(12) United States Patent
Ma et al.

(10) Patent No.: US 11,034,684 B2
(45) Date of Patent: *Jun. 15, 2021

(54) ISOXAZOLE ANALOGS AS FXR AGONISTS AND METHODS OF USE THEREOF

(71) Applicant: Enanta Pharmaceuticals, Inc., Watertown, MA (US)

(72) Inventors: Jun Ma, Belmont, MA (US); Guoqiang Wang, Belmont, MA (US); Bin Wang, Newton, MA (US); Xuechao Xing, Wilmington, MA (US); Ruichao Shen, Belmont, MA (US); Jing He, Somerville, MA (US); Yat Sun Or, Waltham, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 90 days.

This patent is subject to a terminal disclaimer.

(21) Appl. No.: 16/569,819

(22) Filed: Sep. 13, 2019

(65) Prior Publication Data

US 2020/0079764 A1 Mar. 12, 2020

Related U.S. Application Data

(63) Continuation of application No. 15/724,919, filed on Oct. 4, 2017, now Pat. No. 10,450,306.

(60) Provisional application No. 62/404,059, filed on Oct. 4, 2016.

(51) Int. Cl.
  *C07D 417/14* (2006.01)
  *C07D 413/14* (2006.01)
  *C07D 261/08* (2006.01)
  *C07D 413/12* (2006.01)

(52) U.S. Cl.
  CPC ......... *C07D 413/14* (2013.01); *C07D 261/08* (2013.01); *C07D 413/12* (2013.01); *C07D 417/14* (2013.01)

(58) Field of Classification Search
  CPC .................................................. C07D 417/14
  See application file for complete search history.

(56) References Cited

U.S. PATENT DOCUMENTS

| | | | |
|---|---|---|---|
| 5,571,809 A | 11/1996 | Hargrave et al. |
| 6,974,830 B2 | 12/2005 | Giegrich et al. |
| 7,319,109 B2 | 1/2008 | Boggs et al. |
| 7,846,960 B2 | 12/2010 | Bell et al. |
| 7,863,302 B2 | 1/2011 | Bell et al. |
| 7,897,773 B2 | 3/2011 | Aletru et al. |
| 7,902,373 B2 | 3/2011 | Blake et al. |
| 8,952,042 B2 | 2/2015 | Kremoser et al. |
| 9,751,874 B2 | 9/2017 | Gege et al. |
| 10,450,306 B2 * | 10/2019 | Ma .................. C07D 413/14 |
| 2004/0048316 A1 | 3/2004 | Haffner et al. |
| 2007/0054902 A1 | 3/2007 | Fukui et al. |
| 2007/0142340 A1 | 6/2007 | Pellicciari et al. |
| 2008/0167356 A1 | 7/2008 | Caldwell et al. |
| 2009/0163474 A1 | 6/2009 | Zhang et al. |
| 2010/0063697 A1 | 3/2010 | Lindgren et al. |
| 2010/0099703 A1 | 4/2010 | Garcia-López et al. |
| 2010/0120775 A1 | 5/2010 | Bass, III et al. |
| 2010/0152166 A1 | 6/2010 | Genin et al. |
| 2010/0184809 A1 | 7/2010 | Kremoser et al. |
| 2010/0210660 A1 | 8/2010 | Kremoser et al. |
| 2010/0249179 A1 | 9/2010 | Deaton et al. |
| 2010/0292212 A1 | 11/2010 | Ackermann et al. |
| 2011/0034507 A1 | 2/2011 | Akwabi-Ameyaw et al. |
| 2011/0275595 A1 | 11/2011 | Eckhardt et al. |
| 2012/0004164 A1 | 1/2012 | Dales et al. |
| 2013/0261108 A1 | 10/2013 | Tully et al. |
| 2014/0038947 A1 | 2/2014 | Glick et al. |
| 2014/0221659 A1 | 8/2014 | Kinzel et al. |
| 2015/0299210 A1 | 10/2015 | Bailey et al. |
| 2015/0366856 A1 | 12/2015 | Mutnick et al. |
| 2016/0130297 A1 | 5/2016 | Xing et al. |
| 2017/0298068 A1 | 10/2017 | Gege et al. |
| 2017/0304270 A1 | 10/2017 | Or et al. |

(Continued)

FOREIGN PATENT DOCUMENTS

| | | |
|---|---|---|
| CN | 106588804 A | 4/2017 |
| CN | 106632294 A | 5/2017 |

(Continued)

OTHER PUBLICATIONS

"Pubchem CID 123486225" Create Date: Jan. 25, 2017 (Jan. 25, 2017) Date Accessed: Apr. 1, 2019 (Apr. 1, 2019).

(Continued)

*Primary Examiner* — Laura L Stockton

(74) *Attorney, Agent, or Firm* — Edgar W. Harlan; Carolyn S. Elmore; Elmore Patent Law Group, P.C.

(57) ABSTRACT

The present invention provides compounds of Formula I,

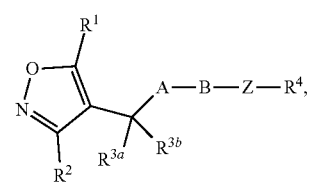

pharmaceutical compositions comprising these compounds and methods of using these compounds to prevent or treat FXR-mediated or TGR5-mediated diseases or conditions.

22 Claims, No Drawings

(56) References Cited

U.S. PATENT DOCUMENTS

| | | |
|---|---|---|
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0030003 A1 | 2/2018 | Wang et al. |
| 2018/0099957 A1 | 4/2018 | Ma et al. |
| 2018/0141941 A1 | 5/2018 | He et al. |
| 2019/0248777 A1 | 8/2019 | Shen et al. |

FOREIGN PATENT DOCUMENTS

| | | | |
|---|---|---|---|
| CN | 106946867 | A | 7/2017 |
| CN | 106995416 | A | 8/2017 |
| CN | 107021957 | A | 8/2017 |
| CN | 108017636 | A | 5/2018 |
| CN | 108341822 | A | 7/2018 |
| CN | 109053751 | A | 12/2018 |
| WO | 2004046162 | A2 | 6/2004 |
| WO | 2007089768 | A2 | 8/2007 |
| WO | 2008115385 | A2 | 9/2008 |
| WO | 2009012125 | A1 | 1/2009 |
| WO | 2009127321 | A1 | 10/2009 |
| WO | 2009149795 | A2 | 12/2009 |
| WO | 2011020615 | A1 | 2/2011 |
| WO | 2011021645 | A1 | 2/2011 |
| WO | 2012087519 | A1 | 6/2012 |
| WO | 2012087520 | A1 | 6/2012 |
| WO | 2012087521 | A1 | 6/2012 |
| WO | 2013007387 | A1 | 1/2013 |
| WO | 2013037482 | A1 | 3/2013 |
| WO | 2013166176 | A1 | 11/2013 |
| WO | 2015036442 | A1 | 3/2015 |
| WO | 2017118294 | A1 | 7/2017 |
| WO | 2017128896 | A1 | 8/2017 |
| WO | 2017145041 | A1 | 8/2017 |
| WO | 2017133521 | A1 | 10/2017 |
| WO | 2017201150 | A1 | 11/2017 |
| WO | 2018024224 | A1 | 2/2018 |
| WO | 2018039386 | A1 | 3/2018 |
| WO | 2018067704 | A1 | 4/2018 |
| WO | 2018075207 | A1 | 4/2018 |
| WO | 2018085148 | A1 | 5/2018 |
| WO | 2018133730 | A1 | 7/2018 |
| WO | 2018170173 | A1 | 9/2018 |
| WO | 2018190643 | A1 | 10/2018 |
| WO | 2018214959 | A1 | 11/2018 |
| WO | 2019007418 | A1 | 1/2019 |

OTHER PUBLICATIONS

Medline Plus. Hardening of the Arteries. (2018). Web: http://www.nlm.nih.gov/medlineplus/ency/article/000171.html.

Merck Manual, Diabetes Mellitus. (2017. Web: http://www.merck.com/mmpe/print/sec12/ch_158b.html.

Buijsman, et al., "Non-Steroidal Steroid Receptor Modulators", Current Medicinal Chemistry, 12, 2005, 1017-1075.

Crawley, , "Farnesoid X Receptor Modulators: a patent review", Expert Opinion on Therapeutic Patents, 20(8), 2010, 1047-1057.

Ruano, J.L. G. et al., "4-(diethoxymethyl)-3-pyridin-3-ylisoxazole-5-carboxylates: useful scaffold for highly functionalised 3-(pyridin-3-yl)isoxazole", Tetrahedron, 61(18), 2005, 4363-4371.

Sepe, et al., "Farnesoid X receptor modulators (2011-2014): a patent review", Expert Opinion on Therapeutic Patents, 25:8, 2015, 885-896.

\* cited by examiner

ISOXAZOLE ANALOGS AS FXR AGONISTS AND METHODS OF USE THEREOF

RELATED APPLICATIONS

This application is a continuation of U.S. application Ser. No. 15/724,919, filed on Oct. 4, 2017, which claims the benefit of U.S. Provisional Application No. 62/404,059, filed on Oct. 4, 2016. The entire teachings of the above applications are incorporated herein by reference.

TECHNICAL FIELD

The present invention relates generally to compounds and pharmaceutical compositions useful as FXR modulators. Specifically, the present invention relates to isoxazole derivatives useful as agonists for FXR, and methods for their preparation and use.

BACKGROUND OF THE INVENTION

Farnesoid X Receptor (FXR) is an orphan nuclear receptor initially identified from a rat liver cDNA library (BM. Forman, et al., *Cell,* 1995, 81(5), 687-693) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., *Cell,* 1995, 83(6), 841-850). The relevant physiological ligands of FXR are bile acids (D. Parks et al., Science, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., *Genes Dev.,* 2003, 17(13), 1581-1591; T. Inagaki et al., *Cell Metab.,* 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/116054, WO 2016/103037, WO 2016/096116, WO 2016/096115, WO 2016/097933, WO 2016/081918, WO 2016/127924, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/133521, WO 2017/156024. Further small molecule FXR modulators have been recently reviewed (R. C. Buijsman, et al., *Curr. Med. Chem.* 2005, 12(9), 1017-1075; Crawley, M. L. *Expert Opin. Ther. Patents* 2010, 20(8), 1047-1057; V. Sepe, et al., *Expert Opin. Ther. Patents* 2015, 25(8), 885-896.

There is a need for the development of FXR modulators for the treatment and prevention of disease. The present invention has identified compounds which modulate FXR as well as methods of using these compounds to treat disease.

SUMMARY OF THE INVENTION

In one aspect, the invention provides compounds represented by Formula I, and pharmaceutically acceptable salts thereof:

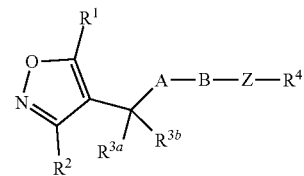

wherein:

$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted $C_3$-$C_6$ cycloalkyl or optionally substituted 3- to 6-membered heterocycloalkyl. Preferably, $R^1$ is isopropyl, tert-butyl, or cyclopropyl.

$R^2$ is optionally substituted aryl, optionally substituted heteroaryl, optionally substituted —$C_3$-$C_{12}$ cycloalkyl or optionally substituted 3- to 12-membered heterocycloalkyl;

$R^{3a}$ and $R^{3b}$ are independently selected from group consisting of hydrogen, halogen, —$C_1$-$C_6$ alkyl, halo-$C_1$-$C_6$ alkyl, —$C_1$-$C_6$ alkoxy or halo-$C_1$-$C_6$ alkoxy, —$C_3$-$C_6$ cycloalkyl, halo-$C_3$-$C_6$ cycloalkyl. Alternatively, $R^{3a}$ and $R^{3b}$ are taken together with the carbon atom to which they are attached to form an optionally substituted —$C_3$-$C_6$ cycloalkyl, optionally substituted 3- to 6-membered heterocycloalkyl, or optionally substituted —$C_3$-$C_6$ cycloalkenyl.

A is selected from the group consisting of:

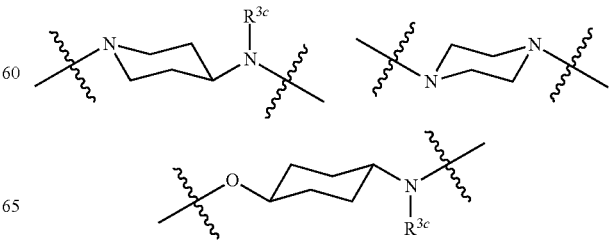

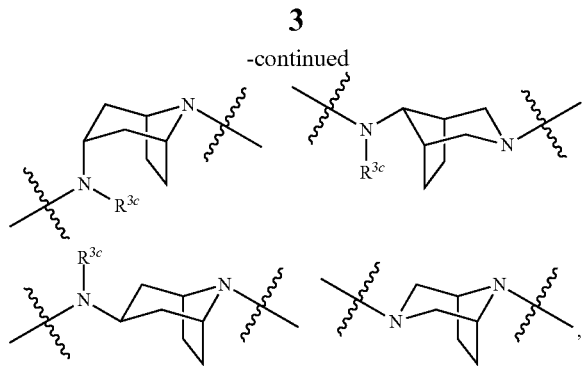

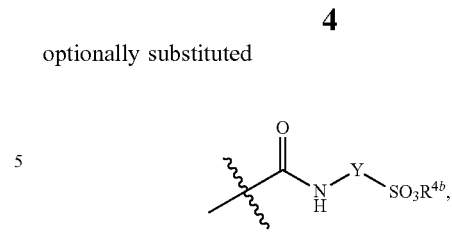

wherein one of the indicated valences is the point of attachment to the carbon atom of —CHR$^{3a}$R$^{3b}$ and the other is the point of attachment to B; R$^{3c}$ is selected from group consisting of hydrogen, optionally substituted —C$_1$-C$_6$ alkyl, optionally substituted —C$_3$-C$_6$ cycloalkyl, formyl, and acetyl; B is optionally substituted aryl, optionally substituted biaryl, optionally substituted 3- to 12 membered heterocycle or optionally substituted heteroaryl;

Z is selected from the group consisting of:
 1) Absent;
 2) Optionally substituted —C$_1$-C$_6$ alkyl;
 3) Optionally substituted —C$_2$-C$_6$ alkenyl;
 4) Optionally substituted —C$_2$-C$_6$ alkynyl;
 5) Optionally substituted —C$_3$-C$_8$ cycloalkyl;
 6) Optionally substituted 3- to 8-membered heterocycloalkyl;
 7) Optionally substituted —C$_3$-C$_8$ cycloalkenyl;
 8) Optionally substituted aryl; and
 9) Optionally substituted heteroaryl;

R$^4$ is hydroxy, protected hydroxy, —O-(hydroxy prodrug group), tetrazol, cyano, —CO$_2$R$^5$, —O—Y—CO$_2$R$^5$, —NR$^{4b}$—Y—CO$_2$R$^5$, —CONR$^{4a}$R$^{4b}$, optionally substituted

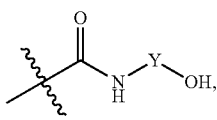

optionally substituted

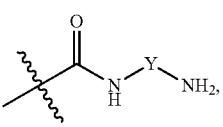

optionally substitute

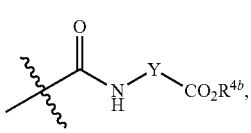

optionally substituted

[structure with —C(O)—NH—Y—SO$_3$R$^{4b}$]

optionally substituted

[structure with —C(O)—NH—S(O)$_2$—R$^7$]

optionally substituted

[structure with —NH—C(O)—NH—S(O)$_2$—R$^7$]

or optionally substituted

[structure with —O—C(O)—NH—S(O)$_2$—R$^7$];

wherein,
 Y is absent or optionally substituted —C$_1$-C$_6$ alkyl;
 R$^4$ and R$^{4b}$ are independently selected from the group consisting of:
  1) Hydrogen;
  2) Optionally substituted —C$_1$-C$_8$ alkyl;
  3) Optionally substituted —C$_2$-C$_8$ alkenyl;
  4) Optionally substituted —C$_2$-C$_8$ alkynyl; and
  5) Optionally substituted —C$_3$-C$_8$ cycloalkyl;
 R$^5$ is selected from the group consisting of:
  1) Hydrogen;
  2)

[sugar structure with OH, OH, OH, and CO$_2$H]

3) Optionally substituted —C$_1$-C$_8$ alkyl;
  4) Optionally substituted —C$_2$-C$_8$ alkenyl;
  5) Optionally substituted —C$_2$-C$_8$ alkynyl; and
  6) Optionally substituted —C$_3$-C$_8$ cycloalkyl; R$^7$ is selected from the groups consisting of:
  1) Optionally substituted —C$_1$-C$_8$ alkyl;
  2) Optionally substituted —C$_2$-C$_8$ alkenyl;
  3) Optionally substituted —C$_2$-C$_8$ alkynyl;
  4) Optionally substituted —C$_3$-C$_8$ cycloalkyl;
  5) Optionally substituted —C$_3$-C$_8$ cycloalkenyl;
  6) Optionally substituted 3- to 8-membered heterocycloalkyl;

7) Optionally substituted 3- to 8-membered heterocycloalkenyl;
8) Optionally substituted aryl;
9) Optionally substituted —$C_1$-$C_8$ arylalkyl;
10) Optionally substituted heteroaryl;
11) Optionally substituted —$C_1$-$C_8$ heteroarylalkyl; and
12) $NR^9R^{10}$; wherein $R^9$ and $R^{10}$ are each independently selected from hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted aryl, optionally substituted alkylaryl, optionally substituted 3- to 8-membered heterocycloalkyl, optionally substituted heteroaryl, optionally substituted alkylheteroaryl; alternatively, $R^9$ and $R^{10}$ are taken together with the nitrogen atom to which they are attached to form a heterocyclic ring.

In certain embodiments, the said hydroxy prodrug group is phosphate or sulfamate. In certain embodiments, the said hydroxy prodrug group is an acyl group derived from an amino acid, preferably an α-amino acid.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

DETAILED DESCRIPTION OF THE INVENTION

In one embodiment the present invention provides a compound of Formula (I) as described above, or a pharmaceutically acceptable salt thereof.

In certain embodiments, the present invention relates to compounds of Formula (I), and pharmaceutically acceptable salts thereof, wherein $R^1$ is optionally substituted isopropyl, cyclopropyl, or tert-butyl.

In certain embodiments, the present invention relates to compounds of Formula (I), and pharmaceutically acceptable salts thereof, wherein $R^2$ is optionally substituted cyclohexyl, cyclopentyl, or cyclopropyl.

In certain embodiments, the present invention relates to compounds of Formula (I), and pharmaceutically acceptable salts thereof, wherein $R^2$ is cyclohexyl or cyclopentyl, each of which is optionally substituted with up to 3 groups which are independently selected from of halogen, —$C_1$-$C_6$ alkyl, halo-$C_1$-$C_6$ alkyl, —$C_1$-$C_6$ alkoxy, halo-$C_1$-$C_6$ alkoxy, —$C_3$-$C_6$ cycloalkyl, halo-$C_3$-$C_6$ cycloalkyl, —$C_3$-$C_6$ cycloalkenyl, halo-$C_3$-$C_6$ cycloalkenyl, optionally substituted aryl, or optionally substituted heteroaryl.

In certain embodiments, the present invention relates to compounds of Formula (I), and pharmaceutically acceptable salts thereof, wherein $R^2$ is cyclopropyl which is optionally substituted with up to 2 groups which are independently selected from of halogen, —$C_1$-$C_6$ alkyl, halo-$C_1$-$C_6$ alkyl, —$C_1$-$C_6$ alkoxy, halo-$C_1$-$C_6$ alkoxy, —$C_3$-$C_6$ cycloalkyl, halo-$C_3$-$C_6$ cycloalkyl, —$C_3$-$C_6$ cycloalkenyl, or halo-$C_3$-$C_6$ cycloalkenyl, optionally substituted aryl, or optionally substituted heteroaryl.

In certain embodiments, the present invention relates to compounds of Formula (I), and pharmaceutically acceptable salts thereof, wherein $R^2$ is optionally substituted phenyl.

In certain embodiments, the present invention relates to compounds of Formula (I), and pharmaceutically acceptable salts thereof, wherein $R^2$ is optionally substituted heteroaryl.

In certain embodiments, the present invention relates to compounds of Formula (I), and pharmaceutically acceptable salts thereof, wherein $R^2$ is selected from the groups set forth below:

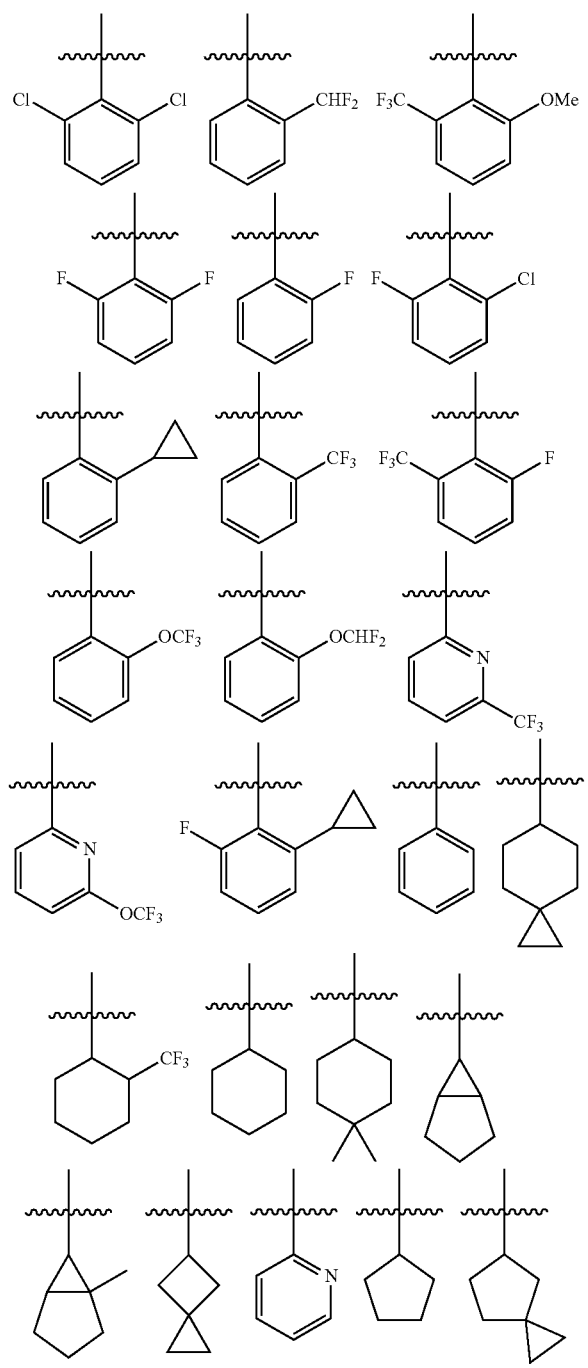

-continued

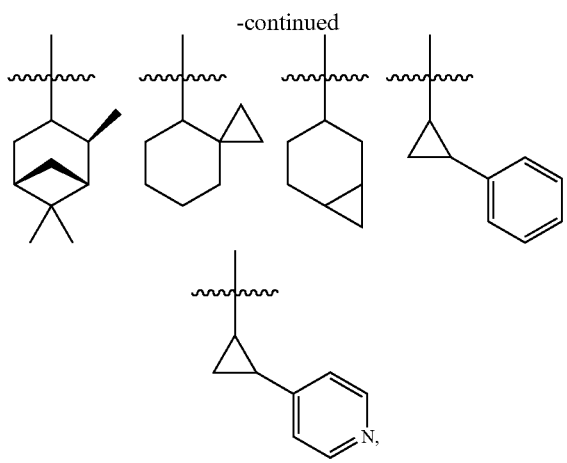

wherein each of above groups can be optionally further substituted. The preferred substituents are halogen, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein one of $R^{3'}$ and $R^{3b}$ is hydrogen or halogen; In certain embodiments, the present invention relates to compounds of Formula (I), and pharmaceutically acceptable salts thereof, wherein both $R^{3a}$ and $R^{3b}$ are independently hydrogen or halogen.

In certain embodiments, the present invention relates to compounds of Formula (I), and pharmaceutically acceptable salts thereof, wherein A is

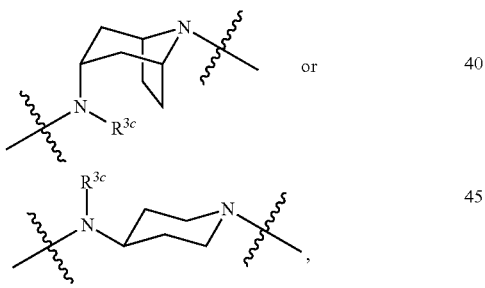

or and $R^{3c}$ is as previously defined; preferably, $R^{3c}$ is hydrogen, methyl, or formyl.

In certain embodiments, the present invention relates to compounds of Formula (I), and pharmaceutically acceptable salts thereof, wherein B is optionally substituted phenyl, pyridyl, pyrimidinyl, pyrazolyl, thienyl, thiazolyl, triazolyl, isothiazolyl, pyrrolyl, pyrazolyl, oxazolyl, oxadiazolyl, imidazolyl, furanyl, indolyl, benzothienyl, naphthyl, quinolyl, naphthyridyl, quinoxalinyl, pyridopyrazolyl, pyridooxazolyl, pyridothiazolyl, isoquinolyl, pyridofuranyl, indazolyl, benzisoxazolyl, benzofuranyl, benzotriazolyl, or benzothiazolyl. Preferred substituents include halogen, —CN, —NO$_2$, —NH$_2$, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein B is an optionally substituted biaryl group. In this embodiment, A and Z, or $R^4$ when Z is absent, are attached to atoms of different rings in the biaryl group. In certain embodiments, B is optionally substituted pyrimidylphenyl, pyrimidylpyridyl, pyrimidyloxadiazolyl. Preferred substituents include halogen, —CN, —NO$_2$, —NH$_2$, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein B is selected from, but not limited to the groups set forth below:

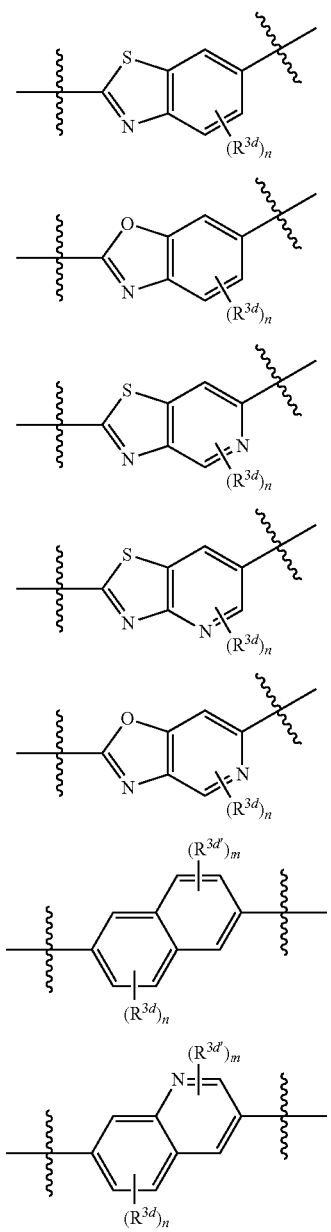

-continued
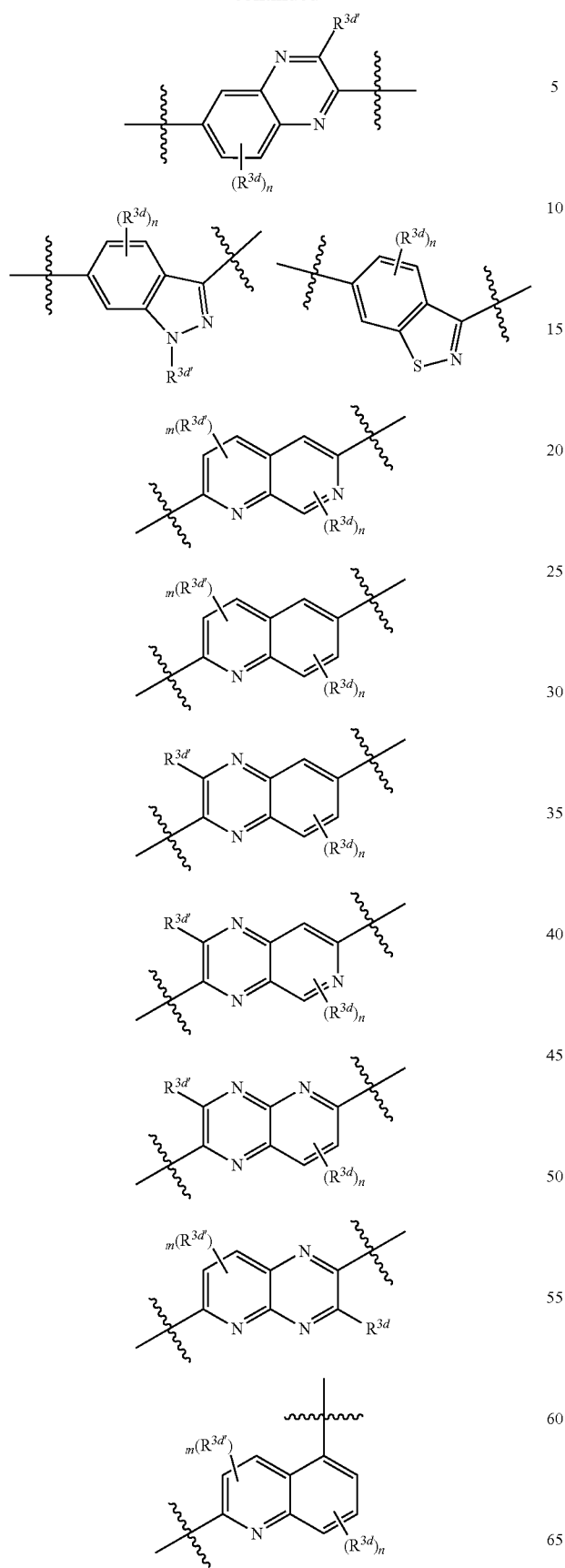
-continued
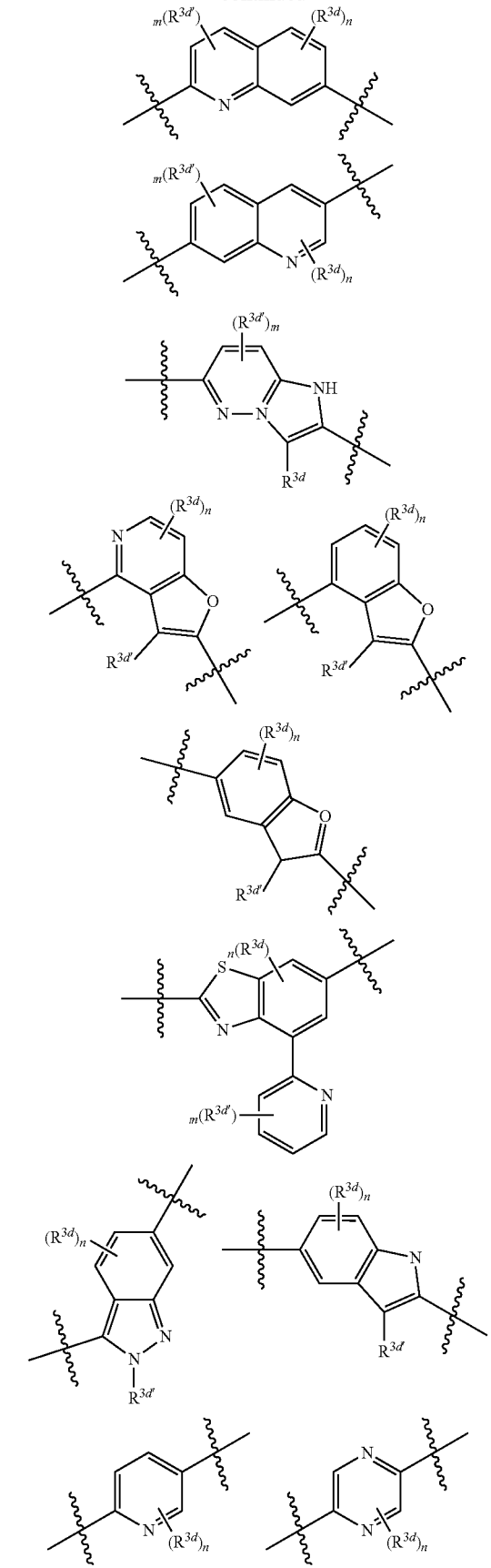

-continued

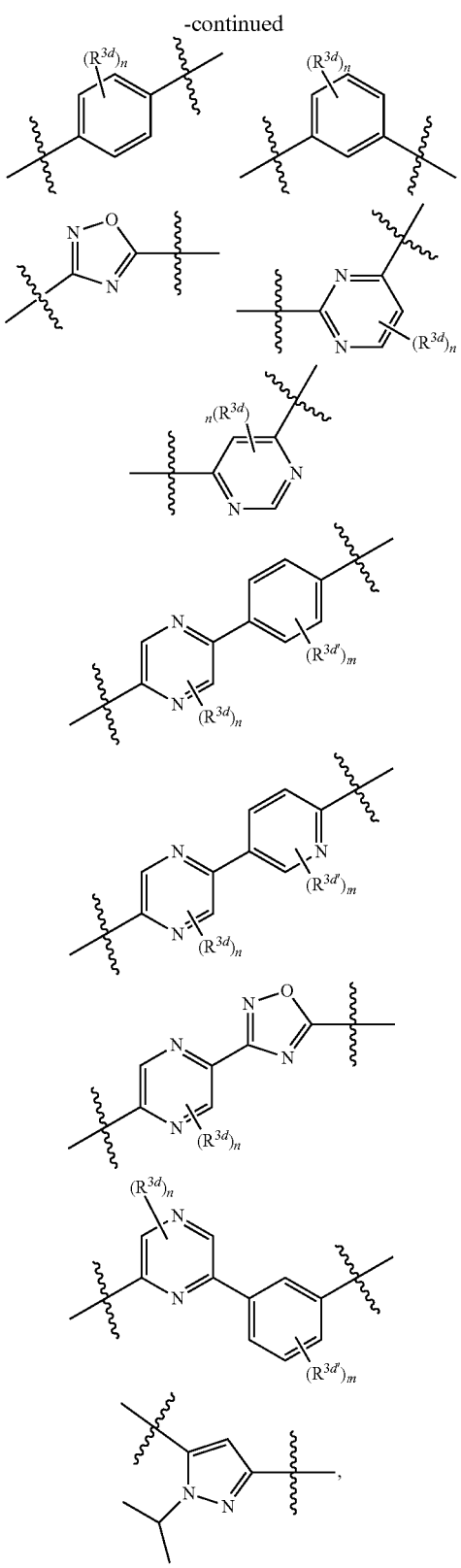

wherein, one of the indicated valences is the point of attachment to A and the other is the point of attachment to Z; $R^{3d}$ and $R^{3e}$ are independently selected from the group consisting of halogen, —CN, —NO$_2$, —NH$_2$, optionally substituted C$_1$-C$_6$ alkyl, optionally substituted C$_1$-C$_6$ alkoxy, optionally substituted C$_3$-C$_6$ cycloalkyl, optionally substituted C$_3$-C$_6$ cycloalkenyl, optionally substituted aryl, and optionally substituted heteroaryl; m and n are independently 0, 1, 2 or 3, preferably, m and n are independently 0 or 1, more preferably, m and n are both 0.

In certain embodiments, the present invention relates to compounds of Formula (I), and pharmaceutically acceptable salts thereof, wherein Z is absent. In certain embodiments, the present invention relates to compounds of Formula (I), and pharmaceutically acceptable salts thereof, wherein Z is optionally substituted —CH$_2$—; preferably, Z is —CH$_2$—, —CHF—, or —CF$_2$—. In certain embodiments, the present invention relates to compounds of Formula (I), and pharmaceutically acceptable salts thereof, wherein Z is optionally substituted —CH$_2$CH$_2$—. In certain embodiments, the present invention relates to compounds of Formula (I), and pharmaceutically acceptable salts thereof, wherein Z is optionally substituted cyclopropyl or cyclohexyl.

In certain embodiments, the present invention relates to compounds of Formula (I), and pharmaceutically acceptable salts thereof, wherein Z is optionally substituted

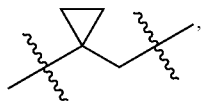

wherein, one of the indicated valences is the point of attachment to B and the other is the point of attachment to $R^4$.

In certain embodiments, the present invention relates to compounds of Formula (I), and pharmaceutically acceptable salts thereof, wherein Z is optionally substituted aryl; preferably Z is optionally substituted phenyl. In certain embodiments, the present invention relates to compounds of Formula (I), and pharmaceutically acceptable salts thereof, wherein Z is optionally substituted heteroaryl; preferably Z is optionally substituted pyridyl.

In certain embodiments, the present invention relates to compounds of Formula (I), and pharmaceutically acceptable salts thereof, wherein $R^4$ is —CO$_2$R$^5$, and $R^5$ is previously defined. Preferably $R^5$ is hydrogen, methyl, ethyl, t-butyl, or OH

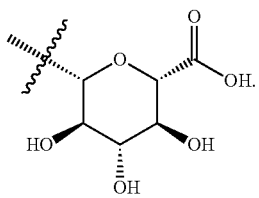

In certain embodiments, the present invention relates to compounds of Formula (I), and pharmaceutically acceptable salts thereof, wherein $R^4$ is

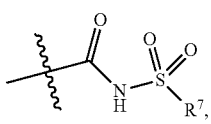

and $R^7$ is previously defined.

In certain embodiments, the present invention relates to compounds of Formula (I), and pharmaceutically acceptable salts thereof, wherein R is optionally substituted cyclopropyl; $R^2$ is selected from

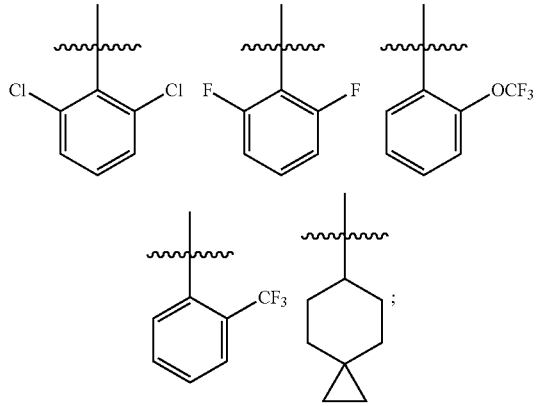

$R^{3a}$ is hydrogen; $R^{3b}$ is hydrogen; A is

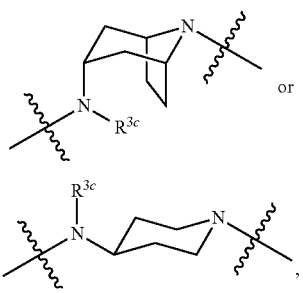

$R^{3c}$ is hydrogen, or methyl; B is selected from:

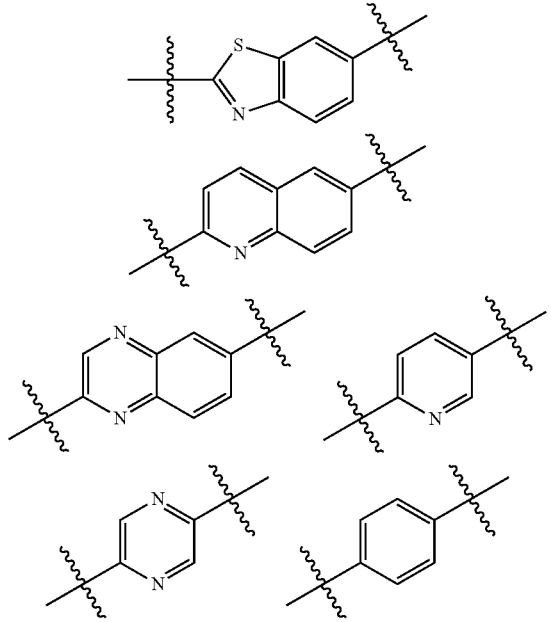

-continued

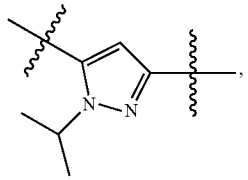

and B is optionally substituted; Z is absent; and $R^4$ is

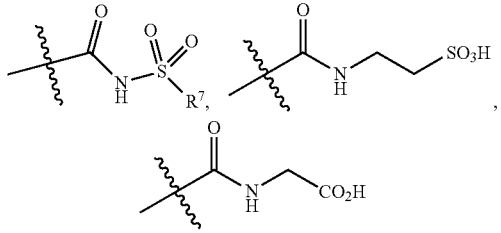

or —$CO_2R^5$; $R^7$ is as previously defined and $R^5$ is hydrogen, methyl, ethyl, t-butyl, or

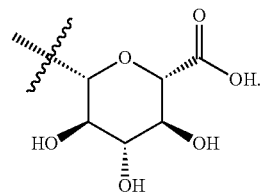

In another embodiment, the compound of Formula (I) is represented by Formula (IIa) or Formula (IIb) or a pharmaceutically acceptable salt thereof:

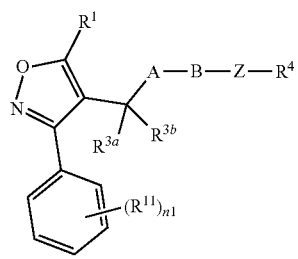

(IIa)

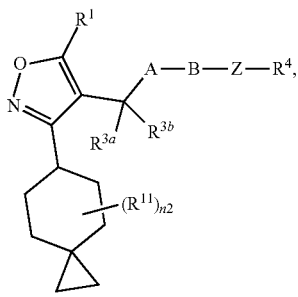

(IIb)

wherein $R^1$, $R^{3a}$, $R^{3b}$, A, B, Z and $R^4$ are as previously defined; $R^{11}$ at each occurrence is independently selected from the group consisting of halogen, optionally substituted —$C_1$-$C_6$ alkyl, optionally substituted —$C_1$-$C_6$ alkoxy, optionally substituted —$C_3$-$C_6$ cycloalkyl, optionally substituted —$C_3$-$C_6$ cycloalkenyl, optionally substituted aryl, or optionally substituted heteroaryl; n1 is 0, 1, 2, 3, 4, or 5: and n2 is 0, 1, or 2.

In another embodiment, the compound of Formula (I) is represented by Formula (IIa-1), (IIa-2), (IIa-3), (IIb-1), (IIb-2), (IIb-3), or a pharmaceutically acceptable salt thereof:

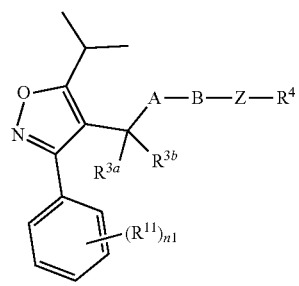

(IIa-1)

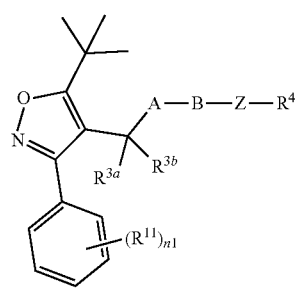

(IIa-2)

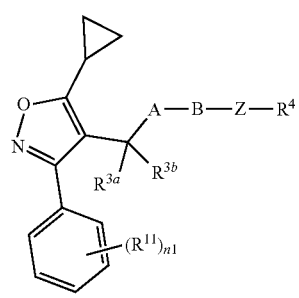

(IIa-3)

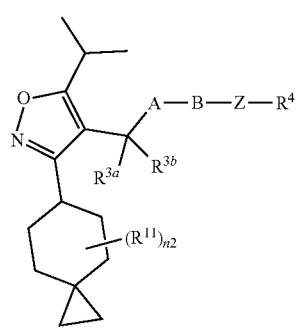

(IIb-1)

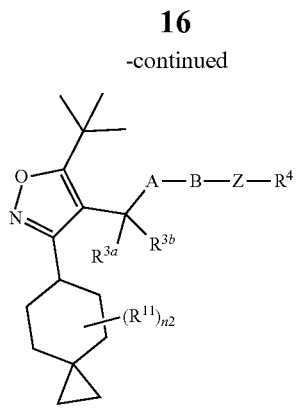

(IIb-2)

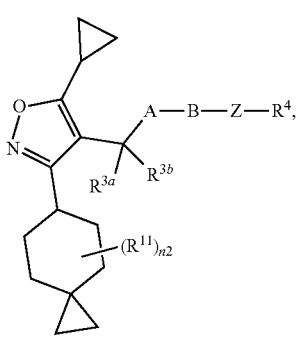

(IIb-3)

wherein $R^{3a}$, $R^{3b}$, A, B, Z, $R^4$, $R^{11}$, n1 and n2 are as previously defined.

In another embodiment, the compound of Formula (I) is represented by Formula (IIIa) or Formula (IIIb) or a pharmaceutically acceptable salt thereof:

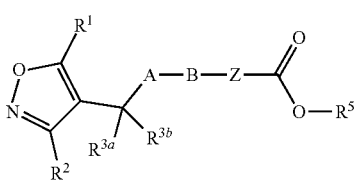

(IIIa)

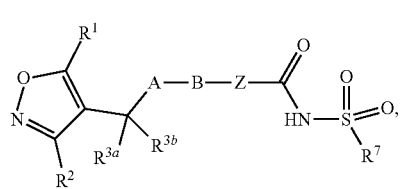

(IIIb)

wherein A, B, Z, $R^1$, $R^2$, $R^{3a}$, $R^{3b}$, $R^5$, and $R^7$ are as previously defined.

In another embodiment, the compound of Formula (I) is represented by Formula (IVa) or Formula (IVb) or a pharmaceutically acceptable salt thereof:

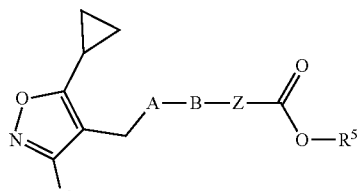
(IVa)

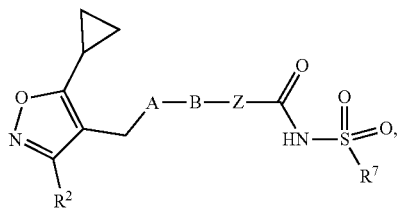
(IVb)

wherein A, B, Z, $R^2$, $R^5$, and $R^7$ are as previously defined.

In another embodiment, the compound of Formula (I) is represented by Formula (Va) or Formula (Vb) or a pharmaceutically acceptable salt thereof:

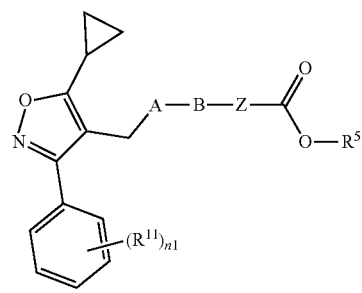
(Va)

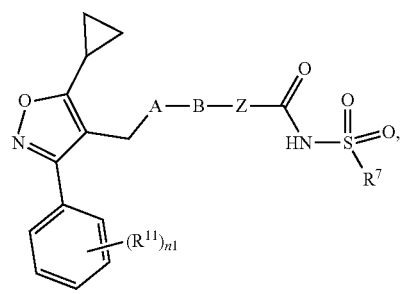
(Vb)

wherein A, B, Z, $R^3$, $R^7$, $R^{11}$, and n are as previously defined.

In another embodiment, the compound of Formula (I) is represented by Formula (VIa) or Formula (VIb) or a pharmaceutically acceptable salt thereof:

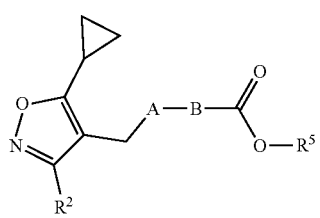
(VIa)

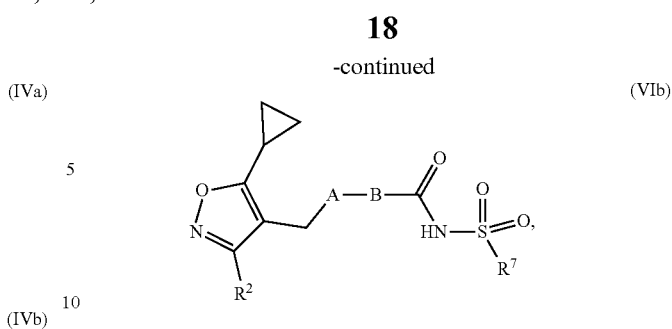
(VIb)

wherein A, B, $R^2$, $R^5$, and $R^7$ are as previously defined.

In another embodiment, the compound of Formula (I) is represented by Formula (VIIa) or Formula (VIb) or a pharmaceutically acceptable salt thereof:

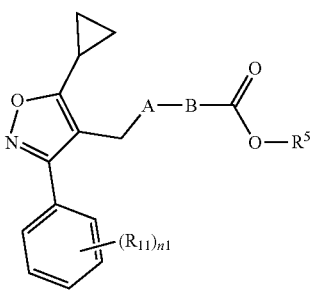
(VIIa)

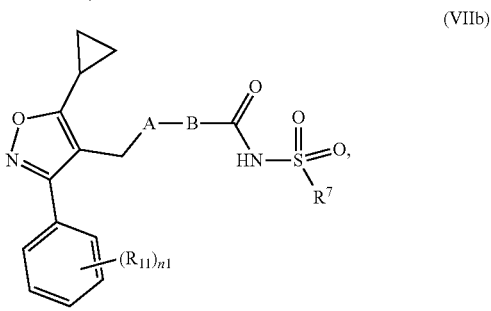
(VIIb)

wherein A, B, $R^5$, $R^7$, $R^1$, and n1 are as previously defined.

In another embodiment, the compound of Formula (I) is represented by Formula (VIII) or a pharmaceutically acceptable salt thereof:

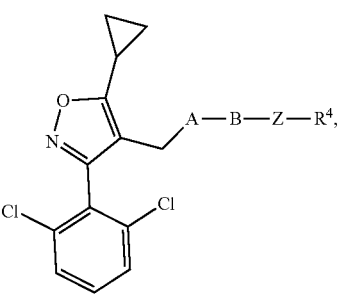
(VIII)

wherein A, B, Z, and $R^4$ are as previously defined.

Representative compounds of the invention include, but are not limited to, compounds according to Formula (VIII), and pharmaceutically acceptable salts thereof, wherein A, B, and Z—$R^4$ are delineated for each compound in Table 1.

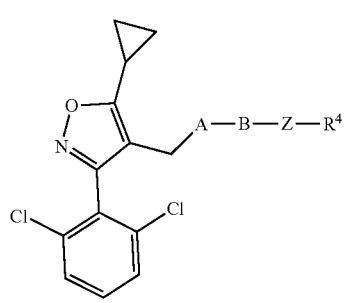

(VIII)

TABLE 1

| Compound | A | B | —Z—R⁴ |
|---|---|---|---|
| 1 | 3-amino-8-azabicyclo[3.2.1]octane (NH/N) | 2,6-benzothiazolediyl | C(=O)OEt |
| 2 | 3-amino-8-azabicyclo[3.2.1]octane (NH/N) | 2,6-benzothiazolediyl | C(=O)OH |
| 3 | 3-amino-8-azabicyclo[3.2.1]octane (NH/N) | 2,6-benzothiazolediyl, 4-F | C(=O)OMe |
| 4 | 3-amino-8-azabicyclo[3.2.1]octane (NH/N) | 2,6-benzothiazolediyl, 4-F | C(=O)OH |
| 5 | 3-amino-8-azabicyclo[3.2.1]octane (NH/N) | 2,6-benzothiazolediyl, 4-OMe | C(=O)OMe |
| 6 | 3-amino-8-azabicyclo[3.2.1]octane (NH/N) | 2,6-benzothiazolediyl, 4-OMe | C(=O)OH |

TABLE 1-continued

| Compound | A | B | —Z—R⁴ |
|---|---|---|---|
| 7 | [azabicyclic amine with NH] | [2,4-disubstituted benzothiazole with methyl] | C(=O)OMe |
| 8 | [azabicyclic amine with NH] | [2,4-disubstituted benzothiazole with methyl] | C(=O)OH |
| 9 | [azabicyclic amine with NH] | [benzothiazole with Br] | C(=O)OMe |
| 10 | [azabicyclic amine with NH] | [benzothiazole with Br] | C(=O)OH |
| 11 | [azabicyclic amine with NH] | [benzothiazole with Cl] | C(=O)OMe |
| 12 | [azabicyclic amine with NH] | [benzothiazole with Cl] | C(=O)OH |
| 13 | [azabicyclic amine with NH] | [benzofuran with methyl] | C(=O)OEt |

TABLE 1-continued

| Compound | A | B | —Z—R⁴ |
|---|---|---|---|
| 14 | bicyclic amine | methyl-benzofuran | —C(CH₃)₂COOH |
| 15 | bicyclic amine | benzothiazole-CF₃ | —C(CH₃)₂C(O)OMe |
| 16 | bicyclic amine | benzothiazole-CF₃ | —C(CH₃)₂COOH |
| 17 | bicyclic amine | benzothiazole-OCF₃ | —C(CH₃)₂C(O)OMe |
| 18 | bicyclic amine | benzothiazole-OCF₃ | —C(CH₃)₂COOH |
| 19 | bicyclic amine | benzoxazole | —C(CH₃)₂C(O)OMe |
| 20 | bicyclic amine | benzoxazole | —C(CH₃)₂COOH |

TABLE 1-continued

| Compound | A | B | —Z—R⁴ |
|---|---|---|---|
| 21 | bicyclic amine with NH | fluorobenzoxazole | methyl ester (C(CH₃)₂C(O)OMe) |
| 22 | bicyclic amine with NH | fluorobenzoxazole | carboxylic acid (C(CH₃)₂C(O)OH) |
| 23 | bicyclic amine with NH | methoxybenzoxazole | methyl ester |
| 24 | bicyclic amine with NH | methoxybenzoxazole | carboxylic acid |
| 25 | bicyclic amine with NH | benzisothiazole | methyl ester |
| 26 | bicyclic amine with NH | benzisothiazole | carboxylic acid |
| 27 | bicyclic amine with NH | fluorobenzisothiazole | methyl ester |

TABLE 1-continued

| Compound | A | B | —Z—R⁴ |
|---|---|---|---|
| 28 | [bicyclic amine with NH] | [fluoro benzisothiazole] | [C(Me)₂C(O)OH] |
| 29 | [bicyclic amine with NH] | [pyrazolo[1,5-a]pyrimidine] | [C(Me)₂C(O)OMe] |
| 30 | [bicyclic amine with NH] | [pyrazolo[1,5-a]pyrimidine] | [C(Me)₂C(O)OH] |
| 31 | [bicyclic amine with NH] | [imidazo[1,2-a]pyridine] | [C(Me)₂C(O)OMe] |
| 32 | [bicyclic amine with NH] | [imidazo[1,2-a]pyridine] | [C(Me)₂C(O)OH] |
| 33 | [bicyclic amine with NH] | [naphthalene] | [C(Me)₂C(O)OMe] |
| 34 | [bicyclic amine with NH] | [isoquinoline] | [C(Me)₂C(O)OH] |

TABLE 1-continued

| Compound | A | B | —Z—R⁴ |
|---|---|---|---|
| 35 | [bicyclic amine with NH] | quinoline | C(Me)₂C(O)OMe |
| 36 | [bicyclic amine with NH] | quinoline | C(Me)₂C(O)OH |
| 37 | [bicyclic amine with NH] | isoquinoline | C(Me)₂C(O)OMe |
| 38 | [bicyclic amine with NH] | isoquinoline | C(Me)₂C(O)OH |
| 39 | [bicyclic amine with NH] | quinazoline | C(Me)₂C(O)OMe |
| 40 | [bicyclic amine with NH] | quinazoline | C(Me)₂C(O)OH |
| 41 | [bicyclic amine with NH] | fluoro-naphthalene | C(Me)₂C(O)OMe |

TABLE 1-continued

| Compound | A | B | —Z—R⁴ |
|---|---|---|---|
| 42 | bicyclic diamine | 5-fluoro-naphthalene-2,7-diyl | C(CH₃)₂COOH |
| 43 | bicyclic diamine | quinoxaline-2,6-diyl | C(CH₃)₂COOMe |
| 44 | bicyclic diamine | quinoxaline-2,6-diyl | C(CH₃)₂COOH |
| 45 | bicyclic diamine | 8-fluoro-quinoline-2,6-diyl | C(CH₃)₂COOMe |
| 46 | bicyclic diamine | 8-fluoro-quinoline-2,6-diyl | C(CH₃)₂COOH |
| 47 | bicyclic diamine | 5-methoxy-naphthalene-2,7-diyl | C(CH₃)₂COOMe |
| 48 | bicyclic diamine | 4-methoxy-quinoline-2,6-diyl | C(CH₃)₂COOH |

TABLE 1-continued

| Compound | A | B | —Z—R⁴ |
|---|---|---|---|
| 49 | (bicyclic amine with NH) | 2,6-naphthyl | methyl ester (C(Me)₂C(O)OMe) |
| 50 | (bicyclic amine with NH) | 3,7-naphthyl | carboxylic acid (C(Me)₂C(O)OH) |
| 51 | (bicyclic amine with NH) | naphthyl with OMe | methyl ester |
| 52 | (bicyclic amine with NH) | naphthyl with OMe | carboxylic acid |
| 53 | (bicyclic amine with NH) | 2,6-quinolinyl | methyl ester |
| 54 | (bicyclic amine with NH) | 2,6-quinolinyl | carboxylic acid |
| 55 | (bicyclic amine with NH) | 3,7-quinolinyl | methyl ester |

TABLE 1-continued

| Compound | A | B | —Z—R⁴ |
|---|---|---|---|
| 56 | bicyclic amine with NH | quinoline (3,7-linked) | C(Me)₂C(O)OH |
| 57 | bicyclic amine with NH | quinoline (2,6-linked) | C(Me)₂C(O)OMe |
| 58 | bicyclic amine with NH | quinoline (2,6-linked) | C(Me)₂C(O)OH |
| 59 | bicyclic amine with NH | 5-F quinoline (2,6-linked) | C(Me)₂C(O)OMe |
| 60 | bicyclic amine with NH | 5-F quinoline (2,6-linked) | C(Me)₂C(O)OH |
| 61 | bicyclic amine with NH | 7-F quinoline (2,6-linked) | C(Me)₂C(O)OMe |
| 62 | bicyclic amine with NH | 7-F quinoline (2,6-linked) | C(Me)₂C(O)OH |

TABLE 1-continued

| Compound | A | B | —Z—R⁴ |
|---|---|---|---|
| 63 | azabicyclic-NH- | quinoxaline | C(=O)OMe |
| 64 | azabicyclic-NH- | quinoxaline | C(=O)OH |
| 65 | azabicyclic-NH- | 3-Cl-quinoxaline | C(=O)OMe |
| 66 | azabicyclic-NH- | 3-Cl-quinoxaline | C(=O)OH |
| 67 | azabicyclic-NH- | quinoline (2,5-) | C(=O)OMe |
| 68 | azabicyclic-NH- | quinoline (2,5-) | C(=O)OH |
| 69 | azabicyclic-NH- | quinazoline | C(=O)OMe |

TABLE 1-continued

| Compound | A | B | —Z—R⁴ |
|---|---|---|---|
| 70 | [bicyclic amine with NH] | quinazoline | –C(Me)₂–CO₂H |
| 71 | [bicyclic amine with NH] | benzisothiazole | –C(Me)₂–CO₂Me |
| 72 | [bicyclic amine with NH] | benzisothiazole | –C(Me)₂–CO₂H |
| 73 | [bicyclic amine with NH] | benzothiazole | –CO₂Me |
| 74 | [bicyclic amine with NH] | benzothiazole | –CO₂t-Bu |
| 75 | [bicyclic amine with NH] | benzothiazole | –CH₂–CO₂Me |
| 76 | [bicyclic amine with NH] | benzothiazole | –CH₂–CO₂H |

TABLE 1-continued

| Compound | A | B | —Z—R⁴ |
|---|---|---|---|
| 77 | bicyclic amine with NH | benzothiazole | CH₂CH₂C(O)OMe |
| 78 | bicyclic amine with NH | benzothiazole | CH₂CH₂C(O)OH |
| 79 | bicyclic amine with NH | benzothiazole | CH₂OCH₂C(O)OMe |
| 80 | bicyclic amine with NH | benzothiazole | CH₂OCH₂C(O)OH |
| 81 | bicyclic amine with NH | benzothiazole | CH₂NHCH₂C(O)OMe |
| 82 | bicyclic amine with NH | benzothiazole | CH₂NHCH₂C(O)OH |
| 83 | bicyclic amine with NH | benzothiazole | CH₂N(Me)CH₂C(O)OMe |

TABLE 1-continued

| Compound | A | B | —Z—R⁴ |
|---|---|---|---|
| 84 | bicyclic amine with NH | benzothiazole | CH₂N(Me)CH₂CO₂H |
| 85 | bicyclic amine with NH | benzothiazole | C(Me)₂CH₂OH |
| 86 | bicyclic amine with NH | benzothiazole | C(Me)₂CH₂CH₂OH |
| 87 | bicyclic amine with NH | benzothiazole | cyclopropyl-CO₂Me |
| 88 | bicyclic amine with NH | benzothiazole | cyclopropyl-CO₂H |
| 89 | bicyclic amine with NH | benzothiazole | cyclopropyl-CH₂C(O)OMe |
| 90 | bicyclic amine with NH | benzothiazole | cyclopropyl-CH₂C(O)OH |

TABLE 1-continued

| Compound | A | B | —Z—R⁴ |
|---|---|---|---|
| 91 | (bicyclic amine with NH) | (benzothiazole) | C(F)(F)CO₂Me |
| 92 | (bicyclic amine with NH) | (benzothiazole) | C(F)(F)COOH |
| 93 | (bicyclic amine with NH) | (benzothiazole) | CN |
| 94 | (bicyclic amine with NH) | (benzothiazole) | tetrazole |
| 95 | (bicyclic amine with NH) | (benzothiazole) | C(=O)NHCH₂C(=O)O-tBu |
| 96 | (bicyclic amine with NH) | (benzothiazole) | C(=O)NHCH₂COOH |
| 97 | (bicyclic amine with NH) | (benzothiazole) | C(=O)NHC(CH₃)₂COOH |

TABLE 1-continued
| Compound | A | B | —Z—R⁴ |
|---|---|---|---|
| 98 | 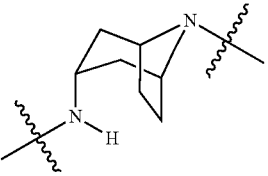 | 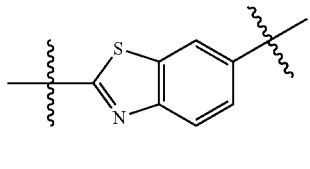 | 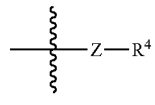 |
| 99 | 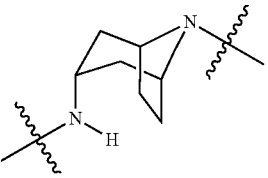 | 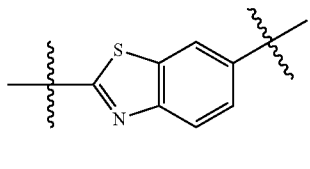 | 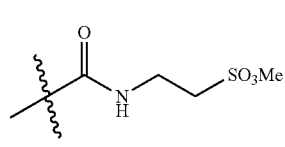 |
| 100 | 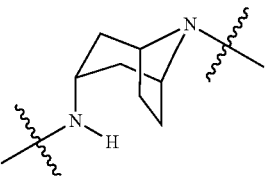 [SMILES: *NC1CC2CCC(C1)CN(*)C2] | 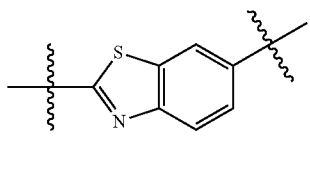 | 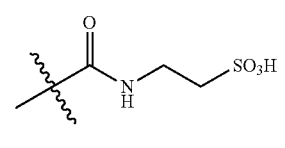 [SMILES: *C(=O)NCCS(=O)(=O)O] |
| 101 | 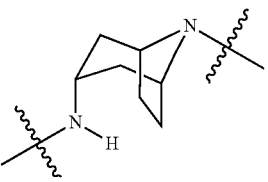 | 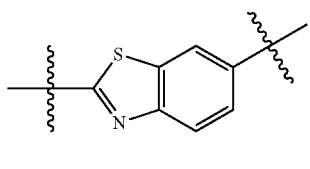 | 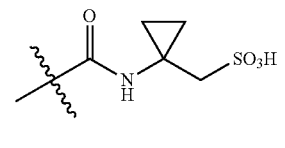 |
| 102 | 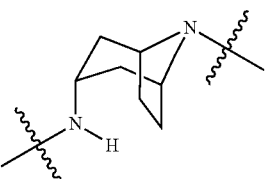 [SMILES: *NC1CC2CCC(C1)CN(*)C2] | 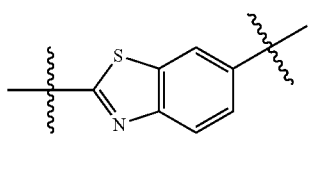 | 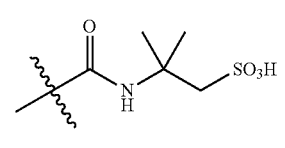 [SMILES: *C(=O)NC(C)(C)CS(=O)(=O)O] |
| 103 | 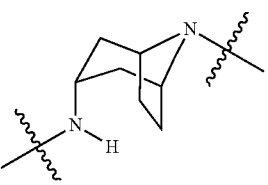 | 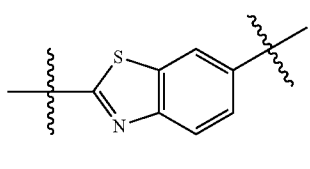 | 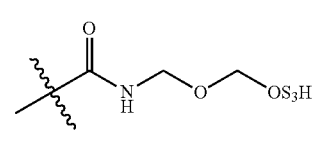 |
| 104 | 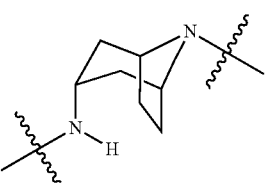 [SMILES: *NC1CC2CCC(C1)CN(*)C2] | 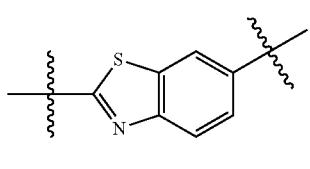 | 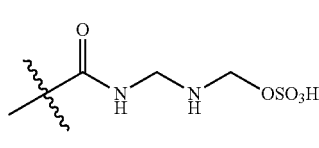 |

TABLE 1-continued

| Compound | A | B | —Z—R⁴ |
|---|---|---|---|
| 105 | [bicyclic amine with NH] | [benzothiazole] | [acyl glucuronide] |
| 106 | [bicyclic amine with NH] | [benzothiazole with OMe] | [acyl glucuronide] |
| 107 | [bicyclic amine with NH] | [benzothiazole with F] | [acyl glucuronide] |
| 108 | [bicyclic amine with NH] | [benzothiazole with Me] | [acyl glucuronide] |
| 109 | [bicyclic amine with NH] | [1,2,4-oxadiazole] | [methyl benzoate] |
| 110 | [bicyclic amine with NH] | [1,2,4-oxadiazole] | [benzoic acid] |
| 111 | [bicyclic amine with NH] | [1,2,4-oxadiazole] | [methyl picolinate] |

TABLE 1-continued

| Compound | A | B | —Z—R⁴ |
|---|---|---|---|
| 112 | [bicyclic amine with NH] | [1,2,4-oxadiazole] | pyridine-2-carboxylic acid (6-position linked) |
| 113 | [bicyclic amine with NH] | [1,2,4-oxadiazole] | methyl benzoate (para-linked) |
| 114 | [bicyclic amine with NH] | [1,2,4-oxadiazole] | benzoic acid (para-linked) |
| 115 | [bicyclic amine with NH] | [1,2,4-oxadiazole] | methyl 4-fluoro-3-substituted benzoate |
| 116 | [bicyclic amine with NH] | [1,2,4-oxadiazole] | 4-fluoro-3-substituted benzoic acid |
| 117 | [bicyclic amine with NH] | [1,2,4-oxadiazole] | methyl cyclohexane-carboxylate (3,5-disubstituted) |
| 118 | [bicyclic amine with NH] | [1,2,4-oxadiazole] | cyclohexane-carboxylic acid (3,5-disubstituted) |

TABLE 1-continued

| Compound | A | B | —Z—R⁴ |
|---|---|---|---|
| 119 | azabicyclic-NH- | pyrazine-2,5-diyl | —CO₂Me |
| 120 | azabicyclic-NH- | pyrazine-2,5-diyl | —C(CH₃)₂CO₂H |
| 121 | azabicyclic-NH- | 3-fluoro-1,4-phenylene | —CO₂Me |
| 122 | azabicyclic-NH- | 3-fluoro-1,4-phenylene | —C(CH₃)₂CO₂H |
| 123 | azabicyclic-NH- | 4-methylpyrimidine-2,6-diyl | —C(CH₃)₂CO₂H |
| 124 | azabicyclic-NH- | pyridine-2,6-diyl | —C(CH₃)₂CO₂H |
| 125 | azabicyclic-NH- | pyridine-2,5-diyl | —C(CH₃)₂CO₂H |

TABLE 1-continued

| Compound | A | B | —Z—R⁴ |
|---|---|---|---|
| 126 | bicyclic amine with NH | 4-fluoropyridine-2,5-diyl | C(CH₃)₂COOH |
| 127 | bicyclic amine with NH | thiazole-2,4-diyl | C(CH₃)₂COOH |
| 128 | bicyclic amine with NH | thiazole-2,5-diyl | C(CH₃)₂COOH |
| 129 | bicyclic amine with NH | 4-methylpyridine-2,5-diyl | C(CH₃)₂COOH |
| 130 | bicyclic amine with NH | pyridine-2,6-diyl | C(CH₃)₂COOH |
| 131 | bicyclic amine with NH | 3-methylpyridine-2,5-diyl | C(CH₃)₂COOH |
| 132 | bicyclic amine with NH | 3-fluoropyridine-2,5-diyl | C(CH₃)₂COOH |

TABLE 1-continued

| Compound | A | B | —Z—R⁴ |
|---|---|---|---|
| 133 | [bicyclic amine with NH] | 3-cyclopropylpyridine-2,5-diyl | —C(CH₃)₂—COOH |
| 134 | [bicyclic amine with NH] | 2,6-difluoro-1,4-phenylene | —C(CH₃)₂—COOH |
| 135 | [bicyclic amine with NH] | pyrazine-2,5-diyl | —CH(CH₃)—CN |
| 136 | [bicyclic amine with NH] | pyrazine-2,5-diyl | tetrazole |
| 137 | [bicyclic amine with NH] | 2-fluoro-1,4-phenylene | —CH(CH₃)—CN |
| 138 | [bicyclic amine with NH] | 2-fluoro-1,4-phenylene | tetrazole |
| 139 | [bicyclic amine with NH] | 2-methoxy-1,4-phenylene | —CH(CH₃)—CN |

TABLE 1-continued

| Compound | A | B | —⸨Z—R⁴⸩— |
|---|---|---|---|
| 140 | (bicyclic amine with NH) | 2-methoxy-1,4-phenylene | 2H-tetrazol-5-yl |
| 141 | (bicyclic amine with NH) | benzothiazole-2,6-diyl | tert-butoxycarbonyl-NH-SO₂-(4-isopropoxyphenyl) |
| 142 | (bicyclic amine with NH) | 4-fluorobenzothiazole-2,6-diyl | tert-butoxycarbonyl-NH-SO₂-(4-isopropoxyphenyl) |
| 143 | (bicyclic amine with NH) | 4-methoxybenzothiazole-2,6-diyl | tert-butoxycarbonyl-NH-SO₂-(4-isopropoxyphenyl) |
| 144 | (bicyclic amine with NH) | 4-chlorobenzothiazole-2,6-diyl | tert-butoxycarbonyl-NH-SO₂-(4-isopropoxyphenyl) |
| 145 | (bicyclic amine with NH) | benzothiazole-2,6-diyl | tert-butoxycarbonyl-NH-SO₂-(4-tert-butoxyphenyl) |
| 146 | (bicyclic amine with NH) | 4-fluorobenzothiazole-2,6-diyl | tert-butoxycarbonyl-NH-SO₂-(4-tert-butoxyphenyl) |

TABLE 1-continued

| Compound | A | B | —Z—R⁴ |
|---|---|---|---|
| 147 | [azabicyclic amine] | [benzothiazole with OMe] | [carbamate sulfonamide phenyl O-tBu] |
| 148 | [azabicyclic amine] | [benzothiazole with Cl] | [carbamate sulfonamide phenyl O-tBu] |
| 149 | [azabicyclic amine] | [benzothiazole] | [carbamate sulfonamide pyridyl piperidine] |
| 150 | [azabicyclic amine] | [benzothiazole with F] | [carbamate sulfonamide pyridyl piperidine] |
| 151 | [azabicyclic amine] | [benzothiazole with OMe] | [carbamate sulfonamide pyridyl piperidine] |
| 152 | [azabicyclic amine] | [benzothiazole with Cl] | [carbamate sulfonamide pyridyl piperidine] |
| 153 | [azabicyclic amine] | [benzothiazole] | [carbamate sulfonamide phenyl O-tBu] |

TABLE 1-continued

| Compound | A | B | ⌇—Z—R⁴ |
|---|---|---|---|
| 154 | [bicyclic amine with NH] | [benzothiazole, F-substituted] | [O-C(O)-NH-SO₂-C₆H₄-O-tBu] |
| 155 | [bicyclic amine with NH] | [benzothiazole, OMe-substituted] | [O-C(O)-NH-SO₂-C₆H₄-O-tBu] |
| 156 | [bicyclic amine with NH] | [benzothiazole, Cl-substituted] | [O-C(O)-NH-SO₂-C₆H₄-O-tBu] |
| 157 | [bicyclic amine with NH] | [benzothiazole] | [NH-C(O)-NH-SO₂-C₆H₄-tBu] |
| 158 | [bicyclic amine with NH] | [benzothiazole, F-substituted] | [NH-C(O)-NH-SO₂-C₆H₄-tBu] |
| 159 | [bicyclic amine with NH] | [benzothiazole, OMe-substituted] | [NH-C(O)-NH-SO₂-C₆H₄-tBu] |
| 160 | [bicyclic amine with NH] | [benzothiazole, Cl-substituted] | [NH-C(O)-NH-SO₂-C₆H₄-tBu] |

TABLE 1-continued

| Compound | A | B | —Z—R⁴ |
|---|---|---|---|
| 161 | 3-aminoazabicyclo[3.3.1] (NH) | benzothiazol-2,6-diyl | CH₂NHC(O)NHSO₂-C₆H₄-tBu |
| 162 | 3-aminoazabicyclo[3.3.1] (NH) | 4-F-benzothiazol-2,6-diyl | CH₂NHC(O)NHSO₂-C₆H₄-tBu |
| 163 | 3-aminoazabicyclo[3.3.1] (NH) | 4-OMe-benzothiazol-2,6-diyl | CH₂NHC(O)NHSO₂-C₆H₄-tBu |
| 164 | 3-(N-methylamino)azabicyclo[3.3.1] | 4-Cl-benzothiazol-2,6-diyl | CH₂NHC(O)NHSO₂-C₆H₄-tBu |
| 165 | 3-(N-methylamino)azabicyclo[3.3.1] | benzothiazol-2,6-diyl | C(CH₃)₂C(O)OEt |
| 166 | 3-(N-methylamino)azabicyclo[3.3.1] | benzothiazol-2,6-diyl | C(CH₃)₂C(O)OH |
| 167 | 3-(N-formylamino)azabicyclo[3.3.1] | benzothiazol-2,6-diyl | C(CH₃)₂C(O)OEt |

TABLE 1-continued
| Compound | A | B | -Z-R⁴ |
|---|---|---|---|
| 168 | 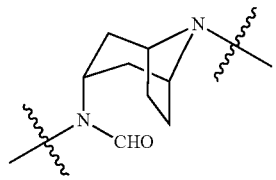 [SMILES: *N1CC2CCC(CC(N(*)C=O)C2)C1] | 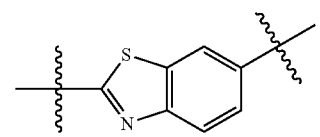 | 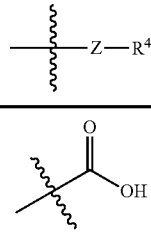 |
| 169 | 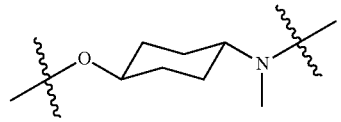 [SMILES: *OC1CCC(N(*)C)CC1] | 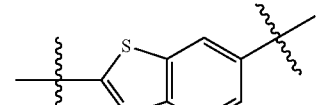 | 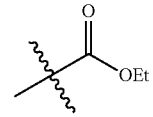 [SMILES: *C(=O)OCC] |
| 170 | 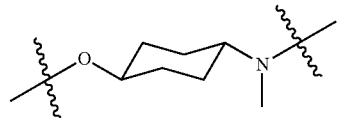 [SMILES: *OC1CCC(N(*)C)CC1] | 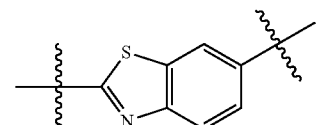 | 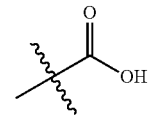 [SMILES: *C(=O)O] |
| 171 | 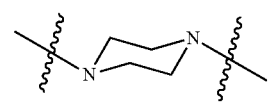 [SMILES: *N1CCN(*)CC1] | 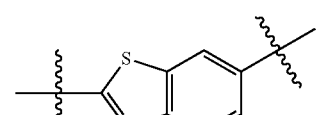 | 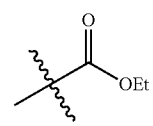 |
| 172 | 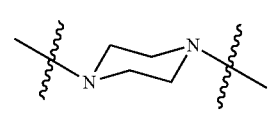 [SMILES: *N1CCN(*)CC1] | 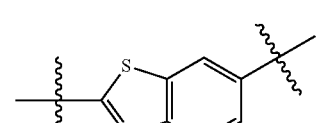 | 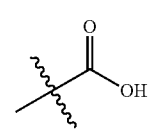 [SMILES: *C(=O)O] |
| 173 | 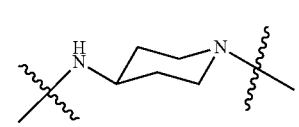 [SMILES: *NC1CCN(*)CC1] | 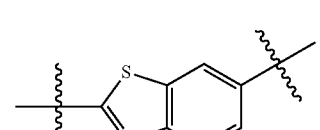 | 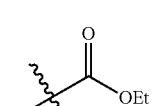 |
| 174 | 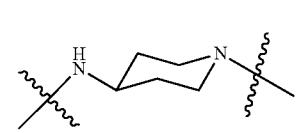 | 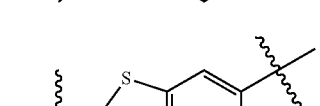 | 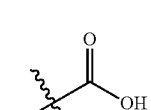 |
| 175 | 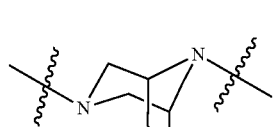 | 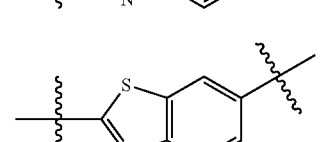 | 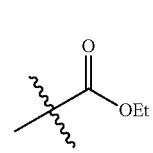 [SMILES: *C(=O)OCC] |
| 176 | 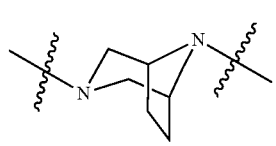 [SMILES: *N1CC2CCC(C1)CN(*)C2] | 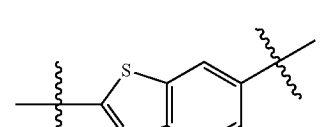 | 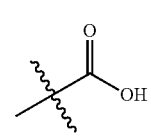 [SMILES: *C(=O)O] |
| 177 | 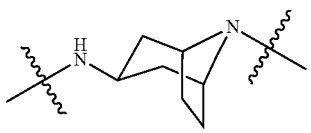 [SMILES: *NC1CC2CCC(C1)CN(*)C2] | 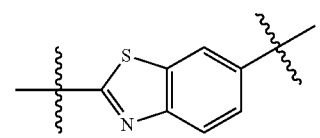 | 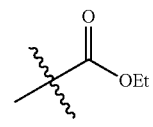 |

TABLE 1-continued

| Compound | A | B | —Z—R⁴ |
|---|---|---|---|
| 178 | 3-aminotropane (NH) | benzothiazol-2,6-diyl | C(=O)OH |
| 179 | 3-(methylamino)tropane | benzothiazol-2,6-diyl | C(=O)OMe |
| 180 | 3-(methylamino)tropane | benzothiazol-2,6-diyl | C(=O)OH |
| 181 | piperazine-1,4-diyl | 1,3-phenylene | C(=O)OMe |
| 182 | piperazine-1,4-diyl | 1,3-phenylene | C(=O)OH |
| 183 | 4-aminopiperidine (NH) | benzothiazol-2,6-diyl | C(=O)OEt |
| 184 | 4-aminopiperidine (NH) | benzothiazol-2,6-diyl | C(=O)OH |
| 185 | 4-(methylamino)piperidine | benzothiazol-2,6-diyl | C(=O)OEt |
| 186 | 4-(methylamino)piperidine | benzothiazol-2,6-diyl | C(=O)OH |
| 187 | piperazine-1,4-diyl | 1,3-phenylene | C(=O)OMe |

TABLE 1-continued

| Compound | A | B | ⸺Z—R⁴ |
|---|---|---|---|
| 188 | piperazine | 1,3-phenylene | C(Me)₂COOH |
| 189 | 3-aminomethyl-8-azabicyclo | 4-(OCHF₂)-benzothiazole-2,6-diyl | C(Me)₂COOMe |
| 190 | 3-aminomethyl-8-azabicyclo | 4-(OCHF₂)-benzothiazole-2,6-diyl | C(Me)₂COOH |
| 191 | 3-aminomethyl-8-azabicyclo | 4-(OCH₂F)-benzothiazole-2,6-diyl | C(Me)₂COOMe |
| 192 | 3-aminomethyl-8-azabicyclo | 4-(OCH₂F)-benzothiazole-2,6-diyl | C(Me)₂COOH |
| 193 | 3-aminomethyl-8-azabicyclo | 5-Me-benzothiazole-2,6-diyl | C(Me)₂COOMe |
| 194 | 3-aminomethyl-8-azabicyclo | 5-Me-benzothiazole-2,6-diyl | C(Me)₂COOH |
| 195 | 3-aminomethyl-8-azabicyclo | 7-Me-benzothiazole-2,6-diyl | C(Me)₂COOMe |

TABLE 1-continued

| Compound | A | B | —Z—R⁴ |
|---|---|---|---|
| 196 | azabicyclic-NH | 7-Me-benzothiazol-2,6-diyl | C(Me)₂COOH |
| 197 | azabicyclic-NH | 3-MeO-quinoxaline-2,6-diyl | C(Me)₂COOMe |
| 198 | azabicyclic-NH | 3-MeO-quinoxaline-2,6-diyl | C(Me)₂COOH |
| 199 | azabicyclic-NH | 3-Cl-quinoxaline-2,6-diyl | C(Me)₂COOMe |
| 200 | azabicyclic-NH | 3-Cl-quinoxaline-2,6-diyl | C(Me)₂COOH |
| 200-1 | azabicyclic-NH | 4-F-benzothiazol-2,6-diyl | C(Me)₂C(O)NHCH₂CH₂SO₃H |
| 200-2 | azabicyclic-NH | quinoxaline-2,6-diyl | C(Me)₂COOMe |

TABLE 1-continued

| Compound | A | B | ⁀Z—R⁴ |
|---|---|---|---|
| 200-3 | 4-aminopiperidine | 2,6-disubstituted-4-OiPr-benzothiazole | C(=O)OMe (α,α-dimethyl) |
| 200-4 | 4-aminopiperidine | 2,6-disubstituted-4-OiPr-benzothiazole | C(=O)OH (α,α-dimethyl) |
| 200-5 | 4-aminopiperidine | 2,6-disubstituted-4-F-benzothiazole | C(=O)OMe (α,α-dimethyl) |
| 200-6 | 4-aminopiperidine | 2,6-disubstituted-4-F-benzothiazole | C(=O)OH (α,α-dimethyl) |
| 200-7 | 3-amino-8-azabicyclo[3.2.1]octane | 2,6-disubstituted-5-OMe-benzothiazole | C(=O)OMe (α,α-dimethyl) |
| 200-8 | 3-amino-8-azabicyclo[3.2.1]octane | 2,6-disubstituted-5-OMe-benzothiazole | C(=O)OH (α,α-dimethyl) |
| 200-9 | 3-amino-8-azabicyclo[3.2.1]octane | 2,6-disubstituted-4-OEt-benzothiazole | C(=O)OMe (α,α-dimethyl) |
| 200-10 | 3-amino-8-azabicyclo[3.2.1]octane | 2,6-disubstituted-4-OEt-benzothiazole | C(=O)OH (α,α-dimethyl) |

TABLE 1-continued

| Compound | A | B | —Z—R⁴ |
|---|---|---|---|
| 200-11 | 3-aminoquinuclidine-like | 2-yl-7-methoxybenzothiazol-6-yl | —C(CH₃)₂C(O)NHCH₂COOH |
| 200-12 | 3-aminoquinuclidine-like | 2-yl-7-methoxybenzothiazol-6-yl | —C(CH₃)₂C(O)NHCH₂CH₂SO₃H |
| 200-13 | 3-aminoquinuclidine-like | 2-yl-7-isopropoxybenzothiazol-6-yl | —C(CH₃)₂C(O)OMe |
| 200-14 | 3-aminoquinuclidine-like | 2-yl-7-isopropoxybenzothiazol-6-yl | —C(CH₃)₂C(O)OH |
| 200-15 | 3-aminoquinuclidine-like | 2-yl-5-fluorobenzothiazol-6-yl | —C(CH₃)₂C(O)OMe |
| 200-16 | 3-aminoquinuclidine-like | 2-yl-5-fluorobenzothiazol-6-yl | —C(CH₃)₂C(O)OH |
| 200-17 | 3-aminoquinuclidine-like | 2-yl-thiazolo[5,4-b]pyrazin-6-yl | —C(CH₃)₂C(O)OMe |

TABLE 1-continued

| Compound | A | B | —Z—R⁴ |
|---|---|---|---|
| 200-18 | bicyclic amine | thiazolo-pyrazine | C(Me)₂COOH |
| 200-19 | bicyclic amine | 5-Br-benzothiazole | C(Me)₂COOMe |
| 200-20 | bicyclic amine | 5-Br-benzothiazole | C(Me)₂COOH |
| 200-21 | bicyclic amine | 4-Br-benzothiazole | C(Me)₂COOMe |
| 200-22 | bicyclic amine | 4-Br-benzothiazole | C(Me)₂COOH |
| 200-23 | bicyclic amine | 5-Ph-benzothiazole | C(Me)₂COOMe |
| 200-24 | bicyclic amine | 5-Ph-benzothiazole | C(Me)₂COOH |

TABLE 1-continued

| Compound | A | B | —Z—R⁴ |
|---|---|---|---|
| 200-25 | azabicyclic-NH | 2-yl-7-Ph-benzothiazole-6-yl | C(Me)₂C(O)OMe |
| 200-26 | azabicyclic-NH | 2-yl-7-Ph-benzothiazole-6-yl | C(Me)₂C(O)OH |
| 200-27 | azabicyclic-NH | naphtho[1,2-d]thiazol-2,5-diyl | C(Me)₂C(O)OMe |
| 200-28 | azabicyclic-NH | naphtho[1,2-d]thiazol-2,5-diyl | C(Me)₂C(O)OH |
| 200-29 | azabicyclic-NH | 2-yl-4-cyclopropyl-benzothiazole-6-yl | C(Me)₂C(O)OMe |
| 200-30 | azabicyclic-NH | 2-yl-4-cyclopropyl-benzothiazole-6-yl | C(Me)₂C(O)OH |
| 200-31 | azabicyclic-NH | isoxazolo-pyrazine diyl | C(Me)₂C(O)OH |

TABLE 1-continued

| Compound | A | B | —Z—R⁴ |
|---|---|---|---|
| 200-32 | | | |
| 200-33 | | | |
| 200-34 | | | |
| 200-35 | | | |
| 200-36 | | | |
| 200-37 | | | |
| 200-38 | | | |

TABLE 1-continued

| Compound | A | B | —Z—R⁴ |
|---|---|---|---|
| 200-39 | [azabicyclic amine with NH] | [quinoxaline, 2,5-disubstituted] | [C(CH₃)₂COOH] |
| 200-40 | [azabicyclic amine with NH] | [quinoxaline, 2,6-disubstituted] | [C(CH₃)₂COOH] |
| 200-41 | [azabicyclic amine with NH] | [quinoxaline, 2,6-disubstituted] | [C(CH₃)₂COOH] |
| 200-42 | [azabicyclic amine with NH] | [quinoxaline, 2,5-disubstituted] | [C(CH₃)₂COOH] |
| 200-43 | [azabicyclic amine with NH] | [3-CF₃-quinoxaline, 2,5-disubstituted] | [C(CH₃)₂COOH] |
| 200-44 | [azabicyclic amine with NH] | [3-CF₃-quinoxaline, 2,6-disubstituted] | [C(CH₃)₂COOH] |
| 200-45 | [azabicyclic amine with NH] | [3-CF₃-quinoxaline, 2,6-disubstituted] | [C(CH₃)₂COOH] |

TABLE 1-continued

| Compound | A | B | —Z—R⁴ |
|---|---|---|---|
| 200-46 | [bicyclic amine with NH] | [F₃C-quinoxaline] | [C(=O)OH with gem-dimethyl] |
| 200-47 | [bicyclic amine with NH] | [OiPr-quinoxaline] | [C(=O)OH with gem-dimethyl] |
| 200-48 | [bicyclic amine with NH] | [OiPr-quinoxaline] | [C(=O)OH with gem-dimethyl] |
| 200-49 | [bicyclic amine with NH] | [OiPr-quinoxaline] | [C(=O)OH with gem-dimethyl] |
| 200-50 | [bicyclic amine with NH] | [OiPr-quinoxaline] | [C(=O)OH with gem-dimethyl] |
| 200-51 | [bicyclic amine with NH] | [MeO-quinoxaline] | [C(=O)OH with gem-dimethyl] |
| 200-52 | [bicyclic amine with NH] | [MeO-quinoxaline] | [C(=O)OH with gem-dimethyl] |

TABLE 1-continued

| Compound | A | B | —Z—R⁴ |
|---|---|---|---|
| 200-53 | | | |
| 200-54 | | | |
| 200-55 | | | |
| 200-56 | | | |
| 200-57 | | | |
| 200-58 | | | |
| 200-59 | | | |

TABLE 1-continued

| Compound | A | B | —Z—R⁴ |
|---|---|---|---|
| 200-60 | azabicyclic-NH- | 3-F-quinolin-2,8-diyl | -C(CH₃)₂-COOH |
| 200-61 | azabicyclic-NH- | 3-OiPr-quinolin-2,5-diyl | -C(CH₃)₂-COOH |
| 200-62 | azabicyclic-NH- | 3-OiPr-quinolin-2,6-diyl | -C(CH₃)₂-COOH |
| 200-63 | azabicyclic-NH- | 3-OiPr-quinolin-2,7-diyl | -C(CH₃)₂-COOH |
| 200-64 | azabicyclic-NH- | 3-OiPr-quinolin-2,8-diyl | -C(CH₃)₂-COOH |
| 200-65 | azabicyclic-NH- | 3-cyclopropyl-pyridin-2,5-diyl | -C(CH₃)₂-COOH |
| 200-66 | azabicyclic-NH- | 3-MeO-pyridin-2,5-diyl | -C(CH₃)₂-COOH |

TABLE 1-continued

| Compound | A | B | —Z—R⁴ |
|---|---|---|---|
| 200-67 | [bicyclic amine with NH] | 4-OMe-2,5-dimethylpyridine | C(CH₃)₂COOH |
| 200-68 | [bicyclic amine with NH] | 4-OiPr-pyridine | C(CH₃)₂COOH |
| 200-69 | [bicyclic amine with NH] | 4-F-pyridine | C(CH₃)₂COOH |
| 200-70 | [bicyclic amine with NH] | 3-F-4-OiPr-pyridine | C(CH₃)₂COOH |
| 200-71 | [bicyclic amine with NH] | cyclopropyl-pyrazine | C(CH₃)₂COOH |
| 200-72 | [bicyclic amine with NH] | cyclopropyl-F-pyrimidine | C(CH₃)₂COOH |
| 200-73 | [bicyclic amine with NH] | 1-isopropyl-pyrazole | C(CH₃)₂COOH |

TABLE 1-continued

| Compound | A | B | ⸝⸝⸝-Z—R⁴ |
|---|---|---|---|
| 200-74 | (bicyclic amine with NH) | 1-cyclopropyl-pyrazole | —C(CH₃)₂COOH |
| 200-75 | (bicyclic amine with NH) | 1-methyl-pyrazole | —C(CH₃)₂COOH |
| 200-76 | (bicyclic amine with NH) | 1H-pyrazole | —C(CH₃)₂COOH |
| 200-77 | (bicyclic diamine, N-methyl) | 2-OiPr-benzothiazole | —C(CH₃)₂COOH |
| 200-78 | (bicyclic diamine, N-CF₃) | 2-OiPr-benzothiazole | —C(CH₃)₂COOH |

In another embodiment, the compound of Formula (I) is represented by Formula (IX) or a pharmaceutically acceptable salt thereof:

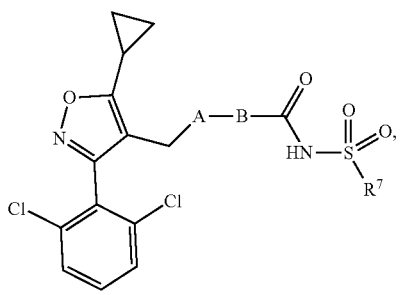

(IX)

wherein A, B, and R⁷ are as previously defined.

Representative compounds of the invention include, but are not limited to, compounds according to Formula (M), and pharmaceutically acceptable salts thereof, wherein, A, B, and R⁷ are delineated for each compound in Table 2.

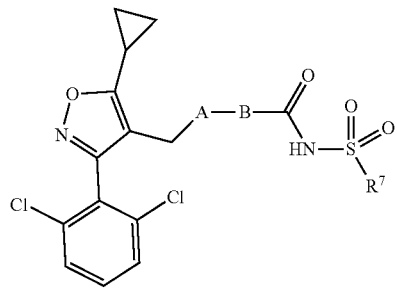

(IX)

TABLE 2

| Compound | A | B | R⁷ |
|---|---|---|---|
| 201 | [bicyclic amine with NH] | [benzothiazole] | cyclopropyl |
| 202 | [bicyclic amine with NH] | [benzothiazole] | 1-methylcyclopropyl |
| 203 | [bicyclic amine with NH] | [benzothiazole] | 1-cyclopropyl-CHO |
| 204 | [bicyclic amine with NH] | [benzothiazole] | 1-cyclopropyl-CD₃ |
| 205 | [bicyclic amine with NH] | [benzothiazole] | 1-cyclopropyl-CH₂OH |
| 206 | [bicyclic amine with NH] | [benzothiazole] | 1-cyclopropyl-CHF₂ |
| 207 | [bicyclic amine with NH] | [benzothiazole] | 1-cyclopropyl-CF₃ |
| 208 | [bicyclic amine with NH] | [benzothiazole] | 1-fluorocyclopropyl |
| 209 | [bicyclic amine with NH] | [benzothiazole] | 1-chlorocyclopropyl |

TABLE 2-continued

| Compound | A | B | R⁷ |
|---|---|---|---|
| 210 | bicyclic amine | benzothiazole | cyclopropyl-CH₂F |
| 211 | bicyclic amine | benzothiazole | cyclopropyl-CH₂OMe |
| 212 | bicyclic amine | benzothiazole | cyclopropyl-CN |
| 213 | bicyclic amine | benzothiazole | cyclopropyl-CH₂OBn |
| 214 | bicyclic amine | benzothiazole | cyclopropyl-CH₂CH₂OH |
| 215 | bicyclic amine | benzothiazole | cyclopropyl-CH₂CH₂N⁺Me₃ |
| 216 | bicyclic amine | benzothiazole | cyclopropyl-CH₂CH₂OCH₂CH₂OH |
| 217 | bicyclic amine | benzothiazole | cyclopropyl-CH₂CH₂OCH₂CH₂N⁺Me₃ |

TABLE 2-continued

| Compound | A | B | R⁷ |
|---|---|---|---|
| 218 | bicyclic amine | benzothiazole | 1-(methoxycarbonyl)cyclopropyl |
| 219 | bicyclic amine | benzothiazole | 1-carboxycyclopropyl |
| 220 | bicyclic amine | benzothiazole | 1-carbamoylcyclopropyl |
| 221 | bicyclic amine | benzothiazole | 1-(N,N-dimethylsulfamoylcarbamoyl)cyclopropyl |
| 222 | bicyclic amine | benzothiazole | 1-(pyrrolidin-1-ylsulfonylcarbamoyl)cyclopropyl |
| 223 | bicyclic amine | benzothiazole | 2,2-difluoro-1-methylcyclopropyl |
| 224 | bicyclic amine | benzothiazole | 2,2-difluorocyclopropyl |
| 225 | bicyclic amine | benzothiazole | N,N-dimethylamino |
| 226 | bicyclic amine | benzothiazole | azetidin-1-yl |

TABLE 2-continued

| Compound | A | B | R⁷ |
|---|---|---|---|
| 227 | bicyclic amine-NH | benzothiazole | pyrrolidine |
| 228 | bicyclic amine-NH | benzothiazole | piperidine |
| 229 | bicyclic amine-NH | benzothiazole | 4,4-difluoropiperidine |
| 230 | bicyclic amine-NH | benzothiazole | NH₂ |
| 231 | bicyclic amine-NH | benzothiazole | cyclopentyl |
| 232 | bicyclic amine-NH | benzothiazole | cyclohexyl |
| 233 | bicyclic amine-NH | benzothiazole | 1-methylcyclopentyl |
| 234 | bicyclic amine-NH | benzothiazole | morpholine |
| 235 | bicyclic amine-NH | benzothiazole | Me |

TABLE 2-continued

| Compound | A | B | R⁷ |
|---|---|---|---|
| 236 | (bicyclic amine with NH) | benzothiazole | -CF₃ |
| 237 | (bicyclic amine with NH) | benzothiazole | -CH(CH₃)₂ (isopropyl) |
| 238 | (bicyclic amine with NH) | benzothiazole | -CH₂-Me (ethyl) |
| 239 | (bicyclic amine with NH) | benzothiazole | -CH₂C(CH₃)₃ (neopentyl) |
| 240 | (bicyclic amine with NH) | benzothiazole | -C(CH₃)₃ (tert-butyl) |
| 241 | (bicyclic amine with NH) | benzothiazole | -CH₂-cyclopropyl |
| 242 | (bicyclic amine with NH) | benzothiazole | -C(CH₃)₂CH₂OBn |
| 243 | (bicyclic amine with NH) | benzothiazole | -CH₂-phenyl (benzyl) |
| 244 | (bicyclic amine with NH) | benzothiazole | -CH₂-CH=CH₂ (allyl) |

TABLE 2-continued

| Compound | A | B | R⁷ |
|---|---|---|---|
| 245 | bicyclic amine (N-H) | benzothiazole | —Bu |
| 246 | bicyclic amine (N-H) | benzothiazole | n-propyl |
| 247 | bicyclic amine (N-H) | benzothiazole | —NH₂ |
| 248 | bicyclic amine (N-H) | benzothiazole | —NHMe |
| 249 | bicyclic amine (N-H) | benzothiazole | —NH-iPr |
| 250 | bicyclic amine (N-H) | benzothiazole | —NHEt |
| 251 | bicyclic amine (N-H) | benzothiazole | —NH-cyclopentyl |
| 252 | bicyclic amine (N-H) | benzothiazole | —NH-cyclopropyl |
| 253 | bicyclic amine (N-H) | benzothiazole | —NH-phenyl |

TABLE 2-continued

| Compound | A | B | R⁷ |
|---|---|---|---|
| 254 | [bicyclic amine with NH] | [benzothiazole] | [cyclohexyl-NH] |
| 255 | [bicyclic amine with NH] | [benzothiazole] | [4-fluorophenyl-NH] |
| 256 | [bicyclic amine with NH] | [benzothiazole] | [pyridin-4-yl-NH] |
| 257 | [bicyclic amine with NH] | [benzothiazole] | [phenyl] |
| 258 | [bicyclic amine with NH] | [benzothiazole] | [2-(OCF₃)phenyl-NH] |
| 259 | [bicyclic amine with NH] | [benzothiazole] | [4-fluorophenyl] |
| 260 | [bicyclic amine with NH] | [benzothiazole] | [4-methylphenyl] |
| 261 | [bicyclic amine with NH] | [benzothiazole] | [pyridin-2-yl] |

TABLE 2-continued

| Compound | A | B | R⁷ |
|---|---|---|---|
| 262 | (bicyclic amine with NH) | benzothiazole | 4-tert-butylphenyl |
| 263 | (bicyclic amine with NH) | benzothiazole | 4-pyridyl |
| 264 | (bicyclic amine with NH) | benzothiazole | 3-pyridyl |
| 265 | (bicyclic amine with NH) | benzothiazole | 5-thiazolyl |
| 266 | (bicyclic amine with NH) | benzothiazole | 5-fluoro-2-pyridyl |
| 267 | (bicyclic amine with NH) | benzothiazole | 1H-imidazol-2-yl |
| 268 | (bicyclic amine with NH) | benzothiazole | 2-thiazolyl |
| 269 | (bicyclic amine with NH) | benzothiazole | 2-(trifluoromethoxy)phenyl |
| 270 | (bicyclic amine with NH) | benzothiazole | 1-methyl-1H-imidazol-2-yl |

TABLE 2-continued

| Compound | A | B | R⁷ |
|---|---|---|---|
| 271 | (bicyclic amine with NH) | (benzothiazole) | (naphthalen-2-yl) |
| 272 | (bicyclic amine with NH) | (benzothiazole) | (2-methoxyphenyl, MeO) |
| 273 | (bicyclic amine with NH) | (benzothiazole) | (biphenyl-4-yl) |
| 274 | (bicyclic amine with NH) | (benzothiazole) | (pyridinyl-pyridinyl) |
| 275 | (bicyclic amine with NH) | (benzothiazole) | (4-(pyridin-4-yl)phenyl) |
| 276 | (bicyclic amine with NH) | (benzothiazole) | (2,3-dihydrobenzo[b][1,4]dioxin-6-yl) |
| 277 | (bicyclic amine with NH) | (benzothiazole) | (benzo[d][1,3]dioxol-5-yl) |
| 278 | (bicyclic amine with NH) | (benzothiazole) | (2,3-dihydro-1H-inden-5-yl) |
| 279 | (cyclohexyl with O and N(Me)) | (benzothiazole) | (N,N-dimethylamino) |

TABLE 2-continued

| Compound | A | B | R⁷ |
|---|---|---|---|
| 280 | | | |
| 281 | | | |
| 282 | | | |
| 283 | | | |
| 284 | | | |
| 285 | | | |
| 286 | | | |
| 287 | | | |
| 288 | | | |
| 289 | | | |
| 290 | | | |

TABLE 2-continued

| Compound | A | B | R⁷ |
|---|---|---|---|
| 291 | [piperidine with NH and N] | [benzothiazole] | [cyclopropyl] |
| 292 | [N-methyl bicyclic amine] | [benzothiazole] | [cyclopropyl] |
| 293 | [N-methyl bicyclic amine] | [benzothiazole] | [methylcyclopropyl] |
| 294 | [N-CHO bicyclic amine] | [benzothiazole] | [methylcyclopropyl] |
| 295 | [NH bicyclic amine] | [fluoro-benzothiazole] | [methylcyclopropyl] |
| 296 | [NH bicyclic amine] | [fluoro-benzothiazole] | [D₃C-methylcyclopropyl] |
| 297 | [NH bicyclic amine] | [fluoro-benzothiazole] | [N(CH₃)₂] |
| 298 | [NH bicyclic amine] | [fluoro-benzothiazole] | [cyclopropyl] |

TABLE 2-continued

| Compound | A | B | R⁷ |
|---|---|---|---|
| 299 | 3-amino-9-azabicyclo[3.3.1]nonane (NH linker) | 4-fluorobenzothiazol-2,6-diyl | 1-formylcyclopropyl (CHO) |
| 300 | 3-amino-9-azabicyclo[3.3.1]nonane (NH linker) | 4-fluorobenzothiazol-2,6-diyl | piperidin-1-yl |
| 301 | 3-amino-9-azabicyclo[3.3.1]nonane (NH linker) | benzoxazol-2,6-diyl | N,N-dimethylamino |
| 302 | 3-amino-9-azabicyclo[3.3.1]nonane (NH linker) | benzoxazol-2,6-diyl | 1-methylcyclopropyl |
| 303 | 3-amino-9-azabicyclo[3.3.1]nonane (NH linker) | 4-methoxybenzothiazol-2,6-diyl | N,N-dimethylamino |
| 304 | 3-amino-9-azabicyclo[3.3.1]nonane (NH linker) | 4-methoxybenzothiazol-2,6-diyl | 1-methylcyclopropyl |
| 305 | 4-aminopiperidine | benzothiazol-2,6-diyl | 1-methylcyclopropyl |
| 306 | 4-aminopiperidine | benzothiazol-2,6-diyl | piperidin-1-yl |
| 307 | 3-amino-9-azabicyclo[3.3.1]nonane (NH linker) | 4-methoxybenzothiazol-2,6-diyl | 1-(difluoromethyl)cyclopropyl |

TABLE 2-continued

| Compound | A | B | R⁷ |
|---|---|---|---|
| 308 | bicyclic amine-NH- | benzothiazole, OMe | pyrrolidine |
| 309 | bicyclic amine-NH- | benzothiazole, OMe | azetidine |
| 310 | bicyclic amine-NH- | benzothiazole, OMe | piperidine |
| 311 | bicyclic amine-NH- | benzothiazole, CHF₃ | 1-methylcyclopropyl |
| 312 | bicyclic amine-NH- | benzothiazole, CHF₃ | 1-(CHF₂)cyclopropyl |
| 313 | bicyclic amine-NH- | benzothiazole, CHF₃ | N(CH₃)₂ |
| 314 | bicyclic amine-NH- | benzothiazole, CHF₃ | azetidine |
| 315 | bicyclic amine-NH- | benzothiazole, CHF₃ | pyrrolidine |

TABLE 2-continued

| Compound | A | B | R⁷ |
|---|---|---|---|
| 316 | bicyclic amine with NH | benzothiazole with CHF₃ | piperidine |
| 317 | bicyclic amine with NH | benzothiazole with OCF₃ | 1-methylcyclopropyl |
| 318 | bicyclic amine with NH | benzothiazole with OCF₃ | cyclopropyl-CHF₂ |
| 319 | bicyclic amine with NH | benzothiazole with OCF₃ | N(CH₃)₂ |
| 320 | bicyclic amine with NH | benzothiazole with OCF₃ | azetidine |
| 321 | bicyclic amine with NH | benzothiazole with OCF₃ | pyrrolidine |
| 322 | bicyclic amine with NH | benzothiazole with OCF₃ | piperidine |
| 323 | bicyclic amine with NH | benzothiazole with OCHF₂ | 1-methylcyclopropyl |

TABLE 2-continued

| Compound | A | B | R⁷ |
|---|---|---|---|
| 324 | bicyclic amine with NH | benzothiazole with OCHF₂ | cyclopropyl-CHF₂ |
| 325 | bicyclic amine with NH | benzothiazole with OCHF₂ | N(CH₃)₂ |
| 326 | bicyclic amine with NH | benzothiazole with OCHF₂ | azetidinyl |
| 327 | bicyclic amine with NH | benzothiazole with OCHF₂ | pyrrolidinyl |
| 328 | bicyclic amine with NH | benzothiazole with OCHF₂ | piperidinyl |
| 329 | bicyclic amine with NH | benzothiazole with CF₃ | cyclopropyl |
| 330 | bicyclic amine with NH | benzothiazole with CF₃ | cyclopropyl-CHF₂ |
| 331 | bicyclic amine with NH | benzothiazole with CF₃ | N(CH₃)₂ |

TABLE 2-continued

| Compound | A | B | R⁷ |
|---|---|---|---|
| 332 | bicyclic amine (NH) | benzothiazole with CF₃ | azetidine |
| 333 | bicyclic amine (NH) | benzothiazole with CF₃ | pyrrolidine |
| 334 | bicyclic amine (NH) | benzothiazole with CF₃ | piperidine |
| 335 | bicyclic amine (NH) | 3-chloroquinoxaline | 1-methylcyclopropyl |
| 336 | bicyclic amine (NH) | 3-chloroquinoxaline | 1-(difluoromethyl)cyclopropyl |
| 337 | bicyclic amine (NH) | 3-chloroquinoxaline | N,N-dimethylamino |
| 338 | bicyclic amine (NH) | 3-chloroquinoxaline | azetidine |
| 339 | bicyclic amine (NH) | 3-chloroquinoxaline | pyrrolidine |

TABLE 2-continued

| Compound | A | B | R⁷ |
|---|---|---|---|
| 340 | [bicyclic amine with NH] | [chloroquinoxaline] | [piperidine] |
| 341 | [bicyclic amine with NH] | [MeO-quinoxaline] | [1-methylcyclopropyl] |
| 342 | [bicyclic amine with NH] | [MeO-quinoxaline] | [1-(difluoromethyl)cyclopropyl] |
| 343 | [bicyclic amine with NH] | [MeO-quinoxaline] | [N,N-dimethylamino] |
| 344 | [bicyclic amine with NH] | [MeO-quinoxaline] | [azetidine] |
| 345 | [bicyclic amine with NH] | [MeO-quinoxaline] | [pyrrolidine] |
| 346 | [bicyclic amine with NH] | [MeO-quinoxaline] | [piperidine] |
| 347 | [bicyclic amine with NH] | [quinoxaline] | [1-methylcyclopropyl] |

TABLE 2-continued

| Compound | A | B | R⁷ |
|---|---|---|---|
| 348 | (bicyclic amine with NH) | quinoxaline | 1-(difluoromethyl)cyclopropyl (F₂HC-) |
| 349 | (bicyclic amine with NH) | quinoxaline | N,N-dimethylamino |
| 350 | (bicyclic amine with NH) | quinoxaline | azetidin-1-yl |
| 351 | (bicyclic amine with NH) | quinoxaline | pyrrolidin-1-yl |
| 352 | (bicyclic amine with NH) | quinoxaline | piperidin-1-yl |
| 353 | (bicyclic amine with NH) | 5-fluoroquinoxaline | 1-methylcyclopropyl |
| 354 | (bicyclic amine with NH) | 5-fluoroquinoxaline | piperidin-1-yl |
| 355 | (bicyclic amine with NH) | 5-fluoroquinoxaline | N,N-dimethylamino |

TABLE 2-continued

| Compound | A | B | R⁷ |
|---|---|---|---|
| 356 | bicyclic NH-amine | quinoxaline, F | azetidine |
| 357 | bicyclic NH-amine | quinoxaline, F | pyrrolidine |
| 358 | bicyclic NH-amine | quinoxaline, F | piperidine |
| 359 | bicyclic NH-amine | quinoxaline, OMe | 1-methylcyclopropyl |
| 360 | bicyclic NH-amine | quinoxaline, OMe | piperidine |
| 361 | bicyclic NH-amine | quinoxaline, OMe | N,N-dimethylamino |
| 362 | bicyclic NH-amine | quinoxaline, OMe | azetidine |
| 363 | bicyclic NH-amine | quinoxaline, OMe | pyrrolidine |

TABLE 2-continued

| Compound | A | B | R⁷ |
|---|---|---|---|
| 364 | bicyclic amine with NH | quinoxaline with OMe | piperidine |
| 365 | bicyclic amine with NH | quinazoline | 1-methylcyclopropyl |
| 366 | bicyclic amine with NH | quinazoline | piperidine |
| 367 | bicyclic amine with NH | quinazoline | N(Me)₂ |
| 368 | bicyclic amine with NH | quinazoline | azetidine |
| 369 | bicyclic amine with NH | quinazoline | pyrrolidine |
| 370 | bicyclic amine with NH | quinazoline | piperidine |
| 371 | bicyclic amine with NH | pyrazolo[1,5-a]pyrimidine | 1-methylcyclopropyl |
| 372 | bicyclic amine with NH | pyrazolo[1,5-a]pyrimidine | piperidine |

TABLE 2-continued

| Compound | A | B | R⁷ |
|---|---|---|---|
| 373 | [bicyclic amine with NH] | [pyrazolo[1,5-a]pyrimidine] | N(CH₃)₂ |
| 374 | [bicyclic amine with NH] | [pyrazolo[1,5-a]pyrimidine] | azetidinyl |
| 375 | [bicyclic amine with NH] | [pyrazolo[1,5-a]pyrimidine] | pyrrolidinyl |
| 376 | [bicyclic amine with NH] | [pyrazolo[1,5-a]pyrimidine] | piperidinyl |
| 377 | [bicyclic amine with NH] | [benzoxazole] | 1-methylcyclopropyl |
| 378 | [bicyclic amine with NH] | [benzoxazole] | piperidinyl |
| 379 | [bicyclic amine with NH] | [oxazolopyridine] | N(CH₃)₂ |
| 380 | [bicyclic amine with NH] | [oxazolopyridine] | azetidinyl |
| 381 | [bicyclic amine with NH] | [oxazolopyridine] | pyrrolidinyl |

TABLE 2-continued

| Compound | A | B | R⁷ |
|---|---|---|---|
| 382 | bicyclic amine-NH | benzoxazole | piperidine |
| 383 | bicyclic amine-NH | quinoline | 1-methylcyclopropyl |
| 384 | bicyclic amine-NH | quinoline | piperidine |
| 385 | bicyclic amine-NH | quinoline | N,N-dimethylamino |
| 386 | bicyclic amine-NH | quinoline | azetidine |
| 387 | bicyclic amine-NH | quinoline | pyrrolidine |
| 388 | bicyclic amine-NH | quinoline | piperidine |
| 389 | bicyclic amine-NH | naphthalene | 1-methylcyclopropyl |

TABLE 2-continued

| Compound | A | B | R⁷ |
|---|---|---|---|
| 390 | bicyclic amine with NH | 2,6-naphthalenediyl | 1-(difluoromethyl)cyclopropyl |
| 391 | bicyclic amine with NH | 2,6-naphthalenediyl | N(CH₃)₂ |
| 392 | bicyclic amine with NH | 2,6-naphthalenediyl | azetidin-1-yl |
| 393 | bicyclic amine with NH | 2,6-naphthalenediyl | pyrrolidin-1-yl |
| 394 | bicyclic amine with NH | 2,6-naphthalenediyl | piperidin-1-yl |
| 395 | bicyclic amine with NH | 2,5-pyrazinediyl | 1-methylcyclopropyl |
| 396 | bicyclic amine with NH | 2,5-pyrazinediyl | 1-(difluoromethyl)cyclopropyl |
| 397 | bicyclic amine with NH | 2,5-pyrazinediyl | N(CH₃)₂ |

TABLE 2-continued

| Compound | A | B | R⁷ |
|---|---|---|---|
| 398 | | | |
| 399 | | | |
| 400 | | | |
| 400-1 | | | |
| 400-2 | | | |
| 400-3 | | | |
| 400-4 | | | |
| 400-5 | | | |

TABLE 2-continued

| Compound | A | B | R⁷ |
|---|---|---|---|
| 400-6 | piperidine-4-ylamine linker | 2-yl-6-yl-benzothiazole, 7-OiPr | piperidin-1-yl |
| 400-7 | piperidine-4-ylamine linker | 2-yl-6-yl-benzothiazole, 7-F | pyrrolidin-1-yl |
| 400-08 | piperidine-4-ylamine linker | 2-yl-6-yl-benzothiazole, 7-F | piperidin-1-yl |
| 400-9 | piperidine-4-ylamine linker | 2-yl-6-yl-benzothiazole, 7-F | cyclopropyl |
| 400-10 | piperidine-4-ylamine linker | 2-yl-6-yl-benzothiazole, 7-F | 1-methylcyclopropyl |
| 400-11 | 8-azabicyclo[3.2.1]octan-3-amine | 2-yl-6-yl-benzothiazole, 5-Me | 1-methylcyclopropyl |
| 400-12 | 8-azabicyclo[3.2.1]octan-3-amine | 2-yl-6-yl-benzothiazole, 5-Me | piperidin-1-yl |
| 400-13 | 8-azabicyclo[3.2.1]octan-3-amine | 2-yl-6-yl-benzothiazole, 7-Me | 1-methylcyclopropyl |

TABLE 2-continued
| Compound | A | B | R⁷ |
|---|---|---|---|
| 400-14 | 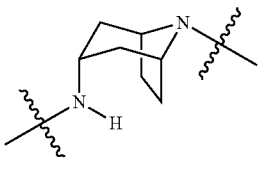 [SMILES: *NC1CC2CCC(C1)N2*] | 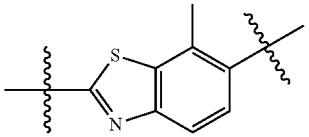 [SMILES: *c1nc2ccc(*)c(C)c2s1] | 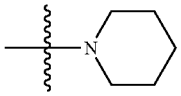 |
| 400-15 | 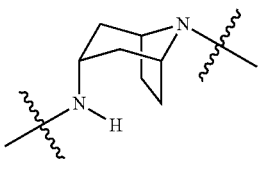 [SMILES: *NC1CC2CCC(C1)N2*] | 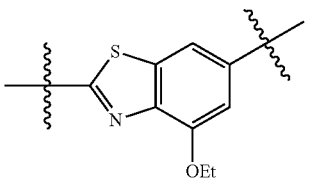 [SMILES: *c1cc(OCC)c2nc(*)sc2c1] | 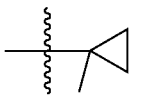 |
| 400-16 | 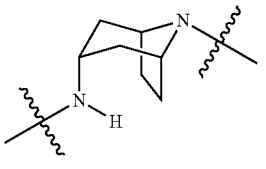 | 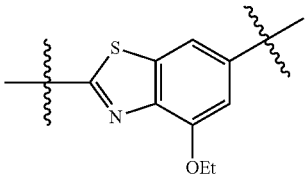 | 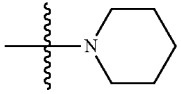 |
| 400-17 | 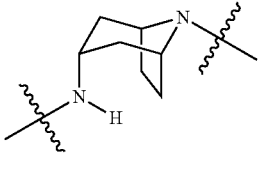 [SMILES: *NC1CC2CCC(C1)N2*] | 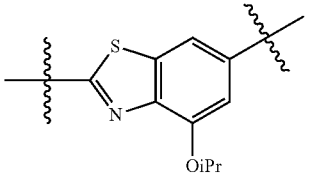 [SMILES: *c1cc(OC(C)C)c2nc(*)sc2c1] | 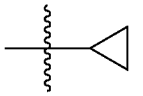 [SMILES: *C1CC1] |
| 400-18 | 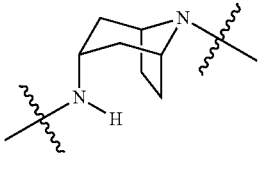 [SMILES: *NC1CC2CCC(C1)N2*] | 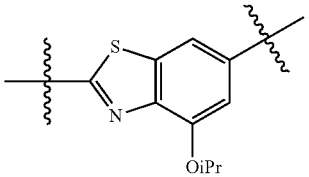 | 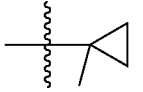 |
| 400-19 | 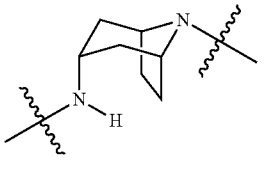 | 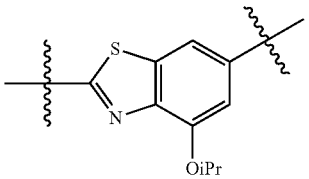 [SMILES: *c1cc(OC(C)C)c2nc(*)sc2c1] | 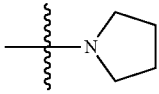 |
| 400-20 | 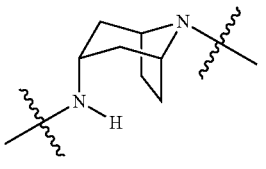 [SMILES: *NC1CC2CCC(C1)N2*] | 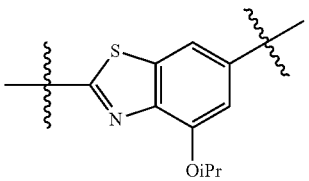 [SMILES: *c1cc(OC(C)C)c2nc(*)sc2c1] | 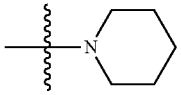 |
| 400-21 | 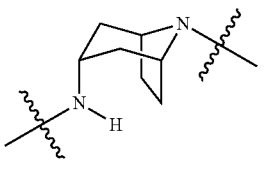 | 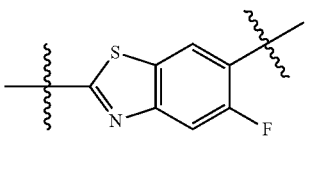 | 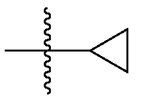 [SMILES: *C1CC1] |

TABLE 2-continued

| Compound | A | B | R⁷ |
|---|---|---|---|
| 400-22 | (bicyclic amine with NH) | benzothiazole with F | 1-methylcyclopropyl |
| 400-23 | (bicyclic amine with NH) | benzothiazole with F | pyrrolidinyl |
| 400-24 | (bicyclic amine with NH) | benzothiazole with F | piperidinyl |
| 400-25 | (bicyclic amine with NH) | thiazolopyrazine | cyclopropyl |
| 400-26 | (bicyclic amine with NH) | thiazolopyrazine | 1-methylcyclopropyl |
| 400-27 | (bicyclic amine with NH) | thiazolopyrazine | pyrrolidinyl |
| 400-28 | (bicyclic amine with NH) | thiazolopyrazine | piperidinyl |
| 400-29 | (bicyclic amine with NH) | methylbenzothiazole | 1-methylcyclopropyl |
| 400-30 | (bicyclic amine with NH) | methylbenzothiazole | piperidinyl |

TABLE 2-continued

| Compound | A | B | R⁷ |
|---|---|---|---|
| 400-31 | | benzothiazole with Ph | 1-methylcyclopropyl |
| 400-32 | | benzothiazole with Ph | piperidinyl |
| 400-33 | | naphthothiazole | 1-methylcyclopropyl |
| 400-34 | | naphthothiazole | piperidinyl |
| 400-35 | | benzothiazole with cyclopropyl | 1-methylcyclopropyl |
| 400-36 | | benzothiazole with cyclopropyl | piperidinyl |
| 400-37 | | pyridine | cyclopropyl |
| 400-38 | | pyridine | 1-methylcyclopropyl |

TABLE 2-continued

| Compound | A | B | $R^7$ |
|---|---|---|---|
| 400-39 | (bicyclic amine with NH) | (pyridine) | (pyrrolidine) |
| 400-40 | (bicyclic amine with NH) | (pyridine) | (piperidine) |

In another embodiment, the compound of Formula (I) is represented by Formula (VIII) or a pharmaceutically acceptable salt thereof:

Representative compounds of the invention include, but are not limited to, compounds according to Formula (X), and pharmaceutically acceptable salts thereof, wherein A, B, and Z—$R^4$ are delineated for each compound in Table 3.

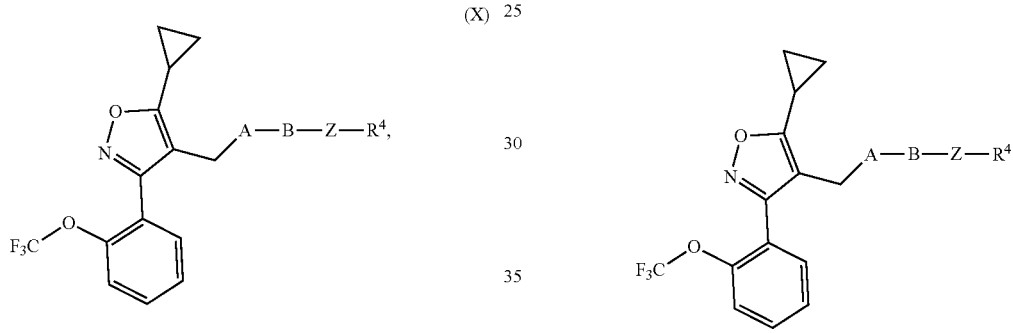

wherein A, B, and $R^4$ are as previously defined.

TABLE 3

| Compound | A | B | $Z-R^4$ |
|---|---|---|---|
| 401 | (bicyclic amine with NH) | (benzothiazole) | (C(O)OMe with gem-dimethyl) |
| 402 | (bicyclic amine with NH) | (benzothiazole) | (C(O)OH with gem-dimethyl) |
| 403 | (bicyclic amine with NH) | (fluoro-benzothiazole) | (C(O)OMe with gem-dimethyl) |

TABLE 3-continued

| Compound | A | B | —Z—R⁴ |
|---|---|---|---|
| 404 | bicyclic amine-NH | benzothiazole, F substituent | C(Me)₂COOH |
| 405 | bicyclic amine-NH | benzothiazole, OMe substituent | C(Me)₂COOMe |
| 406 | bicyclic amine-NH | benzothiazole, OMe substituent | C(Me)₂COOH |
| 407 | bicyclic amine-NH | benzothiazole, OCF₃ substituent | C(Me)₂COOMe |
| 408 | bicyclic amine-NH | benzothiazole, OCF₃ substituent | C(Me)₂COOH |
| 409 | bicyclic amine-NH | benzothiazole, CHF₂ substituent | C(Me)₂COOMe |
| 410 | bicyclic amine-NH | benzothiazole, CHF₂ substituent | C(Me)₂COOH |

TABLE 3-continued

| Compound | A | B | ⸙—Z—R⁴ |
|---|---|---|---|
| 411 | [bicyclic amine with NH] | [benzothiazole with CH₂F] | -C(=O)OMe |
| 412 | [bicyclic amine with NH] | [benzothiazole with CH₂F] | -C(=O)OH |
| 413 | [bicyclic amine with NH] | [benzothiazole with OiPr] | -C(=O)OMe |
| 414 | [bicyclic amine with NH] | [benzothiazole with OiPr] | -C(=O)OH |
| 415 | [bicyclic amine with NH] | [benzothiazole with OEt] | -C(=O)OMe |
| 416 | [bicyclic amine with NH] | [benzothiazole with OEt] | -C(=O)OH |
| 417 | [bicyclic amine with NH] | [benzothiazole with OH] | -C(=O)OMe |

TABLE 3-continued

| Compound | A | B | ⸾⸾⸾—Z—R⁴ |
|---|---|---|---|
| 418 | [bicyclic amine with NH] | 2-yl-6-yl-benzothiazole, 4-OH | –C(Me)₂–C(O)OH |
| 419 | [bicyclic amine with NH] | 2-yl-6-yl-benzothiazole, 4-NH₂ | –C(Me)₂–C(O)OMe |
| 420 | [bicyclic amine with NH] | 2-yl-6-yl-benzothiazole, 4-NH₂ | –C(Me)₂–C(O)OH |
| 421 | [bicyclic amine with NH] | 2-yl-6-yl-benzothiazole, 4-NMe₂ | –C(Me)₂–C(O)OMe |
| 422 | [bicyclic amine with NH] | 2-yl-6-yl-benzothiazole, 4-NMe₂ | –C(Me)₂–C(O)OH |
| 423 | [bicyclic amine with NH] | 2-yl-6-yl-benzothiazole, 4-(pyridin-2-yl) | –C(Me)₂–C(O)OMe |
| 424 | [bicyclic amine with NH] | 2-yl-6-yl-benzothiazole, 4-(pyridin-2-yl) | –C(Me)₂–C(O)OH |

TABLE 3-continued

| Compound | A | B | —Z—R⁴ |
|---|---|---|---|
| 425 | (bridged bicyclic amine with NH) | benzothiazole with Me | C(=O)OMe |
| 426 | (bridged bicyclic amine with NH) | benzothiazole with Me | C(=O)OH |
| 427 | (bridged bicyclic amine with NH) | benzothiazole with Me | C(=O)OMe |
| 428 | (bridged bicyclic amine with NH) | benzothiazole with Me | C(=O)OH |
| 429 | (bridged bicyclic amine with NH) | benzothiazole with Me | C(=O)OMe |
| 430 | (bridged bicyclic amine with NH) | benzothiazole with Me | C(=O)OH |
| 431 | (bridged bicyclic amine with NH) | benzothiazole with Br | C(=O)OMe |
| 432 | (bridged bicyclic amine with NH) | benzothiazole with Br | C(=O)OH |

TABLE 3-continued

| Compound | A | B | $-Z-R^4$ |
|---|---|---|---|
| 433 | bicyclic amine (N-H) | benzothiazole, Cl-substituted | C(=O)OMe |
| 434 | bicyclic amine (N-H) | benzothiazole, Cl-substituted | C(=O)OH |
| 435 | bicyclic amine (N-H) | benzofuran, Me-substituted | C(=O)OEt |
| 436 | bicyclic amine (N-H) | benzofuran, Me-substituted | C(=O)OH |
| 437 | bicyclic amine (N-H) | benzothiazole, $CF_3$-substituted | C(=O)OMe |
| 438 | bicyclic amine (N-H) | benzothiazole, $CF_3$-substituted | C(=O)OH |
| 439 | bicyclic amine (N-H) | benzothiazole, $CHF_2$-substituted | C(=O)OMe |
| 440 | bicyclic amine (N-H) | benzothiazole, $CHF_2$-substituted | C(=O)OH |

TABLE 3-continued

| Compound | A | B | —Z—R⁴ |
|---|---|---|---|
| 441 | azabicyclic-NH- | benzothiazole with CH₂F | C(=O)OMe |
| 442 | azabicyclic-NH- | benzothiazole with CH₂F | C(=O)OH |
| 443 | azabicyclic-NH- | benzoxazole | C(=O)OMe |
| 444 | azabicyclic-NH- | benzoxazole | C(=O)OH |
| 445 | azabicyclic-NH- | benzoxazole with F | C(=O)OMe |
| 446 | azabicyclic-NH- | benzoxazole with F | C(=O)OH |
| 447 | azabicyclic-NH- | benzoxazole with OMe | C(=O)OMe |
| 448 | azabicyclic-NH- | benzoxazole with OMe | C(=O)OH |

TABLE 3-continued

| Compound | A | B | ⁒-Z-R⁴ |
|---|---|---|---|
| 449 | [bicyclic amine-NH-] | [benzisothiazole] | -C(Me)₂-C(O)OMe |
| 450 | [bicyclic amine-NH-] | [benzisothiazole] | -C(Me)₂-C(O)OH |
| 451 | [bicyclic amine-NH-] | [F-benzisothiazole] | -C(Me)₂-C(O)OMe |
| 452 | [bicyclic amine-NH-] | [F-benzisothiazole] | -C(Me)₂-C(O)OH |
| 453 | [bicyclic amine-NH-] | [pyrazolo[1,5-a]pyrimidine] | -C(Me)₂-C(O)OMe |
| 454 | [bicyclic amine-NH-] | [pyrazolo[1,5-a]pyrimidine] | -C(Me)₂-C(O)OH |
| 455 | [bicyclic amine-NH-] | [imidazo[1,2-a]pyridine] | -C(Me)₂-C(O)OMe |
| 456 | [bicyclic amine-NH-] | [imidazo[1,2-a]pyridine] | -C(Me)₂-C(O)OH |

TABLE 3-continued

| Compound | A | B | $-Z-R^4$ |
|---|---|---|---|
| 457 | [3-azabicyclic amine] | naphthalene-2,6-diyl | $-C(Me)_2C(O)OMe$ |
| 458 | [3-azabicyclic amine] | naphthalene-2,6-diyl | $-C(Me)_2C(O)OH$ |
| 459 | [3-azabicyclic amine] | quinoline-2,5-diyl | $-C(Me)_2C(O)OMe$ |
| 460 | [3-azabicyclic amine] | quinoline-2,5-diyl | $-C(Me)_2C(O)OH$ |
| 461 | [3-azabicyclic amine] | isoquinoline-3,7-diyl | $-C(Me)_2C(O)OMe$ |
| 462 | [3-azabicyclic amine] | isoquinoline-3,7-diyl | $-C(Me)_2C(O)OH$ |
| 463 | [3-azabicyclic amine] | quinazoline-2,6-diyl | $-C(Me)_2C(O)OMe$ |
| 464 | [3-azabicyclic amine] | quinazoline-2,6-diyl | $-C(Me)_2C(O)OH$ |

TABLE 3-continued

| Compound | A | B | —Z—R⁴ |
|---|---|---|---|
| 465 | bicyclic amine-NH- | 2-MeO-quinoxaline-6,3-diyl | -C(=O)OMe |
| 466 | bicyclic amine-NH- | 2-MeO-quinoxaline-6,3-diyl | -C(=O)OH |
| 467 | bicyclic amine-NH- | 2-Cl-quinoxaline-6,3-diyl | -C(=O)OMe |
| 468 | bicyclic amine-NH- | 2-Cl-quinoxaline-6,3-diyl | -C(=O)OH |
| 469 | bicyclic amine-NH- | quinoxaline-6,2-diyl | -C(=O)OMe |
| 470 | bicyclic amine-NH- | quinoxaline-6,2-diyl | -C(=O)OH |
| 471 | bicyclic amine-NH- | 5-Me-quinoxaline-6,2-diyl | -C(=O)OMe |
| 472 | bicyclic amine-NH- | 5-Me-quinoxaline-6,2-diyl | -C(=O)OH |

TABLE 3-continued

| Compound | A | B | —Z—R⁴ |
|---|---|---|---|
| 473 | bicyclic amine (NH) | quinoxaline, 6-Me | C(O)OMe |
| 474 | bicyclic amine (NH) | quinoxaline, 6-Me | C(O)OH |
| 475 | bicyclic amine (NH) | quinoxaline, 5-Me | C(O)OMe |
| 476 | bicyclic amine (NH) | quinoxaline, 5-Me | C(O)OH |
| 477 | bicyclic amine (NH) | quinoxaline, 8-Cl | C(O)OMe |
| 478 | bicyclic amine (NH) | quinoxaline, 8-Cl | C(O)OH |
| 479 | bicyclic amine (NH) | quinoxaline, 8-F | C(O)OMe |
| 480 | bicyclic amine (NH) | quinoxaline, 8-F | C(O)OH |

TABLE 3-continued

| Compound | A | B | |
|---|---|---|---|
| 481 | bicyclic amine with NH | quinoxaline with OMe | —C(=O)OMe |
| 482 | bicyclic amine with NH | quinoxaline with OMe | —C(=O)OH |
| 483 | bicyclic amine with NH | quinoxaline with OCF₃ | —C(=O)OMe |
| 484 | bicyclic amine with NH | quinoxaline with OCF₃ | —C(=O)OH |
| 485 | bicyclic amine with NH | quinoxaline with OCHF₂ | —C(=O)OMe |
| 486 | bicyclic amine with NH | quinoxaline with OCHF₂ | —C(=O)OH |
| 487 | bicyclic amine with NH | quinoxaline with CN | —C(=O)OMe |

TABLE 3-continued

| Compound | A | B | —Z—R⁴ |
|---|---|---|---|
| 488 | [bicyclic amine NH] | quinoxaline with CN | C(=O)OH |
| 489 | [bicyclic amine NH] | quinoxaline with CF₃ | C(=O)OMe |
| 490 | [bicyclic amine NH] | quinoxaline with CF₃ | C(=O)OH |
| 491 | [bicyclic amine NH] | quinoxaline with F | C(=O)OMe |
| 492 | [bicyclic amine NH] | quinoxaline with F | C(=O)OH |
| 493 | [bicyclic amine NH] | quinoxaline with OMe | C(=O)OMe |
| 494 | [bicyclic amine NH] | quinoxaline with OMe | C(=O)OH |
| 495 | [bicyclic amine NH] | quinoxaline with F | C(=O)OMe |

TABLE 3-continued

| Compound | A | B | $Z-R^4$ |
|---|---|---|---|
| 496 | [bicyclic amine-NH] | fluoroquinoxaline | -C(O)OH |
| 497 | [bicyclic amine-NH] | fluoronaphthalene | -C(O)OMe |
| 498 | [bicyclic amine-NH] | fluoronaphthalene | -C(O)OH |
| 499 | [bicyclic amine-NH] | quinoxaline | -C(O)OMe |
| 500 | [bicyclic amine-NH] | quinoxaline | -C(O)OH |
| 501 | [bicyclic amine-NH] | fluoroquinoline | -C(O)OMe |
| 502 | [bicyclic amine-NH] | fluoroquinoline | -C(O)OH |
| 503 | [bicyclic amine-NH] | methoxynaphthalene | -C(O)OMe |

TABLE 3-continued

| Compound | A | B | ⸺Z⸺R⁴ |
|---|---|---|---|
| 504 | [bicyclic amine with NH] | methoxy-naphthalene | C(=O)OH |
| 505 | [bicyclic amine with NH] | naphthalene (2,6) | C(=O)OMe |
| 506 | [bicyclic amine with NH] | naphthalene (2,6) | C(=O)OH |
| 507 | [bicyclic amine with NH] | OMe-naphthalene | C(=O)OMe |
| 508 | [bicyclic amine with NH] | OMe-naphthalene | C(=O)OH |
| 509 | [bicyclic amine with NH] | quinoline (2,6) | C(=O)OMe |
| 510 | [bicyclic amine with NH] | quinoline (2,6) | C(=O)OH |
| 511 | [bicyclic amine with NH] | quinoline (3,7) | C(=O)OMe |

TABLE 3-continued

| Compound | A | B | Z—R⁴ |
|---|---|---|---|
| 512 | bicyclic amine-NH | quinoline (3,7) | CH(COOH) |
| 513 | bicyclic amine-NH | quinoline (2,6) | CH(COOMe) |
| 514 | bicyclic amine-NH | quinoline (2,6) | CH(COOH) |
| 515 | bicyclic amine-NH | 5-F-quinoline (2,6) | CH(COOMe) |
| 516 | bicyclic amine-NH | 5-F-quinoline (2,6) | CH(COOH) |
| 517 | bicyclic amine-NH | 7-F-quinoline (2,6) | CH(COOMe) |
| 518 | bicyclic amine-NH | 7-F-quinoline (2,6) | CH(COOH) |
| 519 | bicyclic amine-NH | quinazoline (2,6) | CH(COOMe) |

TABLE 3-continued

| Compound | A | B | —Z—R⁴ |
|---|---|---|---|
| 520 | (bicyclic amine with NH) | quinazoline-2,6-diyl | —C(=O)OH |
| 521 | (bicyclic amine with NH) | 4-Me-quinazoline-2,6-diyl | —C(=O)OMe |
| 522 | (bicyclic amine with NH) | 4-Me-quinazoline-2,6-diyl | —C(=O)OH |
| 523 | (bicyclic amine with NH) | quinoline-2,5-diyl | —C(=O)OMe |
| 524 | (bicyclic amine with NH) | quinoline-2,5-diyl | —C(=O)OH |
| 525 | (bicyclic amine with NH) | quinazoline-4,7-diyl | —C(=O)OMe |
| 526 | (bicyclic amine with NH) | quinazoline-4,7-diyl | —C(=O)OH |

TABLE 3-continued

| Compound | A | B | ⸺Z—R⁴ |
|---|---|---|---|
| 527 | (bicyclic amine with NH) | benzisothiazole | —C(=O)OMe |
| 528 | (bicyclic amine with NH) | benzisothiazole | —C(=O)OH |
| 529 | (bicyclic amine with NH) | benzothiazole | —CO₂Me |
| 530 | (bicyclic amine with NH) | benzothiazole | —CO₂t-Bu |
| 531 | (bicyclic amine with NH) | benzothiazole | —CH₂CO₂Me |
| 532 | (bicyclic amine with NH) | benzothiazole | —CH₂CO₂H |
| 533 | (bicyclic amine with NH) | benzothiazole | —CH₂CH₂C(=O)OMe |
| 534 | (bicyclic amine with NH) | benzothiazole | —CH₂CH₂C(=O)OH |

TABLE 3-continued

| Compound | A | B | ⸝⸝⸝-Z—R⁴ |
|---|---|---|---|
| 535 | [bicyclic amine with NH] | [benzothiazole] | -O-CH₂-C(O)OMe |
| 536 | [bicyclic amine with NH] | [benzothiazole] | -O-CH₂-C(O)OH |
| 537 | [bicyclic amine with NH] | [benzothiazole] | -NH-CH₂-C(O)OMe |
| 538 | [bicyclic amine with NH] | [benzothiazole] | -NH-CH₂-C(O)OH |
| 539 | [bicyclic amine with NH] | [benzothiazole] | -N(Me)-CH₂-C(O)OMe |
| 540 | [bicyclic amine with NH] | [benzothiazole] | -N(Me)-CH₂-C(O)OH |
| 541 | [bicyclic amine with NH] | [benzothiazole] | -N(CHO)-CH₂-C(O)OMe |
| 542 | [bicyclic amine with NH] | [benzothiazole] | -N(CHO)-CH₂-C(O)OH |

TABLE 3-continued

| Compound | A | B | ╱╲Z—R⁴ |
|---|---|---|---|
| 543 | (bicyclic diamine, NH) | (benzothiazole) | cyclopropyl-C(CO₂Me) |
| 544 | (bicyclic diamine, NH) | (benzothiazole) | cyclopropyl-C(CO₂H) |
| 545 | (bicyclic diamine, NH) | (benzothiazole) | cyclopropyl-CH₂C(O)OMe |
| 546 | (bicyclic diamine, NH) | (benzothiazole) | cyclopropyl-CH₂C(O)OH |
| 547 | (bicyclic diamine, NH) | (benzothiazole) | CF₂-CO₂Me |
| 548 | (bicyclic diamine, NH) | (benzothiazole) | CF₂-C(O)OH |
| 549 | (bicyclic diamine, NH) | (benzothiazole) | CN |
| 550 | (bicyclic diamine, NH) | (benzothiazole) | tetrazole |

TABLE 3-continued

| Compound | A | B | ⸻Z—R⁴ |
|---|---|---|---|
| 551 | | | tert-butyl ester of N-acyl glycine |
| 552 | | | N-acyl glycine (COOH) |
| 553 | | | N-acyl 2-aminoisobutyric acid |
| 554 | | | N-acyl alanine |
| 555 | | | N-acyl taurine methyl ester (SO₃Me) |
| 556 | | | N-acyl taurine (SO₃H) |
| 557 | | | N-acyl 1-(sulfomethyl)cyclopropylamine |
| 558 | | | N-acyl 2-methyl-2-aminopropanesulfonic acid |

TABLE 3-continued

| Compound | A | B | |
|---|---|---|---|
| 559 | [bicyclic amine with NH] | [benzothiazole] | [C(=O)NHCH₂OCH₂OSO₃H] |
| 560 | [bicyclic amine with NH] | [benzothiazole] | [C(=O)NHCH₂NHCH₂OSO₃H] |
| 561 | [bicyclic amine with NH] | [benzothiazole] | [acyl glucuronide] |
| 562 | [bicyclic amine with NH] | [benzothiazole with OMe] | [acyl glucuronide] |
| 563 | [bicyclic amine with NH] | [benzothiazole with F] | [acyl glucuronide] |
| 564 | [bicyclic amine with NH] | [benzothiazole with CH₃] | [acyl glucuronide] |
| 565 | [bicyclic amine with NH] | [benzothiazole with CF₃] | [acyl glucuronide] |

TABLE 3-continued

| Compound | A | B | —Z—R⁴ |
|---|---|---|---|
| 566 | (diazabicyclic amine with NH) | benzothiazole-OEt | glucuronide ester |
| 567 | (diazabicyclic amine with NH) | benzothiazole-OiPr | glucuronide ester |
| 568 | (diazabicyclic amine with NH) | benzothiazole-OCHF₂ | glucuronide ester |
| 569 | (diazabicyclic amine with NH) | quinoline | glucuronide ester |
| 570 | (diazabicyclic amine with NH) | quinoxaline | glucuronide ester |
| 571 | (diazabicyclic amine with NH) | quinoxaline-F | glucuronide ester |
| 572 | (diazabicyclic amine with NH) | quinoxaline-OMe | glucuronide ester |

TABLE 3-continued
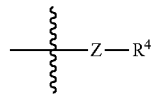
| Compound | A | B | |
|---|---|---|---|
| 573 | | | |
| 574 | | | |
| 575 | | | |
| 576 | | | |
| 577 | | | |
| 578 | | | |
| 579 | | | |

TABLE 3-continued
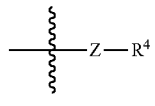
| Compound | A | B | ⸺Z—R⁴ |
|---|---|---|---|
| 580 | | | 4-carboxyphenyl |
| 581 | | | methyl 4-fluoro-3-substituted benzoate |
| 582 | | | 4-fluoro-3-carboxyphenyl |
| 583 | | | methyl cyclohexanecarboxylate |
| 584 | | | cyclohexanecarboxylic acid |
| 585 | | | methyl 4-benzoate |
| 586 | | | methyl 4-benzoate |

TABLE 3-continued

| Compound | A | B | —Z—R⁴ |
|---|---|---|---|
| 587 | bicyclic amine-NH- | pyrazine | methyl pyridine-carboxylate (6-position) |
| 588 | bicyclic amine-NH- | pyrazine | methyl pyridine-carboxylate (6-position) |
| 589 | bicyclic amine-NH- | pyrazine | methyl pyridine-2,6-dicarboxylate |
| 590 | bicyclic amine-NH- | pyrazine | methyl pyridine-2,6-dicarboxylate |
| 591 | bicyclic amine-NH- | pyrazine | —C(Me)₂—CO₂Me |
| 592 | bicyclic amine-NH- | pyrazine | —C(Me)₂—CO₂H |
| 593 | bicyclic amine-NH- | 2-fluoro-1,4-phenylene | —C(Me)₂—CO₂Me |
| 594 | bicyclic amine-NH- | 2-fluoro-1,4-phenylene | —C(Me)₂—CO₂H |

TABLE 3-continued

| Compound | A | B | ⸺Z—R⁴ |
|---|---|---|---|
| 595 | (bicyclic amine with NH) | methylpyrimidine | COOH |
| 596 | (bicyclic amine with NH) | pyridine (2,6) | COOH |
| 597 | (bicyclic amine with NH) | pyridine (2,5) | COOH |
| 598 | (bicyclic amine with NH) | 4-fluoropyridine | COOH |
| 599 | (bicyclic amine with NH) | thiazole (2,4) | COOH |
| 600 | (bicyclic amine with NH) | thiazole (2,5) | COOH |
| 601 | (bicyclic amine with NH) | methylpyridine | COOH |
| 602 | (bicyclic amine with NH) | pyridine (2,6) | COOH |

TABLE 3-continued

| Compound | A | B | $-Z-R^4$ |
|---|---|---|---|
| 603 | 8-azabicyclo[3.2.1] with NH | 3-methyl-pyridine-2,5-diyl | -C(CH₃)₂-COOH |
| 604 | 8-azabicyclo[3.2.1] with NH | 3-fluoro-pyridine-2,5-diyl | -C(CH₃)₂-COOH |
| 605 | 8-azabicyclo[3.2.1] with NH | 3-cyclopropyl-pyridine-2,5-diyl | -C(CH₃)₂-COOH |
| 606 | 8-azabicyclo[3.2.1] with NH | 2,6-difluoro-phenylene | -C(CH₃)₂-COOH |
| 607 | 8-azabicyclo[3.2.1] with NH | pyrazine-2,5-diyl | -C(CH₃)₂-CN |
| 608 | 8-azabicyclo[3.2.1] with NH | pyrazine-2,5-diyl | -C(CH₃)₂-tetrazole |
| 609 | 8-azabicyclo[3.2.1] with NH | 3-fluoro-phenylene | -C(CH₃)₂-CN |
| 610 | 8-azabicyclo[3.2.1] with NH | 3-fluoro-phenylene | -C(CH₃)₂-tetrazole |

TABLE 3-continued
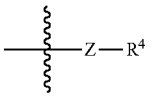
| Compound | A | B | |
|---|---|---|---|
| 611 | | | CN |
| 612 | | | tetrazole |
| 613 | | | |
| 614 | | | |
| 615 | | | |
| 616 | | | |
| 617 | | | |
| 618 | | | |

US 11,034,684 B2

TABLE 3-continued

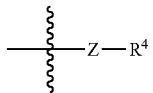

| Compound | A | B | —Z—R⁴ |
|---|---|---|---|
| 619 | bicyclic amine | benzothiazole with OMe | carbamate sulfonamide phenyl O-tBu |
| 620 | bicyclic amine | benzothiazole with Cl | carbamate sulfonamide phenyl O-tBu |
| 621 | bicyclic amine | benzothiazole | carbamate sulfonamide pyridyl piperidine |
| 622 | bicyclic amine | benzothiazole with F | carbamate sulfonamide pyridyl piperidine |
| 623 | bicyclic amine | benzothiazole with OMe | carbamate sulfonamide pyridyl piperidine |
| 624 | bicyclic amine | benzothiazole with Cl | carbamate sulfonamide pyridyl piperidine |
| 625 | bicyclic amine | benzothiazole | carbamate sulfonamide phenyl O-tBu |
| 626 | bicyclic amine | benzothiazole with F | carbamate sulfonamide phenyl O-tBu |

TABLE 3-continued

| Compound | A | B | $Z-R^4$ |
|---|---|---|---|
| 627 | [bicyclic amine with NH] | [benzothiazole with OMe] | [−O−C(O)−NH−SO2−C6H4−O−tBu] |
| 628 | [bicyclic amine with NH] | [benzothiazole with Cl] | [−O−C(O)−NH−SO2−C6H4−O−tBu] |
| 629 | [bicyclic amine with NH] | [benzothiazole] | [−NH−C(O)−NH−SO2−C6H4−tBu] |
| 630 | [bicyclic amine with NH] | [benzothiazole with F] | [−NH−C(O)−NH−SO2−C6H4−tBu] |
| 631 | [bicyclic amine with NH] | [benzothiazole with OMe] | [−NH−C(O)−NH−SO2−C6H4−tBu] |
| 632 | [bicyclic amine with NH] | [benzothiazole with Cl] | [−NH−C(O)−NH−SO2−C6H4−tBu] |
| 633 | [bicyclic amine with NH] | [benzothiazole] | [−CH2−NH−C(O)−NH−SO2−C6H4−tBu] |
| 634 | [bicyclic amine with NH] | [benzothiazole with F] | [−CH2−NH−C(O)−NH−SO2−C6H4−tBu] |

TABLE 3-continued

| Compound | A | B | ⸺Z—R⁴ |
|---|---|---|---|
| 635 | (bicyclic amine with N, NH) | benzothiazole, 7-OMe | CH₂-NH-C(O)-NH-SO₂-C₆H₄-tBu |
| 636 | (bicyclic amine with N, NH) | benzothiazole, 7-Cl | CH₂-NH-C(O)-NH-SO₂-C₆H₄-tBu |
| 637 | 4-aminopiperidine | benzothiazole | C(O)OMe |
| 638 | 4-aminopiperidine | benzothiazole | C(O)OH |
| 639 | 4-aminopiperidine | benzothiazole, 7-OiPr | C(O)OMe |
| 640 | 4-aminopiperidine | benzothiazole, 7-OiPr | C(O)OH |
| 641 | 4-aminopiperidine | benzothiazole, 7-F | C(O)OMe |
| 642 | 4-aminopiperidine | benzothiazole, 7-F | C(O)OH |

TABLE 3-continued

| Compound | A | B | -Z-R⁴ |
|---|---|---|---|
| 643 | [bicyclic amine with NH] | [benzothiazole with cyclopropyl] | C(=O)OMe |
| 644 | [bicyclic amine with NH] | [benzothiazole with cyclopropyl] | C(=O)OH |
| 645 | [bicyclic amine with NH] | [difluorophenyl] | C(=O)OMe |
| 646 | [bicyclic amine with NH] | [difluorophenyl] | C(=O)OH |
| 647 | [bicyclic amine with NH] | [isoxazolo-pyrazine] | C(=O)OH |
| 648 | [bicyclic amine with NH] | [imidazo-pyridine] | C(=O)OH |
| 649 | [bicyclic amine with NH] | [imidazo-pyridine] | C(=O)OH |
| 650 | [bicyclic amine with NH] | [pyrrolo-pyridine] | C(=O)OH |

TABLE 3-continued

| Compound | A | B | —Z—R⁴ |
|---|---|---|---|
| 651 | (bicyclic amine)-NH- | cyclopropyl-quinoxaline | -C(CH₃)₂-COOH |
| 652 | (bicyclic amine)-NH- | cyclopropyl-quinoxaline | -C(CH₃)₂-COOH |
| 653 | (bicyclic amine)-NH- | cyclopropyl-quinoxaline | -C(CH₃)₂-COOH |
| 654 | (bicyclic amine)-NH- | cyclopropyl-quinoxaline | -C(CH₃)₂-COOH |
| 655 | (bicyclic amine)-NH- | quinoxaline | -C(CH₃)₂-COOH |
| 656 | (bicyclic amine)-NH- | quinoxaline | -C(CH₃)₂-COOH |
| 657 | (bicyclic amine)-NH- | quinoxaline | -C(CH₃)₂-COOH |

TABLE 3-continued

| Compound | A | B | ⌇—Z—R⁴ |
|---|---|---|---|
| 658 | [bicyclic amine, NH] | [quinoxaline] | [C(CH₃)₂COOH] |
| 659 | [bicyclic amine, NH] | [F₃C-quinoxaline] | [C(CH₃)₂COOH] |
| 660 | [bicyclic amine, NH] | [F₃C-quinoxaline] | [C(CH₃)₂COOH] |
| 661 | [bicyclic amine, NH] | [F₃C-quinoxaline] | [C(CH₃)₂COOH] |
| 662 | [bicyclic amine, NH] | [F₃C-quinoxaline] | [C(CH₃)₂COOH] |
| 663 | [bicyclic amine, NH] | [OiPr-quinoxaline] | [C(CH₃)₂COOH] |
| 664 | [bicyclic amine, NH] | [OiPr-quinoxaline] | [C(CH₃)₂COOH] |

TABLE 3-continued

| Compound | A | B | 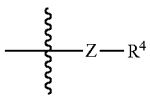 |
|---|---|---|---|
| 665 | (bridged bicyclic amine with NH) | quinoxaline with OiPr | C(CH3)2COOH |
| 666 | (bridged bicyclic amine with NH) | quinoxaline with OiPr (different substitution) | C(CH3)2COOH |
| 667 | (bridged bicyclic amine with NH) | quinoxaline with MeO | C(CH3)2COOH |
| 668 | (bridged bicyclic amine with NH) | quinoxaline with MeO | C(CH3)2COOH |
| 669 | (bridged bicyclic amine with NH) | quinoxaline with MeO | C(CH3)2COOH |
| 670 | (bridged bicyclic amine with NH) | quinoline | C(CH3)2COOH |
| 671 | (bridged bicyclic amine with NH) | quinoline | C(CH3)2COOH |

TABLE 3-continued
| Compound | A | B | 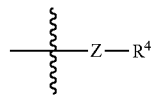 |
|---|---|---|---|
| 672 | | | |
| 673 | | | |
| 674 | | | |
| 675 | | | |
| 676 | | | |
| 677 | | | |
| 678 | | | |

TABLE 3-continued

| Compound | A | B | $\text{---}Z\text{---}R^4$ |
|---|---|---|---|
| 679 | bicyclic amine-NH- | 3-OiPr, 7-linked quinoline, 2-linked | -C(CH₃)₂-COOH |
| 680 | bicyclic amine-NH- | 3-OiPr, 8-linked quinoline, 2-linked | -C(CH₃)₂-COOH |
| 681 | bicyclic amine-NH- | 3-cyclopropyl-pyridine, 2,5-linked | -C(CH₃)₂-COOH |
| 682 | bicyclic amine-NH- | 3-MeO-pyridine, 2,5-linked | -C(CH₃)₂-COOH |
| 683 | bicyclic amine-NH- | 4-OMe pyridine | -C(CH₃)₂-COOH |
| 684 | bicyclic amine-NH- | 4-OiPr-pyridine, 2,5-linked | -C(CH₃)₂-COOH |
| 685 | bicyclic amine-NH- | 4-F-pyridine, 2,5-linked | -C(CH₃)₂-COOH |
| 686 | bicyclic amine-NH- | 3-F, 4-OiPr-pyridine, 2,5-linked | -C(CH₃)₂-COOH |

TABLE 3-continued
| Compound | A | B | 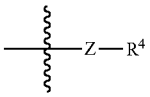 |
|---|---|---|---|
| 687 | | | |
| 688 | | | |
| 689 | | | |
| 690 | | | |
| 691 | | | |
| 692 | | | |
| 693 | | | |

TABLE 3-continued

| Compound | A | B | ![Z—R⁴] |
|---|---|---|---|
| 694 | [bicyclic diamine with N-CF₃] | [benzothiazole with OiPr] | -C(O)OH (gem-dimethyl) |
| 695 | [bicyclic amine with NH] | [thiazolopyrazine] | -C(O)OH (gem-dimethyl) |
| 696 | [bicyclic amine with NH] | [benzothiazole] | -C(O)OEt (gem-dimethyl) |

In another embodiment, the compound of Formula (I) is represented by Formula (XI) or a pharmaceutically acceptable salt thereof:

Representative compounds of the invention include, but are not limited to, compounds according to Formula (XI), and pharmaceutically acceptable salts thereof, wherein, A, B, and $R^7$ are delineated for each compound in Table 4.

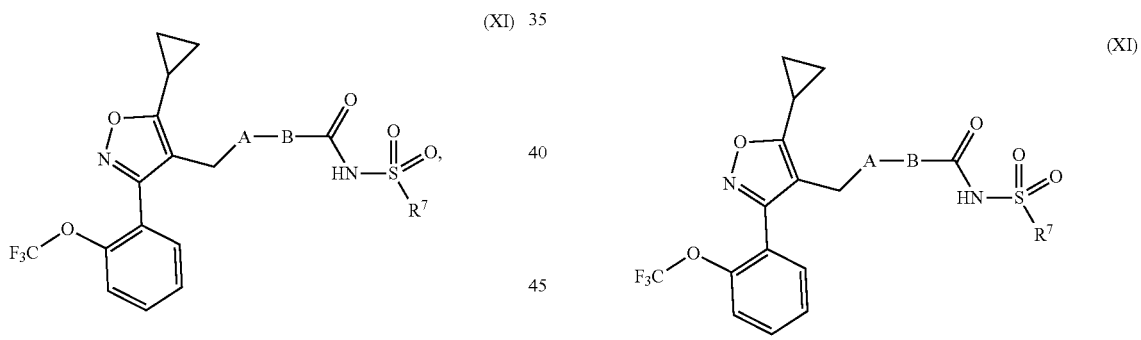

(XI)

wherein A, B, and $R^7$ are as previously defined.

TABLE 4

| Compound | A | B | $R^7$ |
|---|---|---|---|
| 701 | [bicyclic amine with NH] | [benzothiazole] | cyclopropyl |
| 702 | [bicyclic amine with NH] | [benzothiazole] | cyclopropylmethyl |

TABLE 4-continued

| Compound | A | B | R⁷ |
|---|---|---|---|
| 703 | [9-azabicyclic amine] | [benzothiazol-2,6-diyl] | cyclopropyl-CHO |
| 704 | [9-azabicyclic amine] | [benzothiazol-2,6-diyl] | cyclopropyl-CD₃ |
| 705 | [9-azabicyclic amine] | [benzothiazol-2,6-diyl] | cyclopropyl-CH₂OH |
| 706 | [9-azabicyclic amine] | [benzothiazol-2,6-diyl] | cyclopropyl-CHF₂ |
| 707 | [9-azabicyclic amine] | [benzothiazol-2,6-diyl] | cyclopropyl-CF₃ |
| 708 | [9-azabicyclic amine] | [benzothiazol-2,6-diyl] | cyclopropyl-F |
| 709 | [9-azabicyclic amine] | [benzothiazol-2,6-diyl] | cyclopropyl-Cl |
| 710 | [9-azabicyclic amine] | [benzothiazol-2,6-diyl] | cyclopropyl-CH₂F |
| 711 | [9-azabicyclic amine] | [benzothiazol-2,6-diyl] | cyclopropyl-CH₂OMe |

TABLE 4-continued

| Compound | A | B | R⁷ |
|---|---|---|---|
| 712 | | | cyclopropyl-CN |
| 713 | | | cyclopropyl-CH₂OBn |
| 714 | | | cyclopropyl-CH₂OH |
| 715 | | | cyclopropyl-CH₂NMe₃⁺ |
| 716 | | | cyclopropyl-CH₂OCH₂CH₂OH |
| 717 | | | cyclopropyl-CH₂OCH₂CH₂NMe₃⁺ |
| 718 | | | cyclopropyl-C(O)OMe |
| 719 | | | cyclopropyl-C(O)OH |

TABLE 4-continued

| Compound | A | B | R⁷ |
|---|---|---|---|
| 720 | bicyclic amine | benzothiazole | 1-carbamoylcyclopropyl |
| 721 | bicyclic amine | benzothiazole | 1-(N,N-dimethylsulfamoylcarbamoyl)cyclopropyl |
| 722 | bicyclic amine | benzothiazole | 1-(pyrrolidin-1-ylsulfonylcarbamoyl)cyclopropyl |
| 723 | bicyclic amine | benzothiazole | 2,2-difluoro-1-methylcyclopropyl |
| 724 | bicyclic amine | benzothiazole | 2,2-difluorocyclopropyl |
| 725 | bicyclic amine | benzothiazole | N,N-dimethylamino |
| 726 | bicyclic amine | benzothiazole | azetidin-1-yl |
| 727 | bicyclic amine | benzothiazole | pyrrolidin-1-yl |
| 728 | bicyclic amine | benzothiazole | piperidin-1-yl |

TABLE 4-continued

| Compound | A | B | R⁷ |
|---|---|---|---|
| 729 | [bicyclic amine with NH] | [benzothiazole] | [4,4-difluoropiperidinyl] |
| 730 | [bicyclic amine with NH] | [benzothiazole] | [NH₂] |
| 731 | [bicyclic amine with NH] | [benzothiazole] | [cyclopentyl] |
| 732 | [bicyclic amine with NH] | [benzothiazole] | [cyclohexyl] |
| 733 | [bicyclic amine with NH] | [benzothiazole] | [1-methylcyclopentyl] |
| 734 | [bicyclic amine with NH] | [benzothiazole] | [morpholinyl] |
| 735 | [bicyclic amine with NH] | [benzothiazole] | Me |
| 736 | [bicyclic amine with NH] | [benzothiazole] | CF₃ |
| 737 | [bicyclic amine with NH] | [benzothiazole] | [isopropyl] |

TABLE 4-continued

| Compound | A | B | R⁷ |
|---|---|---|---|
| 738 | (bicyclic amine with NH) | benzothiazole | -CH₂-Me (ethyl) |
| 739 | (bicyclic amine with NH) | benzothiazole | -CH₂-C(Me)₂-... (neopentyl-like) |
| 740 | (bicyclic amine with NH) | benzothiazole | -CH₂-C(Me)₃ (neopentyl) |
| 741 | (bicyclic amine with NH) | benzothiazole | -CH₂-cyclopropyl |
| 742 | (bicyclic amine with NH) | benzothiazole | -CH₂-C(Me)₂-CH₂-OBn |
| 743 | (bicyclic amine with NH) | benzothiazole | -CH₂-Ph (benzyl) |
| 744 | (bicyclic amine with NH) | benzothiazole | -CH₂-CH=CH₂ (allyl) |
| 745 | (bicyclic amine with NH) | benzothiazole | -Bu |
| 746 | (bicyclic amine with NH) | benzothiazole | -CH₂CH₂CH₂CH₃ (n-butyl chain) |

TABLE 4-continued

| Compound | A | B | R⁷ |
|---|---|---|---|
| 747 | bicyclic amine | benzothiazole | —NH₂ |
| 748 | bicyclic amine | benzothiazole | —NH—CH₃ |
| 749 | bicyclic amine | benzothiazole | —NH—iPr |
| 750 | bicyclic amine | benzothiazole | —NH—Et |
| 751 | bicyclic amine | benzothiazole | —NH—cyclopentyl |
| 752 | bicyclic amine | benzothiazole | —NH—cyclopropyl |
| 753 | bicyclic amine | benzothiazole | —NH—phenyl |
| 754 | bicyclic amine | benzothiazole | —NH—cyclohexyl |

TABLE 4-continued

| Compound | A | B | R⁷ |
|---|---|---|---|
| 755 | bicyclic amine with NH | benzothiazole | 4-fluorophenyl-NH |
| 756 | bicyclic amine with NH | benzothiazole | pyridin-4-yl-NH |
| 757 | bicyclic amine with NH | benzothiazole | phenyl |
| 758 | bicyclic amine with NH | benzothiazole | 2-(OCF₃)phenyl-NH |
| 759 | bicyclic amine with NH | benzothiazole | 4-fluorophenyl |
| 760 | bicyclic amine with NH | benzothiazole | 4-methylphenyl |
| 761 | bicyclic amine with NH | benzothiazole | pyridin-2-yl |
| 762 | bicyclic amine with NH | benzothiazole | 4-tert-butylphenyl |

TABLE 4-continued

| Compound | A | B | R⁷ |
|---|---|---|---|
| 763 | [bicyclic amine with NH] | [benzothiazole] | [pyridin-4-yl] |
| 764 | [bicyclic amine with NH] | [benzothiazole] | [pyridin-3-yl] |
| 765 | [bicyclic amine with NH] | [benzothiazole] | [thiazol-5-yl] |
| 766 | [bicyclic amine with NH] | [benzothiazole] | [5-fluoropyridin-2-yl] |
| 767 | [bicyclic amine with NH] | [benzothiazole] | [1H-imidazol-2-yl] |
| 768 | [bicyclic amine with NH] | [benzothiazole] | [thiazol-5-yl] |
| 769 | [bicyclic amine with NH] | [benzothiazole] | [2-(trifluoromethoxy)phenyl] |
| 770 | [bicyclic amine with NH] | [benzothiazole] | [1-methyl-1H-imidazol-2-yl] |
| 771 | [bicyclic amine with NH] | [benzothiazole] | [isoquinolin-7-yl] |

TABLE 4-continued

| Compound | A | B | R⁷ |
|---|---|---|---|
| 772 | [bicyclic diamine structure] | [benzothiazole] | [2-methoxyphenyl] |
| 773 | [bicyclic diamine structure] | [benzothiazole] | [biphenyl] |
| 774 | [bicyclic diamine structure] | [benzothiazole] | [2,4'-bipyridyl] |
| 775 | [bicyclic diamine structure] | [benzothiazole] | [4-(pyridin-4-yl)phenyl] |
| 776 | [bicyclic diamine structure] | [benzothiazole] | [2,3-dihydrobenzo[1,4]dioxine] |
| 777 | [bicyclic diamine structure] | [benzothiazole] | [benzo[1,3]dioxole] |
| 778 | [bicyclic diamine structure] | [benzothiazole] | [indane] |
| 779 | [4-(N-methylamino)cyclohexyloxy] | [benzothiazole] | [N,N-dimethylamino] |
| 780 | [bicyclic diamine structure] | [benzothiazole] | [N,N-dimethylamino] |

TABLE 4-continued

| Compound | A | B | R⁷ |
|---|---|---|---|
| 781 | piperazine | 2,6-benzothiazolyl | N(CH₃)₂ |
| 782 | 4-aminopiperidine | 2,6-benzothiazolyl | N(CH₃)₂ |
| 783 | 3,8-diazabicyclo[3.2.1]octane | 2,6-benzothiazolyl | N(CH₃)₂ |
| 784 | 3,8-diazabicyclo[3.2.1]octane | 2,6-benzothiazolyl | 4-tert-butylphenyl |
| 785 | piperazine | 1,3-phenylene | N(CH₃)₂ |
| 786 | piperazine | 1,3-phenylene | 4-tert-butylphenyl |
| 787 | 4-(methylamino)piperidine | 2,6-benzothiazolyl | N(CH₃)₂ |
| 788 | 4-(methylamino)piperidine | 2,6-benzothiazolyl | 4-tert-butylphenyl |
| 789 | 4-aminopiperidine | 2,6-benzothiazolyl | N(CH₃)₂ |
| 790 | 4-aminopiperidine | 2,6-benzothiazolyl | 4-tert-butylphenyl |
| 791 | 4-aminopiperidine | 2,6-benzothiazolyl | cyclopropyl |

TABLE 4-continued

| Compound | A | B | R⁷ |
|---|---|---|---|
| 792 | | | |
| 793 | | | |
| 794 | | | |
| 795 | | | |
| 796 | | | |
| 797 | | | |
| 798 | | | |
| 799 | | | |

TABLE 4-continued

| Compound | A | B | R⁷ |
|---|---|---|---|
| 800 | [bicyclic amine with NH] | [benzothiazole with F] | [piperidine] |
| 801 | [bicyclic amine with NH] | [benzoxazole] | [N(Me)₂] |
| 802 | [bicyclic amine with NH] | [benzoxazole] | [1-methylcyclopropyl] |
| 803 | [bicyclic amine with NH] | [benzothiazole with OMe] | [N(Me)₂] |
| 804 | [bicyclic amine with NH] | [benzothiazole with OMe] | [1-methylcyclopropyl] |
| 805 | [piperidine with NH] | [benzothiazole] | [1-methylcyclopropyl] |
| 806 | [piperidine with NH] | [benzothiazole] | [piperidine] |
| 807 | [bicyclic amine with NH] | [benzothiazole with OMe] | [1-(difluoromethyl)cyclopropyl] |
| 808 | [bicyclic amine with NH] | [benzothiazole with OMe] | [pyrrolidine] |

TABLE 4-continued

| Compound | A | B | R⁷ |
|---|---|---|---|
| 809 | [bicyclic amine with NH] | [benzothiazole with OMe] | [azetidine] |
| 810 | [bicyclic amine with NH] | [benzothiazole with OMe] | [piperidine] |
| 811 | [bicyclic amine with NH] | [benzothiazole with CHF₃] | [1-methylcyclopropyl] |
| 812 | [bicyclic amine with NH] | [benzothiazole with CHF₃] | [1-(CHF₂)cyclopropyl] |
| 813 | [bicyclic amine with NH] | [benzothiazole with CHF₃] | [N(CH₃)₂] |
| 814 | [bicyclic amine with NH] | [benzothiazole with CHF₃] | [azetidine] |
| 815 | [bicyclic amine with NH] | [benzothiazole with CHF₃] | [pyrrolidine] |
| 816 | [bicyclic amine with NH] | [benzothiazole with CHF₃] | [piperidine] |

TABLE 4-continued

| Compound | A | B | R⁷ |
|---|---|---|---|
| 817 | [bicyclic amine with NH] | [benzothiazole with OCF₃] | [cyclopropyl] |
| 818 | [bicyclic amine with NH] | [benzothiazole with OCF₃] | [cyclopropyl with F₂HC] |
| 819 | [bicyclic amine with NH] | [benzothiazole with OCF₃] | [N(CH₃)₂] |
| 820 | [bicyclic amine with NH] | [benzothiazole with OCF₃] | [azetidinyl] |
| 821 | [bicyclic amine with NH] | [benzothiazole with OCF₃] | [pyrrolidinyl] |
| 822 | [bicyclic amine with NH] | [benzothiazole with OCF₃] | [piperidinyl] |
| 823 | [bicyclic amine with NH] | [benzothiazole with OCHF₂] | [cyclopropyl] |
| 824 | [bicyclic amine with NH] | [benzothiazole with OCHF₂] | [cyclopropyl with F₂HC] |

TABLE 4-continued

| Compound | A | B | R⁷ |
|---|---|---|---|
| 825 | bicyclic amine with NH | benzothiazole with OCHF₂ | N(CH₃)₂ |
| 826 | bicyclic amine with NH | benzothiazole with OCHF₂ | azetidinyl |
| 827 | bicyclic amine with NH | benzothiazole with OCHF₂ | pyrrolidinyl |
| 828 | bicyclic amine with NH | benzothiazole with OCHF₂ | piperidinyl |
| 829 | bicyclic amine with NH | benzothiazole with CF₃ | 1-methylcyclopropyl |
| 830 | bicyclic amine with NH | benzothiazole with CF₃ | 1-(difluoromethyl)cyclopropyl |
| 831 | bicyclic amine with NH | benzothiazole with CF₃ | N(CH₃)₂ |
| 832 | bicyclic amine with NH | benzothiazole with CF₃ | azetidinyl |

TABLE 4-continued

| Compound | A | B | R⁷ |
|---|---|---|---|
| 833 | [bicyclic amine with NH] | [benzothiazole with CF₃] | pyrrolidine |
| 834 | [bicyclic amine with NH] | [benzothiazole with CF₃] | piperidine |
| 835 | [bicyclic amine with NH] | [chloroquinoxaline] | 1-methylcyclopropyl |
| 836 | [bicyclic amine with NH] | [chloroquinoxaline] | 1-(difluoromethyl)cyclopropyl |
| 837 | [bicyclic amine with NH] | [chloroquinoxaline] | N,N-dimethylamino |
| 838 | [bicyclic amine with NH] | [chloroquinoxaline] | azetidine |
| 839 | [bicyclic amine with NH] | [chloroquinoxaline] | pyrrolidine |
| 840 | [bicyclic amine with NH] | [chloroquinoxaline] | piperidine |

TABLE 4-continued

| Compound | A | B | R⁷ |
|---|---|---|---|
| 841 | bicyclic amine with NH | 3-MeO-quinoxaline | 1-methylcyclopropyl |
| 842 | bicyclic amine with NH | 3-MeO-quinoxaline | 1-(difluoromethyl)cyclopropyl |
| 843 | bicyclic amine with NH | 3-MeO-quinoxaline | N(CH₃)₂ |
| 844 | bicyclic amine with NH | 3-MeO-quinoxaline | azetidinyl |
| 845 | bicyclic amine with NH | 3-MeO-quinoxaline | pyrrolidinyl |
| 846 | bicyclic amine with NH | 3-MeO-quinoxaline | piperidinyl |
| 847 | bicyclic amine with NH | quinoxaline | 1-methylcyclopropyl |
| 848 | bicyclic amine with NH | quinoxaline | 1-(difluoromethyl)cyclopropyl |

TABLE 4-continued

| Compound | A | B | R⁷ |
|---|---|---|---|
| 849 | [bicyclic amine with NH] | [quinoxaline] | -N(CH₃)₂ |
| 850 | [bicyclic amine with NH] | [quinoxaline] | -N(azetidine) |
| 851 | [bicyclic amine with NH] | [quinoxaline] | -N(pyrrolidine) |
| 852 | [bicyclic amine with NH] | [quinoxaline] | -N(piperidine) |
| 853 | [bicyclic amine with NH] | [quinoxaline, F-substituted] | -cyclopropyl |
| 854 | [bicyclic amine with NH] | [quinoxaline, F-substituted] | -C(CHF₂)(cyclopropyl) |
| 855 | [bicyclic amine with NH] | [quinoxaline, F-substituted] | -N(CH₃)₂ |
| 856 | [bicyclic amine with NH] | [quinoxaline, F-substituted] | -N(azetidine) |

TABLE 4-continued

| Compound | A | B | R⁷ |
|---|---|---|---|
| 857 | [bicyclic amine with NH] | [quinoxaline with F] | [pyrrolidine] |
| 858 | [bicyclic amine with NH] | [quinoxaline with F] | [piperidine] |
| 859 | [bicyclic amine with NH] | [quinoxaline with OMe] | [1-methylcyclopropyl] |
| 860 | [bicyclic amine with NH] | [quinoxaline with OMe] | [1-(difluoromethyl)cyclopropyl] |
| 861 | [bicyclic amine with NH] | [quinoxaline with OMe] | [N,N-dimethylamino] |
| 862 | [bicyclic amine with NH] | [quinoxaline with OMe] | [azetidine] |
| 863 | [bicyclic amine with NH] | [quinoxaline with OMe] | [pyrrolidine] |
| 864 | [bicyclic amine with NH] | [quinoxaline with OMe] | [piperidine] |

TABLE 4-continued

| Compound | A | B | R⁷ |
|---|---|---|---|
| 865 | bicyclic amine with NH | quinazoline | cyclopropyl (methyl) |
| 866 | bicyclic amine with NH | quinazoline | 1-(difluoromethyl)cyclopropyl |
| 867 | bicyclic amine with NH | quinazoline | N,N-dimethylamino |
| 868 | bicyclic amine with NH | quinazoline | azetidin-1-yl |
| 869 | bicyclic amine with NH | quinazoline | pyrrolidin-1-yl |
| 870 | bicyclic amine with NH | quinazoline | piperidin-1-yl |
| 871 | bicyclic amine with NH | pyrazolo[1,5-a]pyrimidine | cyclopropyl (methyl) |
| 872 | bicyclic amine with NH | pyrazolo[1,5-a]pyrimidine | 1-(difluoromethyl)cyclopropyl |
| 873 | bicyclic amine with NH | pyrazolo[1,5-a]pyrimidine | N,N-dimethylamino |

TABLE 4-continued

| Compound | A | B | R⁷ |
|---|---|---|---|
| 874 | bicyclic amine-NH- | pyrazolo[1,5-a]pyrimidine | N-azetidinyl |
| 875 | bicyclic amine-NH- | pyrazolo[1,5-a]pyrimidine | N-pyrrolidinyl |
| 876 | bicyclic amine-NH- | pyrazolo[1,5-a]pyrimidine | N-piperidinyl |
| 877 | bicyclic amine-NH- | benzoxazole | 1-methylcyclopropyl |
| 878 | bicyclic amine-NH- | benzoxazole | 1-(difluoromethyl)cyclopropyl |
| 879 | bicyclic amine-NH- | benzoxazole | N,N-dimethylamino |
| 880 | bicyclic amine-NH- | oxazolopyridine | N-azetidinyl |
| 881 | bicyclic amine-NH- | oxazolopyridine | N-pyrrolidinyl |
| 882 | bicyclic amine-NH- | oxazolopyridine | N-piperidinyl |

TABLE 4-continued

| Compound | A | B | R⁷ |
|---|---|---|---|
| 883 | (bicyclic amine with NH) | quinoline-2,6-diyl | 1-methylcyclopropyl |
| 884 | (bicyclic amine with NH) | quinoline-2,6-diyl | 1-(difluoromethyl)cyclopropyl |
| 885 | (bicyclic amine with NH) | quinoline-2,6-diyl | N,N-dimethylamino |
| 886 | (bicyclic amine with NH) | quinoline-2,6-diyl | azetidin-1-yl |
| 887 | (bicyclic amine with NH) | quinoline-2,6-diyl | pyrrolidin-1-yl |
| 888 | (bicyclic amine with NH) | quinoline-2,6-diyl | piperidin-1-yl |
| 889 | (bicyclic amine with NH) | naphthalene-2,6-diyl | 1-methylcyclopropyl |
| 890 | (bicyclic amine with NH) | naphthalene-2,6-diyl | 1-(difluoromethyl)cyclopropyl |

TABLE 4-continued

| Compound | A | B | R⁷ |
|---|---|---|---|
| 891 | bicyclic amine with NH | 2,6-naphthalenediyl | N(CH₃)₂ |
| 892 | bicyclic amine with NH | 2,6-naphthalenediyl | azetidinyl |
| 893 | bicyclic amine with NH | 2,6-naphthalenediyl | pyrrolidinyl |
| 894 | bicyclic amine with NH | 2,6-naphthalenediyl | piperidinyl |
| 895 | bicyclic amine with NH | 2,5-pyrazinediyl | cyclopropyl |
| 896 | bicyclic amine with NH | 2,5-pyrazinediyl | 1-(difluoromethyl)cyclopropyl |
| 897 | bicyclic amine with NH | 2,5-pyrazinediyl | N(CH₃)₂ |
| 898 | bicyclic amine with NH | 2,5-pyrazinediyl | azetidinyl |

TABLE 4-continued

| Compound | A | B | R⁷ |
|---|---|---|---|
| 899 | | | pyrrolidine |
| 900 | | | piperidine |
| 900-1 | | benzothiazole | 1-methylcyclopropyl |
| 900-2 | | 4-F-benzothiazole | 1-methylcyclopropyl |
| 900-3 | | 4-F-benzothiazole | cyclopropyl |
| 900-4 | | 4-F-benzothiazole | 1-methylcyclopropyl |
| 900-5 | | 4-OiPr-benzothiazole | cyclopropyl |
| 900-6 | | 4-OiPr-benzothiazole | 1-methylcyclopropyl |

TABLE 4-continued

| Compound | A | B | R⁷ |
|---|---|---|---|
| 900-7 | piperidine-NH linker | 2,6-disubstituted-4-OiPr-benzothiazole | pyrrolidinyl |
| 900-8 | piperidine-NH linker | 2,6-disubstituted-4-OiPr-benzothiazole | piperidinyl |
| 900-9 | bicyclic diamine (NH) | 2,6-disubstituted-4-cyclopropyl-benzothiazole | cyclopropyl |
| 900-10 | bicyclic diamine (NH) | 2,6-disubstituted-4-cyclopropyl-benzothiazole | piperidinyl |
| 900-11 | bicyclic diamine (NH) | 2,3-difluorophenyl | cyclopropyl |
| 900-12 | bicyclic diamine (NH) | 2,3-difluorophenyl | 1-methylcyclopropyl |
| 900-13 | bicyclic diamine (NH) | 2,5-disubstituted pyridine | cyclopropyl |
| 900-14 | bicyclic diamine (NH) | 2,5-disubstituted pyridine | 1-methylcyclopropyl |

TABLE 4-continued

| Compound | A | B | R[7] |
|---|---|---|---|
| 900-15 | 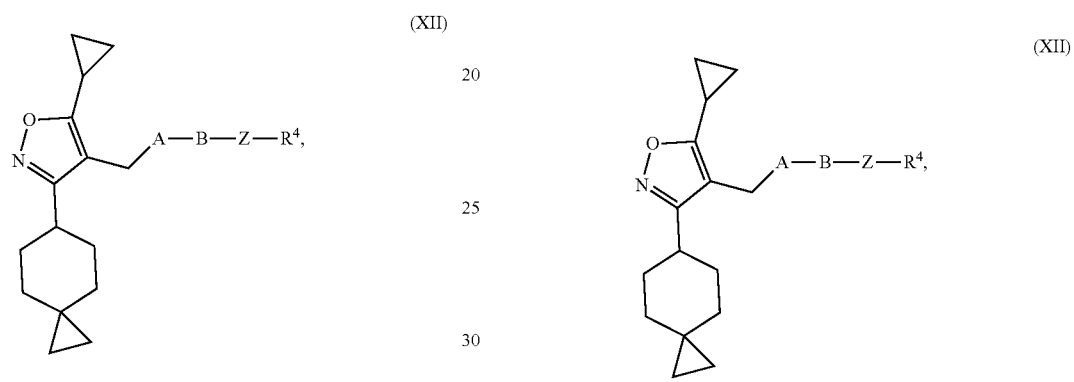 | | |

In another embodiment, the compound of Formula (I) is represented by Formula (XII) or a pharmaceutically acceptable salt thereof:

(XII)

wherein A, B, Z, and R[4] are as previously defined.

Representative compounds of the invention include, but are not limited to, compounds according to Formula (XII), and pharmaceutically acceptable salts thereof, wherein A, B, and Z—R[4] are delineated for each compound in Table 5.

(XII)

TABLE 5

| Compound A | B | —Z—R[4] |
|---|---|---|
| 901 | | |
| 902 | | |
| 903 | | |

TABLE 5-continued
| Compound A | | B | Z—R⁴ |
|---|---|---|---|
| 904 | 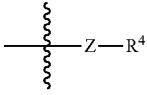 | 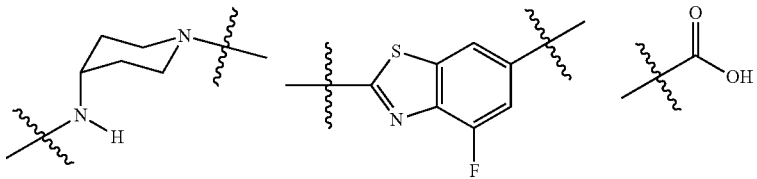 (F) | 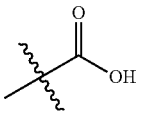 (OH) |
| 905 | 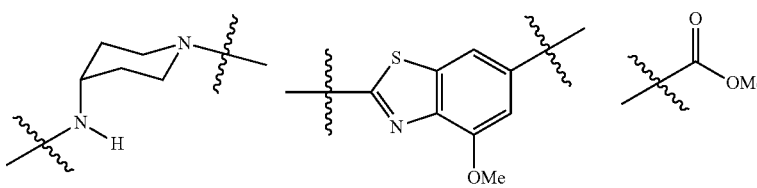 | 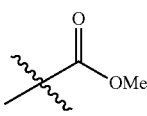 [SMILES: *C(=O)OC] (OMe) | 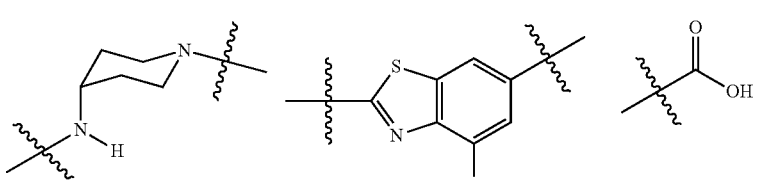 (OMe) |
| 906 | 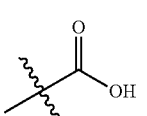 | 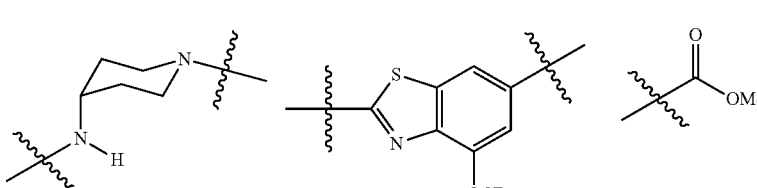 (OMe) | 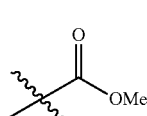 (OH) |
| 907 | 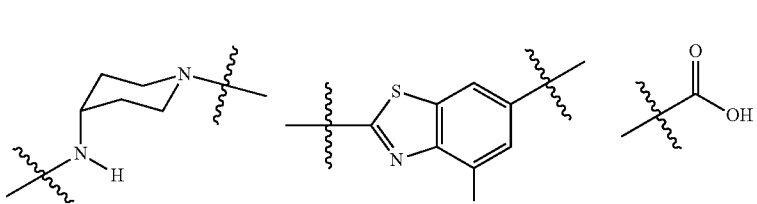 | 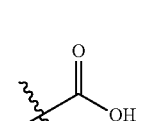 (OCF₃) | 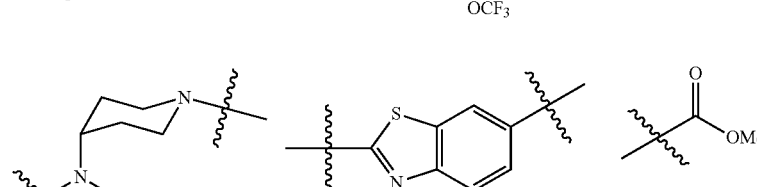 (OMe) |
| 908 | | 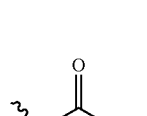 (OCF₃) | (OH) |
| 909 | | 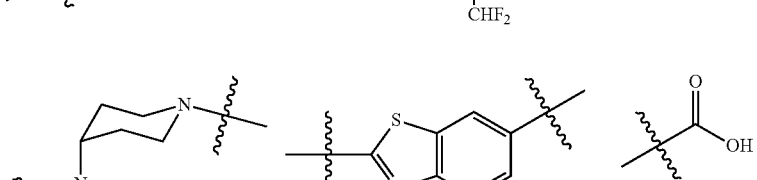 (CHF₂) | (OMe) |
| 910 | | 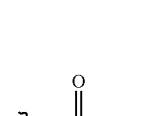 (CHF₂) | (OH) |

TABLE 5-continued
| Compound A | | B | | |
|---|---|---|---|---|
| 911 |  |  | | 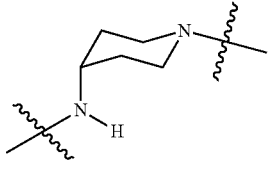 [SMILES: *NC1CCN(*)CC1] |
| 912 | 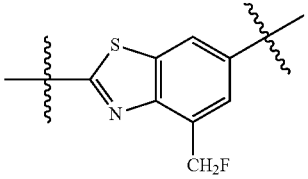 | 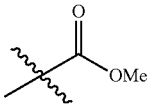 [SMILES: *C(=O)OC] | | 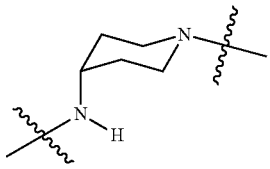 |
| 913 | 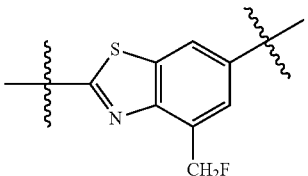 | 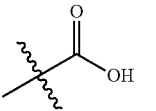 [SMILES: *C(=O)O] | | 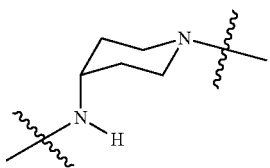 |
| 914 | 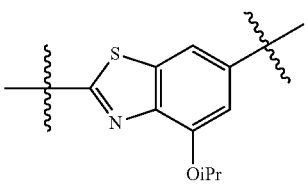 | 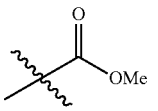 | | 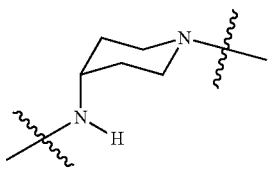 [SMILES: *NC1CCN(*)CC1] |
| 915 | 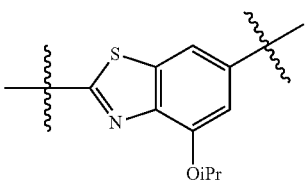 | 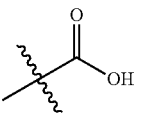 | | 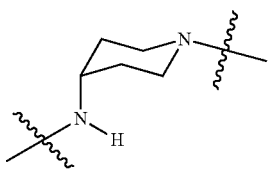 [SMILES: *NC1CCN(*)CC1] |
| 916 | 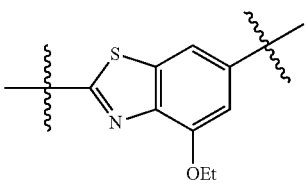 | 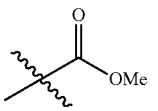 [SMILES: *C(=O)OC] | | 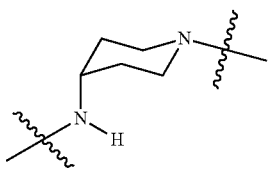 [SMILES: *NC1CCN(*)CC1] |
| 917 | 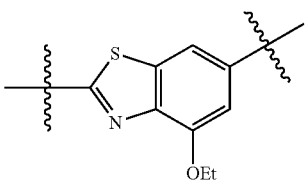 | 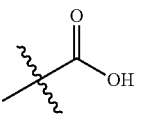 | | 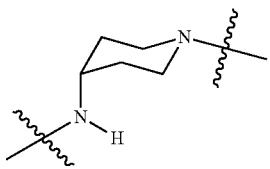 |
| 918 | 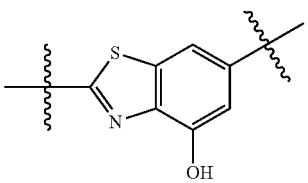 | 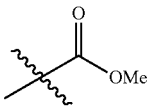 [SMILES: *C(=O)OC] | | 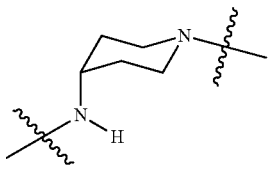 [SMILES: *NC1CCN(*)CC1] |

TABLE 5-continued
| Compound | A | B | Z—R⁴ |
|---|---|---|---|
| 919 | 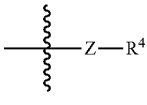 | 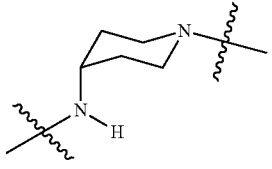 [SMILES: *NC1CCN(*)CC1] | 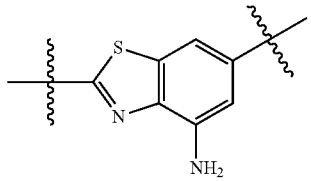 |
| 920 | 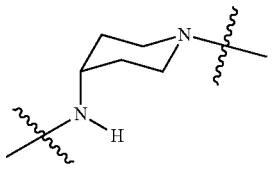 [SMILES: *NC1CCN(*)CC1] | 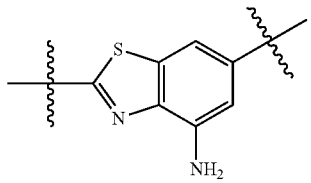 | 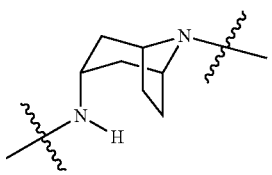 [SMILES: *NC1CC2CCC(C1)N2*] |
| 921 | 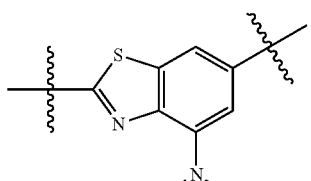 | 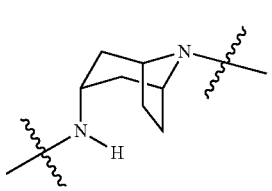 [SMILES: *NC1CC2CCC(C1)N2*] | 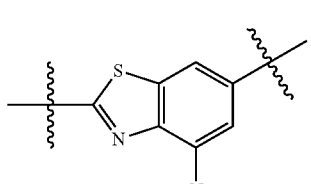 |
| 922 | 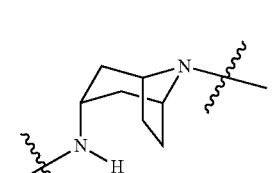 | 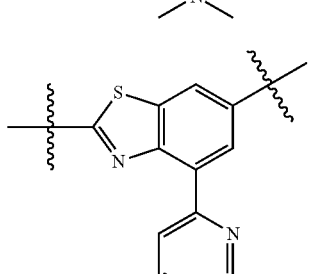 | 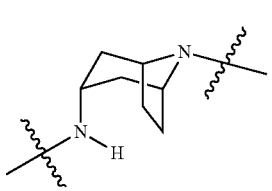 [SMILES: *NC1CC2CCC(C1)N2*] |
| 923 | 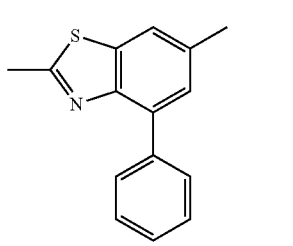 | 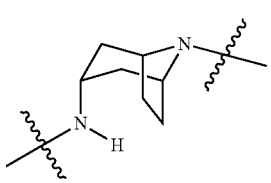 [SMILES: *NC1CC2CCC(C1)N2*] | 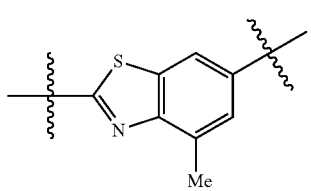 |
| 924 | | | |
| 925 | | | |

TABLE 5-continued
| Compound A | | B | | |
|---|---|---|---|---|
| 926 | 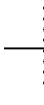 |  | | 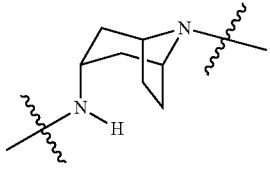 [SMILES: *NC1CC2CCC(C1)N2*] |
| 927 | 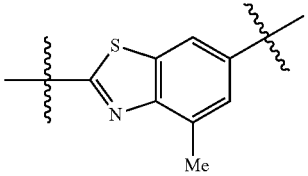 | 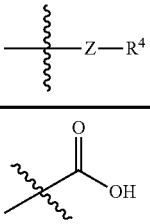 | | 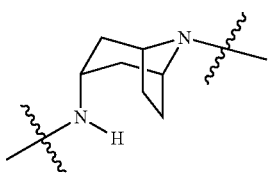 [SMILES: *NC1CC2CCC(C1)N2*] |
| 928 | 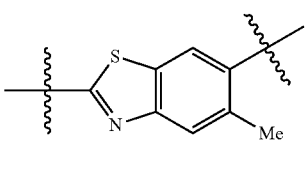 | 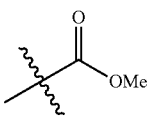 [SMILES: *C(=O)OC] | | 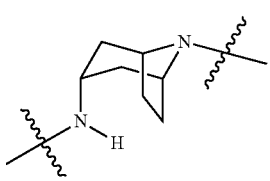 [SMILES: *NC1CC2CCC(C1)N2*] |
| 929 | 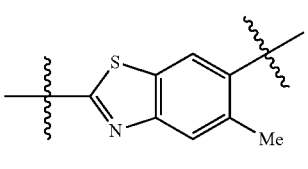 [SMILES: *c1nc2cc(C)c(*)cc2s1] | 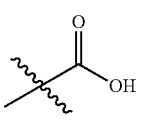 | | 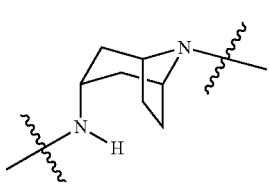 [SMILES: *NC1CC2CCC(C1)N2*] |
| 930 | 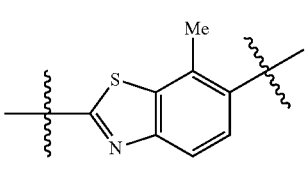 | 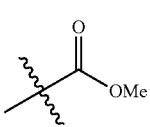 [SMILES: *C(=O)OC] | | 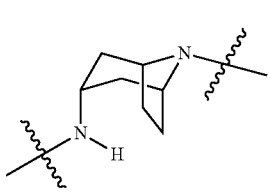 [SMILES: *NC1CC2CCC(C1)N2*] |
| 931 | 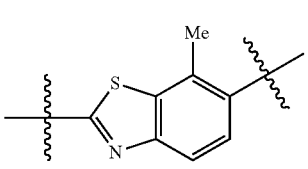 | 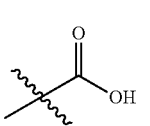 | | 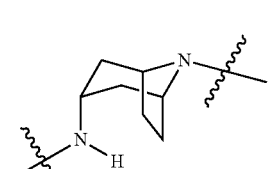 |
| 932 | 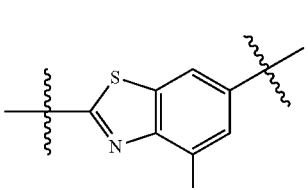 | 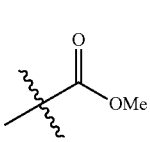 [SMILES: *C(=O)OC] | | 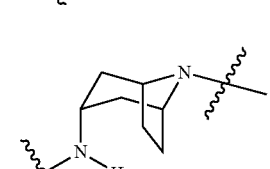 |
| 933 | 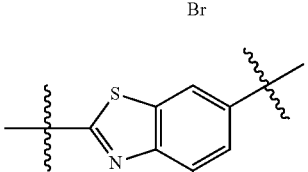 | 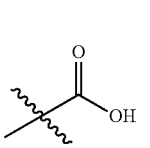 [SMILES: *C(=O)O] | | 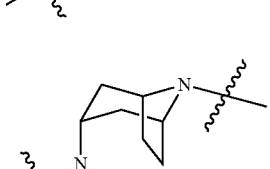 |

TABLE 5-continued

| Compound A | B | Z—R⁴ |
|---|---|---|
| 934 | [bicyclic amine]-NH / [benzothiazole with Cl] | -C(=O)OH |
| 935 | [bicyclic amine]-NH / [dihydrobenzofuran with Me] | -C(=O)OEt |
| 936 | [bicyclic amine]-NH / [benzofuran with Me] | -C(=O)OH |
| 937 | [bicyclic amine]-NH / [benzothiazole with CF₃] | -C(=O)OMe |
| 938 | [bicyclic amine]-NH / [benzothiazole with CF₃] | -C(=O)OH |
| 939 | [bicyclic amine]-NH / [benzothiazole with CH₂F] | -C(=O)OMe |
| 940 | [bicyclic amine]-NH / [benzothiazole with CHF₂] | -C(=O)OH |

TABLE 5-continued
| Compound A | | B | | |
|---|---|---|---|---|
| 941 |  |  | | 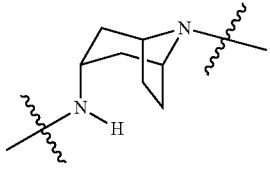 [SMILES: *NC1CC2CCC(C1)N2*] |
| 942 | 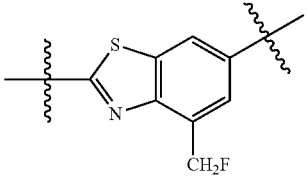 | 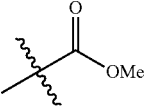 [SMILES: *C(=O)OC] | | 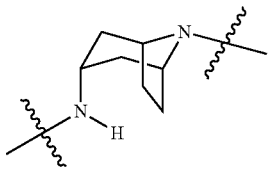 [SMILES: *NC1CC2CCC(C1)N2*] |
| 943 | 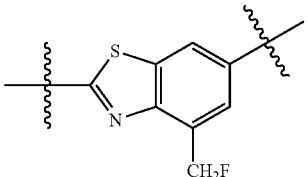 [SMILES: *c1cc(Cl)c2nc(*)sc2c1] | 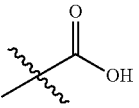 [SMILES: *C(=O)O] | | 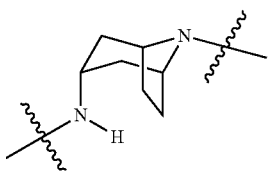 [SMILES: *NC1CC2CCC(C1)N2*] |
| 944 | 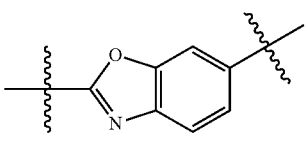 | 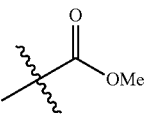 [SMILES: *C(=O)OC] | | 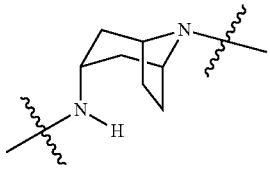 |
| 945 | 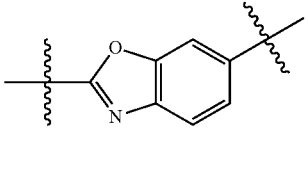 | 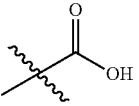 | | 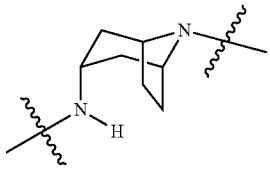 [SMILES: *NC1CC2CCC(C1)N2*] |
| 946 | 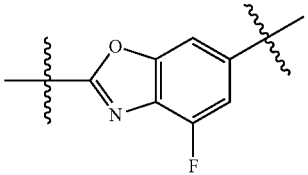 | 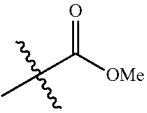 [SMILES: *C(=O)OC] | | 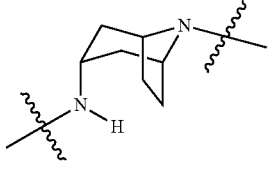 [SMILES: *NC1CC2CCC(C1)N2*] |
| 947 | 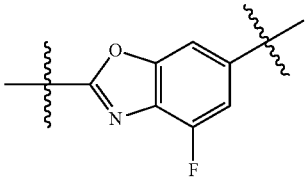 [SMILES: *c1cc(F)c2nc(*)oc2c1] | 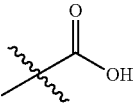 | | 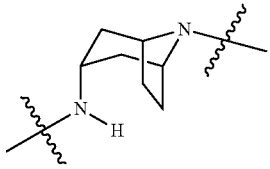 [SMILES: *NC1CC2CCC(C1)N2*] |
| 948 | 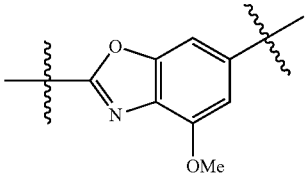 | 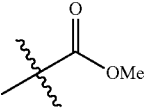 [SMILES: *C(=O)OC] | | 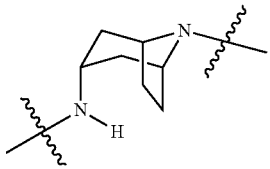 [SMILES: *NC1CC2CCC(C1)N2*] |

TABLE 5-continued
| Compound A | B | -Z—R⁴ |
|---|---|---|
| 949 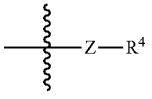 | 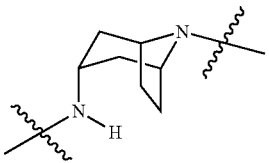 [SMILES: *NC1CC2CCC(C1)N2*] | 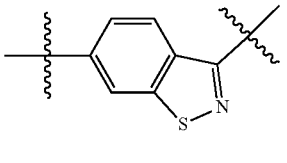 [SMILES: *c1ccc2c(*)nsc2c1] |
| 950 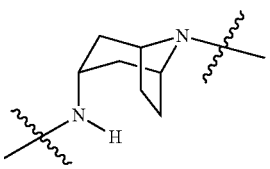 [SMILES: *NC1CC2CCC(C1)N2*] | 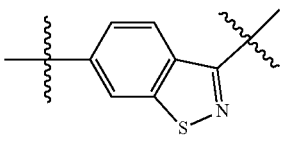 [SMILES: *c1ccc2c(*)nsc2c1] | 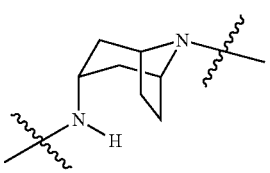 |
| 951 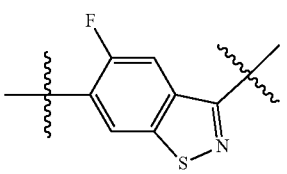 [SMILES: *c1cc2snc(*)c2cc1F] | 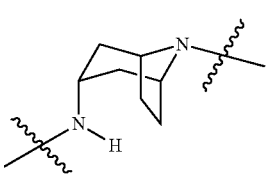 [SMILES: *NC1CC2CCC(C1)N2*] | 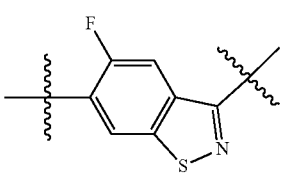 [SMILES: *c1cc2snc(*)c2cc1F] |
| 952 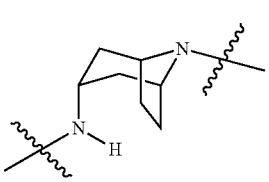 [SMILES: *NC1CC2CCC(C1)N2*] | 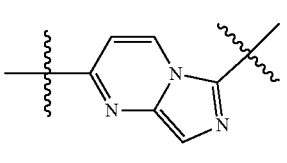 [SMILES: *c1ccn2c(*)ncc2n1] | 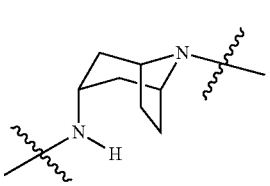 [SMILES: *NC1CC2CCC(C1)N2*] |
| 953 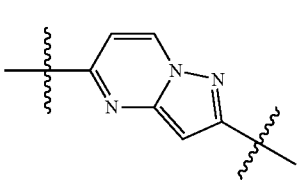 [SMILES: *c1ccn2nc(*)cc2n1] | 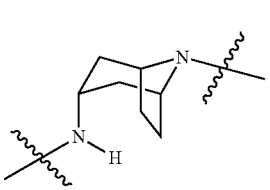 [SMILES: *NC1CC2CCC(C1)N2*] | 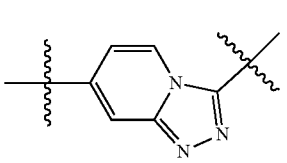 [SMILES: *c1ccn2c(*)nnc2c1] |
| 954 | | 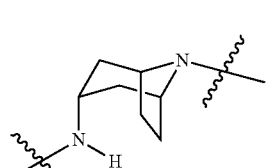 |
| 955 | | |
| 956 | | 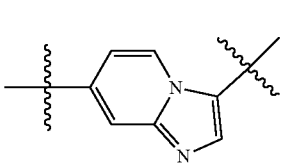 [SMILES: *c1ccn2c(*)cnc2c1] |

TABLE 5-continued
| Compound A | B | −Z−R⁴ |
|---|---|---|
| 957 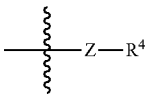 | 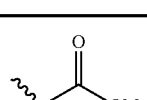 | 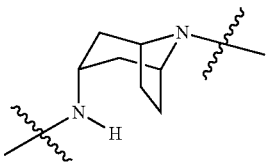 [SMILES: *NC1CC2CCC(C1)N2*] |
| 958 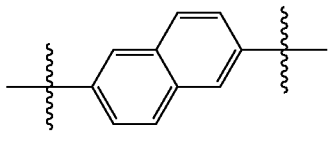 [SMILES: *c1ccc2cc(*)ccc2c1] | 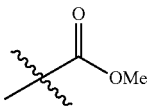 [SMILES: *C(=O)OC] | 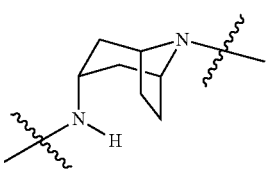 [SMILES: *NC1CC2CCC(C1)N2*] |
| 959 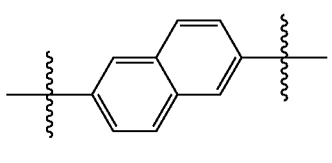 | 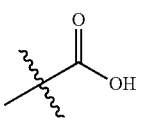 | 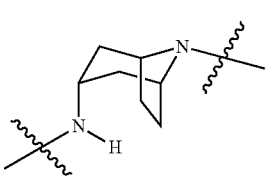 [SMILES: *NC1CC2CCC(C1)N2*] |
| 960 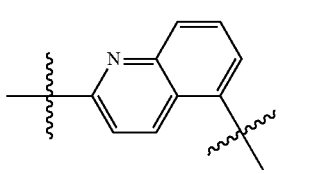 [SMILES: *c1ccc2c(*)cccc2n1] | 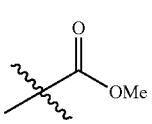 [SMILES: *C(=O)OC] | 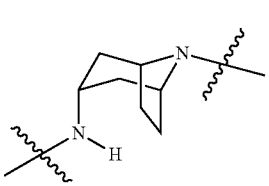 [SMILES: *NC1CC2CCC(C1)N2*] |
| 961 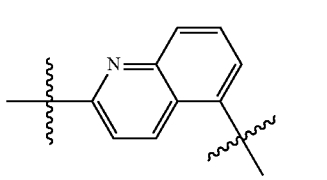 | 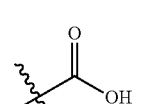 | 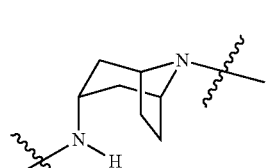 |
| 962 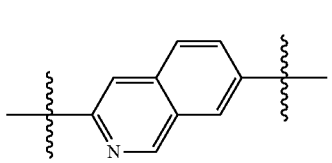 | 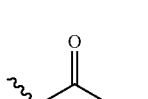 | 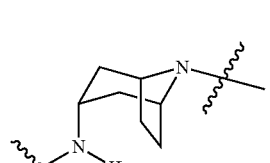 |
| 963 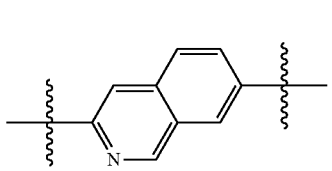 | 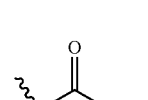 | 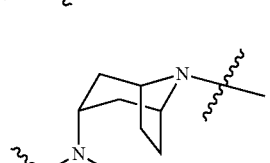 |
| 964 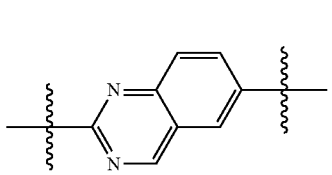 [SMILES: *c1ccc2nc(*)ncc2c1] | 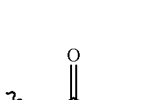 | 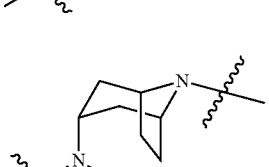 |

TABLE 5-continued
| Compound A | | B | | $-Z-R^4$ | |
|---|---|---|---|---|---|
| 965 | 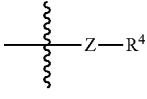 | 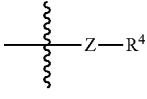 | | 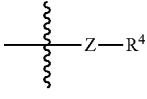 | |
| 966 | 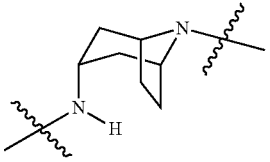 [SMILES: *NC1CC2CCC(C1)N2*] | 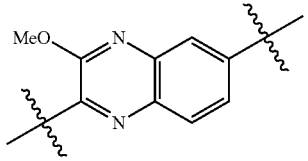 [SMILES: *c1ccc2nc(*)c(OC)nc2c1] | | 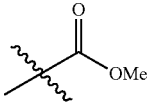 | |
| 967 | 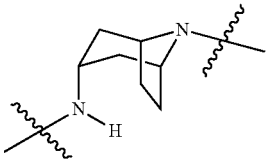 [SMILES: *NC1CC2CCC(C1)N2*] | 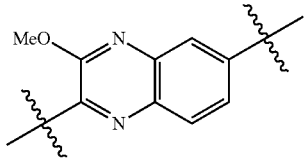 [SMILES: *c1ccc2nc(*)c(OC)nc2c1] | | 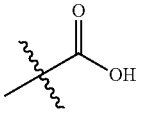 | |
| 968 | 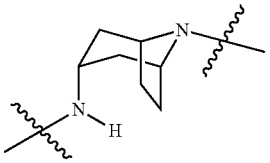 [SMILES: *NC1CC2CCC(C1)N2*] | 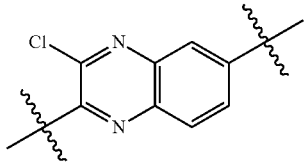 [SMILES: *c1ccc2nc(*)c(Cl)nc2c1] | | 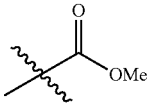 [SMILES: *C(=O)OC] | |
| 969 | 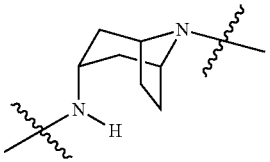 [SMILES: *NC1CC2CCC(C1)N2*] | 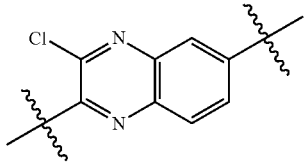 [SMILES: *c1ccc2nc(*)c(Cl)nc2c1] | | 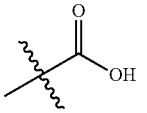 | |
| 970 | 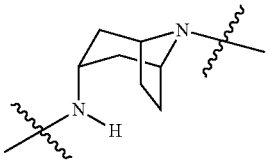 [SMILES: *NC1CC2CCC(C1)N2*] | 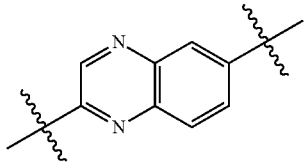 [SMILES: *c1ccc2nc(*)cnc2c1] | | 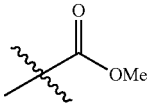 | |
| 971 | 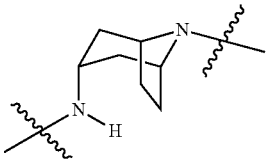 [SMILES: *NC1CC2CCC(C1)N2*] | 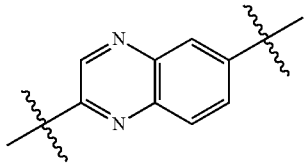 [SMILES: *c1ccc2nc(*)cnc2c1] | | 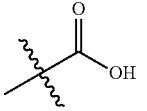 | |
| 972 | 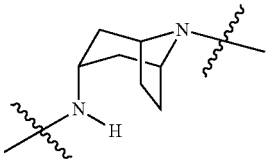 [SMILES: *NC1CC2CCC(C1)N2*] | 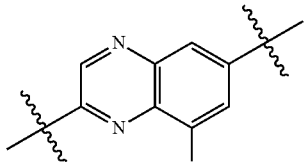 | | 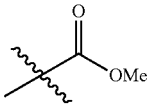 [SMILES: *C(=O)OC] | |

TABLE 5-continued
| Compound A | | B | $-Z-R^4$ |
|---|---|---|---|
| 973 | 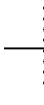 |  | 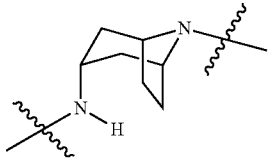 [SMILES: *NC1CC2CCC(C1)N2*] |
| 974 | 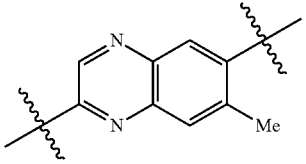 [SMILES: *c1cnc2cc(*)c(C)cc2n1] | 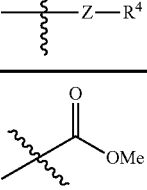 | 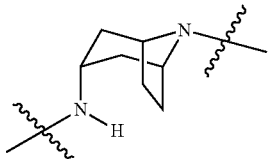 [SMILES: *NC1CC2CCC(C1)N2*] |
| 975 | 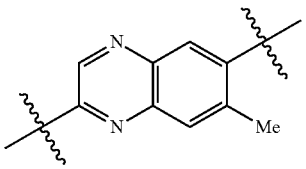 [SMILES: *c1cnc2cc(*)c(C)cc2n1] | 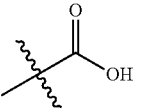 [SMILES: *C(=O)O] | 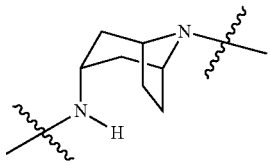 [SMILES: *NC1CC2CCC(C1)N2*] |
| 976 | 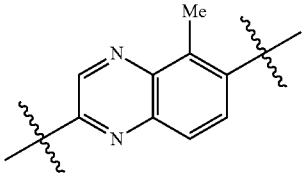 [SMILES: *c1cnc2c(C)c(*)ccc2n1] | 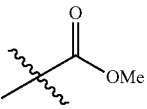 [SMILES: *C(=O)OC] | 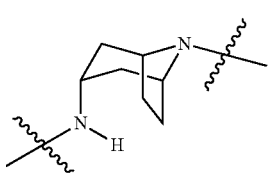 [SMILES: *NC1CC2CCC(C1)N2*] |
| 977 | 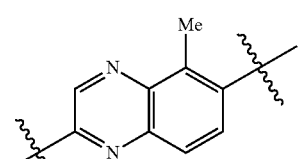 | 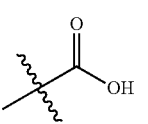 | 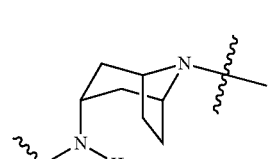 |
| 978 | 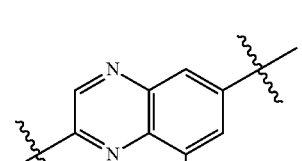 | 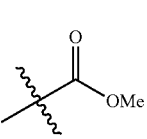 | 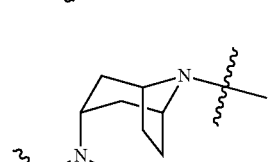 |
| 979 | 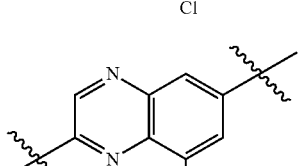 | 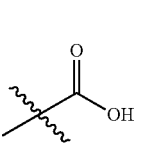 | 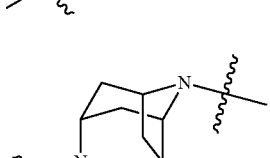 |
| 980 | 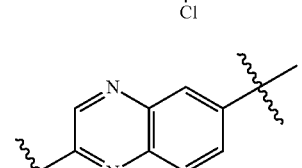 | 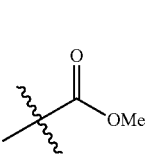 [SMILES: *C(=O)OC] | 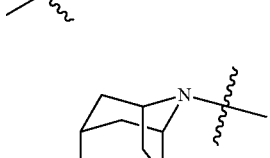 |

TABLE 5-continued
| Compound A | | B | | -Z-R⁴ |
|---|---|---|---|---|
| 981 | 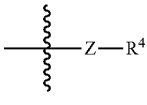 | 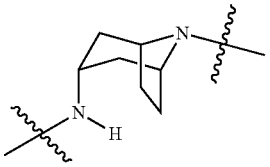 [SMILES: *NC1CC2CCC(C1)N2*] | | 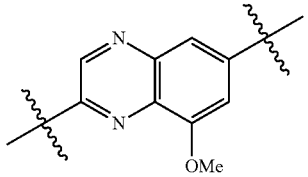 [SMILES: *c1cc(OC)c2nc(*)cnc2c1] |
| 982 | 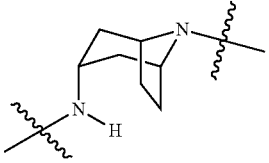 [SMILES: *NC1CC2CCC(C1)N2*] | 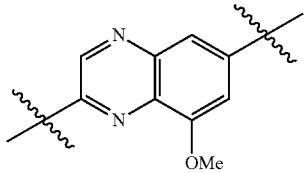 [SMILES: *c1cc(OC)c2nc(*)cnc2c1] | | 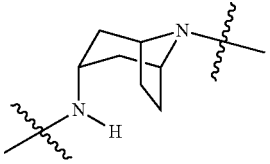 [SMILES: *NC1CC2CCC(C1)N2*] |
| 983 | 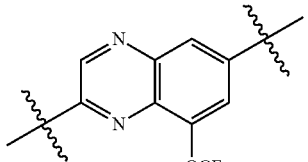 | 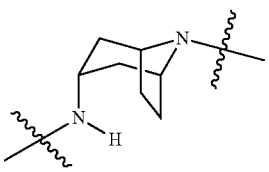 [SMILES: *NC1CC2CCC(C1)N2*] | | 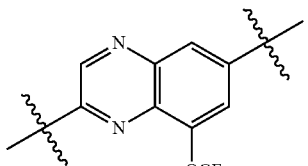 |
| 984 | 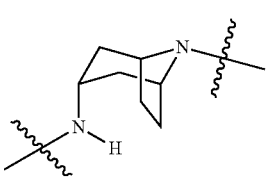 [SMILES: *NC1CC2CCC(C1)N2*] | 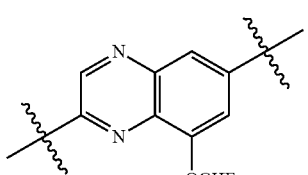 | | 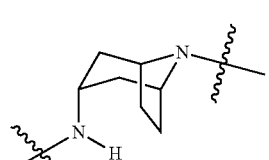 |
| 985 | 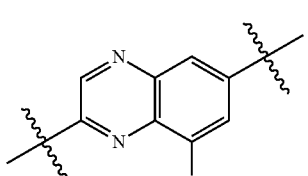 | 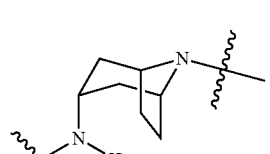 | | 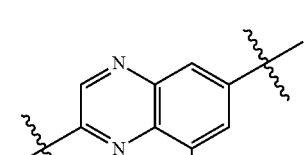 |
| 986 | 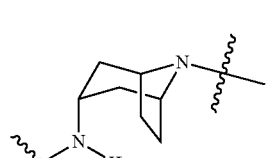 | 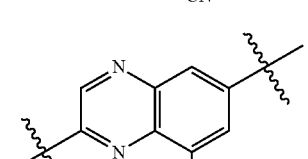 | | |
| 987 | | | | |
| 988 | | | | |

TABLE 5-continued
| Compound A | | B | | —Z—R⁴ |
|---|---|---|---|---|
| 989 | 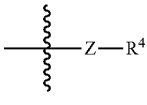 | | 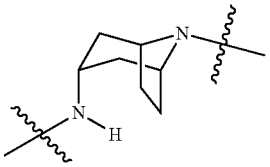 [SMILES: *NC1CC2CCC(C1)N2*] | 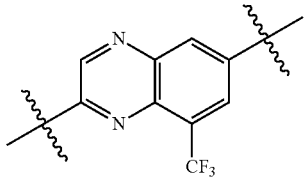 [SMILES: *c1cc(C(F)(F)F)c2nc(*)cnc2c1] |
| 990 | 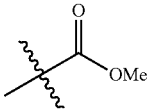 [SMILES: *C(=O)OC] | | 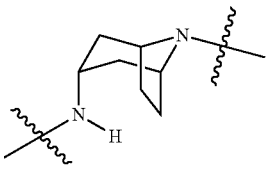 [SMILES: *NC1CC2CCC(C1)N2*] | 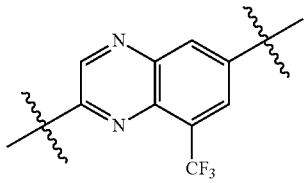 |
| 991 | 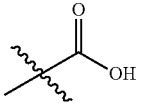 | | 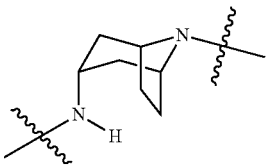 [SMILES: *NC1CC2CCC(C1)N2*] | 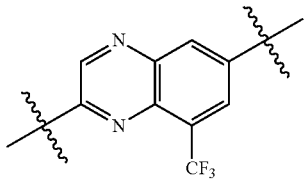 |
| 992 | 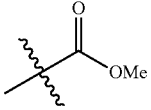 [SMILES: *C(=O)OC] | | 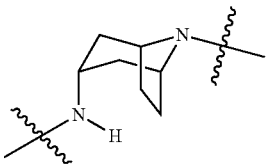 [SMILES: *NC1CC2CCC(C1)N2*] | 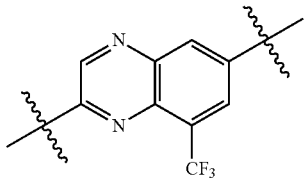 |
| 993 | 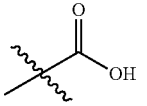 | | 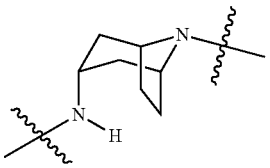 [SMILES: *NC1CC2CCC(C1)N2*] | 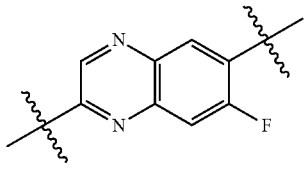 [SMILES: *c1cnc2cc(*)c(F)cc2n1] |
| 994 | 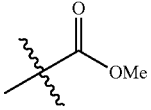 | | 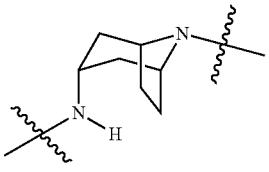 [SMILES: *NC1CC2CCC(C1)N2*] | 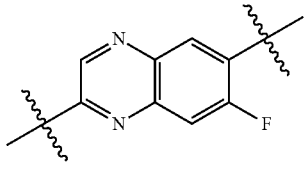 [SMILES: *c1cnc2cc(*)c(F)cc2n1] |
| 995 | 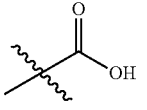 | | 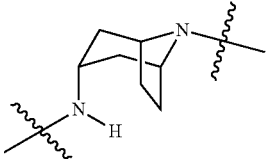 [SMILES: *NC1CC2CCC(C1)N2*] | 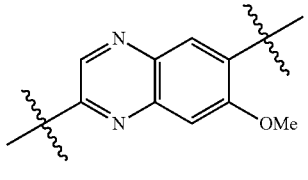 [SMILES: *c1cnc2cc(*)c(OC)cc2n1] |
| 996 | 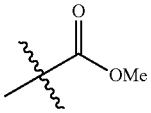 [SMILES: *C(=O)OC] | | 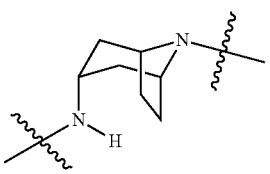 [SMILES: *NC1CC2CCC(C1)N2*] | 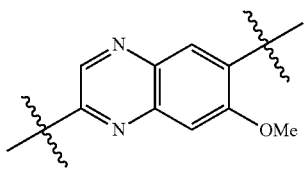 [SMILES: *c1cnc2cc(*)c(OC)cc2n1] |

TABLE 5-continued
| Compound | A | B | -Z-R⁴ |
|---|---|---|---|
| 997 | 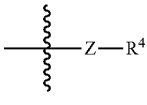 | 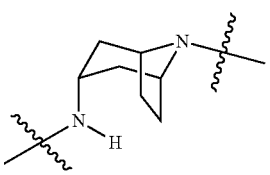 [SMILES: *NC1CC2CCC(C1)N2*] |  |
| 998 | 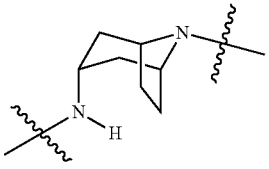 [SMILES: *NC1CC2CCC(C1)N2*] | 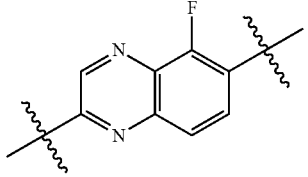 [SMILES: *c1cnc2c(F)c(*)ccc2n1] | 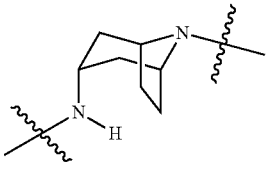 [SMILES: *NC1CC2CCC(C1)N2*] |
| 999 | 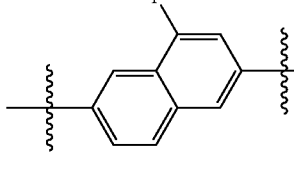 | 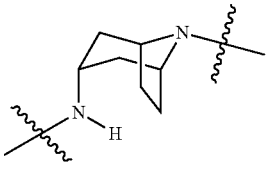 [SMILES: *NC1CC2CCC(C1)N2*] | 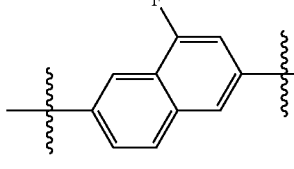 |
| 1000 | 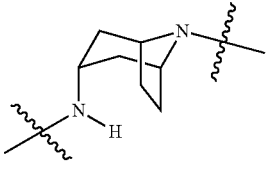 [SMILES: *NC1CC2CCC(C1)N2*] | 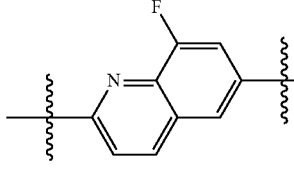 | 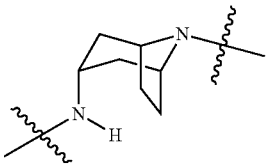 [SMILES: *NC1CC2CCC(C1)N2*] |
| 1001 | 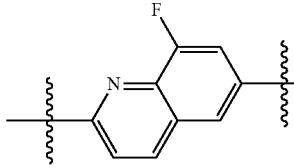 | 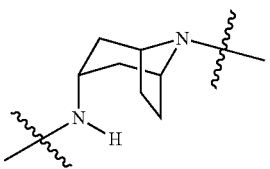 [SMILES: *NC1CC2CCC(C1)N2*] | 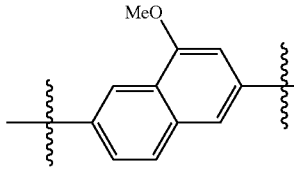 |
| 1002 | 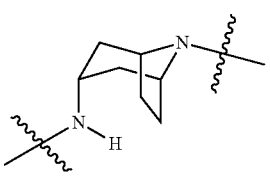 [SMILES: *NC1CC2CCC(C1)N2*] | 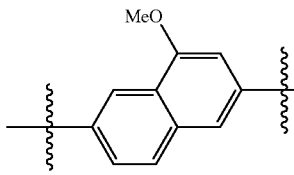 | |
| 1003 | | | |
| 1004 | | | |

TABLE 5-continued
| Compound A | B | ⸺Z—R⁴ |
|---|---|---|
| 1005 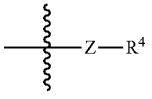 | 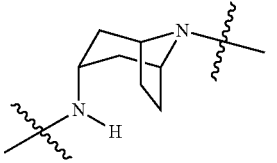 [SMILES: *NC1CC2CCC(C1)N2*] | 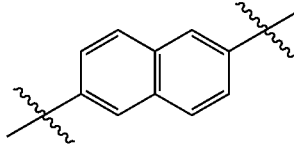 |
| 1006 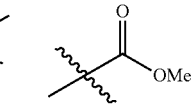 | 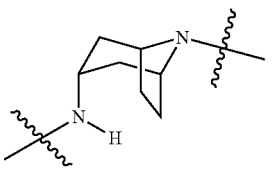 [SMILES: *NC1CC2CCC(C1)N2*] | 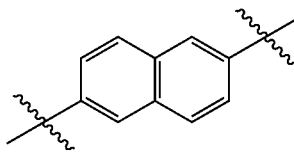 |
| 1007 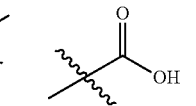 | 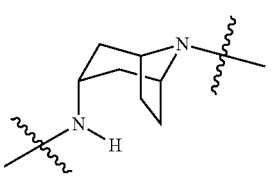 [SMILES: *NC1CC2CCC(C1)N2*] | 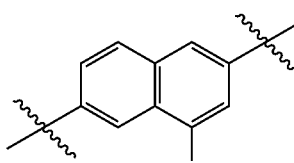 |
| 1008 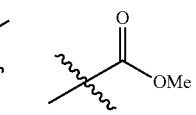 | 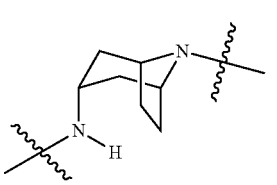 [SMILES: *NC1CC2CCC(C1)N2*] | 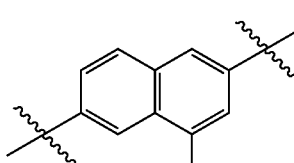 |
| 1009 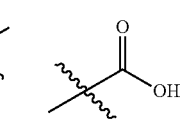 | 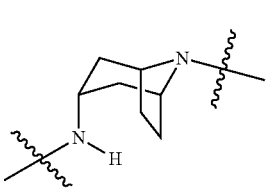 [SMILES: *NC1CC2CCC(C1)N2*] | 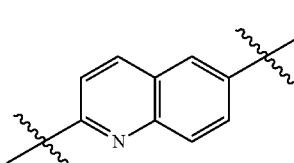 |
| 1010 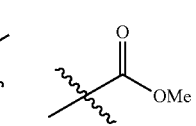 | 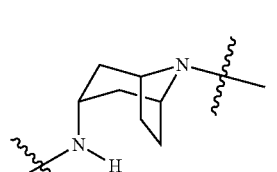 | 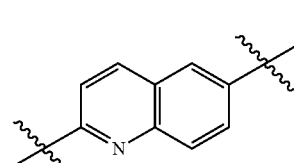 |
| 1011 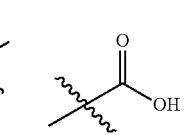 | 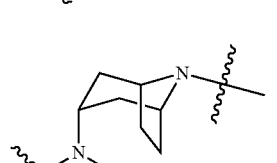 | 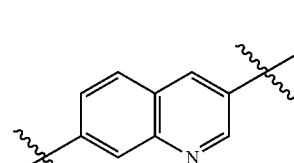 |
| 1012 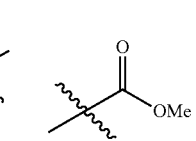 | 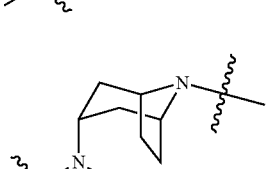 | 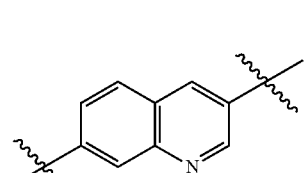 |

TABLE 5-continued
| Compound A | B | —Z—R⁴ |
|---|---|---|
| 1013 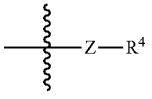 | 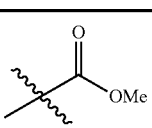 | 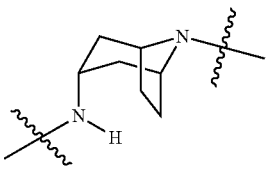 [SMILES: *NC1CC2CCC(C1)N2*] |
| 1014 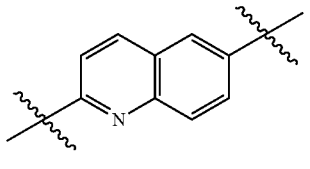 [SMILES: *c1ccc2nc(*)ccc2c1] | 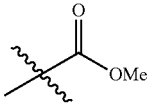 [SMILES: *C(=O)OC] | 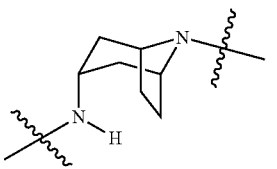 [SMILES: *NC1CC2CCC(C1)N2*] |
| 1015 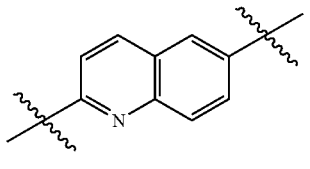 [SMILES: *c1ccc2nc(*)ccc2c1] | 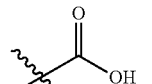 | 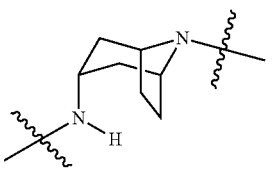 [SMILES: *NC1CC2CCC(C1)N2*] |
| 1016 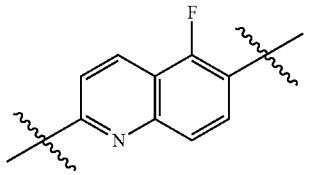 [SMILES: *c1ccc2c(F)c(*)ccc2n1] | 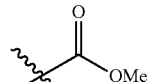 | 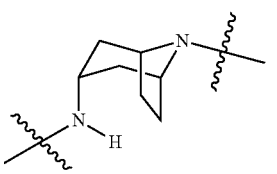 [SMILES: *NC1CC2CCC(C1)N2*] |
| 1017 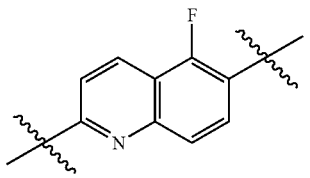 [SMILES: *c1ccc2c(F)c(*)ccc2n1] | 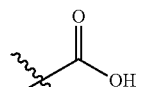 | 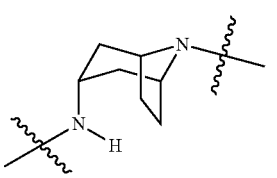 [SMILES: *NC1CC2CCC(C1)N2*] |
| 1018 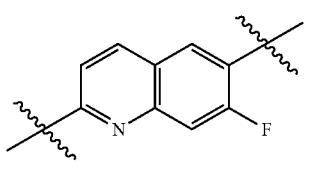 [SMILES: *c1ccc2cc(*)c(F)cc2n1] | 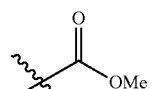 | 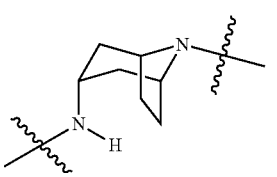 [SMILES: *NC1CC2CCC(C1)N2*] |
| 1019 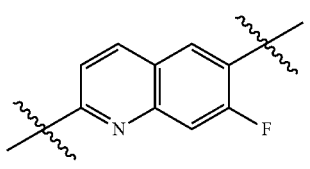 [SMILES: *c1ccc2cc(*)c(F)cc2n1] | 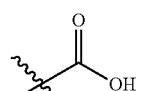 | 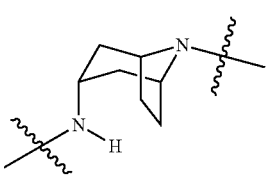 [SMILES: *NC1CC2CCC(C1)N2*] |
| 1020 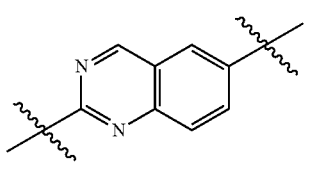 [SMILES: *c1ccc2nc(*)ncc2c1] | 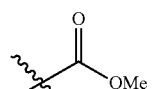 | 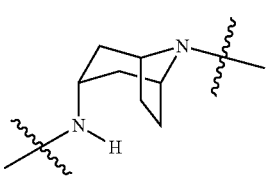 [SMILES: *NC1CC2CCC(C1)N2*] |

TABLE 5-continued

| Compound A | | B | | $-Z-R^4$ |
|---|---|---|---|---|
| 1021 | [bicyclic amine with NH] | [4-Me-quinazoline] | | methyl ester (C(=O)OMe) |
| 1022 | [bicyclic amine with NH] | [4-Me-quinazoline] | | carboxylic acid (C(=O)OH) |
| 1023 | [bicyclic amine with NH] | [quinoline] | | methyl ester (C(=O)OMe) |
| 1024 | [bicyclic amine with NH] | [quinoline] | | carboxylic acid (C(=O)OH) |
| 1025 | [bicyclic amine with NH] | [quinazoline] | | methyl ester (C(=O)OMe) |
| 1026 | [bicyclic amine with NH] | [quinazoline] | | carboxylic acid (C(=O)OH) |
| 1027 | [bicyclic amine with NH] | [benzisothiazole] | | methyl ester (C(=O)OMe) |

TABLE 5-continued

| Compound A | | B | $\text{-Z-R}^4$ |
|---|---|---|---|
| 1028 | [8-azabicyclo[3.2.1]octane with NH] | benzisothiazole | CO2H (gem-dimethyl) |
| 1029 | [8-azabicyclo[3.2.1]octane with NH] | benzothiazole | CO2Me (gem-dimethyl) |
| 1030 | [8-azabicyclo[3.2.1]octane with NH] | benzothiazole | CO2t-Bu |
| 1031 | [8-azabicyclo[3.2.1]octane with NH] | benzothiazole | CH2CO2Me (gem-dimethyl) |
| 1032 | [8-azabicyclo[3.2.1]octane with NH] | benzothiazole | CH2CO2H (gem-dimethyl) |
| 1033 | [8-azabicyclo[3.2.1]octane with NH] | benzothiazole | (CH2)3C(O)OMe |
| 1034 | [8-azabicyclo[3.2.1]octane with NH] | benzoisothiazole | (CH2)3C(O)OH |
| 1035 | [8-azabicyclo[3.2.1]octane with NH] | benzothiazole | CH2OCH2C(O)OMe |

TABLE 5-continued

| Compound A | B | $\text{—Z—R}^4$ |
|---|---|---|
| 1036 | [bicyclic amine]–[benzothiazole]– | –CH(–)–O–CH$_2$–COOH |
| 1037 | [bicyclic amine]–[benzothiazole]– | –CH(–)–NH–CH$_2$–C(O)OMe |
| 1038 | [bicyclic amine]–[benzothiazole]– | –CH(–)–NH–CH$_2$–COOH |
| 1039 | [bicyclic amine]–[benzothiazole]– | –CH(–)–N(Me)–CH$_2$–C(O)OMe |
| 1040 | [bicyclic amine]–[benzothiazole]– | –CH(–)–N(Me)–CH$_2$–COOH |
| 1041 | [bicyclic amine]–[benzothiazole]– | –CH(–)–N(CHO)–CH$_2$–C(O)OMe |
| 1042 | [bicyclic amine]–[benzothiazole]– | –CH(–)–N(CHO)–CH$_2$–COOH |
| 1043 | [bicyclic amine]–[benzothiazole]– | –C(Me)(–)–cyclopropyl–CO$_2$Me |

TABLE 5-continued

| Compound A | B | —Z—R⁴ |
|---|---|---|
| 1044 | | cyclopropyl-CO₂H |
| 1045 | | cyclopropyl-CH₂C(O)OMe |
| 1046 | | cyclopropyl-CH₂C(O)OH |
| 1047 | | -C(F)(F)-CO₂Me |
| 1048 | | -C(F)(F)-C(O)OH |
| 1049 | | -CN |
| 1050 | | 1H-tetrazol-5-yl |
| 1051 | | -C(O)NHCH₂C(O)O-tBu |

(Compound A for entries 1044–1051: 3-aminomethyl-8-azabicyclo[3.2.1]octane fragment with NH; B for entries 1044–1051: benzothiazole linked at 2- and 6-positions.)

TABLE 5-continued
| Compound A | B | —Z—R⁴ |
|---|---|---|
| 1052 | 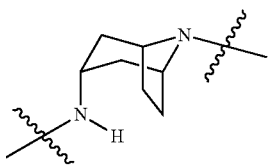 [SMILES: *NC1CC2CCC(C1)N2*] | 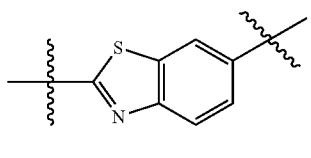 [SMILES: *c1ccc2nc(*)sc2c1] |
| 1053 | | |
| 1054 | | |
| 1055 | | SO₃Me derivative |
| 1056 | | SO₃H derivative |
| 1057 | | cyclopropyl-CH₂-SO₃H derivative |
| 1058 | | C(CH₃)₂-CH₂-SO₃H derivative |
| 1059 | | -NH-CH₂-O-CH₂-OSO₃H derivative |

TABLE 5-continued
| Compound A | B | ⸺Z—R⁴ |
|---|---|---|
| 1060 | | |
| 1061 | | |
| 1062 | | |
| 1063 | | |
| 1064 | | |
| 1065 | | |
| 1066 | | |
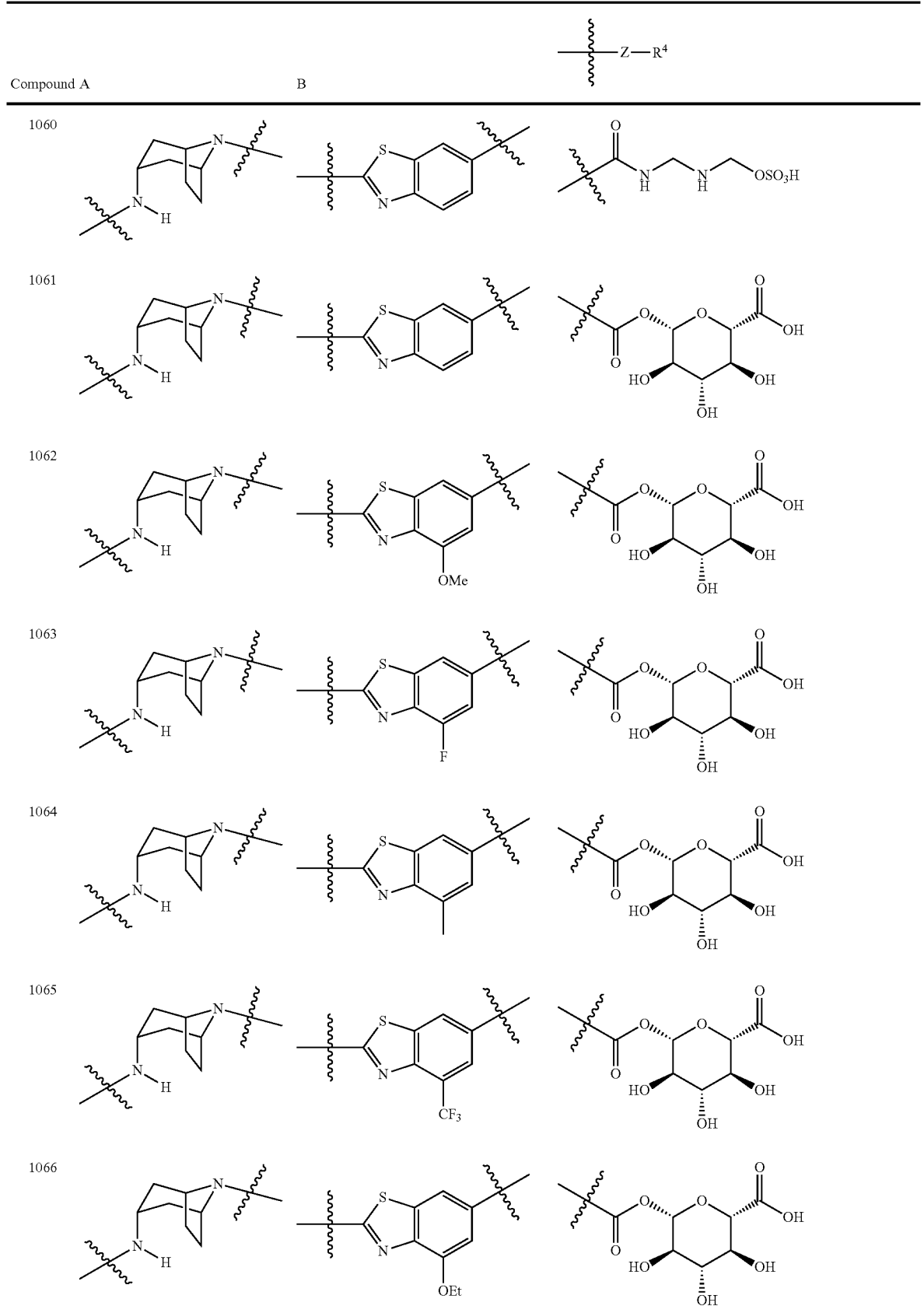

TABLE 5-continued
| Compound A | B | ⸝⸺Z—R⁴ |
|---|---|---|
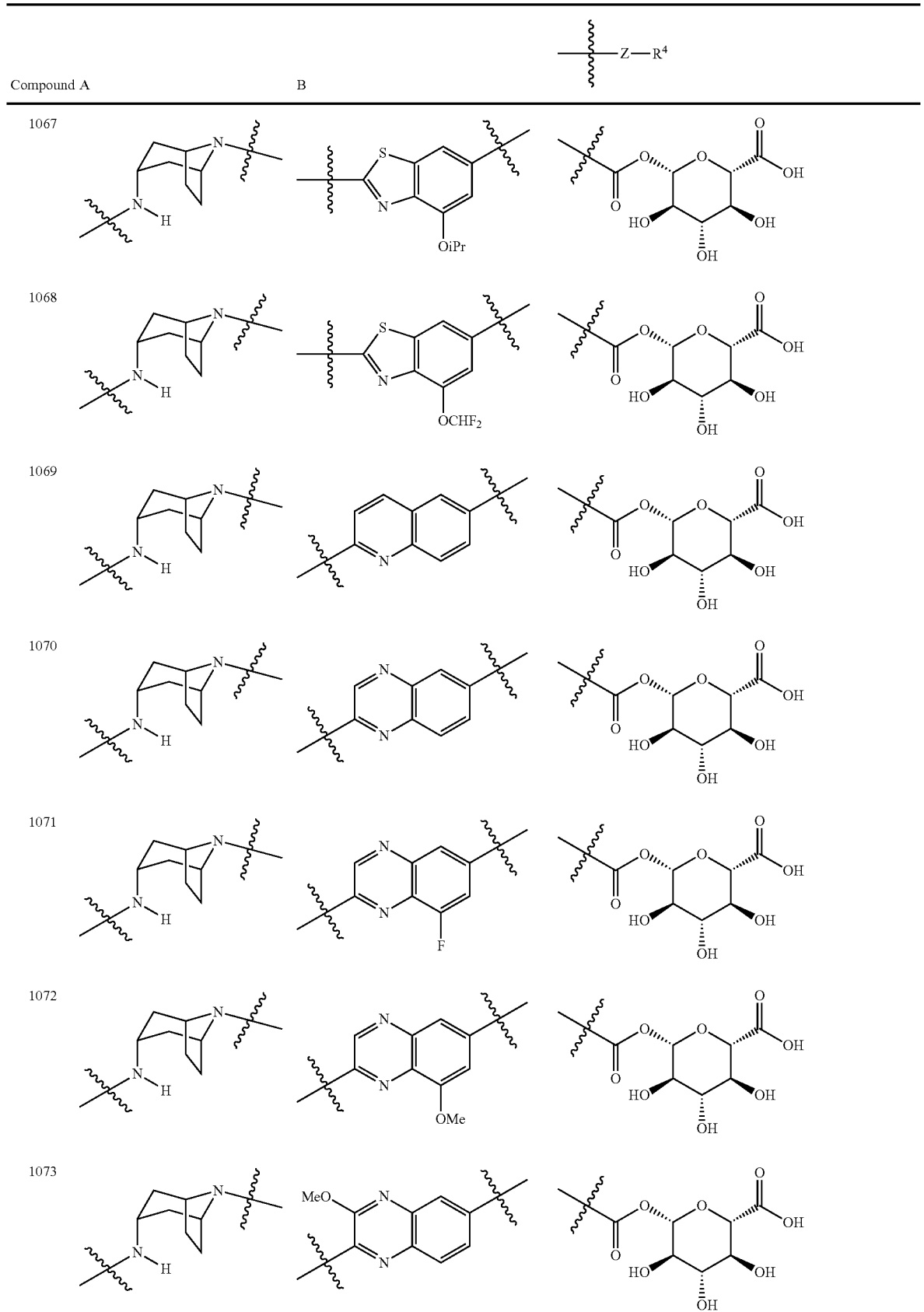

TABLE 5-continued
| Compound A | B | —Z—R⁴ |
|---|---|---|
| 1074 | 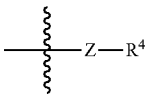 | 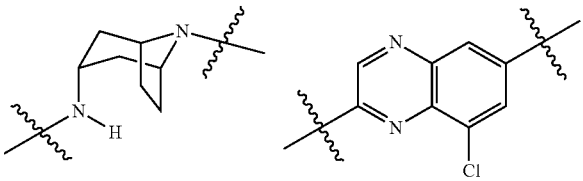 |
| 1075 | 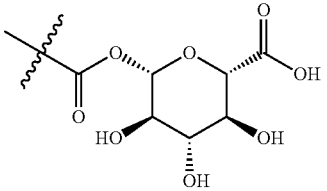 [SMILES: *C(=O)O[C@@H]1O[C@H](C(=O)O)[C@@H](O)[C@H](O)[C@H]1O] | 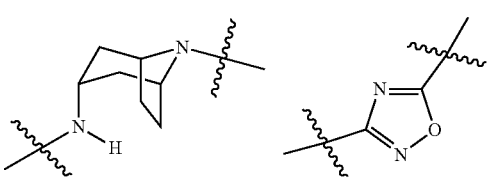 |
| 1076 | 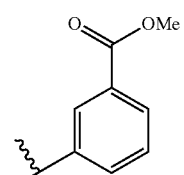 | 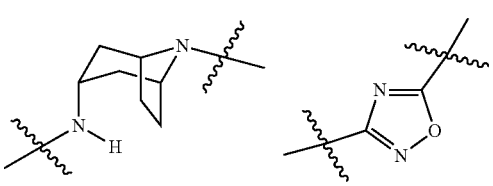 |
| 1077 | 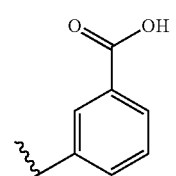 | 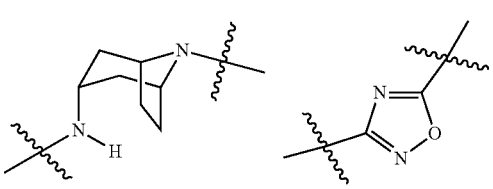 |
| 1078 | 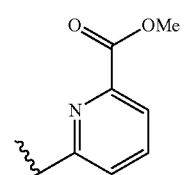 | 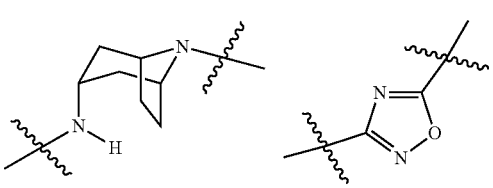 |
| 1079 | 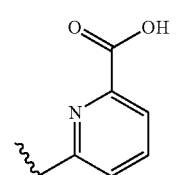 | 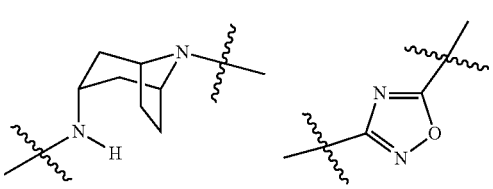 |
| 1080 | 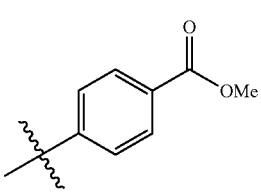 [SMILES: *c1ccc(C(=O)OC)cc1] | 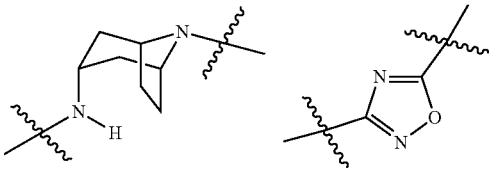 |

TABLE 5-continued

| Compound | A | B | —Z—R⁴ |
|---|---|---|---|
| 1081 | 8-azabicyclic amine | 1,2,4-oxadiazole | methyl 4-fluorobenzoate |
| 1082 | 8-azabicyclic amine | 1,2,4-oxadiazole | 4-fluorobenzoic acid |
| 1083 | 8-azabicyclic amine | 1,2,4-oxadiazole | methyl cyclohexanecarboxylate |
| 1084 | 8-azabicyclic amine | 1,2,4-oxadiazole | cyclohexanecarboxylic acid |
| 1085 | 8-azabicyclic amine | pyrazine | methyl benzoate |
| 1086 | 8-azabicyclic amine | pyrazine | methyl benzoate |
| 1087 | 8-azabicyclic amine | pyrazine | methyl pyridine-carboxylate |

TABLE 5-continued
| Compound A | | B | Z—R⁴ |
|---|---|---|---|
| 1088 | 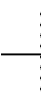 | 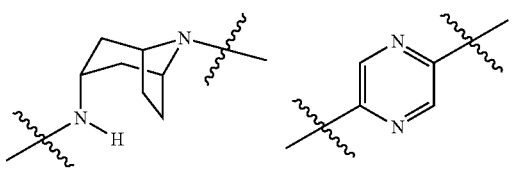 | 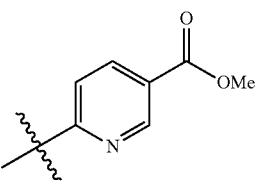 [SMILES: *c1ccc(C(=O)OC)cn1] |
| 1089 | 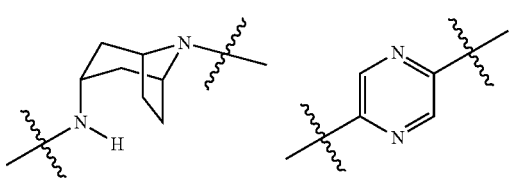 | 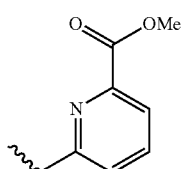 | 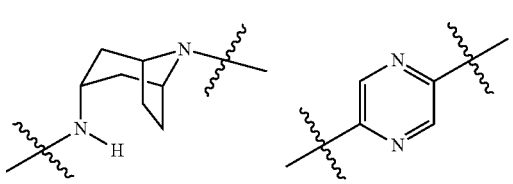 |
| 1090 | 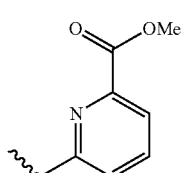 | 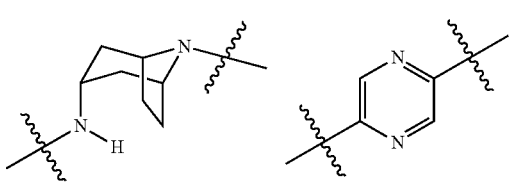 | 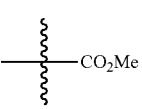 |
| 1091 | 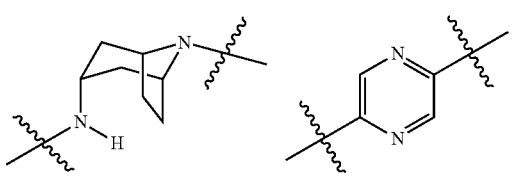 | 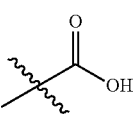 | —CO₂Me |
| 1092 | 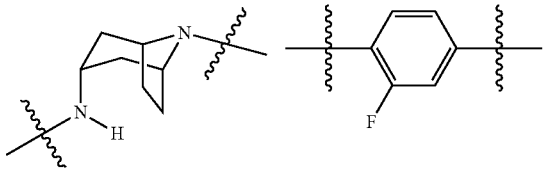 | 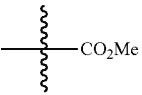 [SMILES: *C(=O)OC] | —COOH |
| 1093 | 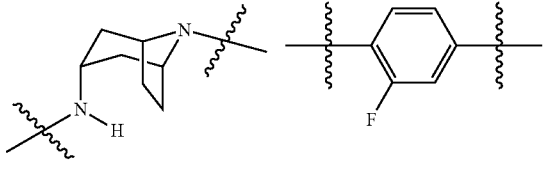 | 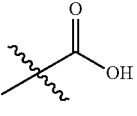 [SMILES: *C(=O)O] (F-substituted phenyl) | —CO₂Me |
| 1094 | 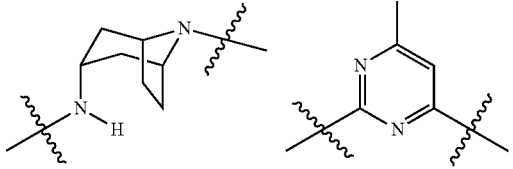 | 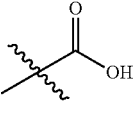 (F-substituted phenyl) | —COOH |
| 1095 | | | —COOH |

TABLE 5-continued
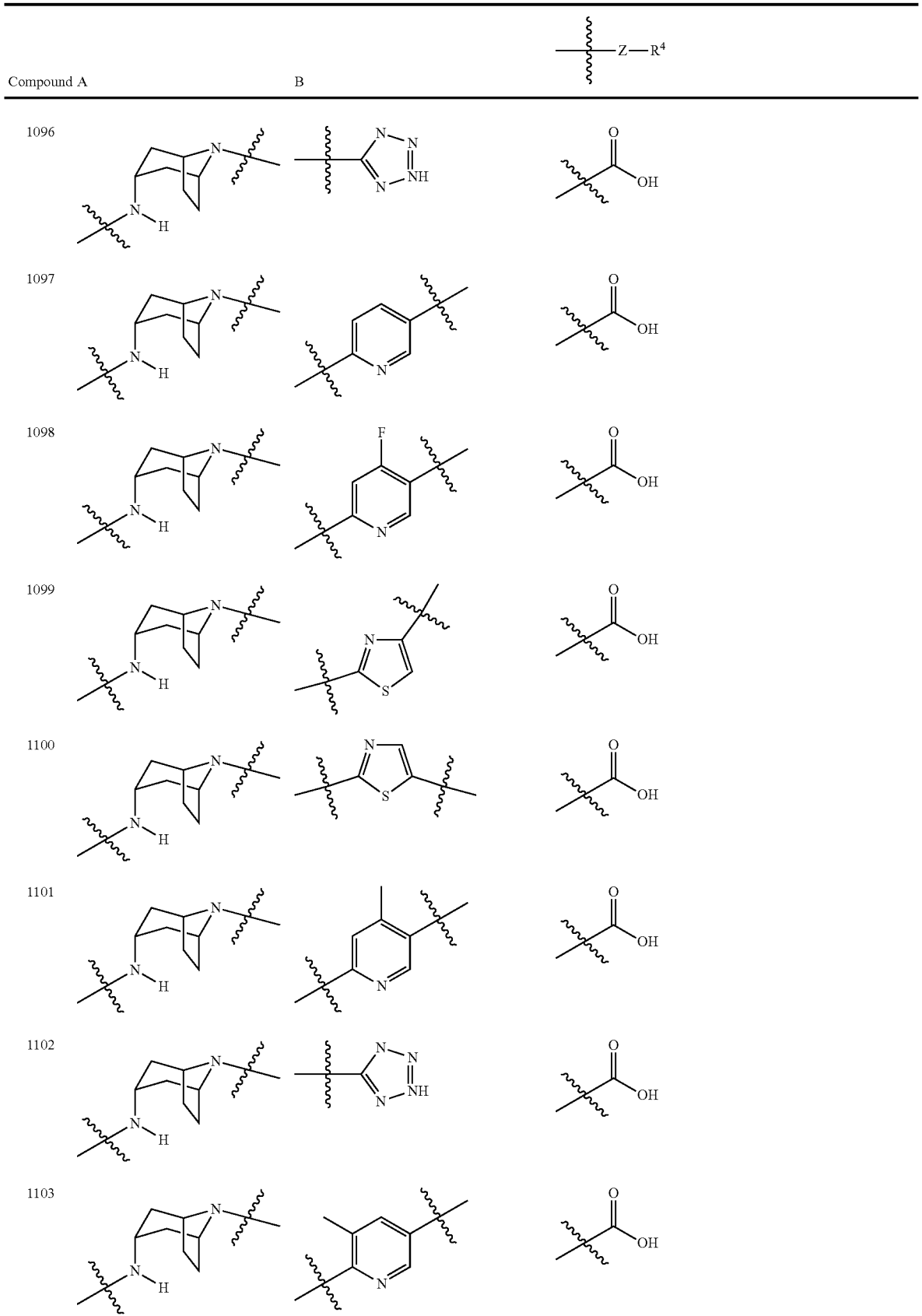

TABLE 5-continued
| Compound A | | B | | —Z—R⁴ |
|---|---|---|---|---|
| 1104 | 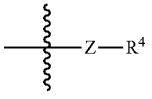 | 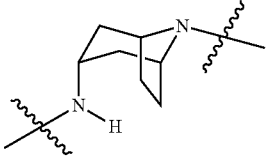 [SMILES: *NC1CC2CCC(C1)N2*] | (F, pyridine) | 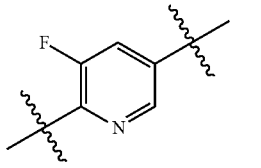 [SMILES: *c1cnc(*)c(F)c1] (COOH) |
| 1105 | 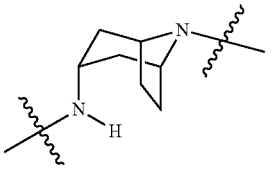 [SMILES: *NC1CC2CCC(C1)N2*] | 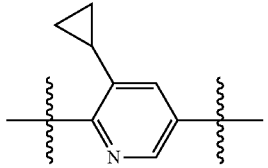 [SMILES: *c1cnc(*)c(C2CC2)c1] | (cyclopropyl, pyridine) | 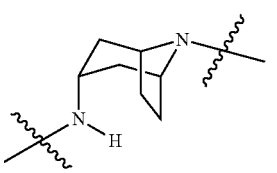 [SMILES: *NC1CC2CCC(C1)N2*] (COOH) |
| 1106 | 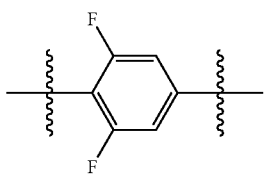 [SMILES: *c1cc(F)c(*)c(F)c1] | 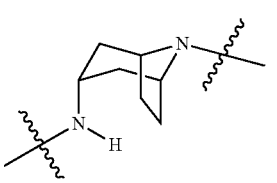 | (2,5-difluorophenyl) | 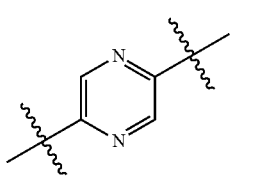 [SMILES: *c1cnc(*)cn1] (COOH) |
| 1107 | 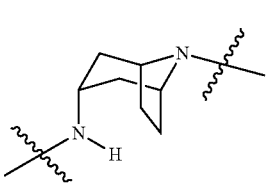 [SMILES: *NC1CC2CCC(C1)N2*] | 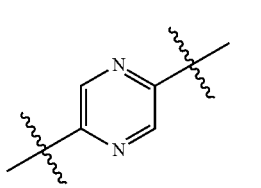 [SMILES: *c1cnc(*)cn1] | (pyrazine) | —CN |
| 1108 | 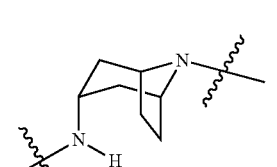 | 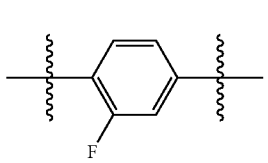 [SMILES: *c1ccc(*)c(F)c1] | (pyrazine) | 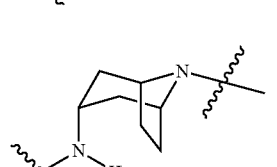 (tetrazole) |
| 1109 | 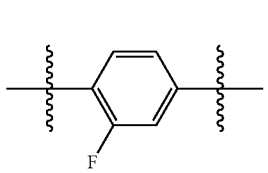 | (F-phenyl) | | —CN |
| 1110 | 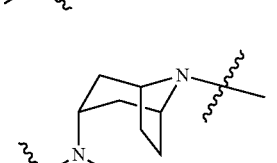 | (F-pyridine) | | (tetrazole) |
| 1111 | 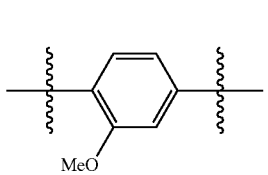 [SMILES: *c1ccc(*)c(OC)c1] | (MeO-phenyl) | | —CN |

TABLE 5-continued
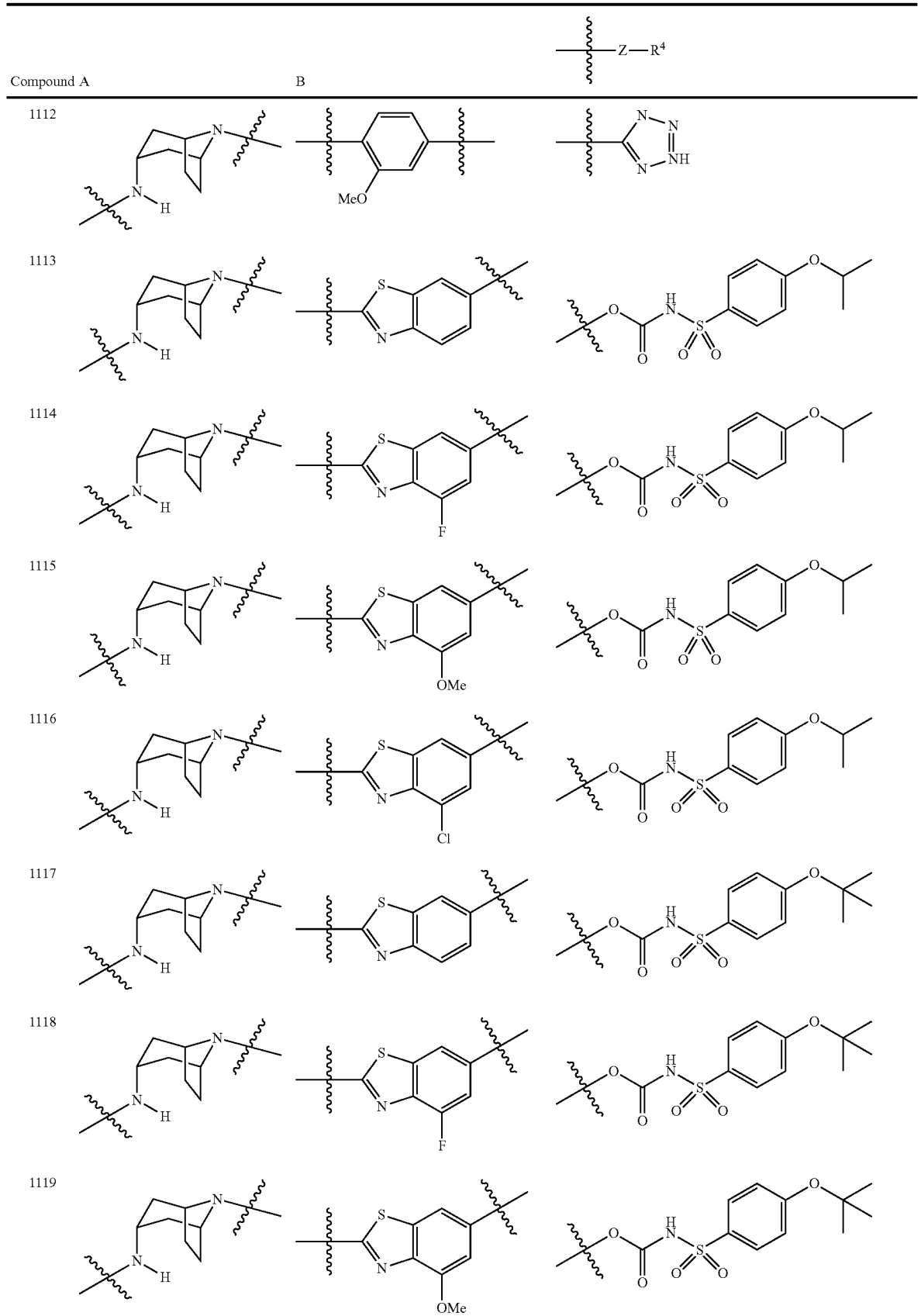

TABLE 5-continued
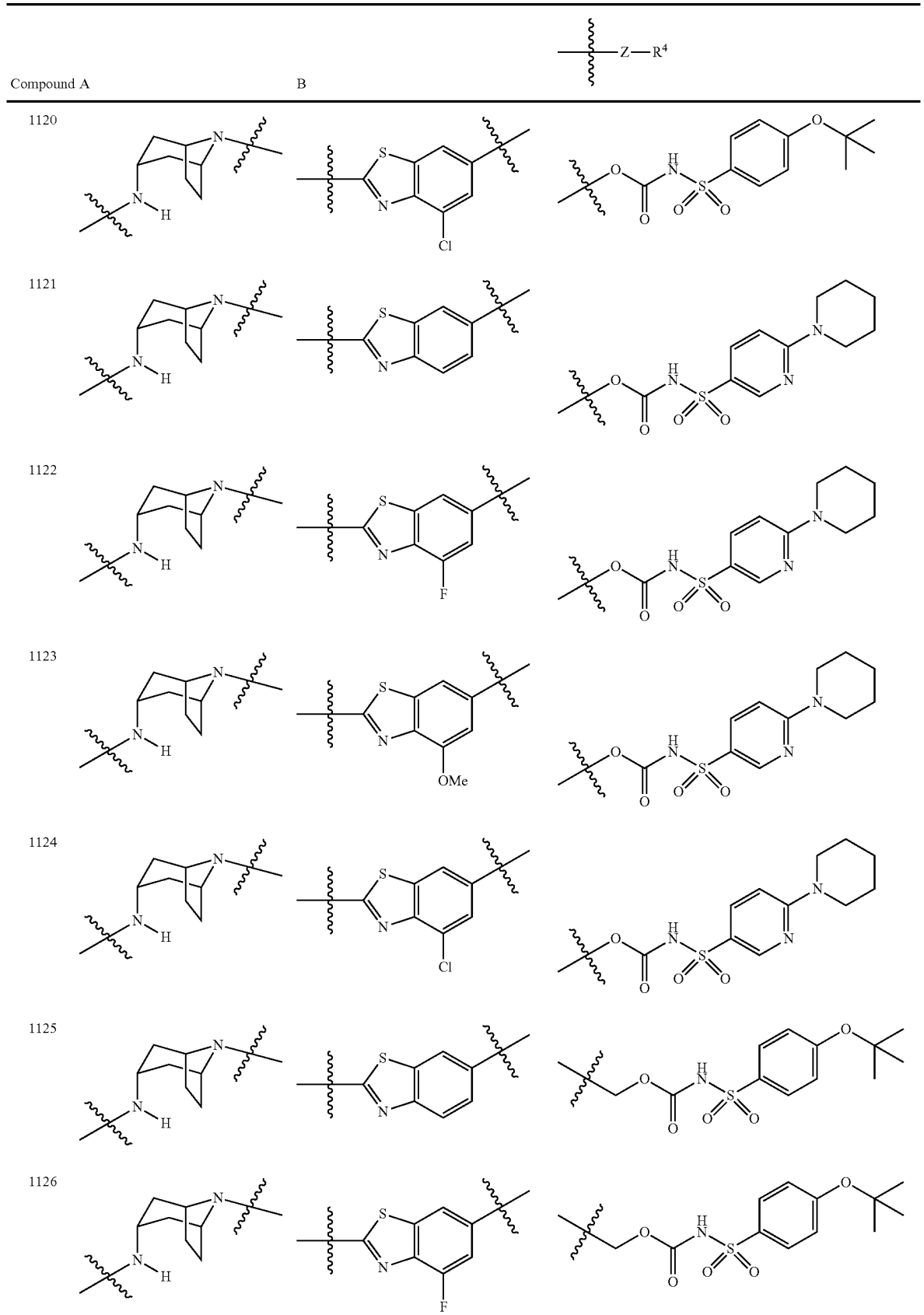

TABLE 5-continued

| Compound A | B | -Z-R⁴ |
|---|---|---|
| 1127 | benzothiazole with OMe | carbamate-SO₂-C₆H₄-O-tBu |
| 1128 | benzothiazole with Cl | carbamate-SO₂-C₆H₄-O-tBu |
| 1129 | benzothiazole | urea-SO₂-C₆H₄-tBu |
| 1130 | benzothiazole with F | urea-SO₂-C₆H₄-tBu |
| 1131 | benzothiazole with OMe | urea-SO₂-C₆H₄-tBu |
| 1132 | benzothiazole with Cl | urea-SO₂-C₆H₄-tBu |
| 1133 | benzothiazole | CH₂-urea-SO₂-C₆H₄-tBu |

TABLE 5-continued

| Compound | A | B | —ξ—Z—R⁴ |
|---|---|---|---|
| 1134 | | (benzothiazole, F) | (urea-sulfonyl-tBu-phenyl) |
| 1135 | | (benzothiazole, OMe) | (urea-sulfonyl-tBu-phenyl) |
| 1136 | | (benzothiazole, Cl) | (urea-sulfonyl-tBu-phenyl) |

In another embodiment, the compound of Formula (I) is represented by Formula (XIII) or a pharmaceutically acceptable salt thereof:

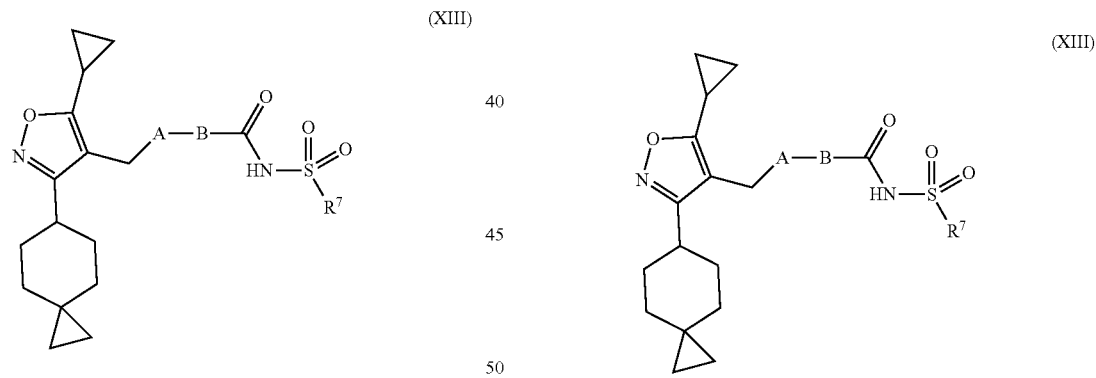

(XIII)

wherein A, B, and R⁷ are as previously defined.

Representative compounds of the invention include, but are not limited to, compounds according to Formula (XIII), and pharmaceutically acceptble salts thereof, wherein, A, B, and R⁷ are delineated for each compound in Table 6

TABLE 6

| Compound | A | B | R⁷ |
|---|---|---|---|
| 1201 | | (benzothiazole) | (cyclopropyl-methyl) |

TABLE 6-continued

| Compound | A | B | R[7] |
|---|---|---|---|
| 1202 | bicyclic amine with NH | benzothiazole | cyclopropyl-CH₃ |
| 1203 | bicyclic amine with NH | benzothiazole | cyclopropyl-CHO |
| 1204 | bicyclic amine with NH | benzothiazole | cyclopropyl-CD₃ |
| 1205 | bicyclic amine with NH | benzothiazole | cyclopropyl-CH₂OH |
| 1206 | bicyclic amine with NH | benzothiazole | cyclopropyl-CHF₂ |
| 1207 | bicyclic amine with NH | benzothiazole | cyclopropyl-CF₃ |
| 1208 | bicyclic amine with NH | benzothiazole | cyclopropyl-F |
| 1209 | bicyclic amine with NH | benzothiazole | cyclopropyl-Cl |
| 1210 | bicyclic amine with NH | benzothiazole | cyclopropyl-CH₂F |

TABLE 6-continued

| Compound | A | B | R⁷ |
|---|---|---|---|
| 1211 | bicyclic amine-NH | benzothiazole | cyclopropyl-CH₂-OMe |
| 1212 | bicyclic amine-NH | benzothiazole | cyclopropyl-CN |
| 1213 | bicyclic amine-NH | benzothiazole | cyclopropyl-CH₂-OBn |
| 1214 | bicyclic amine-NH | benzothiazole | cyclopropyl-CH₂-OH |
| 1215 | bicyclic amine-NH | benzothiazole | cyclopropyl-CH₂-N⁺Me₃ |
| 1216 | bicyclic amine-NH | benzothiazole | cyclopropyl-CH₂-O-CH₂CH₂-OH |
| 1217 | bicyclic amine-NH | benzothiazole | cyclopropyl-CH₂-O-CH₂CH₂-N⁺Me₃ |
| 1218 | bicyclic amine-NH | benzothiazole | cyclopropyl-C(O)-OMe |

TABLE 6-continued

| Compound | A | B | R⁷ |
|---|---|---|---|
| 1219 | bicyclic amine (NH) | benzothiazole | 1-(carboxy)cyclopropyl (COOH) |
| 1220 | bicyclic amine (NH) | benzothiazole | 1-(carboxamide)cyclopropyl (C(O)NH₂) |
| 1221 | bicyclic amine (NH) | benzothiazole | 1-cyclopropyl-C(O)NH-S(O)₂-N(Me)₂ |
| 1222 | bicyclic amine (NH) | benzothiazole | 1-cyclopropyl-C(O)NH-S(O)₂-pyrrolidinyl |
| 1223 | bicyclic amine (NH) | benzothiazole | 2,2-difluoro-1-methylcyclopropyl |
| 1224 | bicyclic amine (NH) | benzothiazole | 2,2-difluorocyclopropyl |
| 1225 | bicyclic amine (NH) | benzothiazole | N(Me)₂ |
| 1226 | bicyclic amine (NH) | benzothiazole | azetidinyl |
| 1227 | bicyclic amine (NH) | benzothiazole | pyrrolidinyl |

TABLE 6-continued

| Compound | A | B | R⁷ |
|---|---|---|---|
| 1228 | [bicyclic amine with NH] | [benzothiazole] | [N-piperidinyl] |
| 1229 | [bicyclic amine with NH] | [benzothiazole] | [NH-NH] |
| 1230 | [bicyclic amine with NH] | [benzothiazole] | [NH-NH] |
| 1231 | [bicyclic amine with NH] | [benzothiazole] | [cyclopentyl] |
| 1232 | [bicyclic amine with NH] | [benzothiazole] | [cyclohexyl] |
| 1233 | [bicyclic amine with NH] | [benzothiazole] | [1-methylcyclopentyl] |
| 1234 | [bicyclic amine with NH] | [benzothiazole] | [morpholinyl] |
| 1235 | [bicyclic amine with NH] | [benzothiazole] | Me |

TABLE 6-continued

| Compound | A | B | R⁷ |
|---|---|---|---|
| 1236 | bicyclic amine with NH | benzothiazole | —CF₃ |
| 1237 | bicyclic amine with NH | benzothiazole | isopropyl |
| 1238 | bicyclic amine with NH | benzothiazole | —CH₂-Me (ethyl) |
| 1239 | bicyclic amine with NH | benzothiazole | neopentyl (CH₂C(Me)₃) |
| 1240 | bicyclic amine with NH | benzothiazole | tert-butyl |
| 1241 | bicyclic amine with NH | benzothiazole | —CH₂-cyclopropyl |
| 1242 | bicyclic amine with NH | benzothiazole | —C(Me)₂CH₂OBn |
| 1243 | bicyclic amine with NH | benzothiazole | —CH₂-phenyl |
| 1244 | bicyclic amine with NH | benzothiazole | —CH₂—CH=CH₂ (allyl) |

TABLE 6-continued

| Compound | A | B | R⁷ |
|---|---|---|---|
| 1245 | (azabicyclic amine with N) | benzothiazole | Bu |
| 1246 | (azabicyclic amine with N) | benzothiazole | propyl |
| 1247 | (bicyclic amine) | benzothiazole | NH₂ |
| 1248 | (bicyclic amine) | benzothiazole | NHMe |
| 1249 | (bicyclic amine) | benzothiazole | NH-iPr |
| 1250 | (bicyclic amine) | benzothiazole | NHEt |
| 1251 | (bicyclic amine) | benzothiazole | NH-cyclopentyl |
| 1252 | (bicyclic amine) | benzothiazole | NH-cyclopropyl |

TABLE 6-continued

| Compound | A | B | R⁷ |
|---|---|---|---|
| 1253 | bicyclic-NH- | benzothiazole | -NH-phenyl |
| 1254 | bicyclic-NH- | benzothiazole | -NH-cyclohexyl |
| 1255 | bicyclic-NH- | benzothiazole | -NH-(4-F-phenyl) |
| 1256 | bicyclic-NH- | benzothiazole | -NH-(pyridin-4-yl) |
| 1257 | bicyclic-NH- | benzothiazole | -phenyl |
| 1258 | bicyclic-NH- | benzothiazole | -NH-(2-OCF₃-phenyl) |
| 1259 | bicyclic-NH- | benzothiazole | -(4-F-phenyl) |
| 1260 | bicyclic-NH- | benzothiazole | -(4-methylphenyl) |

TABLE 6-continued

| Compound | A | B | R⁷ |
|---|---|---|---|
| 1261 | [bicyclic amine] | [benzothiazole] | 2-pyridyl |
| 1262 | [bicyclic amine] | [benzothiazole] | 4-tert-butylphenyl |
| 1263 | [bicyclic amine] | [benzothiazole] | 4-pyridyl |
| 1264 | [bicyclic amine] | [benzothiazole] | 3-pyridyl |
| 1265 | [bicyclic amine] | [benzothiazole] | 5-thiazolyl |
| 1266 | [bicyclic amine] | [benzothiazole] | 5-fluoro-2-pyridyl |
| 1267 | [bicyclic amine] | [benzothiazole] | 2-imidazolyl |
| 1268 | [bicyclic amine] | [benzothiazole] | 2-thiazolyl |

TABLE 6-continued

| Compound | A | B | R⁷ |
|---|---|---|---|
| 1269 | bicyclic amine | benzothiazole | 2-(trifluoromethoxy)phenyl |
| 1270 | bicyclic amine | benzothiazole | 1-methyl-1H-imidazol-2-yl |
| 1271 | bicyclic amine | benzothiazole | naphthalen-2-yl |
| 1272 | bicyclic amine | benzothiazole | 2-methoxyphenyl |
| 1273 | bicyclic amine | benzothiazole | biphenyl-4-yl |
| 1274 | bicyclic amine | benzothiazole | [2,4'-bipyridin]-5-yl |
| 1275 | bicyclic amine | benzothiazole | 4-(pyridin-4-yl)phenyl |
| 1276 | bicyclic amine | benzothiazole | 2,3-dihydrobenzo[b][1,4]dioxin-6-yl |

TABLE 6-continued

| Compound | A | B | R⁷ |
|---|---|---|---|
| 1277 | | | |
| 1278 | | | |
| 1279 | | | |
| 1280 | | | |
| 1281 | | | |
| 1282 | | | |
| 1283 | | | |
| 1284 | | | |
| 1285 | | | |
| 1286 | | | |

TABLE 6-continued

| Compound | A | B | R⁷ |
|---|---|---|---|
| 1287 | N-methylpiperazine linker | 2,6-benzothiazolediyl | N(CH₃)₂ |
| 1288 | N-methylpiperazine linker | 2,6-benzothiazolediyl | 4-tert-butylphenyl |
| 1289 | 4-aminopiperidine linker | 2,6-benzothiazolediyl | N(CH₃)₂ |
| 1290 | 4-aminopiperidine linker | 2,6-benzothiazolediyl | 4-tert-butylphenyl |
| 1291 | 4-aminopiperidine linker (reversed) | 2,6-benzothiazolediyl | cyclopropyl |
| 1292 | N-methyl-bridged bicyclic amine | 2,6-benzothiazolediyl | cyclopropyl |
| 1293 | N-methyl-bridged bicyclic amine | 2,6-benzothiazolediyl | 1-methylcyclopropyl |
| 1294 | N-formyl-bridged bicyclic amine | 2,6-benzothiazolediyl | 1-methylcyclopropyl |
| 1295 | NH-bridged bicyclic amine | 4-fluoro-2,6-benzothiazolediyl | 1-methylcyclopropyl |

TABLE 6-continued

| Compound | A | B | R⁷ |
|---|---|---|---|
| 1296 | [bicyclic amine with NH] | [fluorobenzothiazole] | [cyclopropyl-CD₃] |
| 1297 | [bicyclic amine with NH] | [fluorobenzothiazole] | [N(CH₃)₂] |
| 1298 | [bicyclic amine with NH] | [fluorobenzothiazole] | [cyclopropyl] |
| 1299 | [bicyclic amine with NH] | [fluorobenzothiazole] | [cyclopropyl-CHO] |
| 1300 | [bicyclic amine with NH] | [fluorobenzothiazole] | [piperidinyl] |
| 1301 | [bicyclic amine with NH] | [benzoxazole] | [N(CH₃)₂] |
| 1302 | [bicyclic amine with NH] | [benzoxazole] | [methylcyclopropyl] |
| 1303 | [bicyclic amine with NH] | [methoxybenzothiazole] | [N(CH₃)₂] |

TABLE 6-continued

| Compound | A | B | R⁷ |
| --- | --- | --- | --- |
| 1304 | [bicyclic amine with NH] | [benzothiazole with OMe] | [cyclopropyl] |
| 1305 | [piperidine with NH] | [benzothiazole] | [cyclopropyl] |
| 1306 | [piperidine with NH] | [benzothiazole] | [N-piperidinyl] |
| 1307 | [bicyclic amine with NH] | [benzothiazole with OMe] | [cyclopropyl with $F_2HC$] |
| 1308 | [bicyclic amine with NH] | [benzothiazole with OMe] | [N-pyrrolidinyl] |
| 1309 | [bicyclic amine with NH] | [benzothiazole with OMe] | [N-azetidinyl] |
| 1310 | [bicyclic amine with NH] | [benzothiazole with OMe] | [N-piperidinyl] |
| 1311 | [bicyclic amine with NH] | [benzothiazole with $CHF_2$] | [cyclopropyl] |
| 1312 | [bicyclic amine with NH] | [benzothiazole with $CHF_2$] | [cyclopropyl with $F_2HC$] |

TABLE 6-continued

| Compound | A | B | R⁷ |
|---|---|---|---|
| 1313 | [bicyclic amine with NH] | benzothiazole with CHF₂ | N(CH₃)₂ |
| 1314 | [bicyclic amine with NH] | benzothiazole with CHF₂ | azetidinyl |
| 1315 | [bicyclic amine with NH] | benzothiazole with CHF₂ | pyrrolidinyl |
| 1316 | [bicyclic amine with NH] | benzothiazole with CHF₂ | piperidinyl |
| 1317 | [bicyclic amine with NH] | benzothiazole with OCF₃ | cyclopropyl |
| 1318 | [bicyclic amine with NH] | benzothiazole with OCF₃ | cyclopropyl-CHF₂ |
| 1319 | [bicyclic amine with NH] | benzothiazole with OCF₃ | N(CH₃)₂ |
| 1320 | [bicyclic amine with NH] | benzothiazole with OCF₃ | azetidinyl |

TABLE 6-continued

| Compound | A | B | R⁷ |
|---|---|---|---|
| 1321 | [bicyclic amine with NH] | [benzothiazole with OCF₃] | [pyrrolidine] |
| 1322 | [bicyclic amine with NH] | [benzothiazole with OCF₃] | [piperidine] |
| 1323 | [bicyclic amine with NH] | [benzothiazole with OCHF₂] | [1-methylcyclopropyl] |
| 1324 | [bicyclic amine with NH] | [benzothiazole with OCHF₂] | [1-(difluoromethyl)cyclopropyl] |
| 1325 | [bicyclic amine with NH] | [benzothiazole with OCHF₂] | [N(CH₃)₂] |
| 1326 | [bicyclic amine with NH] | [benzothiazole with OCHF₂] | [azetidine] |
| 1327 | [bicyclic amine with NH] | [benzothiazole with OCHF₂] | [pyrrolidine] |
| 1328 | [bicyclic amine with NH] | [benzothiazole with OCHF₂] | [piperidine] |

TABLE 6-continued

| Compound | A | B | R⁷ |
|---|---|---|---|
| 1329 | [bicyclic amine with NH] | [benzothiazole with CF₃] | [1-methylcyclopropyl] |
| 1330 | [bicyclic amine with NH] | [benzothiazole with CF₃] | [1-(difluoromethyl)cyclopropyl, F₂HC] |
| 1331 | [bicyclic amine with NH] | [benzothiazole with CF₃] | [N(CH₃)₂] |
| 1332 | [bicyclic amine with NH] | [benzothiazole with CF₃] | [azetidinyl] |
| 1333 | [bicyclic amine with NH] | [benzothiazole with CF₃] | [pyrrolidinyl] |
| 1334 | [bicyclic amine with NH] | [benzothiazole with CF₃] | [piperidinyl] |
| 1335 | [bicyclic amine with NH] | [chloroquinoxaline, Cl] | [1-methylcyclopropyl] |
| 1336 | [bicyclic amine with NH] | [chloroquinoxaline, Cl] | [1-(difluoromethyl)cyclopropyl, F₂HC] |

TABLE 6-continued

| Compound | A | B | R⁷ |
|---|---|---|---|
| 1337 | bicyclic amine with NH | 3-Cl quinoxaline | NMe₂ |
| 1338 | bicyclic amine with NH | 3-Cl quinoxaline | azetidinyl |
| 1339 | bicyclic amine with NH | 3-Cl quinoxaline | pyrrolidinyl |
| 1340 | bicyclic amine with NH | 3-Cl quinoxaline | piperidinyl |
| 1341 | bicyclic amine with NH | 3-MeO quinoxaline | 1-methylcyclopropyl |
| 1342 | bicyclic amine with NH | 3-MeO quinoxaline | 1-(CHF₂)cyclopropyl |
| 1343 | bicyclic amine with NH | 3-MeO quinoxaline | NMe₂ |
| 1344 | bicyclic amine with NH | 3-MeO quinoxaline | azetidinyl |

TABLE 6-continued

| Compound | A | B | R⁷ |
|---|---|---|---|
| 1345 | [3,8-diazabicyclo, NH] | [3-MeO-quinoxaline] | [pyrrolidinyl] |
| 1346 | [3,8-diazabicyclo, NH] | [3-MeO-quinoxaline] | [piperidinyl] |
| 1347 | [3,8-diazabicyclo, NH] | [quinoxaline] | [1-methylcyclopropyl] |
| 1348 | [3,8-diazabicyclo, NH] | [quinoxaline] | [1-(difluoromethyl)cyclopropyl] |
| 1349 | [3,8-diazabicyclo, NH] | [quinoxaline] | [N(CH₃)₂] |
| 1350 | [3,8-diazabicyclo, NH] | [quinoxaline] | [azetidinyl] |
| 1351 | [3,8-diazabicyclo, NH] | [quinoxaline] | [pyrrolidinyl] |
| 1352 | [3,8-diazabicyclo, NH] | [quinoxaline] | [piperidinyl] |
| 1353 | [3,8-diazabicyclo, NH] | [F-quinoxaline] | [1-methylcyclopropyl] |

TABLE 6-continued

| Compound | A | B | R⁷ |
|---|---|---|---|
| 1354 | bicyclic amine with NH | quinoxaline, 8-F | 1-(difluoromethyl)cyclopropyl |
| 1355 | bicyclic amine with NH | quinoxaline, 8-F | N(CH₃)₂ |
| 1356 | bicyclic amine with NH | quinoxaline, 8-F | azetidin-1-yl |
| 1357 | bicyclic amine with NH | quinoxaline, 8-F | pyrrolidin-1-yl |
| 1358 | bicyclic amine with NH | quinoxaline, 8-F | piperidin-1-yl |
| 1359 | bicyclic amine with NH | quinoxaline, 8-OMe | 1-methylcyclopropyl |
| 1360 | bicyclic amine with NH | quinoxaline, 8-OMe | 1-(difluoromethyl)cyclopropyl |
| 1361 | bicyclic amine with NH | quinoxaline, 8-OMe | N(CH₃)₂ |

TABLE 6-continued

| Compound | A | B | R⁷ |
|---|---|---|---|
| 1362 | bicyclic amine-NH | quinoxaline with OMe | azetidine |
| 1363 | bicyclic amine-NH | quinoxaline with OMe | pyrrolidine |
| 1364 | bicyclic amine-NH | quinoxaline with OMe | piperidine |
| 1365 | bicyclic amine-NH | quinazoline | 1-methylcyclopropyl |
| 1366 | bicyclic amine-NH | quinazoline | 1-(difluoromethyl)cyclopropyl |
| 1367 | bicyclic amine-NH | quinazoline | N(CH₃)₂ |
| 1368 | bicyclic amine-NH | quinazoline | azetidine |
| 1369 | bicyclic amine-NH | quinazoline | pyrrolidine |

TABLE 6-continued

| Compound | A | B | R⁷ |
|---|---|---|---|
| 1370 | (bicyclic amine with NH) | quinazoline linker | piperidine |
| 1371 | (bicyclic amine with NH) | pyrazolo[1,5-a]pyrimidine | 1-methylcyclopropyl |
| 1372 | (bicyclic amine with NH) | pyrazolo[1,5-a]pyrimidine | 1-(difluoromethyl)cyclopropyl |
| 1373 | (bicyclic amine with NH) | pyrazolo[1,5-a]pyrimidine | N,N-dimethylamino |
| 1374 | (bicyclic amine with NH) | pyrazolo[1,5-a]pyrimidine | azetidine |
| 1375 | (bicyclic amine with NH) | pyrazolo[1,5-a]pyrimidine | pyrrolidine |
| 1376 | (bicyclic amine with NH) | pyrazolo[1,5-a]pyrimidine | piperidine |
| 1377 | (bicyclic amine with NH) | benzoxazole | 1-methylcyclopropyl |
| 1378 | (bicyclic amine with NH) | benzoxazole | 1-(difluoromethyl)cyclopropyl |

TABLE 6-continued

| Compound | A | B | R⁷ |
|---|---|---|---|
| 1379 | bicyclic amine with NH | benzoxazole | N(CH₃)₂ |
| 1380 | bicyclic amine with NH | benzoxazole | azetidinyl |
| 1381 | bicyclic amine with NH | benzoxazole | pyrrolidinyl |
| 1382 | bicyclic amine with NH | benzoxazole | piperidinyl |
| 1383 | bicyclic amine with NH | quinoline | cyclopropyl |
| 1384 | bicyclic amine with NH | quinoline | 1-(difluoromethyl)cyclopropyl (F₂HC) |
| 1385 | bicyclic amine with NH | quinoline | N(CH₃)₂ |
| 1386 | bicyclic amine with NH | quinoline | azetidinyl |

TABLE 6-continued

| Compound | A | B | R⁷ |
|---|---|---|---|
| 1387 | bicyclic amine with NH | 2,6-quinoline (N at 2) | pyrrolidinyl |
| 1388 | bicyclic amine with NH | 2,6-quinoline (N at 2) | piperidinyl |
| 1389 | bicyclic amine with NH | 2,6-naphthalene | cyclopropyl |
| 1390 | bicyclic amine with NH | 2,6-naphthalene | 1-(difluoromethyl)cyclopropyl (F₂HC-) |
| 1391 | bicyclic amine with NH | 2,6-naphthalene | N(CH₃)₂ |
| 1392 | bicyclic amine with NH | 2,6-naphthalene | azetidinyl |
| 1393 | bicyclic amine with NH | 2,6-naphthalene | pyrrolidinyl |
| 1394 | bicyclic amine with NH | 2,6-naphthalene | piperidinyl |

TABLE 6-continued

| Compound | A | B | R⁷ |
|---|---|---|---|
| 1395 | | | |
| 1396 | | | |
| 1397 | | | |
| 1398 | | | |
| 1399 | | | |
| 1400 | | | |

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, cyclooctyl, bicyclo[2.2.1]heptyl, bicyclo[2.2.2]octyl, spiro[2.5]octyl, 3-methylenebicyclo[3.2.1]octyl, spiro[4.4]nonanyl, bicycle[3.1.0]hexanyl, spiro[2.3]hexanyl, bicycle[3.1.1]heptanyl, spiro[2.5]octanyl, bicycle[4.1.0]heptanyl, bicycle[3.1.0]hexan-6-yl, spiro[2.3]hexan-5-yl, bicycle[3.1.1]heptan-3-yl, spiro[2.5]octan-4-yl, and bicycle[4.1.0]heptan-3-yl and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "arylalkyl," as used herein, refers to a functional group wherein an alkylene chain is attached to an aryl group, e.g., —CH$_2$CH$_2$-phenyl. The term "substituted arylalkyl" means an arylalkyl functional group in which the aryl group is substituted. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized, Preferred heteroaryl groups are monocyclic or bicyclic. Heteroaryl groups include, but are not limited to, pyridinyl, pyrazolyl, pyrazinyl, pyrimidinyl, pyrrolyl, pyrazolyl, imidazolyl, thiazolyl, thienyl, triazolyl, isothiazolyl, oxazolyl, isooxazolyl, thiadiazolyl, oxadiazolyl, thiophenyl, furanyl, quinolinyl, isoquinolinyl, benzimidazolyl, benzooxazolyl, benzothienyl, quinoxalinyl, indolyl, indazolyl, benzisoxazolyl, benzofuranyl, benzotriazolyl, benzothiazolyl, and the like.

The term "heteroarylalkyl," as used herein, refers to an alkylene chain is attached to a heteroaryl group. The term "substituted heteroarylalkyl" means a heteroarylalkyl functional group in which the heteroaryl group is substituted. Examples include, but are not limited to, pyridinylmethyl, pyrimidinylethyl and the like.

The term "biaryl", as used herein, refers to a moiety consisting of two aryl groups, two heteroaryl groups or an aryl group and a heteroaryl group, wherein the two groups are connected by a single bond. A substituted biaryl group is a biaryl moiety in which at least one of the connected groups has at least one non-hydrogen substituent. Examples of biaryl groups include biphenyl, pyrimidylphenyl, pyrimidypyridyl, and pyrimidyloxadizolyl groups.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_2$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_2$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)— heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$— aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH—heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_{12}$-alkynyl, —S—$C_3$-$C_{12}$-cycloalkyl, —S-aryl, —S-heteroaryl, —S— heterocycloalkyl, or methylthiomethyl. It is understood that the aryls, heteroaryls, alkyls, cycloalkyls and the like can be further substituted. In some cases, each substituent in a substituted moiety is additionally optionally substituted with one or more groups, each group being independently selected from $C_1$-$C_4$-alkyl, —F, —Cl, —Br, —I, —OH, —$NO_2$, —CN, or —$NH_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

When the compounds described herein contain one or more asymmetric centers they give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in *J. Pharmaceutical Sciences,* 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), Design of Prodrugs, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type.

Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BINAP for 2,2'-bis(diphenylphosphino)-1,1'-binaphthyl;
BrettPhos for 2-(dicyclohexylphosphino)3,6-dimethoxy-2',4',6'-triisopropyl-1,1'-biphenyl;
BOP-Cl for bis(2-oxo-3-oxazolidinyl)phosphinic chloride;
CDI for carbonyldiimidazole;
EDC or EDCI for 1-Ethyl-3-(3-dimethylaminopropyl) carbodiimide;
DavePhos for 2-dicyclohexylphosphino-2'-(N,N-dimethylamino)biphenyl;
DBU for 1,8-diazabicycloundec-7-ene;
DCC for N,N-dicyclohexylcarbodiimide;
DCM for dichloromethane;
DMA for Dimethylacetamide
DMAP for N,N-dimethylaminopyridine;
DMF for N,N-dimethyl formamide;
DPPA for diphenylphosphoryl azide;
DPPF for 1,1'-Ferrocenediyl-bis(diphenylphosphine);
EDC or EDCI for 1-(3-diethylaminopropyl)-3-ethylcarbodiimide hydrochloride;
$Et_3N$ for triethylamine;
EtOAc for ethyl acetate;
HATU for 1-[bis(dimethylamino)methylene]-1H-1,2,3-triazolo[4,5-b]pyridinium 3-oxid hexafluorophosphate;
HCl for hydrochloric acid;
LAH for lithium aluminium hydride;
Mor-Dalphos for Di(1-adamantyl)-2-morpholinophenylphosphine;
NCS for N-Chlorosuccinimide;
NMO for N-Methylmorpholine N-oxide;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
TBAI for tetrabutylammonium iodide;
TFA for trifluoroacetic acid;
TFFH for tetramethylfluoroformamidinium hexafluorophosphate;
THF for tetrahydrofuran;
TPAP for Tetrapropylammonium perruthenate;
Xantphos for 4,5-Bis(diphenylphosphino)-9,9-dimethylxanthene;
XPhos for dicyclohexyl(2',4',6'-triisopropyl-[1,1'-biphenyl]-2-yl)phosphane or
2-Dicyclohexylphosphino-2',4',6'-triisopropylbiphenyl.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

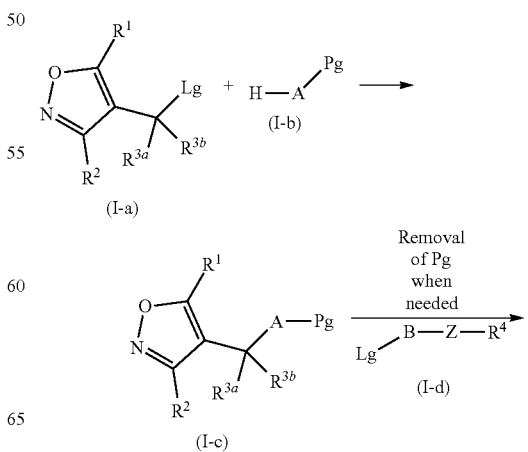

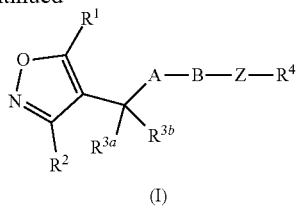

(I)

wherein, $R^1$, $R^2$, $R^{3a}$, $R^{3b}$, A, B, Z and $R^4$ are as previously defined. Lg is a leaving group such as halides, -OMs, -OTf, -OTs, -OAr. Pg is hydrogen or a protecting group for hydroxyl or amine whenever applicable such as, but not limited to, Boc, Cbz and benzyl. The protecting groups are common practices in organic synthesis (see T. W. Greene and P. G. M Wuts, "protective Groups in Organic Chemistry", 4$^{th}$ Ed., Wiley-Interscience, 2006).

As shown in Scheme 1, the compounds of formula (I-c) can be obtained through the coupling between the compounds of formula (I-a) and compounds of formula (I-b) employing suitable base such as but not limited to sodium tert-butoxide, potassium tert-butoxide, or cesium carbonate in the presence or absence of phase transfer reagent such as but not limited to 18-Crown-6, 15-Crown-5 or tetrabutylammonium iodide. The reaction temperature is from −20° C. to 140° C. The protecting group in compounds of formula (I-c) can be removed whenever applicable and coupled with the compounds of formula (I-d) to afford the compounds of formula (I). This coupling can be achieved employing suitable base such as but not limited to sodium tert-butoxide, potassium tert-butoxide, or cesium carbonate in the presence or absence of phase transfer reagent such as but not limited to 18-Crown-6, 15-Crown-5 or tetrabutylammonium iodide. Alternatively, the compounds of formula (I) could also be prepared from the deprotected form of compounds of formula (I-c) and the compounds of formula (I-d) via Buchwald-Hartwig amination. This process employing suitable palladium catalysts such as but not limited to Pd(OAc)$_2$, Pd$_2$(dba)$_3$, PdCl$_2$(P(o-Tolyl)$_3$)$_2$, PdC$_2$(DPPF) and Pd(PPh$_3$)$_4$ in presence or absence of a suitable ligand such as but not limited to XPhos, Xantphos, BINAP, BrettPhos, DavePhos, DPPF, PtBu$_3$, P(o-tolyl)$_3$ and Mor-Dalphos. This amination process may use a suitable base such as but not limited to K$_3$PO$_4$, Cs$_2$CO$_3$, NaOtBu, LiHMDS and NaHMDS. This amination process is carried out in a suitable solvent such as, but not limited to, toluene, dioxane or THF and the temperature can vary from −20° C. to 120° C. More detail about Buchwald-Hartwig amination could be found in literature. (Buchwald, S. L. et al., *Topics in Curr. Chem.*, 2002, 219, 131; Lundgren, R. J. et al., *Aldrichimica Acta*, 2012, 45, 59; Senra, J. D. et al., *Current Organic Synthesis*, 2011, 81, 53).

Scheme 2

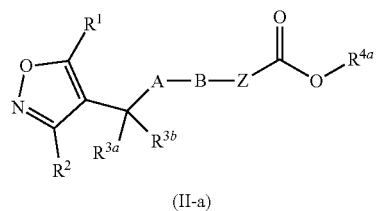

(II-a)

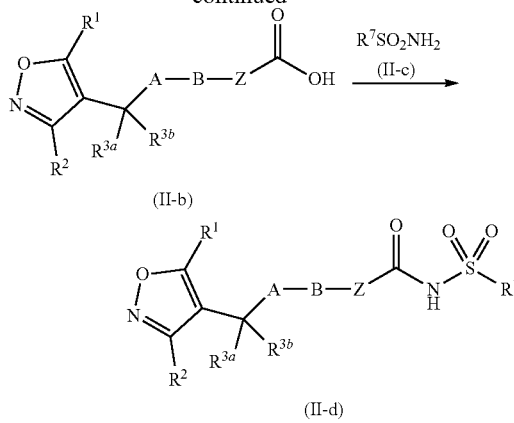

wherein, $R^1$, $R^2$, $R^{3a}$, $R^{3b}$, Z, $R^{4a}$, $R^7$, A and B are as previously defined.

As shown in Scheme 2, the hydrolysis of compounds of Formula (II-a) to the acids of Formula (II-b) can be achieved in the presence of suitable bases such as but not limited to sodium hydroxide, lithium hydroxide or potassium hydroxide. The novel isoxazole acylsulfonamide analogs of the compounds of Formula (II-d) can be prepared from the coupling between compounds of Formula (II-b) and sulfonamide (II-c) using suitable coupling reagents in presence of suitable bases. The coupling reagent can be selected from, but not limited to, DCC, EDCI, CDI, diisopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, DCM, DMF or THF. The reaction temperature can vary from −20° C. to 120° C.

Scheme 3

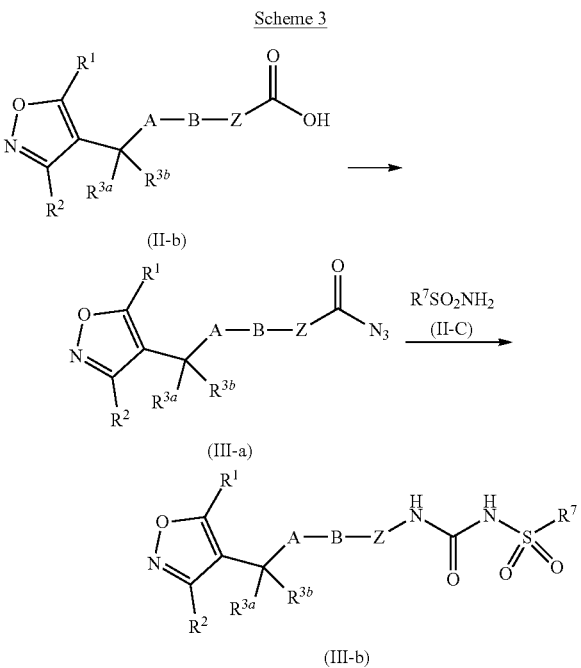

As shown in Scheme 3, novel isoxazole sulfonyl urea analogs of the compound of formula (III-b) are prepared from the compounds of formula (II-b), wherein $R^1$, $R^2$, $R^{3a}$, $R^{3b}$, $R^7$, Z, A and B are as previously defined. Thus, the compounds of formula (II-b) can be converted to the acyl azide compounds of formula (III-a) using suitable reagents such as, but not limited to, DPPA. The reaction solvents can be, but are not limited to, THF, DCM and toluene. The reaction temperature is from −20° C. to 80° C. Alternatively, the acids of formula (II-b) could be transformed to the acyl azides of formula (III-a) via activated acid derivatives such as acyl chlorides or anhydrides in presence of azide source. The reagents for activation of acid includes, but not limited to, tetramethylfluoroformadinium hexafluorophosphate, phenyl dichlorophosphate, $SOCl_2$-DMF, triphosgene, cyanuric chloride, NCS-$Ph_3P$ and $Cl_3CCN$-$Ph_3P$. The azide source includes, but not limited to, sodium azide, tetrabutylammonium azide, trimethylsilyl azide and N,N,N',N'-tetramethylguanidinium azide. Curtius rearrangement of the compounds of formula (III-a) at elevated temperature preferably from 50° C. to 120° C. can lead to the isocyanate intermediates, which then can react with sulfonamides compound of formula (II-c) to afford the compounds of formula (II-b).

with sulfonamides of formula (II-C) employing CDI or phosgene as coupling reagent with or without addition of suitable bases such as, but not limited to, triethylamine, diisopropylethylamine, DBU, N-methylmorpholine and DMAP. Alternatively, this transformation could be achieved via direct coupling of alcohols of formula (IV-a) with isocyanates of formula (IV-b) in the presence or absence of suitable bases such as, but not limited to, triethylamine, diisopropylethylamine, DBU, N-methylmorpholine and DMAP. Moreover, the isocyanates of formula (IV-b) could be generated in situ from compounds of formula (IV-c).

In the reactions described, reactive functional groups such as hydroxyl, amino, imino, thio or carboxy groups, may be protected to avoid unwanted participation in the reactions. These protecting groups may be removed at suitable steps via solovolysis, reduction, photolysis. The protection and deprotection are common practices in organic synthesis (see T. W. Greene and P. G. M Wuts, "protective Groups in Organic Chemistry", 4$^{th}$ Ed., Wiley-Interscience, 2006).

PREPARATIONS AND EXAMPLES

The following preparations and examples are intended for further illustrate the invention only and are not intended to limit the scope of the invention in any way.

Example 1

Step 1a

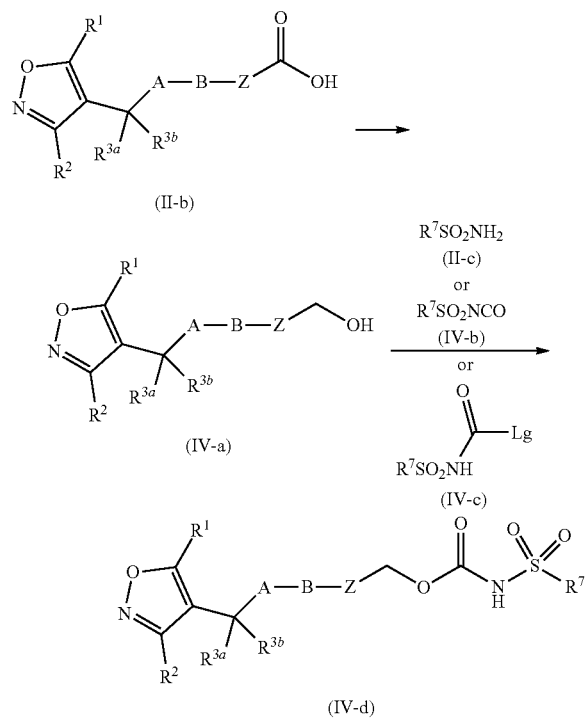

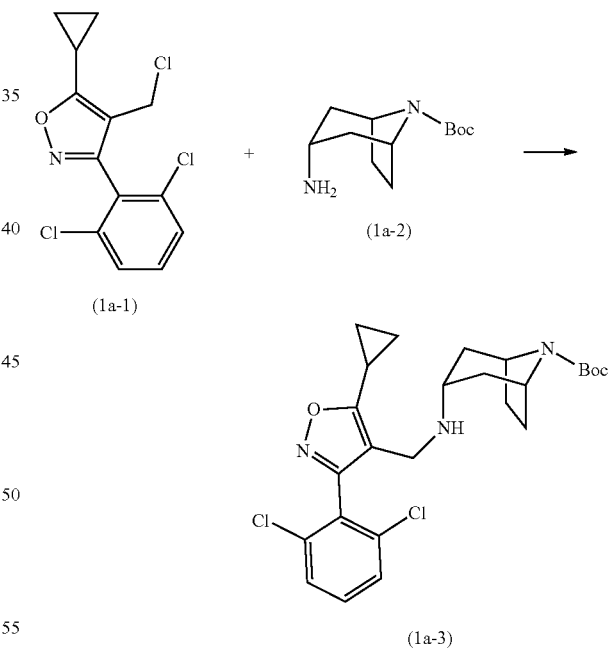

As shown in Scheme 4, the compounds of formula (IV-d) can be prepared from the compounds of formula (II-b), wherein $R^1$, $R^2$, $R^{3a}$, $R^{3b}$, $R^7$, Z, A and B are as previously defined and Lg is a leaving group such as halides, -OMs, -OTf, -OTs, -OAr. Thus, the compounds of formula (II-b) can be converted to alcohols of formula (IV-a) using suitable reducing reagents such as, but not limited to, LAH, $LiBH_4$, $BH_3$. Alternatively, the alcohols of formula (IV-a) can also be synthesized via the reduction of the derivatives of acid of formula (II-V). Such derivatives include, but not limited to, acyl chloride, mixed anhydride or ester derivatives of acids (II-b). The compounds of formula (IV-a) could be transformed to the carbamates of formula (IV-d) via coupling To tert-butyl (1R,3R,5S)-3-amino-8-azabicyclo[3.2.1]octane-8-carboxylate (1a-1) (5 g, 22.09 mmol) and 4-(chloromethyl)-5-cyclopropyl-3-(2,6-dichlorophenyl)isoxazole (1a-2) (7.35 g, 24.30 mmol) in Acetonitrile (50 ml) was added TBAI (0.816 g, 2.209 mmol) and cesium carbonate (18.00 g, 55.2 mmol). The resulting mixture was stirred at 65° C. for 16 h and then concentrated under vacuo to remove most of the solvents. The mixture was diluted with ethyl acetate, washed with water, brine, dried, filtered, and concentrated. The residue was chromatographed by CombiFlash eluting with hexane to 50% acetone/hexane to give tert-butyl (1R,3R,5S)-3-(((5-cyclopropyl-3-(2,6-dichlorophenyl)isoxazol-4-yl)methyl)amino)-8-azabicyclo[3.2.1]octane-8-carboxylate (1a-3) (4.12 g). LC/MS observed [M+H], 492.19; 494.17.

Step 1a-1

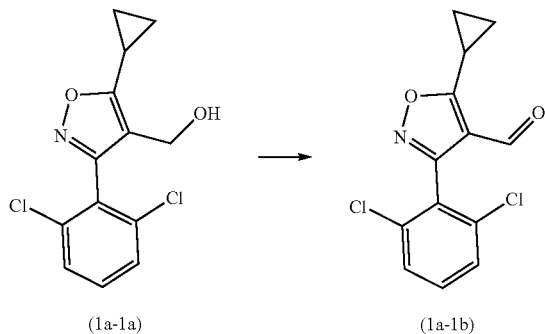 [SMILES: OCc1c(-c2c(Cl)cccc2Cl)noc1C1CC1 ; O=Cc1c(-c2c(Cl)cccc2Cl)noc1C1CC1]

(1a-1a)          (1a-1b)

To (5-cyclopropyl-3-(2,6-dichlorophenyl)isoxazol-4-yl)methanol (1a-1a) (50 g, 176 mmol) in DCM (503 ml) at room temperature was added TPAP (3.09 g, 8.80 mmol) and NMO (51.5 g, 440 mmol). The mixture was stirred for 30 min, and then filtered through a $SiO_2$ pad. The filtrate was concentrated to ~200 mL left, and heptane (300 mL) was added. The mixture was heated at 45° C. under vacuum to remove most of the DCM and colorless solid precipitate was formed. The crystalline product was collected by filtration and rinsed with heptane to give 5-cyclopropyl-3-(2,6-dichlorophenyl)isoxazole-4-carbaldehyde (1a-1b) (42 g, 85%). 1H NMR (400 MHz, Chloroform-d) δ 9.94-9.47 (m, 1H), 7.68-7.38 (m, 3H), 2.84 (tt, J=8.8, 4.9 Hz, 1H), 1.75-1.29 (m, 4H).

Step 1a-2

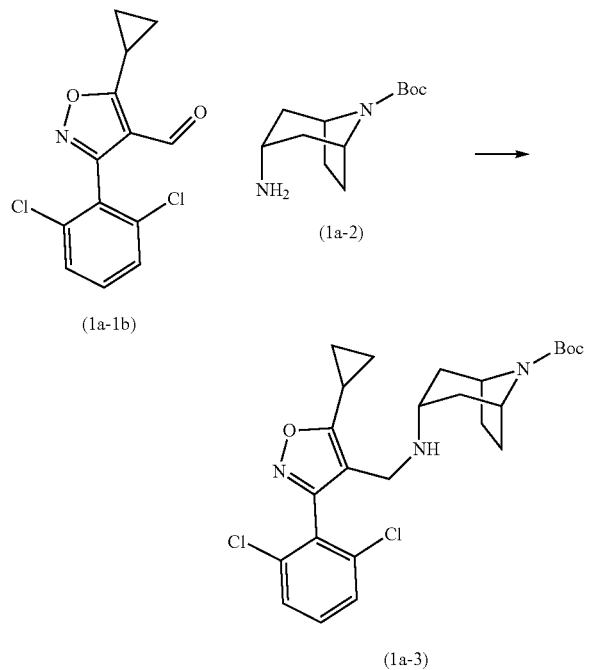

To 5-cyclopropyl-3-(2,6-dichlorophenyl)isoxazole-4-carbaldehyde (1a-1b) (50.1 g, 178 mmol) and tert-butyl (1R,3r,5S)-3-amino-8-azabicyclo[3.2.1]octane-8-carboxylate (38.2 g, 169 mmol) was added 2,2,2-trifluoroethanol (259 ml, 3552 mmol) and the suspension was heated up to 45° C. for 60 min to form a light yellow solution. To this mixture was added sodium borohydride (8.06 g, 213 mmol) in portions over 45 min. The mixture was stirred at 45° C. for 16 h, and the mixture was cooled down and concentrated under vacuum. The filtrate cake was participated in EtOAc/water, organic layer was separated, washed with potassium sodium tartrate, water and brine. The organic layer was combined with the filtrate and concentrated to give crude product. To the crude product was added 20% acetone in heptane (350 ml) and the suspension was heated up to gentle reflux until most of the solid went into solution. The suspension was cooled down to 45° C. and aging for 16 h. Then cooled down to room temperature and the solid was collected by filtration to give tert-butyl (1R,3r,5S)-3-(((5-cyclopropyl-3-(2,6-dichlorophenyl)isoxazol-4-yl)methyl)amino)-8-azabicyclo[3.2.1]octane-8-carboxylate (1a-3) (41.5 g). The mother liquor was concentrated and then recrystallized from acetone/Heptane (1:4) to give another crop of product (1a-3) (21.74 g). LC/MS observed [M+H], 492.18; 1H NMR (500 MHz, Chloroform-d) δ 7.47-7.37 (m, 2H), 7.37-7.29 (m, 1H), 4.03 (d, J=45.6 Hz, 2H), 3.50 (s, 2H), 2.88 (t, J=5.9 Hz, 1H), 2.08 (tt, J=8.4, 5.1 Hz, 1H), 1.93 (d, J=43.8 Hz, 2H), 1.66 (td, J=10.9, 9.8, 6.1 Hz, 4H), 1.44 (s, 9H), 1.31-1.19 (m, 3H), 1.19-1.06 (m, 2H).

Step 1b

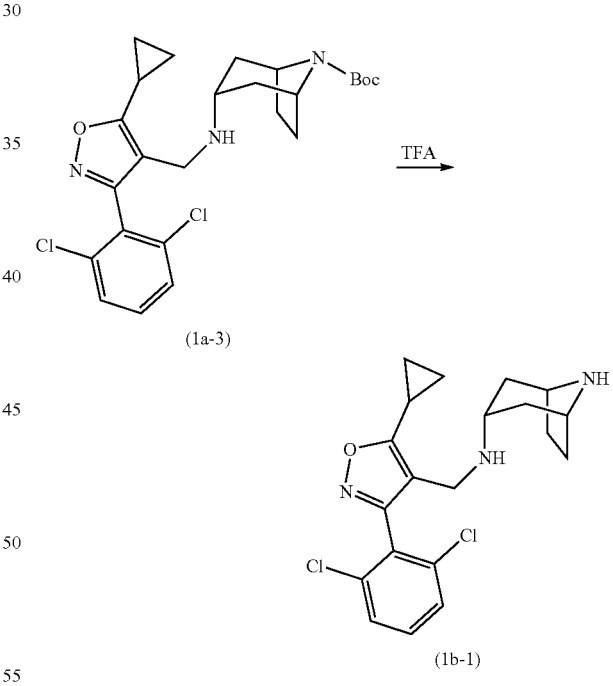

To tert-butyl (1R,3R,5S)-3-(((5-cyclopropyl-3-(2,6-dichlorophenyl)isoxazol-4-yl)methyl)amino)-8-azabicyclo[3.2.1]octane-8-carboxylate (1a-3) (1.43 g, 2.90 mmol) in DCM (8 ml) was added TFA (4.47 ml, 58.1 mmol) and the resulting mixture was stirred at room temperature for 16 h and then concentrated under vacuo. The mixture was diluted with ethyl acetate, washed with 1N NaOH solution, brine, dried, filtered, and concentrated to afford (1R,3R,5S)—N-((5-cyclopropyl-3-(2,6-dichlorophenyl)isoxazol-4-yl)methyl)-8-azabicyclo[3.2.1]octan-3-amine (1b-1) (1.08 g). LC/MS observed [M+H], 392.12.

Step 1c

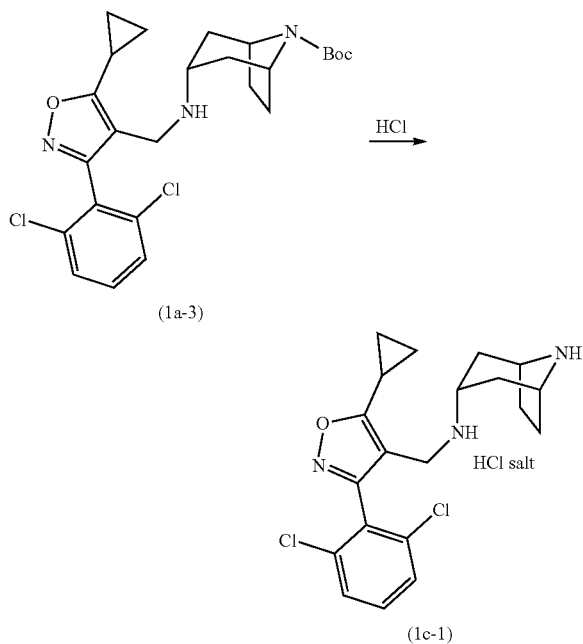

To tert-butyl (1R,3R,5S)-3-(((5-cyclopropyl-3-(2,6-dichlorophenyl)isoxazol-4-yl)methyl)amino)-8-azabicyclo[3.2.1]octane-8-carboxylate (1a-3) (758 mg, 1.539 mmol) in DCM (4 ml) was added HCl (3.85 ml, 15.39 mmol, 4 M in dioxane) and the resulting mixture was stirred at room temperature for 3 h. The mixture was concentrated under vacuo and chased with DCM to afford (1R,3R,5S)—N-((5-cyclopropyl-3-(2,6-dichlorophenyl)isoxazol-4-yl)methyl)-8-azabicyclo[3.2.1]octan-3-amine (1c-1) (785 mg) as HCl salt. LC/MS observed [M+H], 392.13.

Step 1d

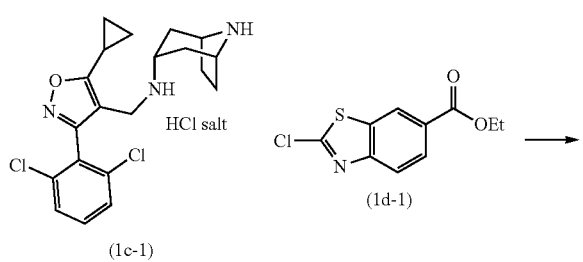

To ethyl 2-chlorobenzo[d]thiazole-6-carboxylate (1d-1) (305 mg, 1.263 mmol) and (1R,3R,5S)—N-((5-cyclopropyl-3-(2,6-dichlorophenyl)isoxazol-4-yl)methyl)-8-azabicyclo[3.2.1]octan-3-amine hydrochloride (1c-1) (430 mg, 0.842 mmol, ~84% by weight) in DMA (5 ml) was added cesium carbonate (686 mg, 2.105 mmol). The resulting mixture was heated up to 60° C. for 16 h, cooled down to room temperature. The mixture was diluted with ethyl acetate, washed with water (4×), brine, dried, filtered, and concentrated. The residue was chromatographed by CombiFlash eluting with hexane to 70% ethyl acetate/hexane to give ethyl 2-((1R,3R,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylate (Example 1) (198 mg). LC/MS observed [M+H], 597.15.

Example 2

Step 2a

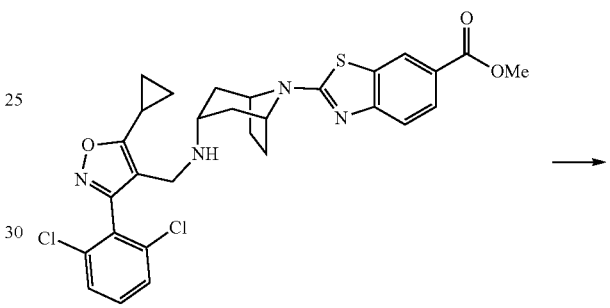

Example 73

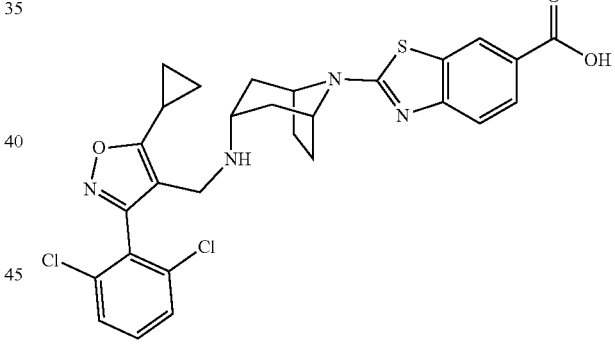

Example 2

To a suspension of methyl 2-((1R,3R,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylate Example 73 (215 mg, 0.368 mmol) in MeOH (3 ml), THF (3 ml) and Water (0.5 ml) was added potassium hydroxide (0.368 ml, 0.737 mmol, 2 M in water), the mixture was stirred at 70° C. for 8 h. Another portion of KOH (0.37 mL), stir at 60° C. for 60 h. The mixture was acidified to slightly acidic with 2N HCl, extracted with EA (3×), organic layer combined, and concentrated under vacuo to give a yellow solid. To this yellow solid was added 20% MeOH/DCM, sonicated for 3 min, filtered, and filtrate was collected and concentrated to give 2-((1R,3R,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylic acid (Example 2) (201 mg). LC/MS observed [M+H], 569.12. A portion of the crude product (35 mg) was purified by CombiFlash DCM to 15% MeOH/DCM to afford Example 2 (24.1 mg). LC/MS observed [M+H], 569.12.

Example 3

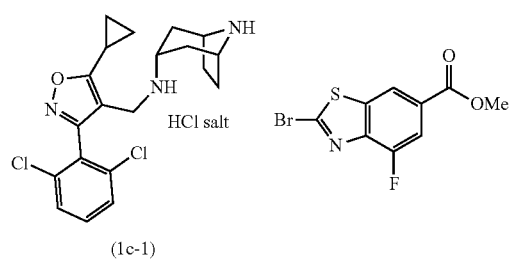

(1c-1)

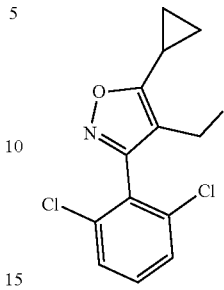

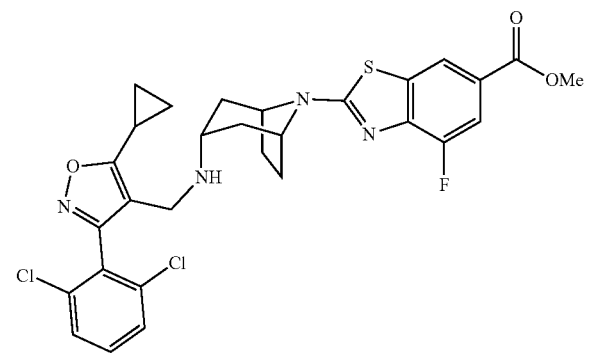

Example 3

Example 3 was prepared from compound (1c-1) and methyl 2-bromo-4-fluorobenzo[d]thiazole-6-carboxylate according to the analogous procedure as in step 1d described for the preparation of Example 1. LC/MS observed [M+H], 601.13.

Example 4

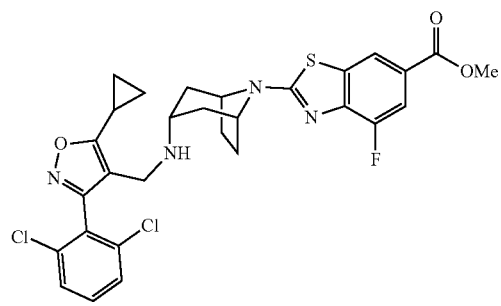

Example 3

-continued

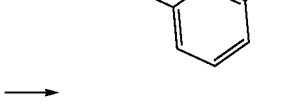

Example 4

Example 4 was prepared from the hydrolysis of Example 3 according to the analogous procedure as in step 2a described for the preparation of Example 2. LC/MS observed [M+H], 587.11.

Example 5

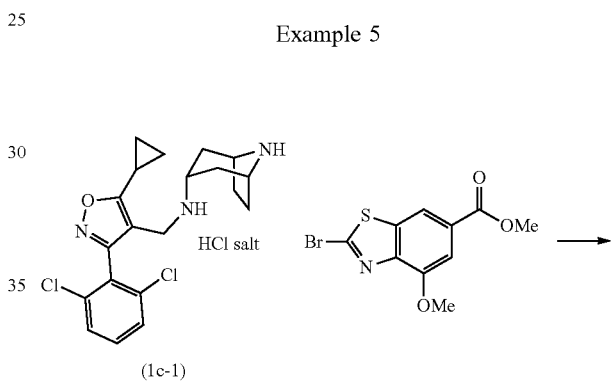

(1c-1)

Example 5

Example 5 was prepared from compound (1c-1) and methyl 2-bromo-4-methoxybenzo[d]thiazole-6-carboxylate according to the analogous procedure as in step 1d described for the preparation of Example 1. LC/MS observed [M+H], 613.15.

Example 6

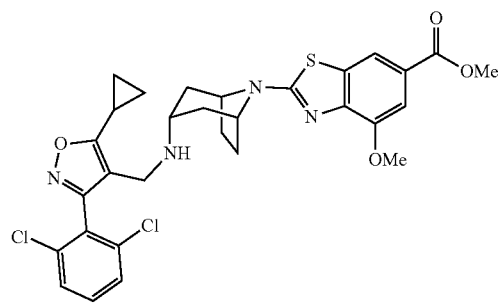
Example 5

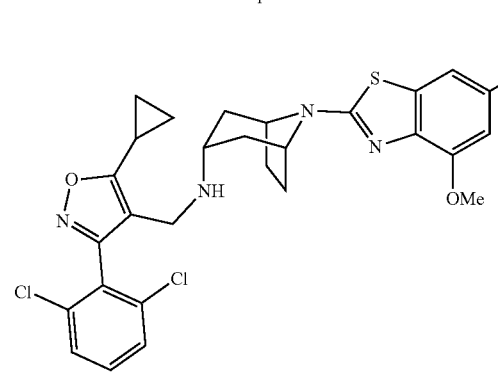
Example 6

Example 6 was prepared according to the analogous procedure as in step 2a described for the preparation of Example 2. LC/MS observed [M+H], 599.13 Example 19

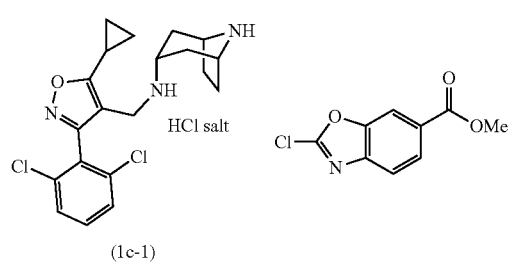
(1c-1)

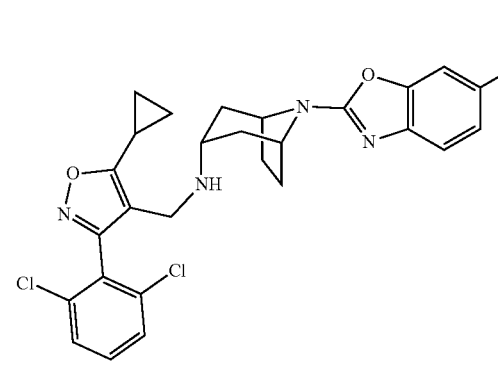
Example 19

Example 19 was prepared from compound (1c-1) and methyl 2-chlorobenzo[d]oxazole-6-carboxylate according to the analogous procedure as in step 1d described for the preparation of Example 1. LC/MS observed [M+H], 567.16.

Example 20

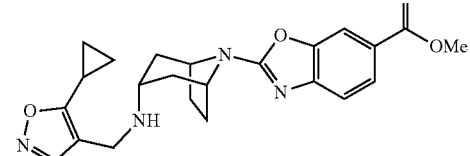
Example 19

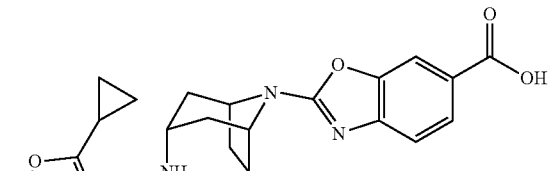
Example 20

Example 20 was prepared according to the analogous procedure as in step 2a described for the preparation of Example 2. LC/MS observed [M+H], 553.15.

Example 73

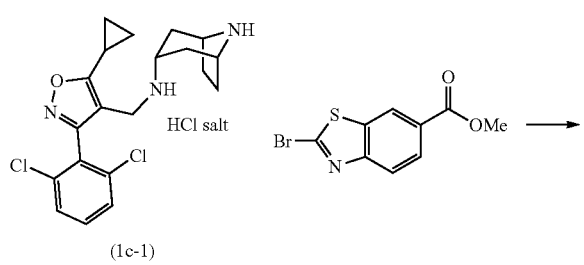
(1c-1)

-continued

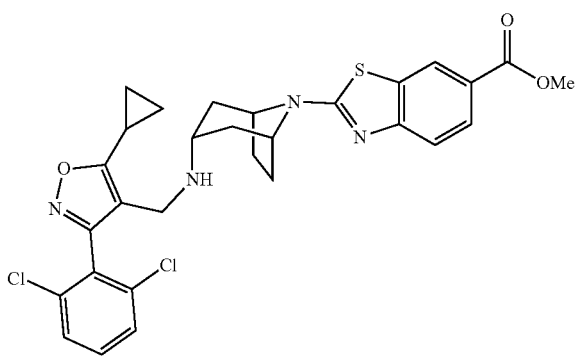

Example 73

Example 73 was prepared from compound (1c-1) and methyl 2-bromobenzo[d]thiazole-6-carboxylate according to the analogous procedure as in step 1d described for the preparation of Example 1. LC/MS observed [M+H], 583.14.

Example 137

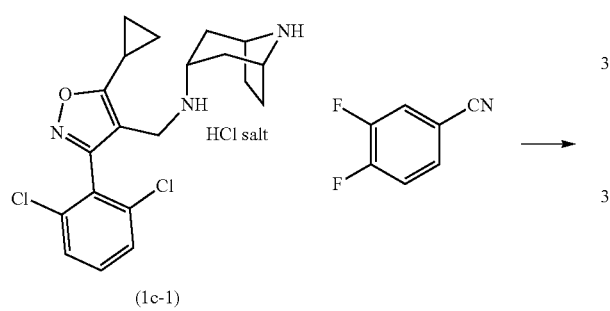

(1c-1)

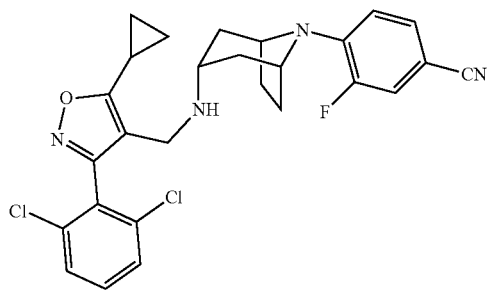

Example 137

To a vial containing compound (1c-1) (123 mg, 0.229 mmol), 3,4-difluorobenzonitrile (958 mg, 6.88 mmol), and cesium carbonate (224 mg, 0.688 mmol), was added N,N-dimethylacetamide (1.4 ml). The mixture was stirred at 110° C. for 24 h. The mixture was treated with water (10 ml). extracted by TBME (3×15 ml). The combined organic layer was dried over Na$_2$SO$_4$, filtered, concentrated to give a crude mixture. The crude mixture was purified by combi-flash (20 g silica gel, 0-50% EtOAc in hexane) to give Example 137 as mild yellow syrup (115 mg, 98% yield). LC/MS observed [M+H], 511.14; 1H NMR (400 MHz, Chloroform-d) δ 7.27-6.99 (m, 5H), 6.56 (t, J=8.8 Hz, 1H), 4.12-4.04 (m, 2H), 3.35 (s, 2H), 2.67 (t, J=5.9 Hz, 1H), 1.92 (ddd, J=8.5, 5.1, 3.3 Hz, 1H), 1.83 (ddd, J=14.7, 5.9, 3.6 Hz, 2H), 1.67-1.55 (m, 4H), 1.28 (d, J=15.0 Hz, 2H), 1.09-1.04 (m, 2H), 0.97-0.90 (m, 2H).

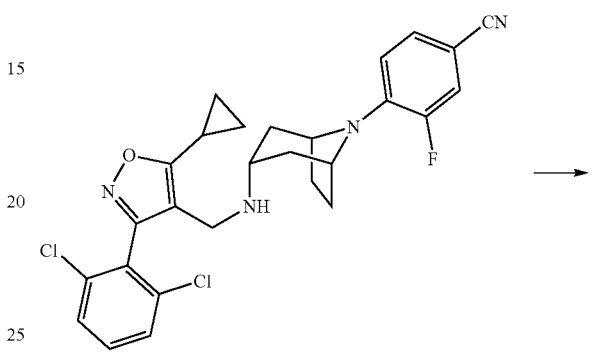

Example 137

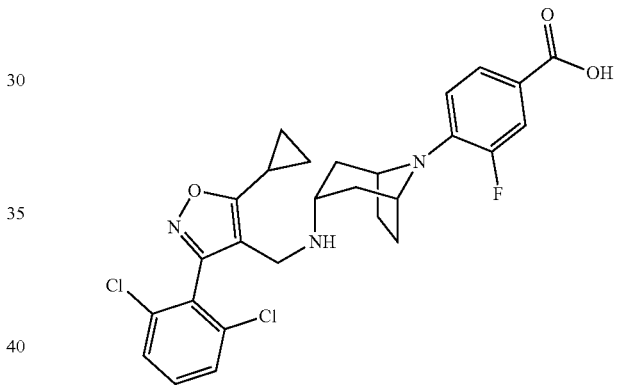

Example 122

To a slurry of Example 137 (47 mg, 0.092 mmol) in MeOH (1 ml), was added aqueous sodium hydroxide solution (50% w, 146 µl, 2.76 mmol) at room temperature and the mixture was stirred at 65° C. for 16 h. Another portion of NaOH (1M, 1 ml), EtOH (2 ml) and DMA (2 ml) was added and the mixture was stirred at 65° C. for 51 h. Reaction mixture was neutralize with HCl (1M) to pH=5. The solvent was removed and then diluted with EtOAc and Water. The organic layer was separated and aqueous layer was extracted by EtOAc (2×). The combined organic layers was washed by Brine, dried (Na$_2$SO$_4$), filtered, and concentrated. The residue was purified by prepHPLC to 4-((1R,3r,5S)-3-(((5-cyclopropyl-3-(2,6-dichlorophenyl)isoxazol-4-yl)methyl)amino)-8-azabicyclo[3.2.]octan-8-yl)-3-fluorobenzoic acid (Example 122) (12 mg) as a white solid. LC/MS observed [M+H], 530.16; 1H NMR (400 MHz, Methanol-d4) δ 7.62-7.38 (m, 5H), 6.88 (t, J=8.8 Hz, 1H), 4.21 (m, 2H), 3.55 (s, 2H), 2.85-2.75 (m, 1H), 2.32-2.19 (m, 1H), 2.11-1.99 (m, 2H), 1.86-1.68 (m, 4H), 1.52-1.39 (m, 2H), 1.17-1.14 (m, 2H), 1.14-1.11 (m, 2H).

Example 138

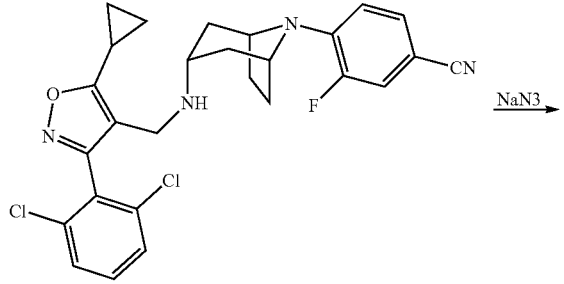

Example 137

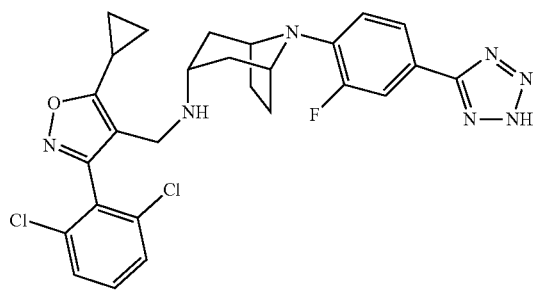

Example 138

To a vial containing Example 137 (62 mg, 0.121 mmol), sodium azide (79 mg, 1.212 mmol), and ammonium chloride (64.8 mg, 1.212 mmol), was added DMA (1.7 ml). The mixture was stirred at 120° C. for 20 h. Upon cooling to room temperature, the reaction mixture was diluted by EtOAc (25 ml), washed by water (2×10 ml), The organic layers was separated, dried, filtered and concentrated to give a crude oil. 1/3 of crude mixture was purified by prepHPLC (reverse column, 0.1% FA in ACN; 0.1% FA in water) to afford Example 138 (9 mg) as a white solid. LC/MS observed [M+H], 554.16; 1H NMR (400 MHz, Chloroform-d) δ 7.97 (bs, 1H), 7.65-7.56 (m, 2H), 7.40 (d, J=7.6 Hz, 2H), 7.32 (dd, J=9.1, 7.0 Hz, 1H), 6.83 (t, J=8.6 Hz, 1H), 4.22 (s, 2H), 3.57-3.43 (m, 2H), 2.88-2.79 (m, 1H), 2.12-2.01 (m, 3H), 1.97-1.50 (m, 4H), 1.43 (d, J=14.4 Hz, 2H), 1.26-1.18 (m, 2H), 1.13-1.03 (m, 2H).

Example 165

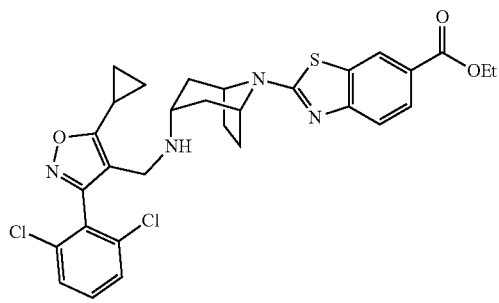

Example 1

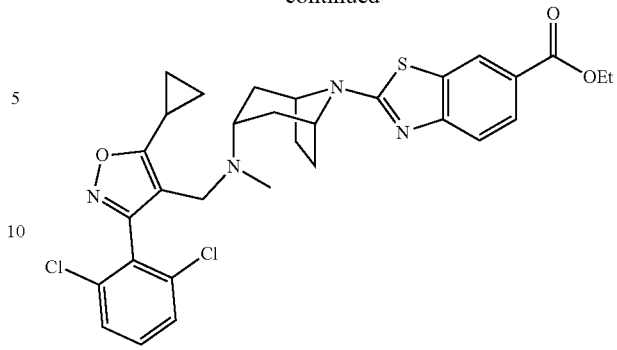

Example 165

To ethyl 2-((1R,3R,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylate (Example 1) (28 mg, 0.047 mmol) in trifluoroethanol (2 ml) was added paraformaldehyde (2.81 mg, 0.094 mmol) and the resulting mixture was heated up to 45° C. Sodium borohydride (3.55 mg, 0.094 mmol) was added and stirred for 30 mins. The mixture was concentrated under vacuo and diluted with ethyl acetate, then washed with 1 N NaOH solution, water, and brine. The organic layer was dried, filtered, and concentrated and the residue was purified by CombiFlash eluting with hexane to 40% ethyl acetate in hexane to give ethyl 2-((1R,3R,5S)-3-(((5-cyclopropyl-3-(2,6-dichlorophenyl)isoxazol-4-yl)methyl)(methyl)amino)-8-azabicyclo[3.2.1]octan-8-yl)benzo[d]thiazole-6-carboxylate (Example 165) (28 mg). LC/MS observed [M+H], 611.17.

Example 169

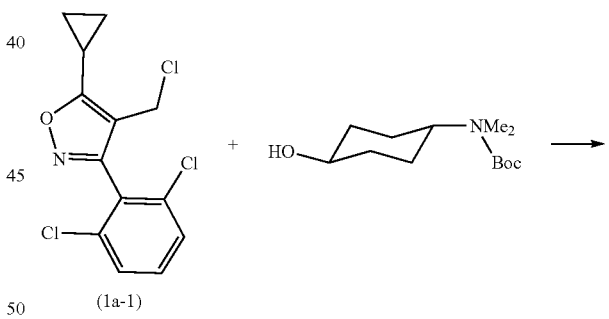

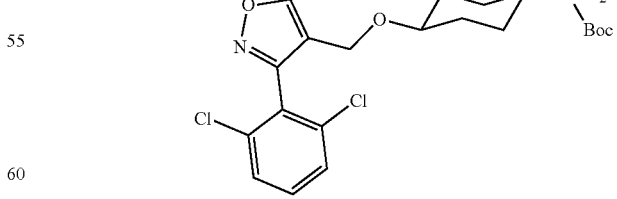

To a solution of tert-butyl ((1R,4R)-4-hydroxycyclohexyl)(methyl)carbamate (182 mg, 0.793 mmol) in THF (3 ml) was added 18-crown-6 (210 mg, 0.793 mmol) and potassium tert-butoxide (104 mg, 0.925 mmol). The resulting mixture was stirred at room temperature for 1 h and to this mixture was added 4-(chloromethyl)-5-cyclopropyl-3-(2,6-dichlorophenyl)isoxazole (1a-1) (200 mg, 0.661 mmol) in THF (2 mL). The resulting mixture was stirred at room temperature for 6 h and was quenched with water and extracted with MTBE (3×). The combined organic layers were washed with brine, dried over Na₂SO₄, and concentrated in vacuo and the residue was purified by CombiFlash eluting with hexane to 30% EtOAc in hexane to give tert-butyl ((1R,4R)-4-((5-cyclopropyl-3-(2,6-dichlorophenyl)isoxazol-4-yl)methoxy)cyclohexyl)(methyl)carbamate (141.2 mg). LC/MS observed [M−tBu+H], 439.12.

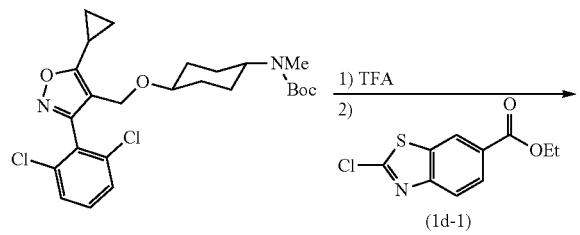

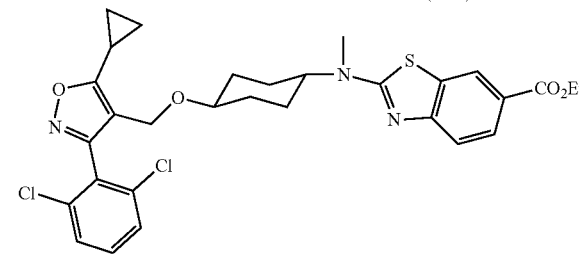

Example 169

Example 169 was prepared from tert-butyl ((1R,4R)-4-((5-cyclopropyl-3-(2,6-dichlorophenyl)isoxazol-4-yl) methoxy)cyclohexyl)(methyl)carbamate according to the analogous procedures as in step 1b and step 1d described for the preparation of Example 1. LC/MS observed [M+H], 600.15.

Example 170

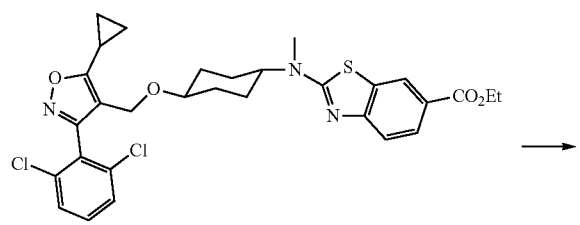

Example 169

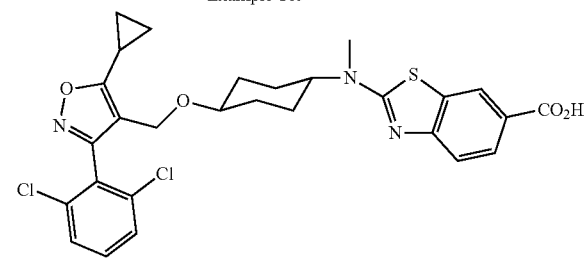

Example 170

Example 170 was prepared according to the analogous procedure as in step 2a described for the preparation of Example 2. LC/MS observed [M+H], 572.12.

Example 171

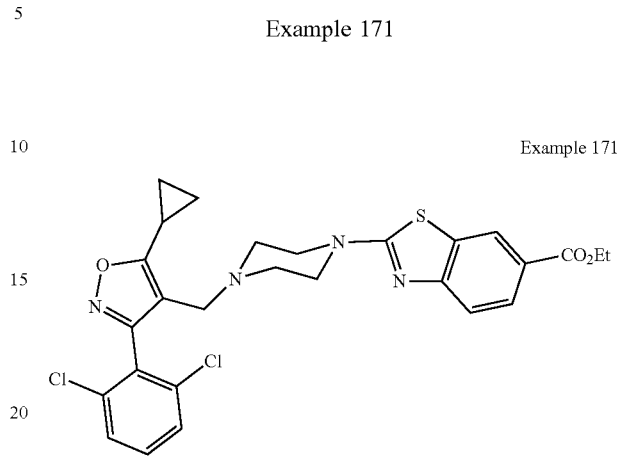

Example 171

Example 171 was prepared from tert-butyl piperazine-1-carboxylate according to the analogous procedures as in step 1a, step 1b and step 1d described for the preparation of Example 1. LC/MS observed [M+H], 557.16.

Example 172

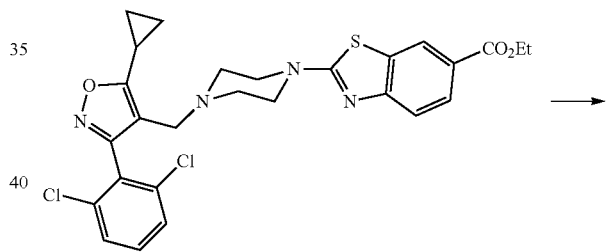

Example 171

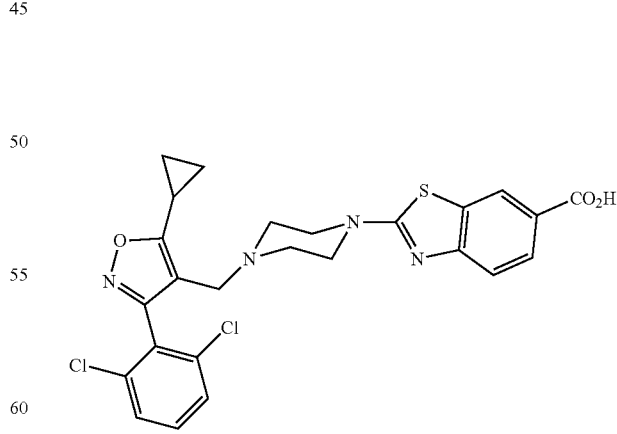

Example 172

Example 172 was prepared according to the analogous procedure as in step 2a described for the preparation of Example 2. LC/MS observed [M+H], 529.13.

Example 173

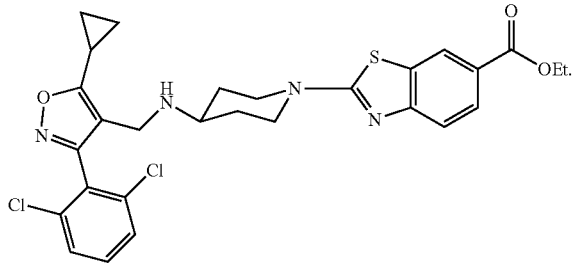

Example 173

Example 173 was prepared from tert-butyl 4-aminopiperidine-1-carboxylate according to the analogous procedures as in step 1a, step 1b and step 1d described for the preparation of Example 1. LC/MS observed [M+H], 571.13.

Example 174

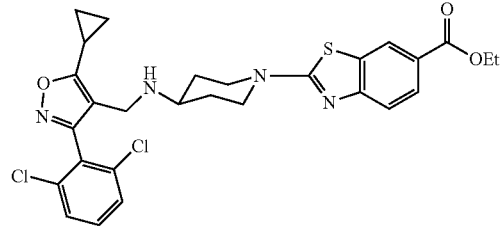

Example 174

Example 174 was prepared according to the analogous procedure as in step 2a described for the preparation of Example 2. LC/MS observed [M+H], 543.18.

Example 175

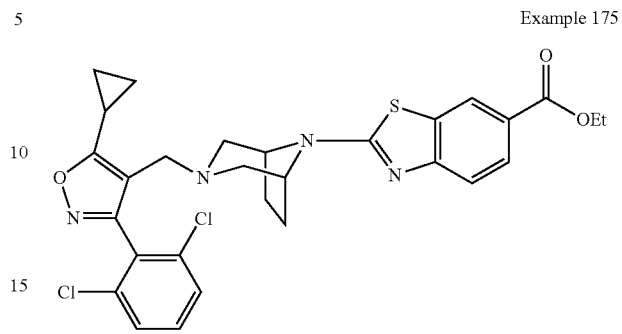

Example 175

Example 175 was prepared from tert-butyl (1R,5S)-3,8-diazabicyclo[3.2.1]octane-8-carboxylate according to the analogous procedures as in step 1a, step 1b and step 1d described for the preparation of Example 1. LC/MS observed [M+H], 571.13.

Example 176

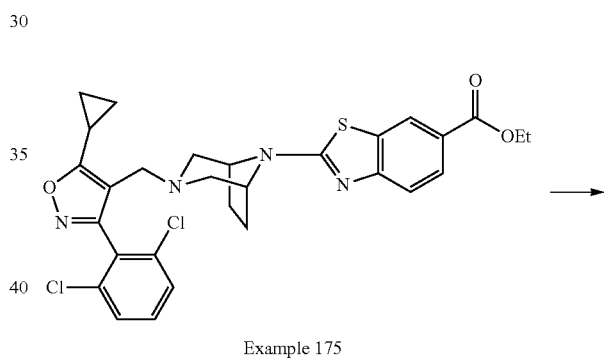

Example 175

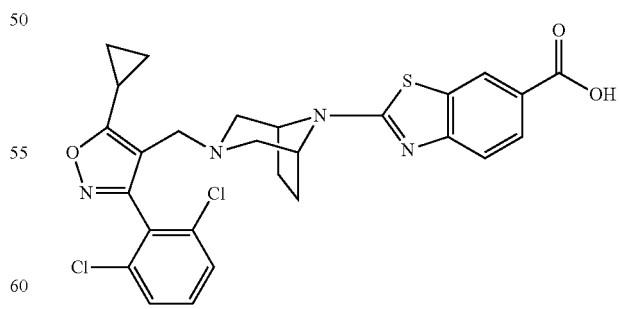

Example 176

Example 176 was prepared according to the analogous procedure as in step 2a described for the preparation of Example 2. LC/MS observed [M+H], 555.10.

Example 177

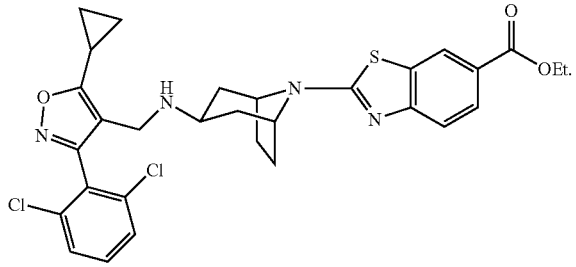

Example 177

Example 177 was prepared from tert-butyl (1R,3S,5S)-3-amino-8-azabicyclo[3.2.1]octane-8-carboxylate according to the analogous procedures as in step 1a, step 1b and step 1d described for the preparation of Example 1. LC/MS observed [M+H], 597.15.

Example 178

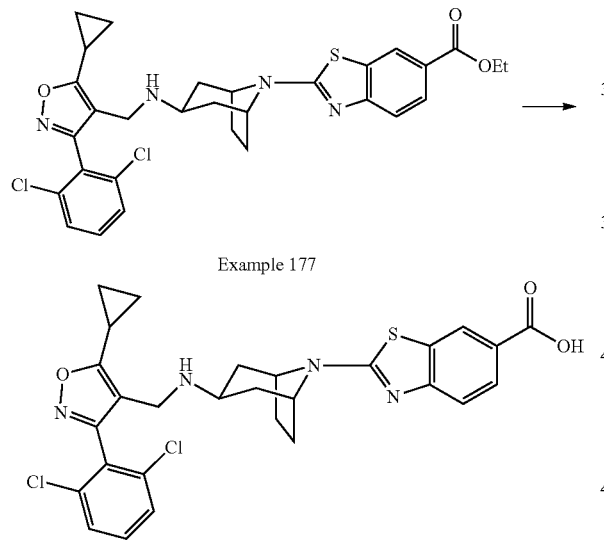

Example 177

Example 178

Example 178 was prepared according to the analogous procedure as in step 2a described for the preparation of Example 2. LC/MS observed [M+H], 569.12.

Example 179

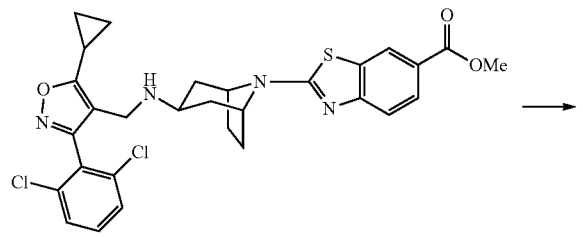

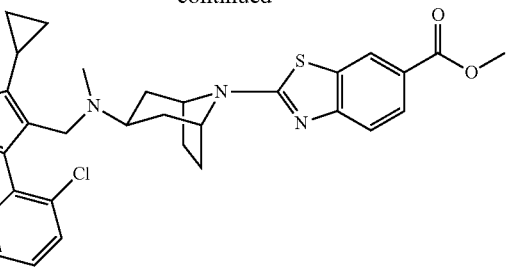

Example 179

To methyl 2-((1R,3S,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylate (17.4 mg, 0.030 mmol) in DCM (0.3 ml) was added MeI (0.019 ml, 0.298 mmol) and Et$_3$N (0.062 ml, 0.447 mmol). The resulting mixture was stirred at room temperature for 20 h and then concentrated. The residue was purified by CombiFlash Purification eluting with Hexane to 40% Acetone in Hexane to give Example 179 (9.5 mg). LC/MS observed [M+H], 597.15.

Example 183

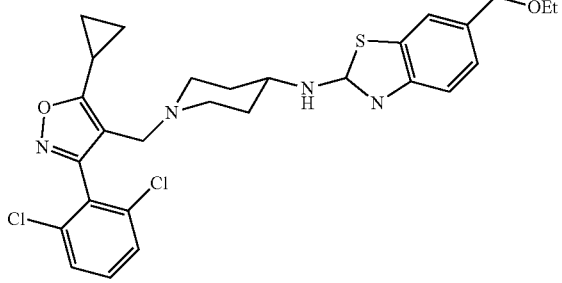

Example 183

Example 183 was prepared from tert-butyl piperidin-4-ylcarbamate according to the analogous procedures as in step 1a, step 1b and step 1d described for the preparation of Example 1. LC/MS observed [M+H], 571.13.

Example 185

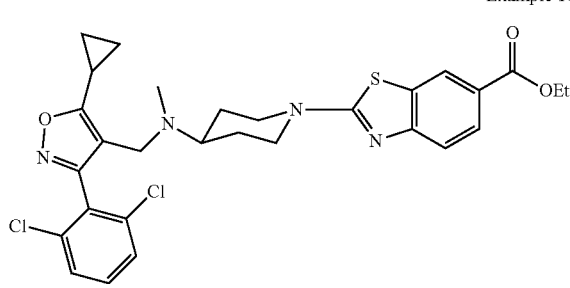

Example 185

Example 185 was prepared from tert-butyl 4-(methylamino)piperidine-1-carboxylate according to the analogous procedures as in step 1a, step 1b and step 1d described for the preparation of Example 1. LC/MS observed [M+H], 585.15.

Example 186

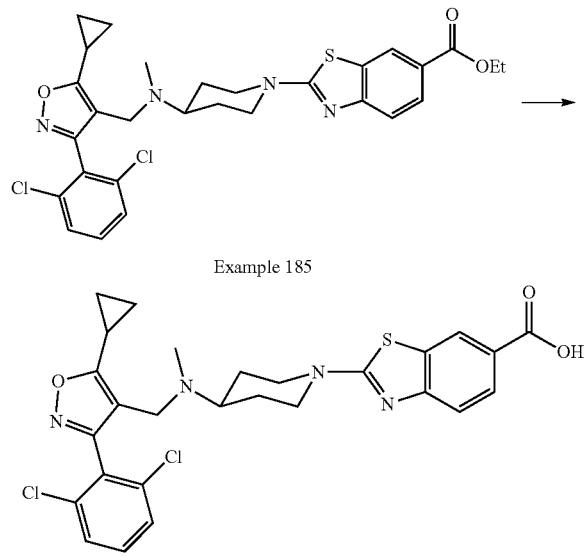

Example 185

Example 186

Example 186 was prepared according to the analogous procedure as in step 2a described for the preparation of Example 2. LC/MS observed [M+H], 557.12.

Example 187

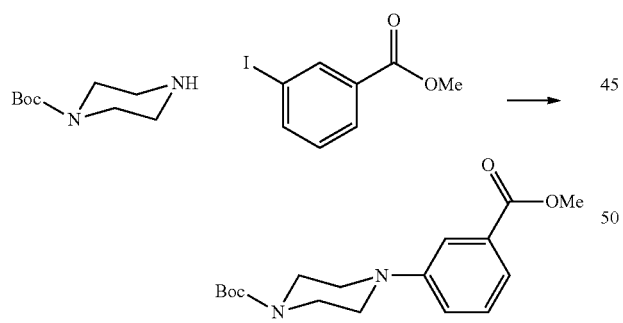

To tert-butyl piperazine-1-carboxylate (500 mg, 2.68 mmol), methyl 3-iodobenzoate (1055 mg, 4.03 mmol), L-proline (124 mg, 1.074 mmol), copper(I) iodide (102 mg, 0.537 mmol) and cesium carbonate (2187 mg, 6.71 mmol) was added DMSO (6 ml) and the resulting mixture was heated up at 90° C. for 7 h. The mixture was diluted with ethyl acetate and filtered through celite. The filtrate was collected and concentrated under vacuo. The residue was purified by CombiFlash eluting with hexane to 40% ethyl acetate in hexane to give tert-butyl 4-(3-(methoxycarbonyl)phenyl)piperazine-1-carboxylate (182 mg). LC/MS observed [M-Boc+H], 221.13.

Step 187-b

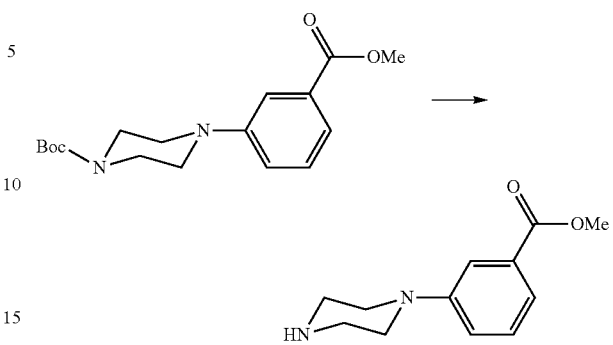

To tert-butyl 4-(3-(methoxycarbonyl)phenyl)piperazine-1-carboxylate (282 mg, 0.880 mmol) in DCM (3 ml) was added HCl (0.267 ml, 8.80 mmol, 4M in dioxane) and the resulting mixture was stirred at RT for 4 h. The mixture was concentrated under vacuo and chased with DCM to give methyl 3-(piperazin-1-yl)benzoate hydrochloride (292 mg).

Step 187-c

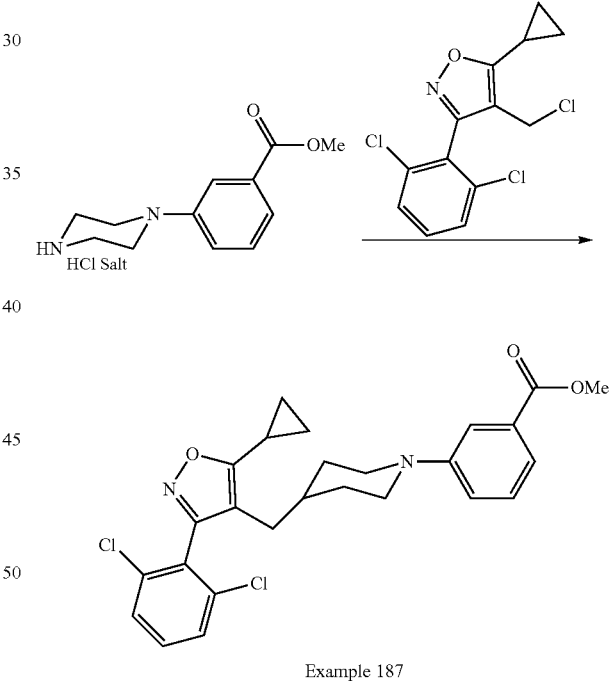

Example 187

To methyl 3-(piperazin-1-yl)benzoate hydrochloride (226 mg, 0.88 mmol), 4-(chloromethyl)-5-cyclopropyl-3-(2,6-dichlorophenyl)isoxazole (306 mg, 1.012 mmol), TBAI (65.0 mg, 0.176 mmol) in Acetonitrile (4 ml) was added cesium carbonate (717 mg, 2.200 mmol) and the resulting mixture was stirred at 60° C. for 24 h. The mixture was concentrated and the residue was diluted with DCM and filtered. The filtrate was collected and concentrated and the residue was purified by CombiFlash eluting with hexane to 35% ethyl acetate in hexane to give Example 187 (170 mg). LC/MS observed [M+H], 486.14.

Example 188

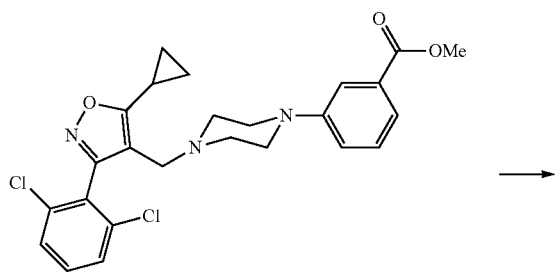

Example 187

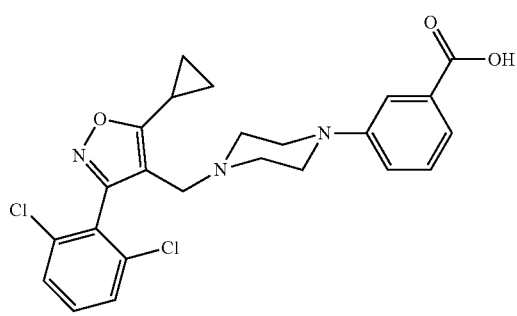

Example 188

Example 188 was prepared according to the analogous procedure as in step 2a described for the preparation of Example 2. LC/MS observed [M+H], 472.12.

Example 200-23

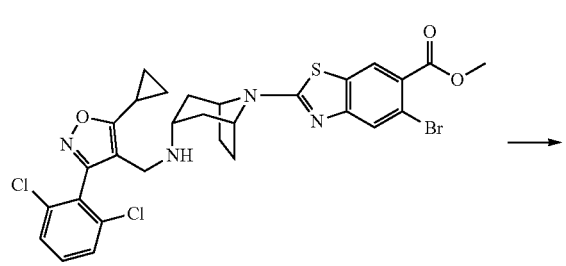

Example 200-19

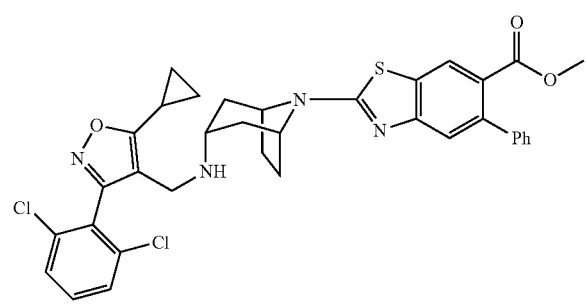

Example 200-23

A mixture of phenylboronic acid (7.90 mg, 0.065 mmol), Example 200-19 (33 mg, 0.050 mmol), cesium carbonate (32.5 mg, 0.100 mmol) and bis(triphenylphosphine)palladium(II) chloride (1.748 mg, 2.491 µmol) in DMF (1 ml) was stirred under argon atmosphere at 80° C. overnight. After cooling down, the most of DMF was removed by N2 blowing. The residue was diluted with ethyl acetate and water and the organic layer was separated. The aqueous layer was extracted with ethyl acetate. The combined organic layer was washed with brine, dried (Na$_2$SO$_4$), filtered and concentrated. The residue was purified by Combiflash (8 g silica gel, 0-50% EtOAc-Hexane) to give a Example 200-23 (10 mg) as colorless oil. LC/MS observed [M+H], 659.17; 1H NMR (500 MHz, Chloroform-d) δ 8.11 (s, 1H), 7.47-7.27 (m, 9H), 4.29-4.17 (m, 2H), 3.59 (s, 3H), 3.52 (s, 2H), 2.92-2.87 (m, 1H), 2.21-2.12 (m, 2H), 2.10-1.99 (m, 1H), 1.89-1.80 (m, 4H), 1.60-1.54 (m, 2H), 1.27-1.18 (m, 2H), 1.12-1.04 (m, 2H).

Example 201

Step 201-a

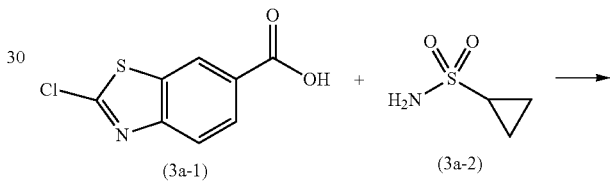

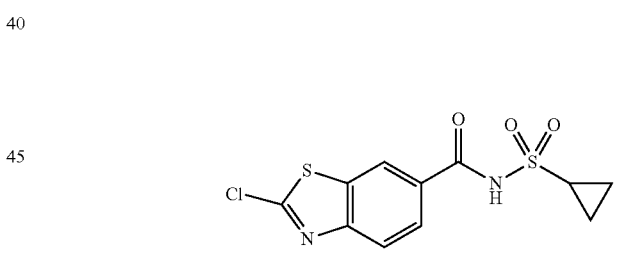

To 2-chlorobenzo[d]thiazole-6-carboxylic acid (200 mg, 0.936 mmol) and cyclopropanesulfonamide (113 mg, 0.936 mmol) in DCM (2 ml) was added EDCI (197 mg, 1.030 mmol) and DMAP (252 mg, 2.060 mmol). The resulting mixture was stirred at room temperature for 16 hrs and then concentrated. The residue was diluted with ethyl acetate and washed with 1N HCl, water. The organic layer contains some white solid and was filtered. The filtrate was collected, dried, and concentrated to give 2-chloro-N-(cyclopropylsulfonyl)benzo[d]thiazole-6-carboxamide (232 mg). This material was used directly to next step without further purification.

Step 201-b

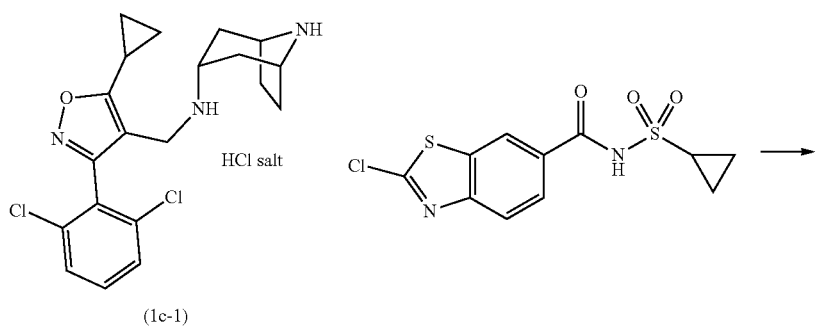

(1c-1)

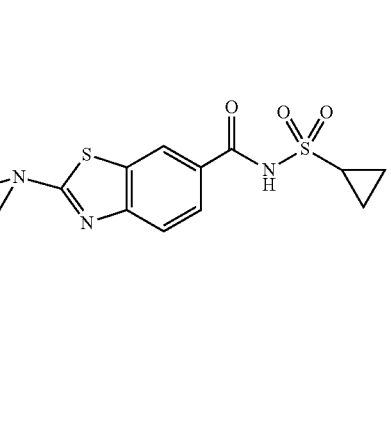

Example 201

To 2-chloro-N-(cyclopropylsulfonyl)benzo[d]thiazole-6-carboxamide (32.5 mg, 0.103 mmol) and (1R,3r,5S)—N-((5-cyclopropyl-3-(2,6-dichlorophenyl)isoxazol-4-yl)methyl)-8-azabicyclo [3.2.1]octan-3-amine hydrochloride (1c-1) (54.4 mg, ~0.093 mmol, ~74% purity by weight) in DMA (1.5 ml) was added cesium carbonate (60.8 mg, 0.187 mmol). The mixture was added stirred at 65° C. for 18 h, then diluted with ethyl acetate, washed with water. The aq. layer was separated, neutralized with 1 N HCl, then extracted extracted back with with ethyl acetate. All the organic layer was combined, washed with water, brine, dried, filtered and concentrated. The residue was purified by CombiFlash eluting with DCM to 40% Acetone/DCM to give Example 201 (20.2 mg). LC/MS observed [M+H], 672.14.

Example 292

Step 292-a

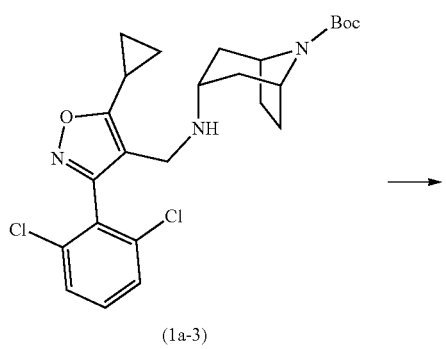

(1a-3)

-continued

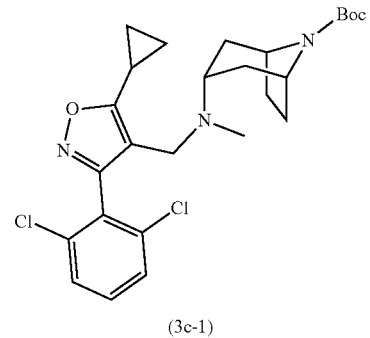

(3c-1)

To paraformaldehyde (4.27 mg, 0.142 mmol) and tert-butyl (1R,3R,5S)-3-(((5-cyclopropyl-3-(2,6-dichlorophenyl)isoxazol-4-yl)methyl)amino)-8-azabicyclo[3.2.1]octane-8-carboxylate (1a-3) (35 mg, 0.071 mmol) in 2,2,2-trifluoroethan-1-ol (1.5 ml, 0.071 mmol) at 45° C. was added sodium borohydride (5.38 mg, 0.142 mmol). The reaction mixture was stirred at 45° C. for 30 min, and then quenched with 1 drop of 1 N HCl. The reaction mixture was concentrated under vacuo and the residue was diluted with ethyl acetate and washed with 1 N NaOH solution, water, brine, dried, filtered, and concentrated to give tert-butyl (1R,3R,5S)-3-(((5-cyclopropyl-3-(2,6-dichlorophenyl)isoxazol-4-yl)methyl)(methyl)amino)-8-azabicyclo[3.2.1]octane-8-carboxylate (3c-1) (39.2 mg). LC/MS observed [M+H], 506.09.

Step 292-b

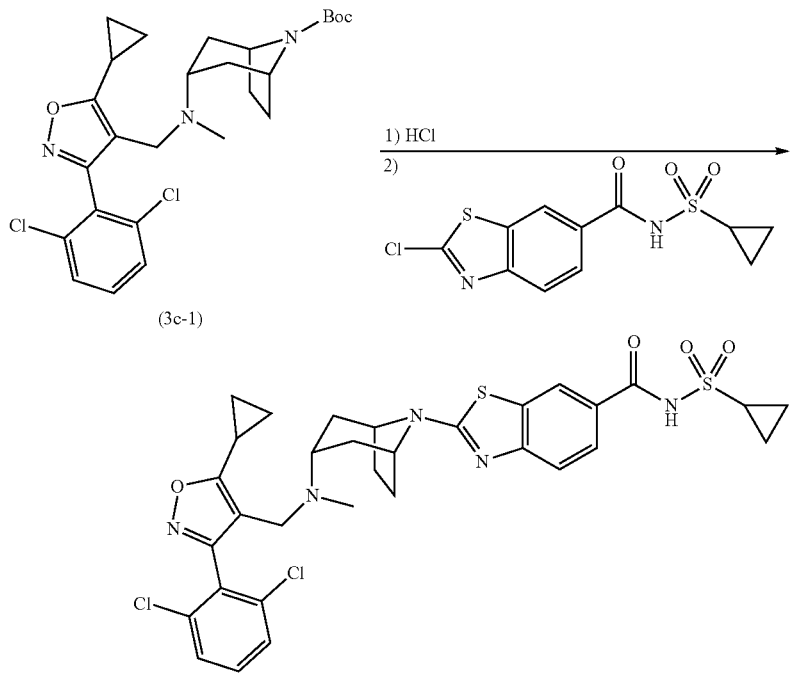

Example 292

Example 292 was prepared from tert-butyl (1R,3R,5S)-3-(((5-cyclopropyl-3-(2,6-dichlorophenyl)isoxazol-4-yl)methyl)(methyl)amino)-8-azabicyclo[3.2.1]octane-8-carboxylate (3c-1) following the analogous procedures described as in step 201-a and step 201-b for the synthesis of Example 201. LC/MS observed [M+H], 686.15.

Example 293

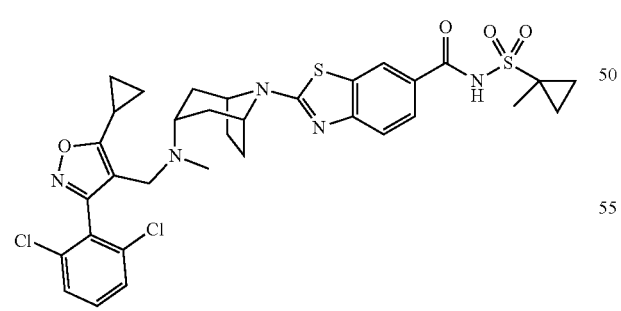

Example 293

Example 293 was prepared from tert-butyl (1R,3R,5S)-3-(((5-cyclopropyl-3-(2,6-dichlorophenyl)isoxazol-4-yl)methyl)(methyl)amino)-8-azabicyclo[3.2.1]octane-8-carboxylate (3c-1) following the analogous procedures described as in step 201-a and step 201-b for the synthesis of Example 201. LC/MS observed [M+H], 700.17.

Example 294

Step 294-a

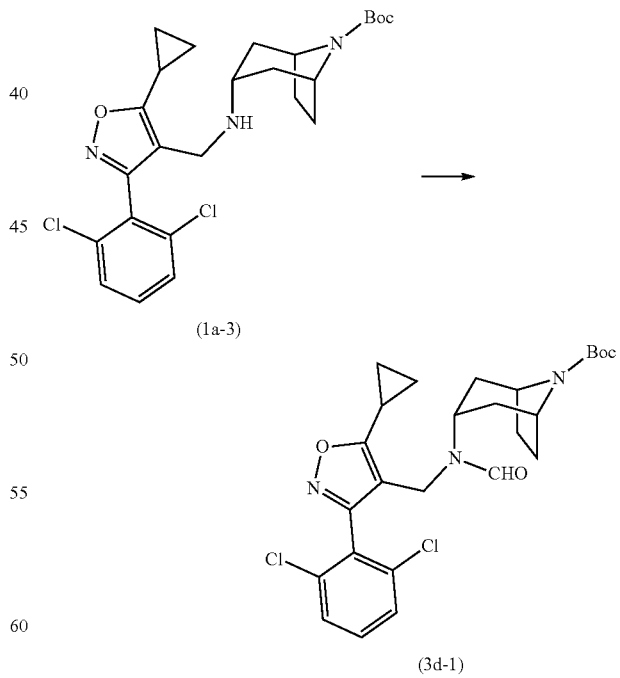

To acetic anhydride (2 ml, 21.20 mmol) was added formic acid (0.88 ml, 22.94 mmol) and the mixture was stirred at reflux for 3 h, cooled down to give the crude acetic formic anhydride (AFA) solution.

To tert-butyl (1R,3r,5S)-3-(((5-cyclopropyl-3-(2,6-dichlorophenyl)isoxazol-4-yl)methyl)amino)-8-azabicyclo[3.2.1]octane-8-carboxylate (1a-3) (150 mg, 0.305 mmol) in DCM (1 ml) was added the AFA solution (0.5 ml) and DMAP (74.4 mg, 0.609 mmol). The resulting mixture was stirred at 60° C. for 1.5 h. Volatile was removed under vacuo and chased with ACN. The residue was diluted with ethyl acetate, washed with 1N NaOH, water, brine, dried, filtered, and concentrated. The residue was purified by CombiFlash eluting with hexane to 50% acetone in hexane to give tert-butyl (1R,3R,5S)-3-(N-((5-cyclopropyl-3-(2,6-dichlorophenyl)isoxazol-4-yl)methyl)formamido)-8-azabicyclo[3.2.1]octane-8-carboxylate (3d-1) (125 mg). LC/MS observed [M−tBu+H], 464.10.

Step 294-b

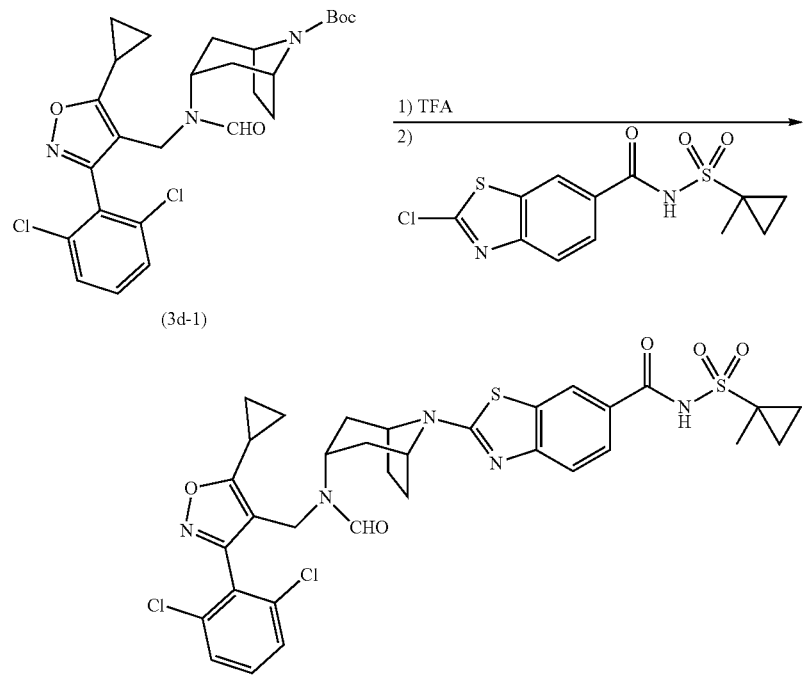

Example 294 was prepared from (1R,3r,5S)-3-(N-((5-cyclopropyl-3-(2,6-dichlorophenyl)isoxazol-4-yl)methyl)formamido)-8-azabicyclo[3.2.1]octane-8-carboxylate (3d-1) following the analogous procedures described as in step 201-a and step 201-b for the synthesis of Example 201. LC/MS observed [M+H], 714.16.

The following examples listed in Table 7 were prepared from (1R,3r,5S)—N-((5-cyclopropyl-3-(2,6-dichlorophenyl)isoxazol-4-yl)methyl)-8-azabicyclo[3.2.1]octan-3-amine hydrochloride (1c-1), 2-chlorobenzo[d]thiazole-6-carboxylic acid and the corresponding sulfonamides following the analogous procedures described as in step 201-a and step 201-b for the synthesis of Example 294.

TABLE 7

| Example # | Structure | MS Data |
|---|---|---|
| 202 | 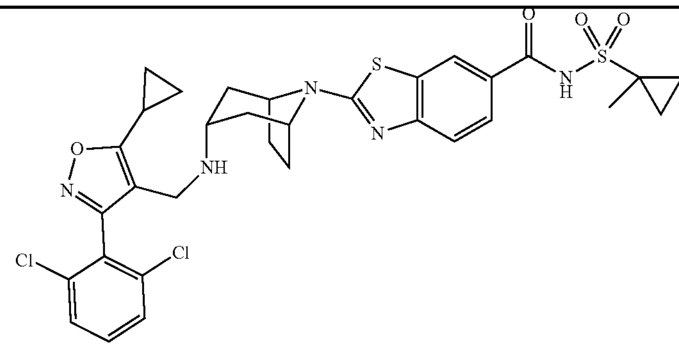 | 686.16 (M + H) |

TABLE 7-continued

| Example # | Structure | MS Data |
|---|---|---|
| 225 | 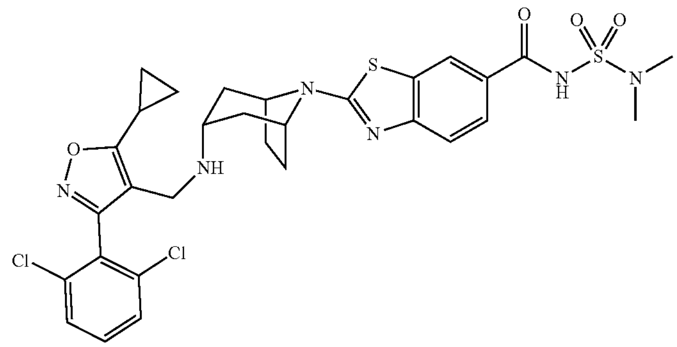 [SMILES: CN(C)S(=O)(=O)NC(=O)c1ccc2nc(N3C4CCC3CC(NCc3c(-c5c(Cl)cccc5Cl)noc3C3CC3)C4)sc2c1] | 675.15 (M + H) |
| 227 | 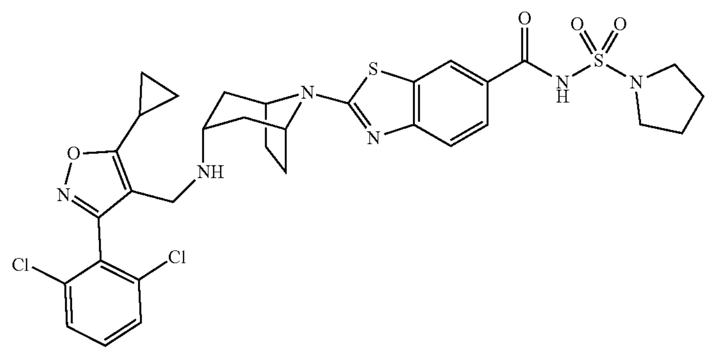 [SMILES: O=C(NS(=O)(=O)N1CCCC1)c1ccc2nc(N3C4CCC3CC(NCc3c(-c5c(Cl)cccc5Cl)noc3C3CC3)C4)sc2c1] | 701.16 (M + H) |
| 228 | 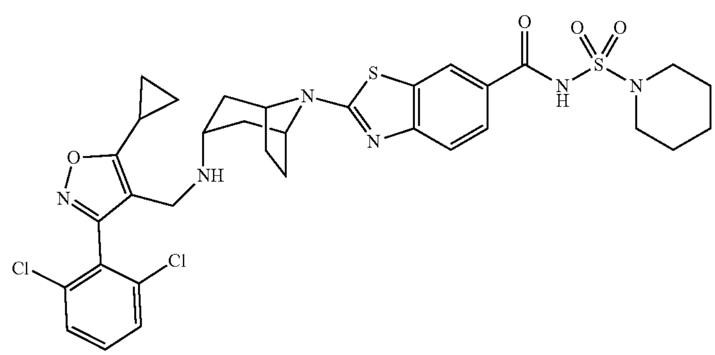 [SMILES: O=C(NS(=O)(=O)N1CCCCC1)c1ccc2nc(N3C4CCC3CC(NCc3c(-c5c(Cl)cccc5Cl)noc3C3CC3)C4)sc2c1] | 715.19 (M + 1) |
| 231 | 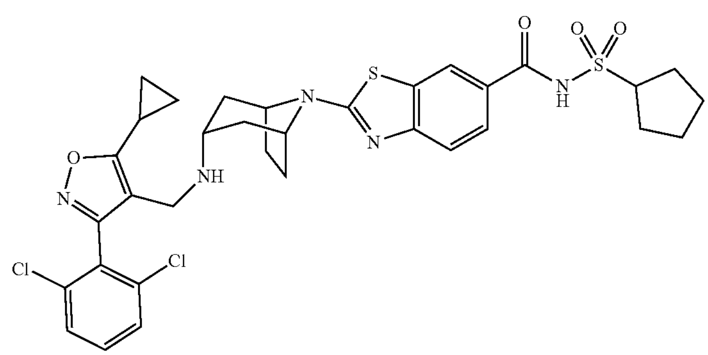 [SMILES: O=C(NS(=O)(=O)C1CCCC1)c1ccc2nc(N3C4CCC3CC(NCc3c(-c5c(Cl)cccc5Cl)noc3C3CC3)C4)sc2c1] | 700.00 (M + H) |

TABLE 7-continued

| Example # | Structure | MS Data |
|---|---|---|
| 234 | 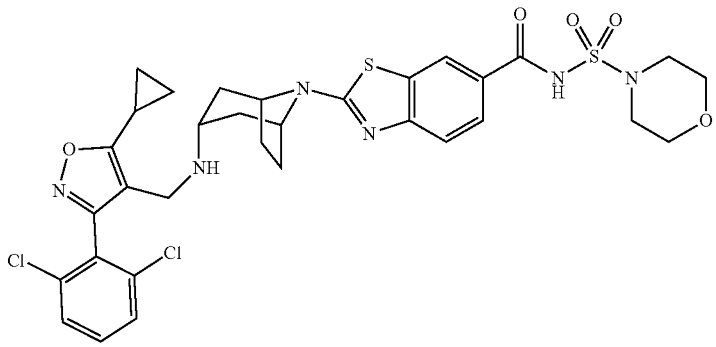 [SMILES: O=C(NS(=O)(=O)N1CCOCC1)c1ccc2nc(N3C4CCC3CC(NCc3c(-c5c(Cl)cccc5Cl)noc3C3CC3)C4)sc2c1] | 717.17 (M + 1) |
| 235 | 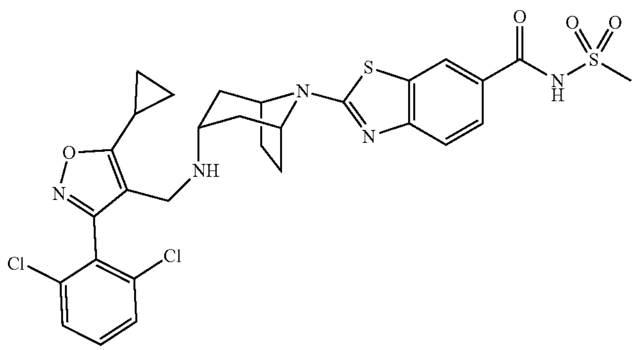 | 672.14 (M + H) |
| 236 | 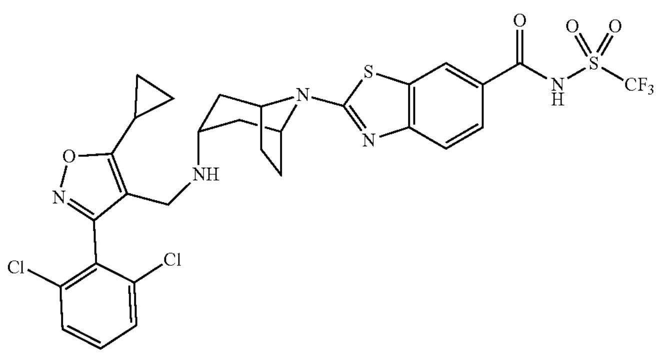 [SMILES: O=C(NS(=O)(=O)C(F)(F)F)c1ccc2nc(N3C4CCC3CC(NCc3c(-c5c(Cl)cccc5Cl)noc3C3CC3)C4)sc2c1] | 700.10 (M + 1) |
| 237 | 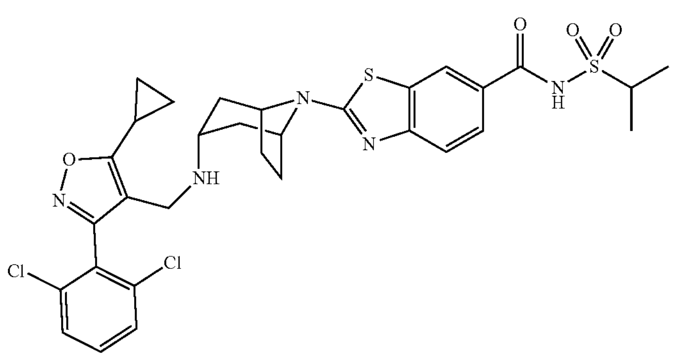 [SMILES: CC(C)S(=O)(=O)NC(=O)c1ccc2nc(N3C4CCC3CC(NCc3c(-c5c(Cl)cccc5Cl)noc3C3CC3)C4)sc2c1] | 674.08 (M + H) |

TABLE 7-continued

| Example # | Structure | MS Data |
|---|---|---|
| 239 | 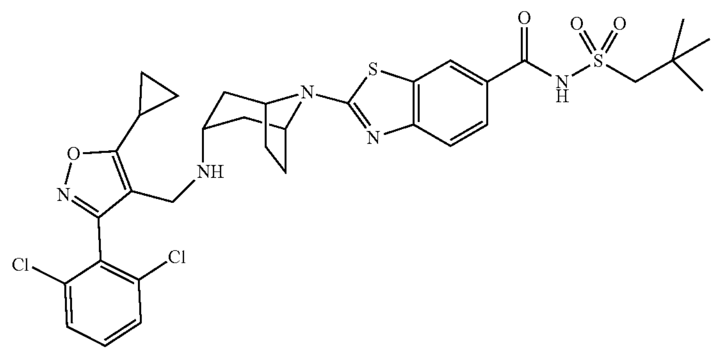 [SMILES: CC(C)(C)CS(=O)(=O)NC(=O)c1ccc2nc(N3C4CCC3CC(NCc3c(-c5c(Cl)cccc5Cl)noc3C3CC3)C4)sc2c1] | 702.11 (M + H) |
| 240 | 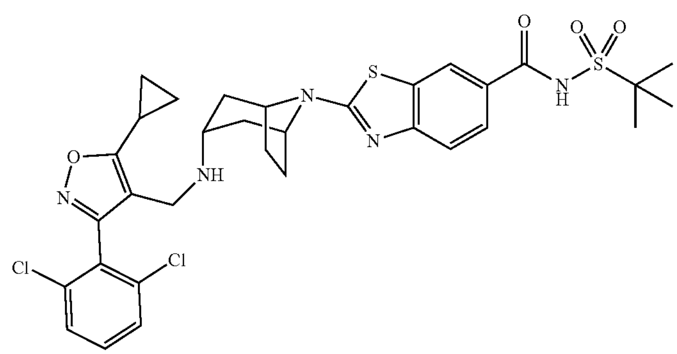 [SMILES: CC(C)(C)S(=O)(=O)NC(=O)c1ccc2nc(N3C4CCC3CC(NCc3c(-c5c(Cl)cccc5Cl)noc3C3CC3)C4)sc2c1] | 688.17 (M + H) |
| 257 | 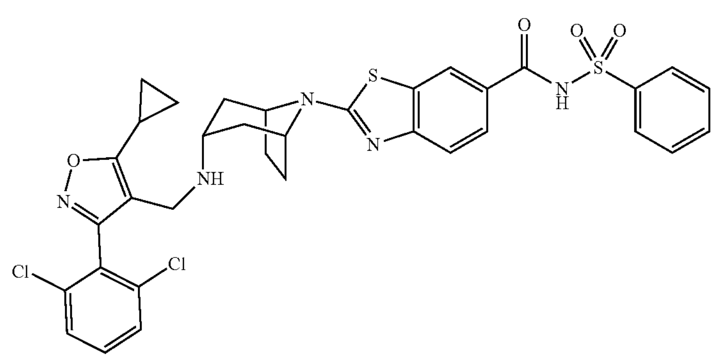 [SMILES: O=C(NS(=O)(=O)c1ccccc1)c1ccc2nc(N3C4CCC3CC(NCc3c(-c5c(Cl)cccc5Cl)noc3C3CC3)C4)sc2c1] | 708.14 (M + H) |
| 262 | 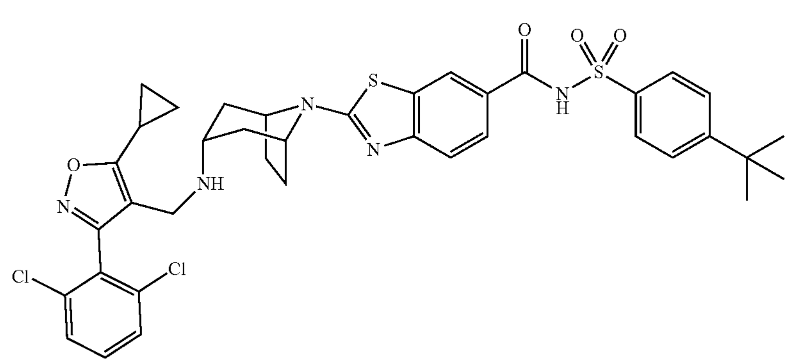 [SMILES: CC(C)(C)c1ccc(S(=O)(=O)NC(=O)c2ccc3nc(N4C5CCC4CC(NCc4c(-c6c(Cl)cccc6Cl)noc4C4CC4)C5)sc3c2)cc1] | 764.04 (M + H) |

| Example # | Structure | MS Data |
|---|---|---|
| 268 | 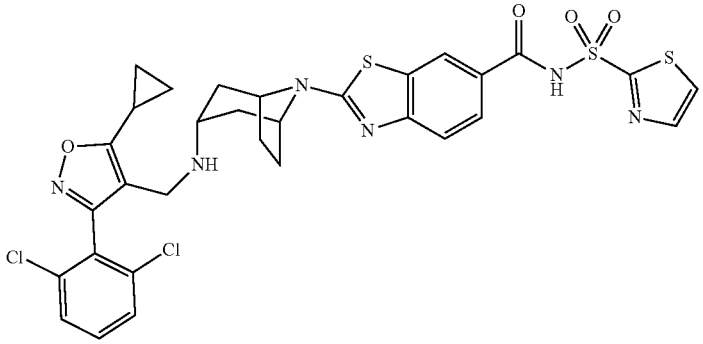 [SMILES: O=C(NS(=O)(=O)c1nccs1)c1ccc2nc(N3C4CCC3CC(NCc3c(-c5c(Cl)cccc5Cl)noc3C3CC3)C4)sc2c1] | 715.10 (M + 1) |

Example 296

Step 296-a

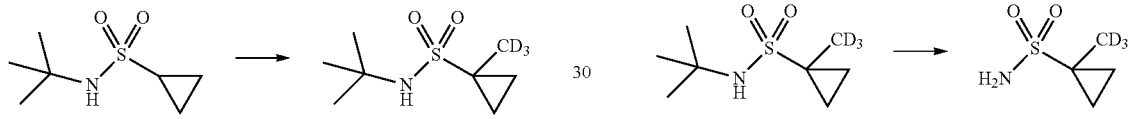

To N-(tert-butyl)cyclopropanesulfonamide (1 g, 5.64 mmol) in Tetrahydrofuran (8 ml) at −78° C. was added butyllithium (8.81 ml, 14.10 mmol) dropwise, and the resulting mixture was stirred at −78° C. for 1 h. To the reaction mixture was added iodomethane-d3 (0.430 ml, 6.77 mmol) and the resulting mixture was stirred at −78° C. for 2 h. The cooling bath was removed and mixture was allowed to warm up to 0° C., quenched with NH₄Cl solution. The mixture was diluted with ethyl acetate, washed with water, brine, dried, and concentrated. The residue purified by CombiFlash eluting with hexane to 40% acetone in hexane to give 1-(methyl-d3)cyclopropane-1-sulfonamide (704 mg).

Step 296-b

To N-(tert-butyl)-1-(methyl-d3)cyclopropane-1-sulfonamide (500 mg, 2.57 mmol) in DCM (6 ml) was added TFA (3 ml, 38.9 mmol), and the resulting mixture was stirred at RT for 16 h. The mixture was concentrated under vacuo and the residue was chased with DCM to give 1-(methyl-d3) cyclopropane-1-sulfonamide (378 mg). This material was directly used to next step without further purification.

Step 296-c

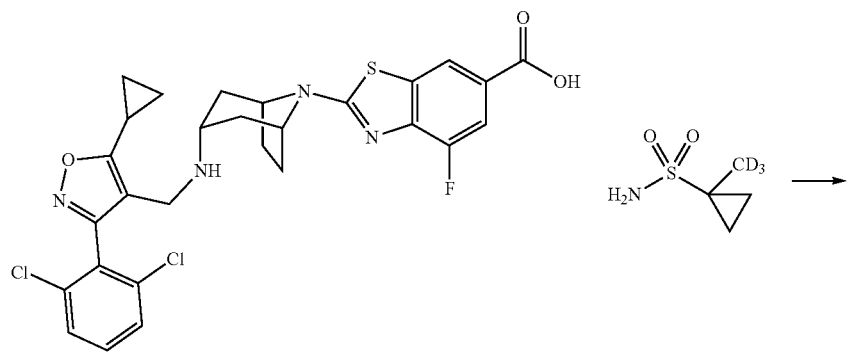

Example 4

-continued

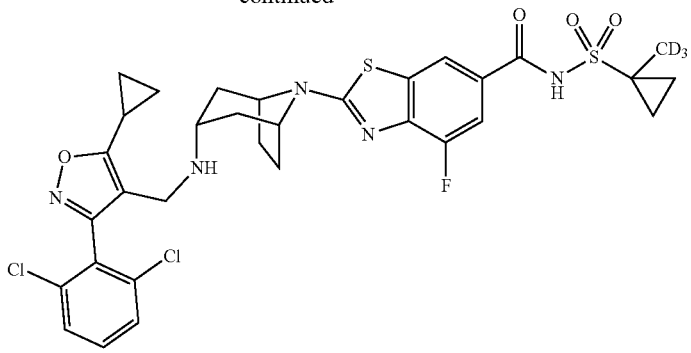

Example 296

To 2-((1R,3R,5S)-3-(((5-cyclopropyl-3-(2,6-dichlorophenyl)isoxazol-4-yl)methyl)amino)-8-azabicyclo[3.2.1]octan-8-yl)-4-fluorobenzo[d]thiazole-6-carboxylic acid (Example 4) (42 mg, 0.071 mmol) and 1-(methyl-d3)cyclopropane-1-sulfonamide (14.82 mg, 0.107 mmol) in DCM (1 ml) was added EDCI (21.93 mg, 0.114 mmol) and DMAP (17.47 mg, 0.143 mmol). The resulting mixture was stirred at RT for 16 h, and then concentrated under vacuo. The residue was purified by CombiFlash eluting with DCM to 50% acetone/DCM to give Example 296 (29.2 mg). LC/MS observed [M+H], 707.17.

The following examples listed in Table 8 were prepared from the corresponding acids and sulfonamides following the analogous procedures described as in step 296-c for the synthesis of Example 296.

TABLE 8

| Example # | Structure | MS Data |
|---|---|---|
| 279 | 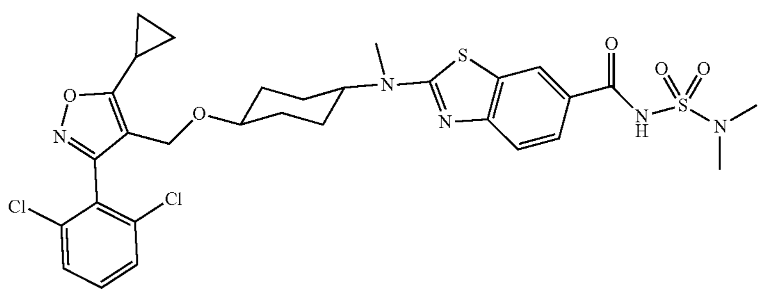 [SMILES: CN(c1nc2ccc(C(=O)NS(=O)(=O)N(C)C)cc2s1)C1CCC(OCc2c(-c3c(Cl)cccc3Cl)noc2C2CC2)CC1] | 678.13 (M + H) |
| 280 | 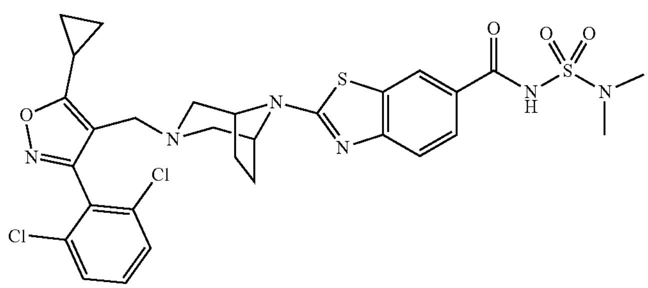 [SMILES: CN(C)S(=O)(=O)NC(=O)c1ccc2nc(N3C4CCC3CN(Cc3c(-c5c(Cl)cccc5Cl)noc3C3CC3)C4)sc2c1] | 661.13 (M + H) |
| 281 | 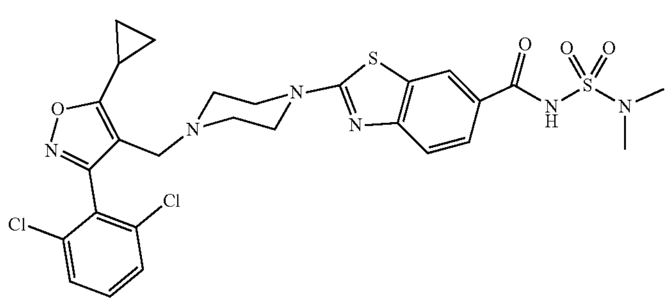 [SMILES: CN(C)S(=O)(=O)NC(=O)c1ccc2nc(N3CCN(Cc4c(-c5c(Cl)cccc5Cl)noc4C4CC4)CC3)sc2c1] | 635.11 (M + H) |

TABLE 8-continued

| Example # | Structure | MS Data |
|---|---|---|
| 282 | 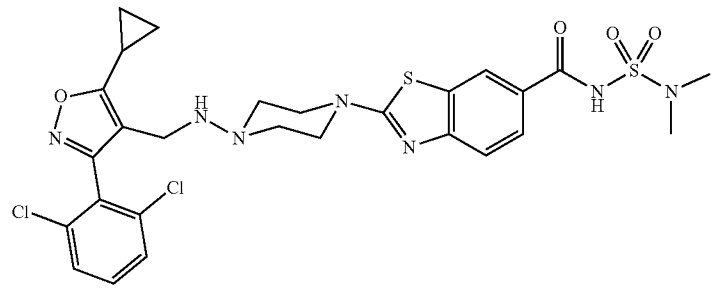 [SMILES: CN(C)S(=O)(=O)NC(=O)c1ccc2nc(N3CCN(NCc4c(-c5c(Cl)cccc5Cl)noc4C4CC4)CC3)sc2c1] | 649.12 (M + H) |
| 283 | 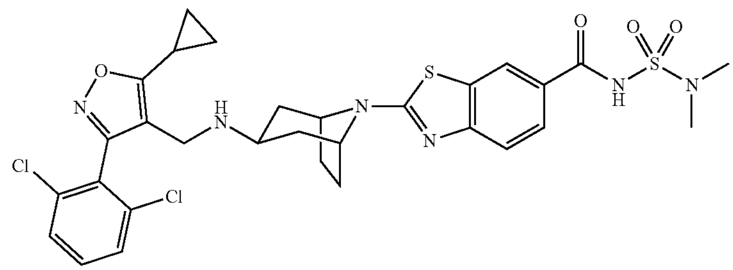 [SMILES: CN(C)S(=O)(=O)NC(=O)c1ccc2nc(N3C4CCC3CC(NCc3c(-c5c(Cl)cccc5Cl)noc3C3CC3)C4)sc2c1] | 675.13 (M + H) |
| 284 | 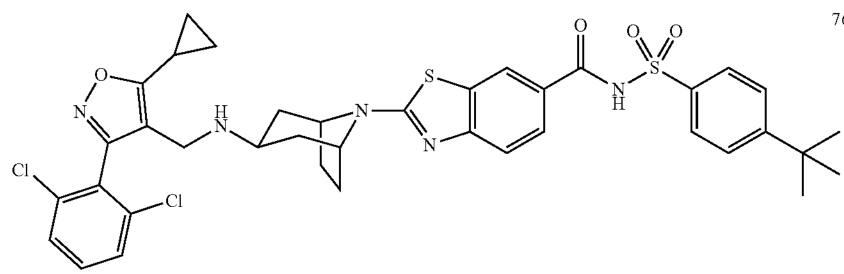 [SMILES: CC(C)(C)c1ccc(S(=O)(=O)NC(=O)c2ccc3nc(N4C5CCC4CC(NCc4c(-c6c(Cl)cccc6Cl)noc4C4CC4)C5)sc3c2)cc1] | 764.18 (M + H) |
| 285 | 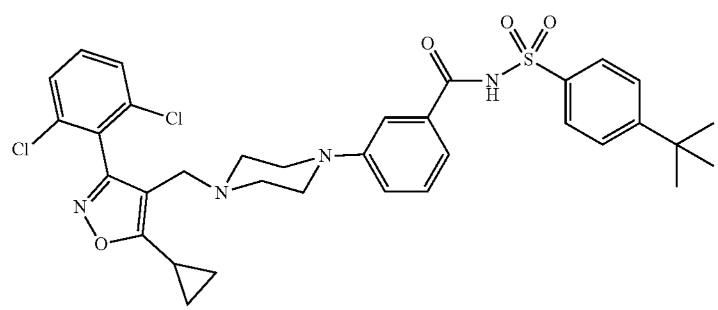 [SMILES: CC(C)(C)c1ccc(S(=O)(=O)NC(=O)c2cccc(N3CCN(Cc4c(-c5c(Cl)cccc5Cl)noc4C4CC4)CC3)c2)cc1] | 667.19 (M + H) |
| 291 | 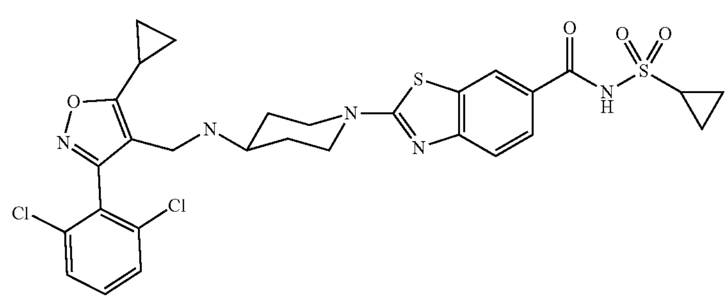 [SMILES: O=C(NS(=O)(=O)C1CC1)c1ccc2nc(N3CCC(NCc4c(-c5c(Cl)cccc5Cl)noc4C4CC4)CC3)sc2c1] | 646.11 (M + H) |

TABLE 8-continued
| Example # | Structure | MS Data |
|---|---|---|
| 295 | 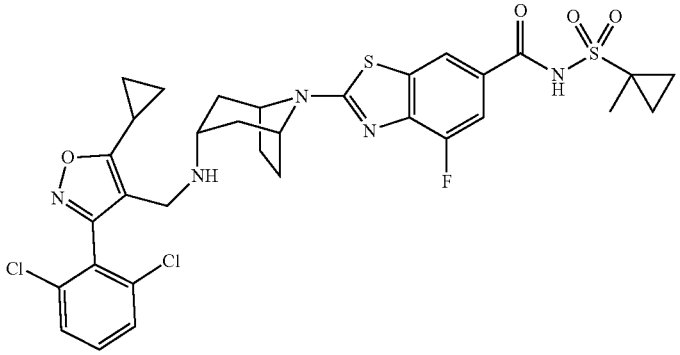 [SMILES: CC1(S(=O)(=O)NC(=O)c2cc(F)c3nc(N4C5CCC4CC(NCc4c(-c6c(Cl)cccc6Cl)noc4C4CC4)C5)sc3c2)CC1] | 704.15 (M + 1) |
| 297 | 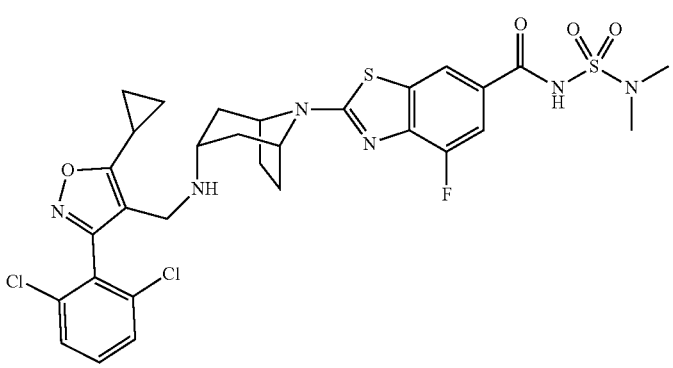 [SMILES: CN(C)S(=O)(=O)NC(=O)c1cc(F)c2nc(N3C4CCC3CC(NCc3c(-c5c(Cl)cccc5Cl)noc3C3CC3)C4)sc2c1] | 693.14 (M + H) |
| 298 | 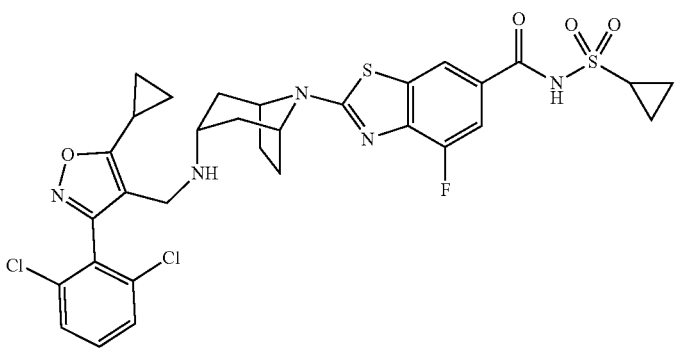 [SMILES: O=C(NS(=O)(=O)C1CC1)c1cc(F)c2nc(N3C4CCC3CC(NCc3c(-c5c(Cl)cccc5Cl)noc3C3CC3)C4)sc2c1] | 690.13 (M + H) |
| 299 | 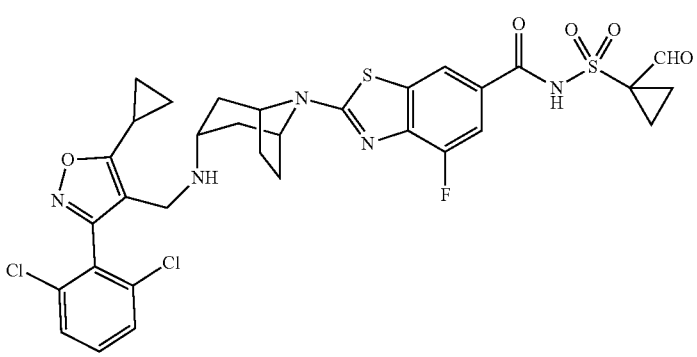 [SMILES: O=CC1(S(=O)(=O)NC(=O)c2cc(F)c3nc(N4C5CCC4CC(NCc4c(-c6c(Cl)cccc6Cl)noc4C4CC4)C5)sc3c2)CC1] | 718.13 (M + H) |

TABLE 8-continued

| Example # | Structure | MS Data |
|---|---|---|
| 300 | 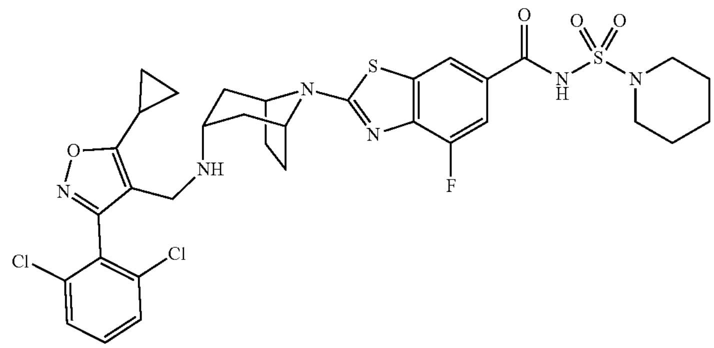 [SMILES: O=C(NS(=O)(=O)N1CCCCC1)c1cc(F)c2nc(N3C4CCC3CC(NCc3c(-c5c(Cl)cccc5Cl)noc3C3CC3)C4)sc2c1] | 733.18 (M + H) |
| 301 | 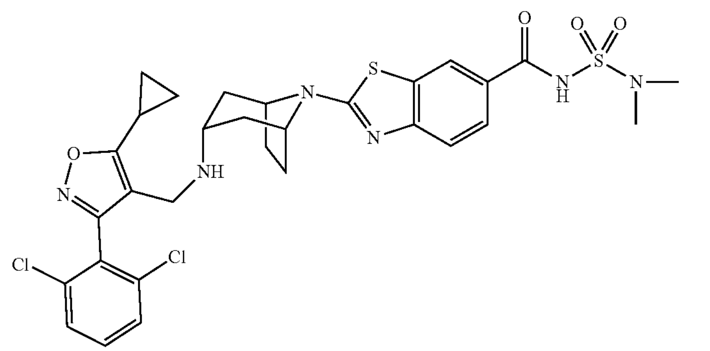 [SMILES: CN(C)S(=O)(=O)NC(=O)c1ccc2nc(N3C4CCC3CC(NCc3c(-c5c(Cl)cccc5Cl)noc3C3CC3)C4)sc2c1] | 657.15 (M − H) |
| 302 | 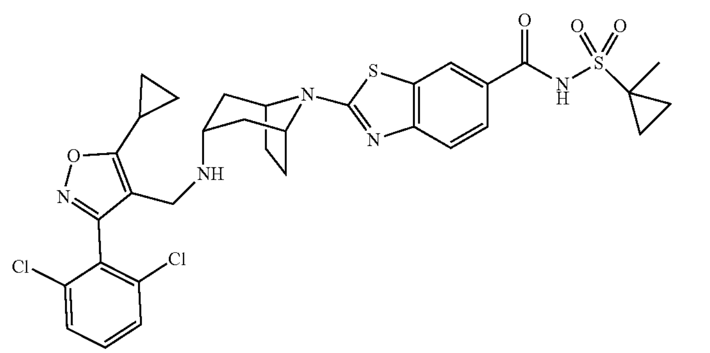 [SMILES: CC1(S(=O)(=O)NC(=O)c2ccc3nc(N4C5CCC4CC(NCc4c(-c6c(Cl)cccc6Cl)noc4C4CC4)C5)sc3c2)CC1] | 668.15 (M − H) |
| 303 | 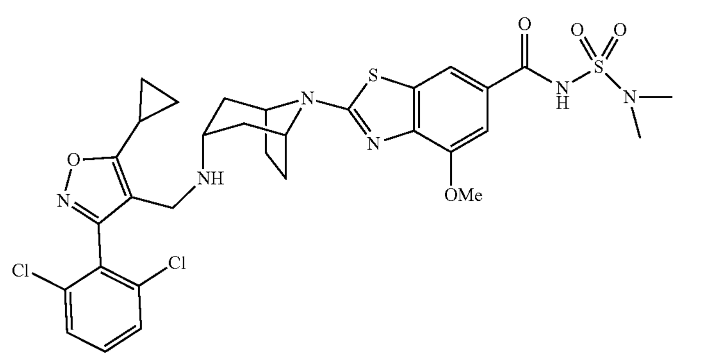 | 716.17 (M + H) |

TABLE 8-continued

| Example # | Structure | MS Data |
|---|---|---|
| 304 | 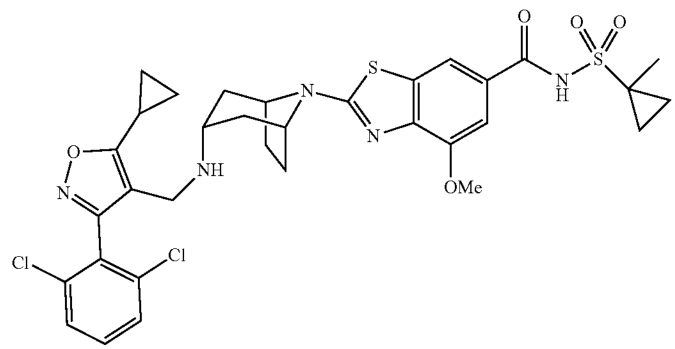 [SMILES: COc1cc(C(=O)NS(=O)(=O)C2(C)CC2)cc2sc(N3C4CCC3CC(NCc3c(-c5c(Cl)cccc5Cl)noc3C3CC3)C4)nc12] | 716.17 (M + H) |
| 305 | 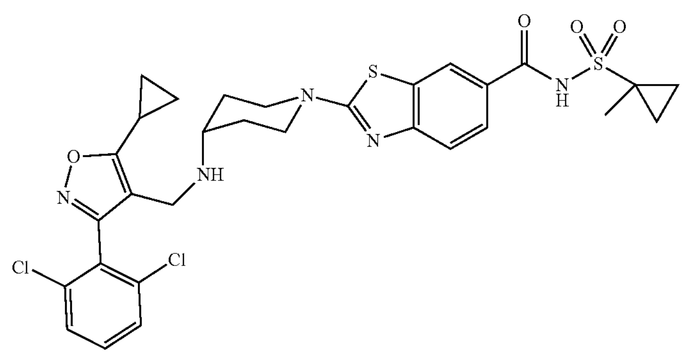 [SMILES: CC1(S(=O)(=O)NC(=O)c2ccc3nc(N4CCC(NCc5c(-c6c(Cl)cccc6Cl)noc5C5CC5)CC4)sc3c2)CC1] | 660.14 (M + H) |

Example 49

A mixture of Pd$_2$(dba)$_3$ (20.42 mg, 0.022 mmol), dicyclohexyl(2',4',6'-triisopropyl-[1,1'-biphenyl]-2-yl)phosphane (XPhos) (21.26 mg, 0.045 mmol), methyl 6-bromo-2-naphthoate (177 mg, 0.669 mmol), cesium carbonate (581 mg, 1.784 mmol) and (1R,3r,5S)—N-((5-cyclopropyl-3-(2,6-dichlorophenyl)isoxazol-4-yl)methyl)-8-azabicyclo[3.2.1]octan-3-amine (175 mg, 0.446 mmol) in toluene (4 ml) was degassed, and then heated to 100° C. under N2 atmosphere. The mixture was stirred for 16 h before cooled down to room temperature. The mixture was diluted with ethyl acetate and filtered through a celite pad. The filtrate was concentrated and the residue was purified by chromatography on silica gel eluting with Hexane to 40% acetone/hexane. The fractions containing Example 49 were combined, concentrated, and further purified by HPLC (0.1% Formic acid in Water/ACN) to give methyl 6-((1R,3R,5S)-3-(((5-cyclopropyl-3-(2,6-dichlorophenyl)isoxazol-4-yl)methyl)amino)-8-azabicyclo[3.2.1]octan-8-yl)-2-naphthoate (58 mg, 0.101 mmol, 22.55% yield). LC/MS observed [M+H], 576.18.

Example 50

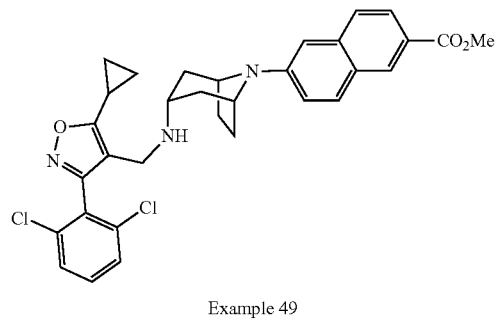

Example 49

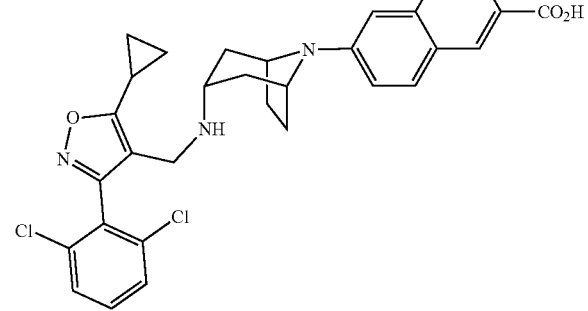

Example 50

Example 50 was prepared according to the analogous procedure as in step 2a described for the preparation of Example 2. LC/MS observed [M+H], 562.17.

Example 85

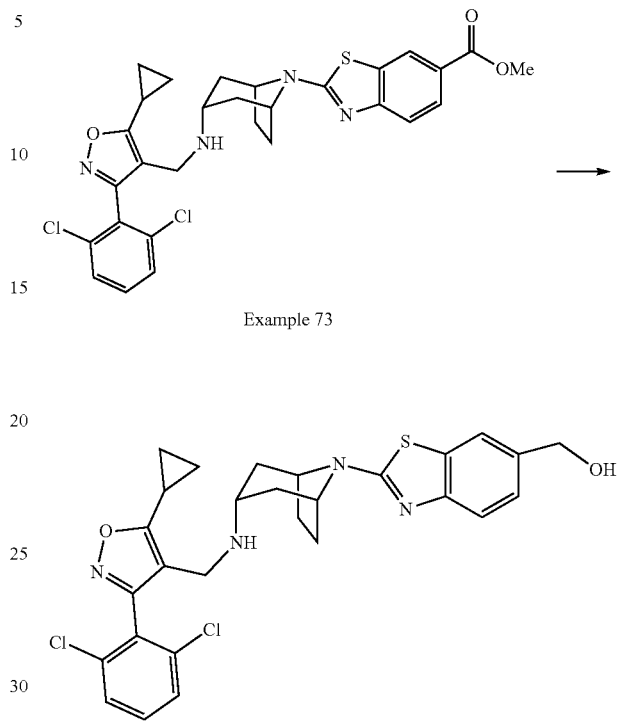

Example 73

Example 85

To methyl 2-((1R,Rr,5S)-3-(((5-cyclopropyl-3-(2,6-dichlorophenyl)isoxazol-4-yl)methyl)amino)-8-azabicyclo[3.2.1]octan-8-yl)benzo[d]thiazole-6-carboxylate (77 mg, 0.132 mmol) in THF (1 ml) was added LAH (0.264 ml, 0.264 mmol, 1 M in THF) at 0° C. The resulting mixture was stirred at 0° C. for 4 h and was then quenched with water, NaHCO$_3$ solution. The mixture was diluted with ethyl acetate and filtered through celite. Organic layer was separated and washed with brine, dried, filtered, and concentrated to Example 85 (68 mg, 0.122 mmol, 93% yield). LC/MS observed [M+H], 555.14.

Example 153

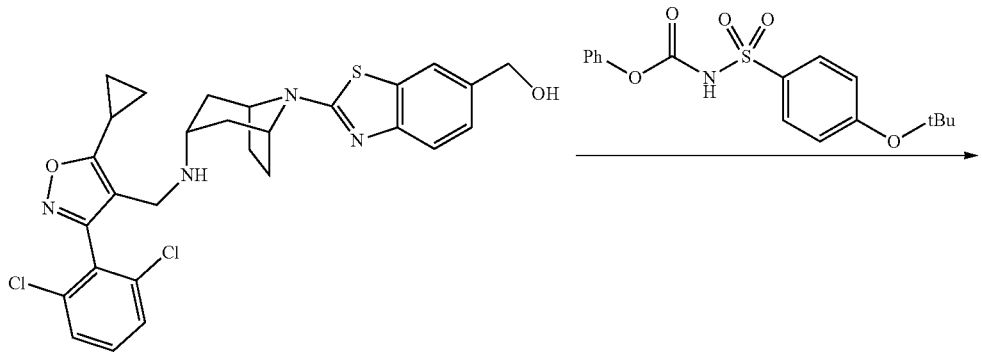

Example 85

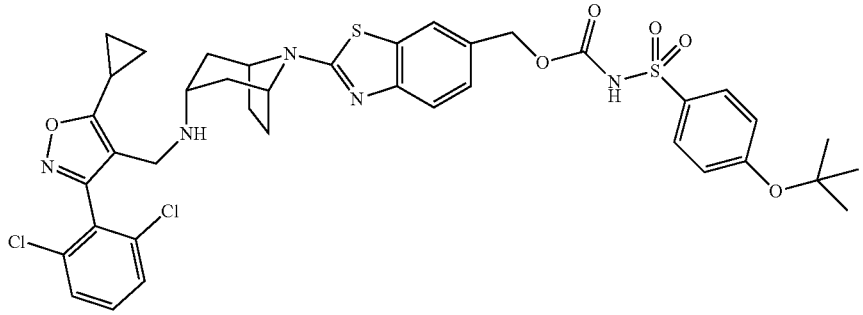

Example 153

To (2-((1R,3R,5S)-3-(((5-cyclopropyl-3-(2,6-dichlorophenyl)isoxazol-4-yl)methyl)amino)-8-azabicyclo[3.2.1]octan-8-yl)benzo[d]thiazol-6-yl)methanol (28 mg, 0.050 mmol) in THF (2 ml) was added triethylamine (0.018 ml, 0.126 mmol), phenyl((4-(tert-butoxy)phenyl) sulfonyl)carbamate (21.13 mg, 0.060 mmol) and DMAP (1.232 mg, 10.08 µmol). The resulting solution was heated up to 50° C. for 16 h. Another portion of phenyl ((4-(tert-butoxy)phenyl) sulfonyl)carbamate (21.13 mg, 0.060 mmol) and DMAP (12 mg) was added and the mixture was stirred at 50° C. for another 4 h. The mixture was concentrated under vacuo and the residue was purified by HPLC (0.1% formic acid in water/ACN) to give Example 153 (11 mg, 0.014 mmol, 26.9% yield). LC/MS observed [M+H], 810.24.

Example 95

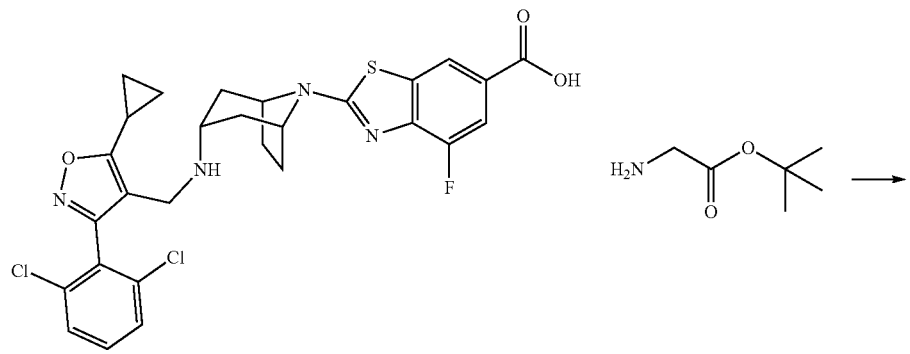

Example 4

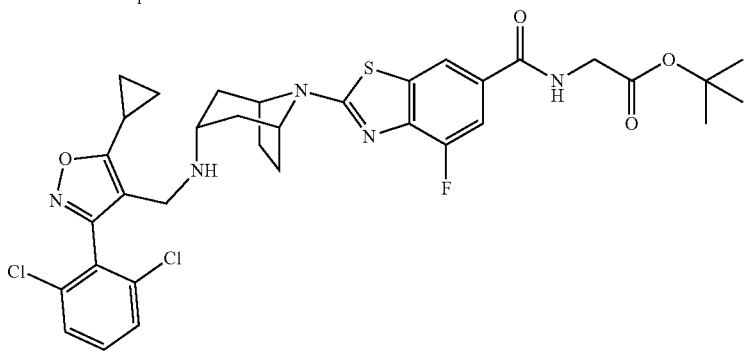

Example 95

To 2-((1R,3R,5S)-3-(((5-cyclopropyl-3-(2,6-dichlorophenyl)isoxazol-4-yl)methyl)amino)-8-azabicyclo[3.2.1]octan-8-yl)-4-fluorobenzo[d]thiazole-6-carboxylic acid (Example 4) (50 mg, 0.085 mmol) and tert-butyl glycinate (16.75 mg, 0.128 mmol) in DCM (1 ml) was added EDC (26.1 mg, 0.136 mmol) and DMAP (20.80 mg, 0.170 mmol). The resulting mixture was stirred at RT for 16 h, and concentrated under vacuo. The residue was purified by CombiFlash eluting with DCM to 40% (10% MeOH in EA) to give Example 95 (31 mg). LC/MS observed [M+H], 700.19.

Example 96

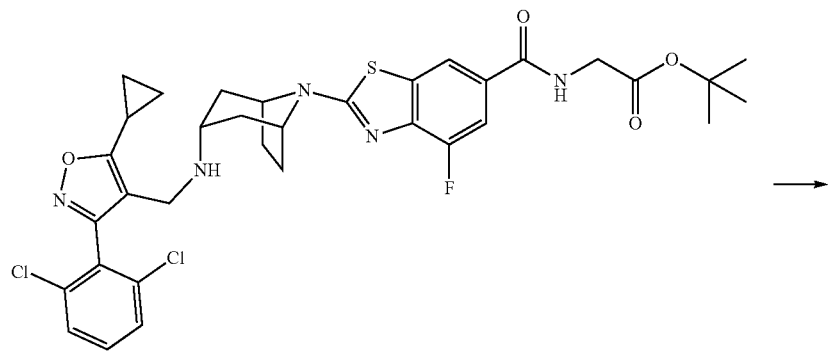

Example 95

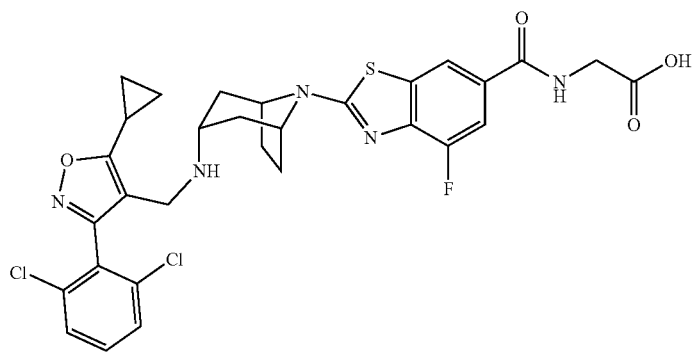

Example 96

To tert-butyl (2-((1R,3r,5S)-3-(((5-cyclopropyl-3-(2,6-dichlorophenyl)isoxazol-4-yl)methyl)amino)-8-azabicyclo[3.2.1]octan-8-yl)-4-fluorobenzo[d]thiazole-6-carbonyl)glycinate (16 mg, 0.023 mmol) in DCM (1 ml) was added HCl (0.228 ml, 0.913 mmol, 4 M in dioxane) and the resulting mixture was stirred at rt for 4 h. The mixture was concentrated under vacuo and chased with DCM to give Example 96 (17 mg). LC/MS observed [M+H], 644.13.

Example 189

Example 189

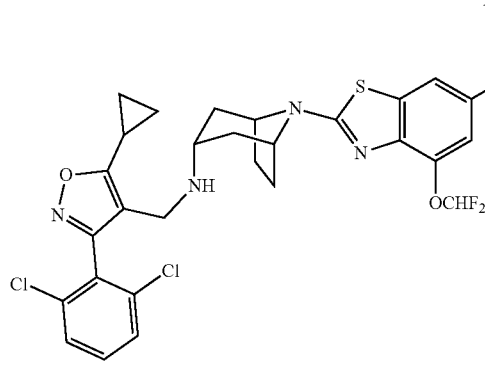

Step 189-a

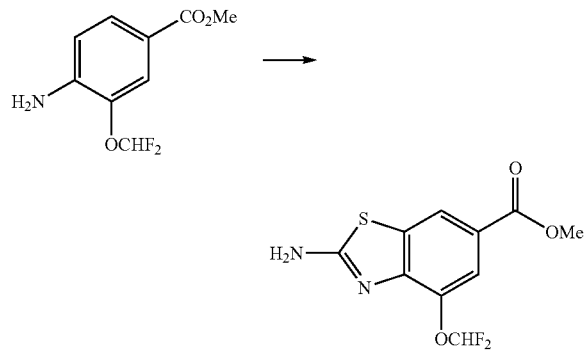

To a solution of sodium thiocyanate (4.78 g, 58.9 mmol) in AcOH (8.67 ml), was added a solution of methyl 4-amino-3-(difluoromethoxy)benzoate (3.2 g, 14.73 mmol) in AcOH (17.34 ml) between 0° C. and rt. Br₂ (0.835 ml, 16.21 mmol) in AcOH (3.47 ml) was added to this mixture dropwise at 0° C. and the resulting mixture was stirred at 0° C. for 15 min. The mixture was allowed to warm up and stirred for 48 h at room temperature. A quarter of reaction mixture was diluted with water (50 ml) and the pH was adjusted to 7 with addition of Na₂CO₃. The resulted yellow slurry was filtered, washed with water and dried under vacuo to give methyl 2-amino-4-(difluoromethoxy)benzo[d]thiazole-6-carboxylate (0.726 g).

Step 189-b

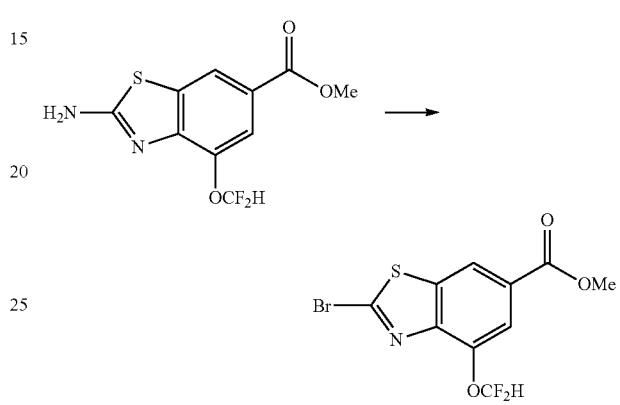

To a suspension of methyl 2-amino-4-(difluoromethoxy)benzo[d]thiazole-6-carboxylate (0.726 g, 2.65 mmol) in acetonitrile (15.57 ml) was added copper(II) bromide (0.887 g, 3.97 mmol). The mixture was cooled down to 0° C. and tert-butyl nitrite (0.734 ml, 6.17 mmol was slowly added) over 10 min. The mixture was warmed up to room temperature and stirred for 15 h. The mixture was diluted with EtOAc (30 ml) and water (20 ml) then filtered through celite. Organic layer was separated and washed with water, brine, dried, filtered, concentrated. The residue was purified by CombiFlash eluting with hexane to 30% EtOAc/hexane to give methyl 2-bromo-4-(difluoromethoxy)benzo[d]thiazole-6-carboxylate (0.4 g) as a white solid. ¹H NMR (400 MHz, Chloroform-d) δ 8.37 (d, J=1.4 Hz, 1H), 7.91 (dt, J=1.5, 0.7 Hz, 1H), 7.03 (t, J=73.6 Hz, 1H), 3.96 (s, 3H).

Step 189-c

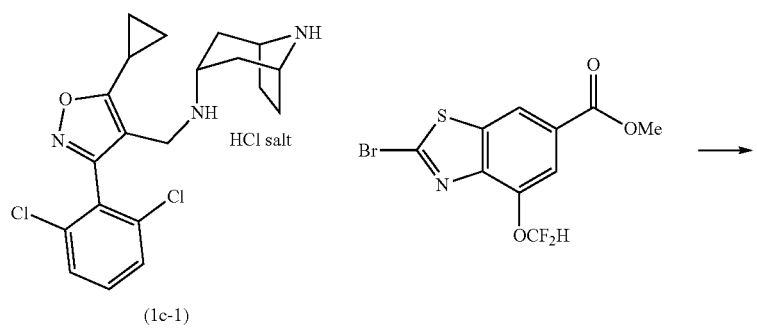

(1c-1)

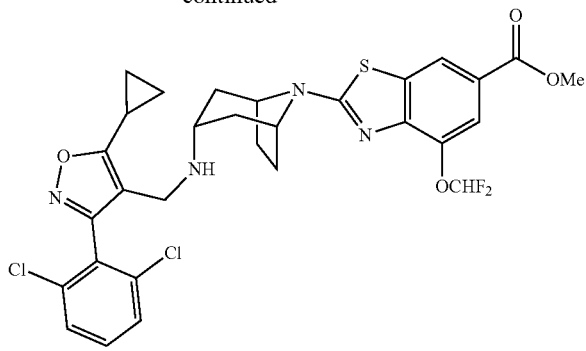

Example 189

Example 189 was prepared from compound (1c-1) and methyl methyl 2-bromo-4-(difluoromethoxy)benzo[d]thiazole-6-carboxylate according to the analogous procedure as in step 1d described for the preparation of Example 1. LC/MS observed [M+H], 649.13.

Example 190

Example 190 was prepared according to the analogous procedure as in step 2a described for the preparation of Example 2. LC/MS observed [M+H], 635.11.

Example 323

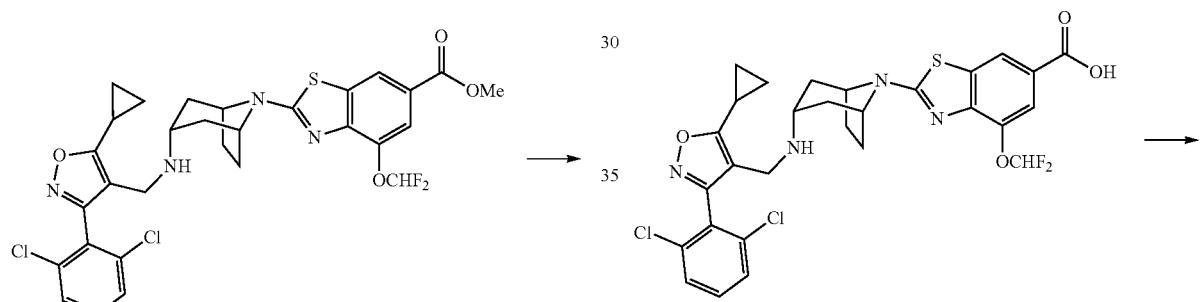

Example 189

Example 190

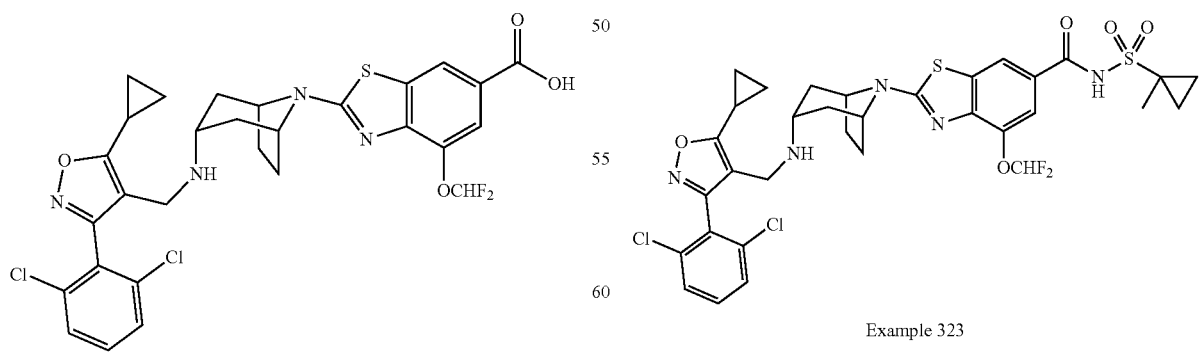

Example 190

Example 323

To 2-(((1R,3r,5S)-3-(((5-cyclopropyl-3-(2,6-dichlorophenyl)isoxazol-4-yl)methyl)amino)-8-azabicyclo[3.2.1]octan-8-yl)-4-(difluoromethoxy)benzo[d]thiazole-6-carboxylic acid (Example 190) (20 m g, 0.031 mmol), DMAP (9.61 mg, 0.079 mmol), and 1-methylcyclopropane-1-sulfonamide (8.51 mg, 0.063 mmol) in DCM (0.629 ml), was added EDC (9.05 mg, 0.047 mmol). The resulting mixture was stirred at rt for 24 h and the volatiles was removed and the residue was purified by HPLC purification (0.1% FA in ACN and water) to give 2-((1R,3r,5S)-3-(((5-cyclopropyl-3-(2,6-dichlorophenyl)isoxazol-4-yl)methyl)amino)-8-azabicyclo[3.2.1]octan-8-yl)-4-(difluoromethoxy)-N-((1-methylcyclopropyl)sulfonyl)benzo[d]thiazole-6-carboxamide (Example 323) (11 mg). LC/MS observed [M+H], 781.16.

Example 693

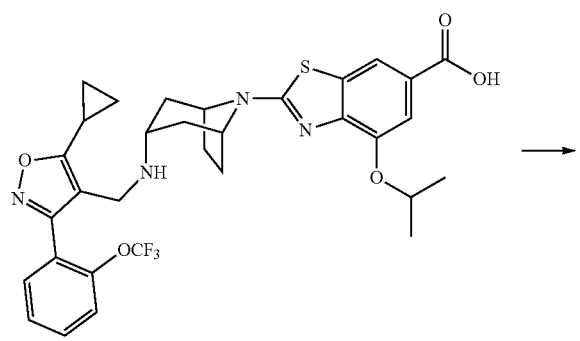

Example 414

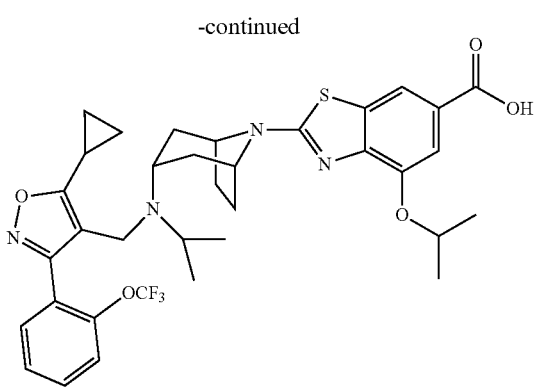

Example 693

To a solution of Example 414 (200 mg, 0.311 mmol) in ACN (1.0 ml) were added acetone (0.12 mL, 1.56 mmol), acetic acid (178 μl, 3.11 mmol) and NaBH$_3$CN (47.8 mg, 0.622 mmol) at 0° C. The resulting mixture was stirred at 0° C. to room temperature for 16 h. Additional portions of acetone (0.12 mL, 1.56 mmol), acetic acid (178 μl, 3.11 mmol) and NaBH$_3$CN (47.8 mg, 0.622 mmol) were added and the reaction mixture continued stirring for another 18 h. The reaction mixture was diluted with EtOAc, washed with water (2×), brine, dried (Na$_2$SO$_4$), and concentrated. The crude sample was purified by reverse phase preparative HPLC using water acetonitrile as mobile phase (solvent A: water with 0.5% formic acid; solvent B: acetonitrile with 0.5% formic acid). The desired product was lyophilized to afford Example 693 as a white solid. LC-MS: 685.29 ([M+1].

TABLE 8a

The following examples listed in TABLE 8a werre prepared according to the procedures described for Example 189, Example 190 and Example 323.

| Example | Structure | MS Data |
| --- | --- | --- |
| 7 | 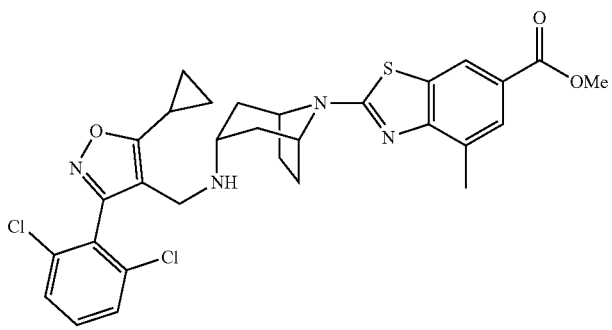 [SMILES: COC(=O)c1cc(C)c2nc(N3C4CCC3CC(NCc3c(-c5c(Cl)cccc5Cl)noc3C3CC3)C4)sc2c1] | 597.15 (M + H) |

TABLE 8a-continued
The following examples listed in TABLE 8a werre prepared according to the procedures described for Example 189, Example 190 and Example 323.
| Example | Structure | MS Data |
|---|---|---|
| 8 | 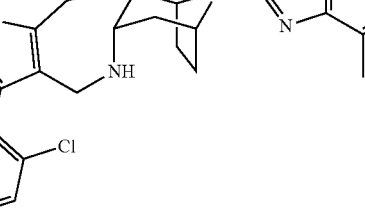 | 583.13 (M + H) |
| 64 | 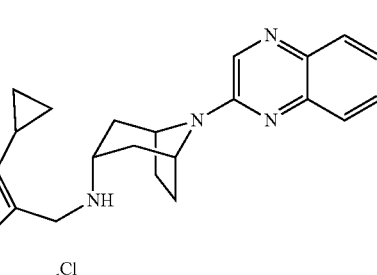 | 578.33 (M + H) |
| 122 | 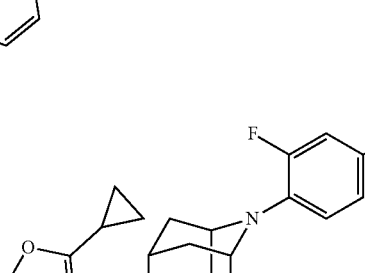 | 530.15 (M + H) |
| 125 | 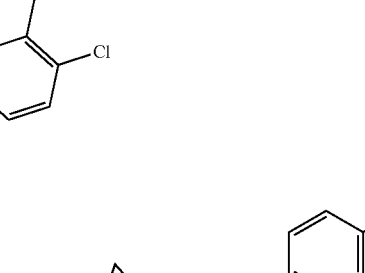 | 513.14 (M + H) |

TABLE 8a-continued

The following examples listed in TABLE 8a werre prepared according to the procedures described for Example 189, Example 190 and Example 323.

| Example | Structure | MS Data |
|---|---|---|
| 194 | 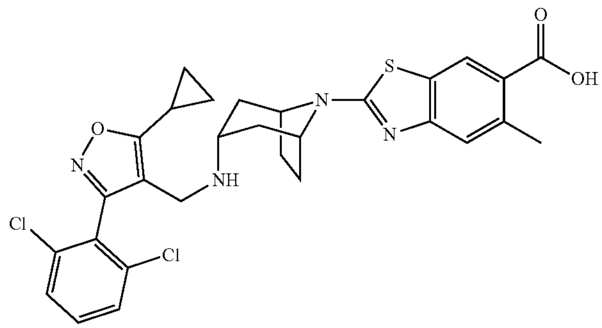 [SMILES: Cc1cc2nc(N3C4CCC3CC(NCc3c(-c5c(Cl)cccc5Cl)noc3C3CC3)C4)sc2cc1C(=O)O] | 583.14 (M + H) |
| 196 | 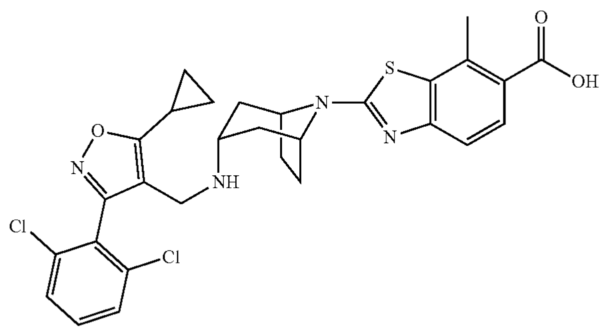 [SMILES: Cc1c(C(=O)O)ccc2nc(N3C4CCC3CC(NCc3c(-c5c(Cl)cccc5Cl)noc3C3CC3)C4)sc12] | 583.14 (M + H) |
| 197 | 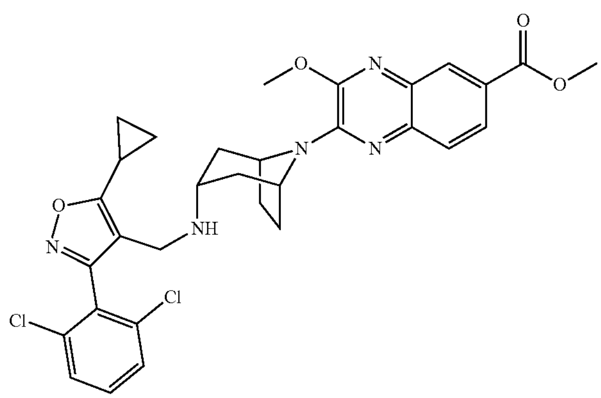 [SMILES: COC(=O)c1ccc2nc(N3C4CCC3CC(NCc3c(-c5c(Cl)cccc5Cl)noc3C3CC3)C4)c(OC)nc2c1] | 608.18 (M + H) |
| 198 | 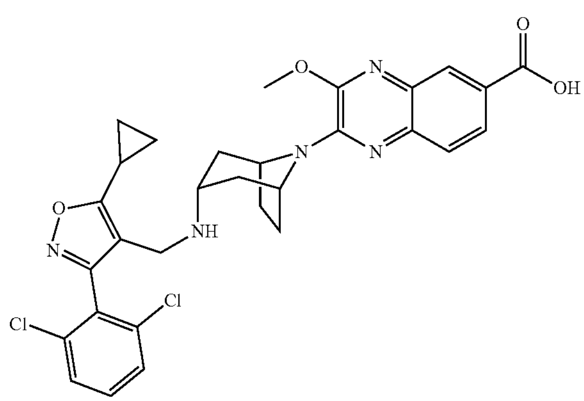 [SMILES: COc1nc2cc(C(=O)O)ccc2nc1N1C2CCC1CC(NCc1c(-c3c(Cl)cccc3Cl)noc1C1CC1)C2] | 594.17 (M + H) |

TABLE 8a-continued
The following examples listed in TABLE 8a werre prepared according to the procedures described for Example 189, Example 190 and Example 323.
| Example | Structure | MS Data |
|---|---|---|
| 199 | 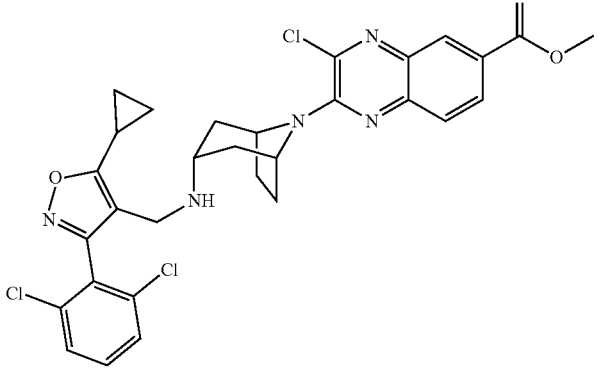 | 614.13 (M + H) |
| 200-1 | 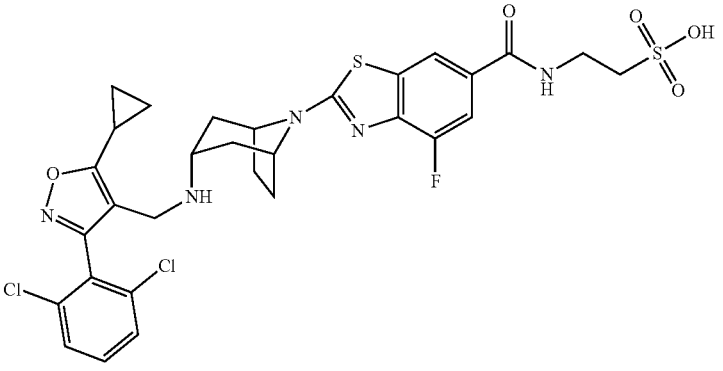 [SMILES: O=C(NCCS(=O)(=O)O)c1cc(F)c2nc(N3C4CCC3CC(NCc3c(-c5c(Cl)cccc5Cl)noc3C3CC3)C4)sc2c1] | 694.11 (M + H) |
| 200-3 | 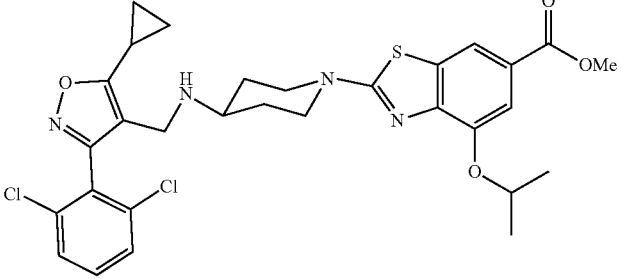 | 615.17 (M + H) |
| 200-4 | 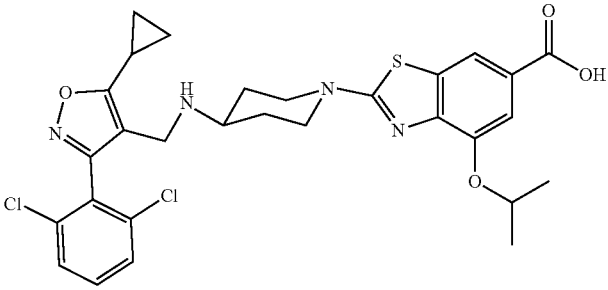 [SMILES: CC(C)Oc1cc(C(=O)O)cc2sc(N3CCC(NCc4c(-c5c(Cl)cccc5Cl)noc4C4CC4)CC3)nc12] | 601.15 (M + H) |

TABLE 8a-continued

The following examples listed in TABLE 8a werre prepared according to the procedures described for Example 189, Example 190 and Example 323.

| Example | Structure | MS Data |
|---|---|---|
| 200-5 | 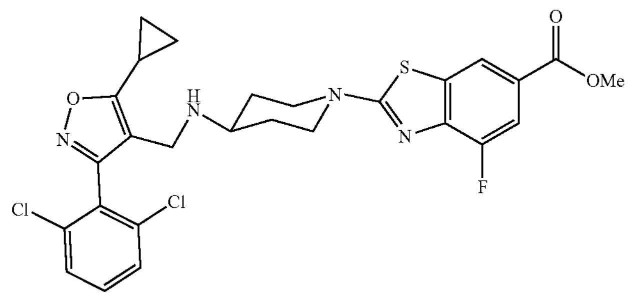 [SMILES: COC(=O)c1cc(F)c2nc(N3CCC(NCc4c(-c5c(Cl)cccc5Cl)noc4C4CC4)CC3)sc2c1] | 575.11 (M + H) |
| 200-6 | 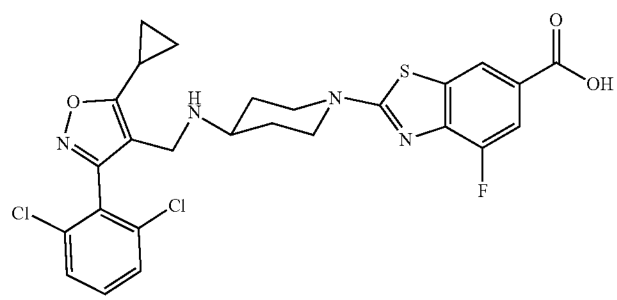 [SMILES: O=C(O)c1cc(F)c2nc(N3CCC(NCc4c(-c5c(Cl)cccc5Cl)noc4C4CC4)CC3)sc2c1] | 561.09 (M + H) |
| 200-7 | 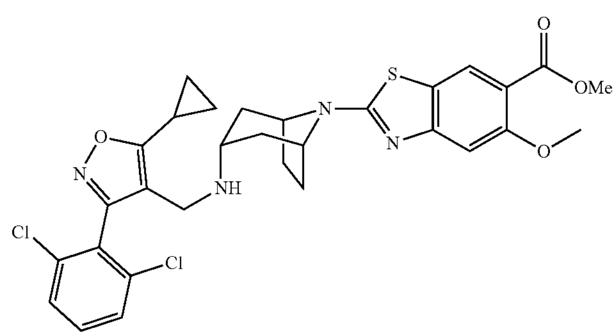 [SMILES: COC(=O)c1cc2sc(N3C4CCC3CC(NCc3c(-c5c(Cl)cccc5Cl)noc3C3CC3)C4)nc2cc1OC] | 613.15 (M + H) |
| 200-8 | 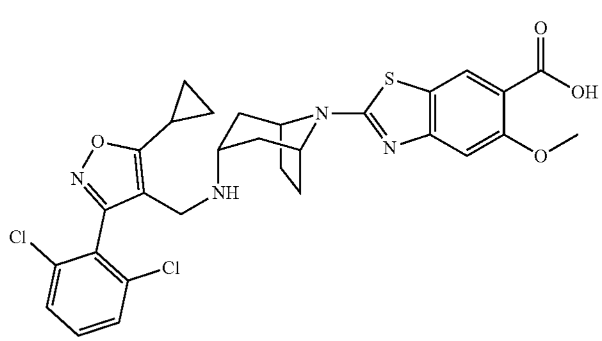 [SMILES: COc1cc2nc(N3C4CCC3CC(NCc3c(-c5c(Cl)cccc5Cl)noc3C3CC3)C4)sc2cc1C(=O)O] | 599.18 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 200-9 | 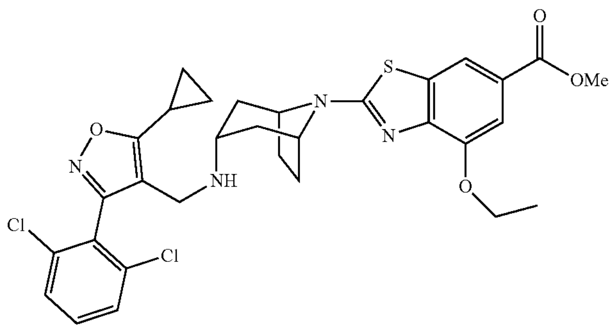 [SMILES: CCOc1cc(C(=O)OC)cc2sc(N3C4CCC3CC(NCc3c(-c5c(Cl)cccc5Cl)noc3C3CC3)C4)nc12] | 627.16 (M + H) |
| 200-10 | 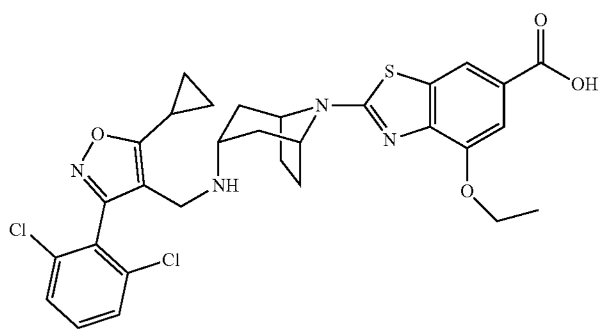 [SMILES: CCOc1cc(C(=O)O)cc2sc(N3C4CCC3CC(NCc3c(-c5c(Cl)cccc5Cl)noc3C3CC3)C4)nc12] | 613.15 (M + H) |
| 200-11 | 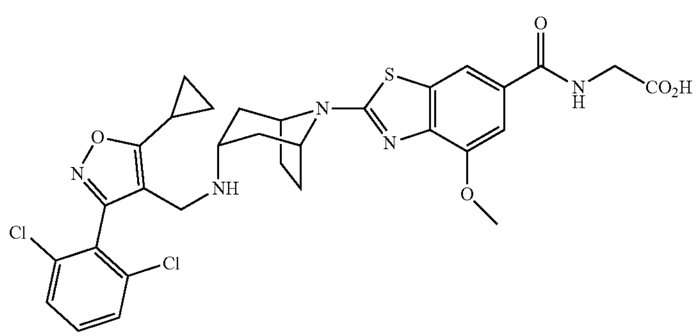 [SMILES: COc1cc(C(=O)NCC(=O)O)cc2sc(N3C4CCC3CC(NCc3c(-c5c(Cl)cccc5Cl)noc3C3CC3)C4)nc12] | 656.15 (M + H) |
| 200-12 | 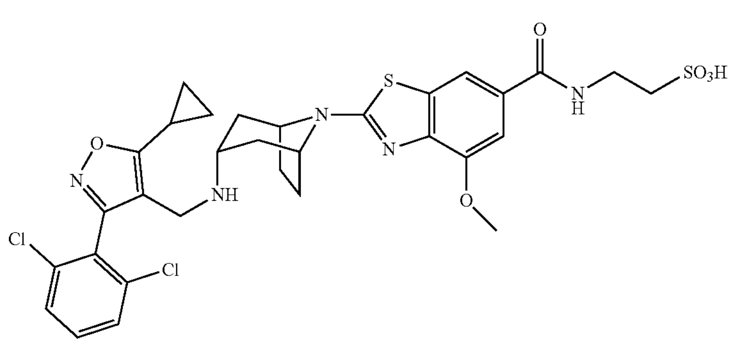 [SMILES: COc1cc(C(=O)NCCS(=O)(=O)O)cc2sc(N3C4CCC3CC(NCc3c(-c5c(Cl)cccc5Cl)noc3C3CC3)C4)nc12] | 706.13 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 200-13 | 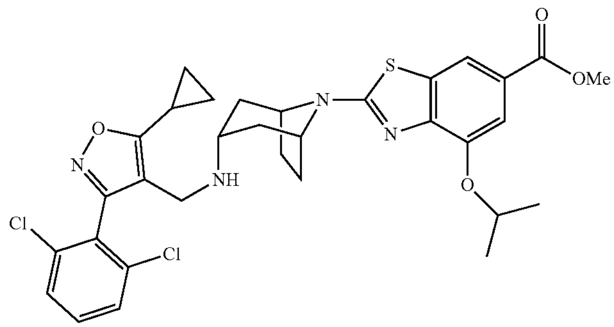 [SMILES: COC(=O)c1cc(OC(C)C)c2nc(N3C4CCC3CC(NCc3c(-c5c(Cl)cccc5Cl)noc3C3CC3)C4)sc2c1] | 641.18 (M + H) |
| 200-14 | 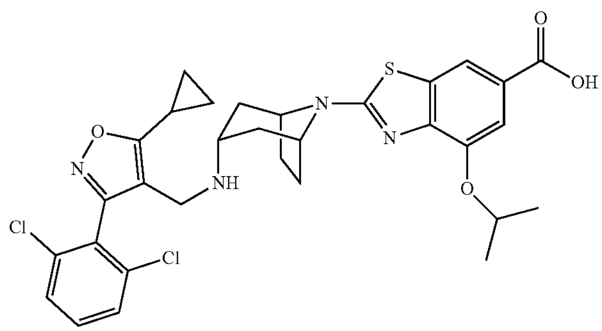 [SMILES: CC(C)Oc1cc(C(=O)O)cc2sc(N3C4CCC3CC(NCc3c(-c5c(Cl)cccc5Cl)noc3C3CC3)C4)nc12] | 627.19 (M + H) |
| 200-15 | 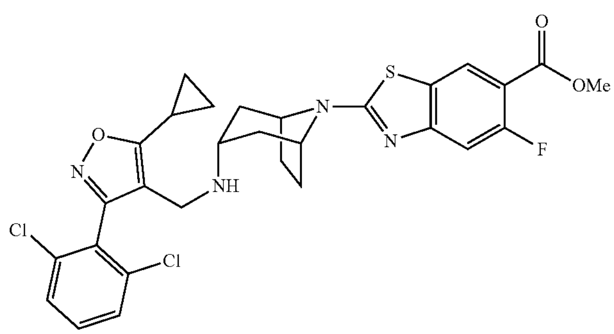 [SMILES: COC(=O)c1cc2sc(N3C4CCC3CC(NCc3c(-c5c(Cl)cccc5Cl)noc3C3CC3)C4)nc2cc1F] | 601.13 (M + H) |
| 200-16 | 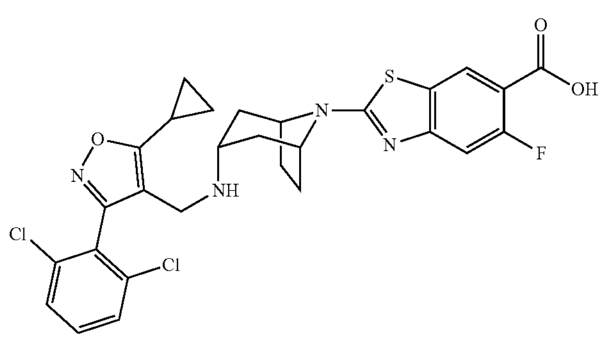 | 587.11 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 200-17 | 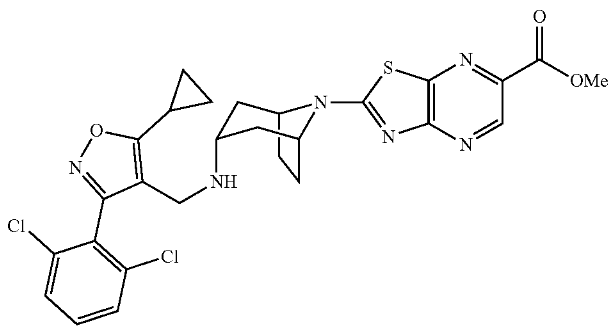 [SMILES: COC(=O)c1cnc2nc(N3C4CCC3CC(NCc3c(-c5c(Cl)cccc5Cl)noc3C3CC3)C4)sc2n1] | 583.13 (M − H) |
| 200-18 | 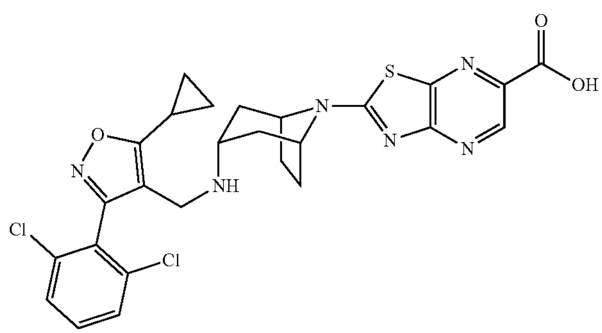 [SMILES: O=C(O)c1cnc2nc(N3C4CCC3CC(NCc3c(-c5c(Cl)cccc5Cl)noc3C3CC3)C4)sc2n1] | 571.11 (M + H) |
| 200-19 | 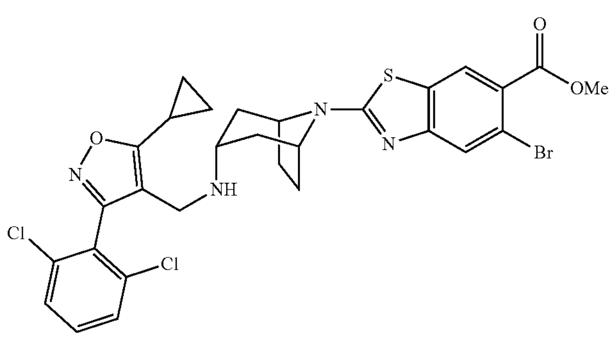 [SMILES: COC(=O)c1cc2sc(N3C4CCC3CC(NCc3c(-c5c(Cl)cccc5Cl)noc3C3CC3)C4)nc2cc1Br] | 663.10 (M + H) |
| 200-21 | 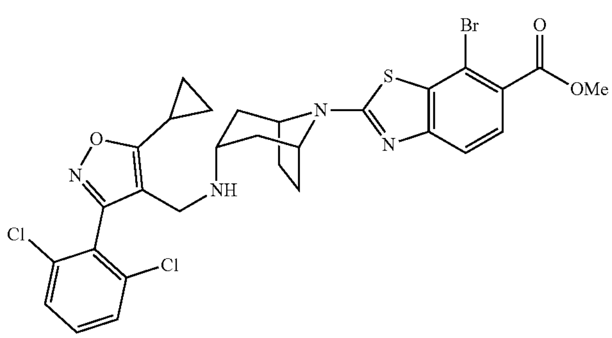 [SMILES: COC(=O)c1ccc2nc(N3C4CCC3CC(NCc3c(-c5c(Cl)cccc5Cl)noc3C3CC3)C4)sc2c1Br] | 663.10, (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 200-23 | 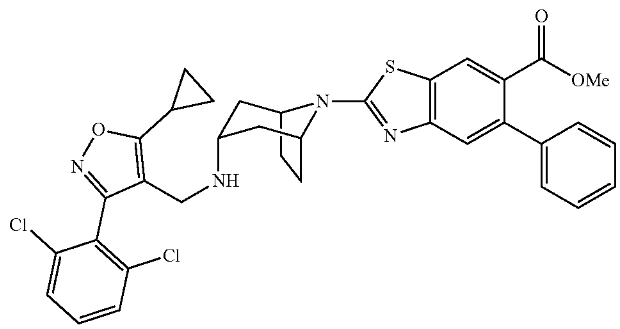 [SMILES: COC(=O)c1cc2sc(N3C4CCC3CC(NCc3c(-c5c(Cl)cccc5Cl)noc3C3CC3)C4)nc2cc1-c1ccccc1] | 659.17 (M + H) |
| 200-24 | 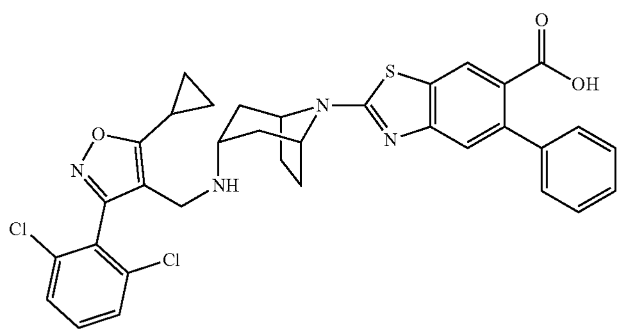 [SMILES: O=C(O)c1cc2sc(N3C4CCC3CC(NCc3c(-c5c(Cl)cccc5Cl)noc3C3CC3)C4)nc2cc1-c1ccccc1] | 645.15 (M + H) |
| 200-25 | 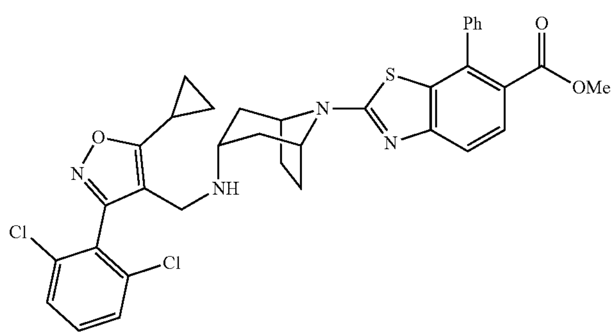 [SMILES: COC(=O)c1ccc2nc(N3C4CCC3CC(NCc3c(-c5c(Cl)cccc5Cl)noc3C3CC3)C4)sc2c1-c1ccccc1] | 659.17 (M + H) |
| 200-27 | 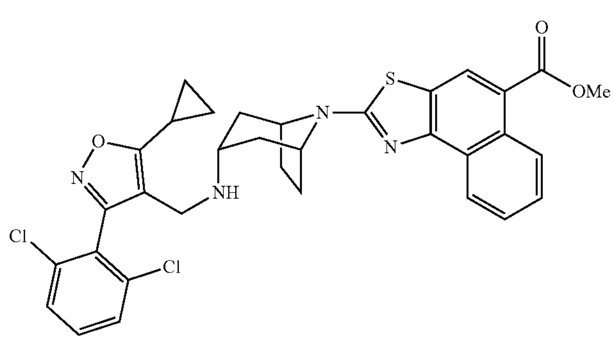 [SMILES: COC(=O)c1cc2sc(N3C4CCC3CC(NCc3c(-c5c(Cl)cccc5Cl)noc3C3CC3)C4)nc2c2ccccc12] | 633.15 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 200-28 | 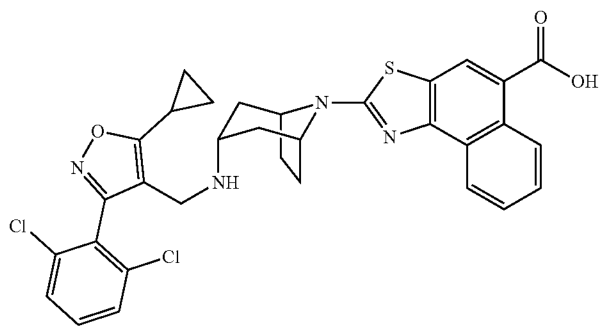 [SMILES: O=C(O)c1cc2sc(N3C4CCC3CC(NCc3c(-c5c(Cl)cccc5Cl)noc3C3CC3)C4)nc2c2ccccc12] | 619.13 (M + H) |
| 200-29 | 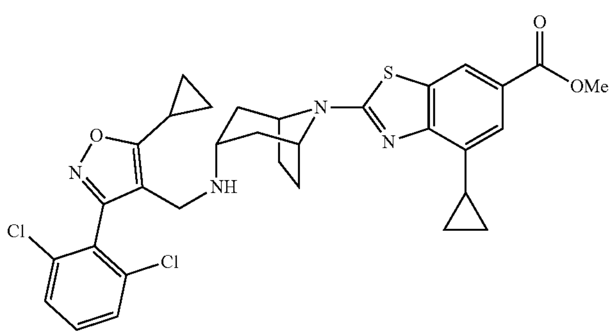 [SMILES: COC(=O)c1cc(C2CC2)c2nc(N3C4CCC3CC(NCc3c(-c5c(Cl)cccc5Cl)noc3C3CC3)C4)sc2c1] | 623.17 (M + H) |
| 200-30 | 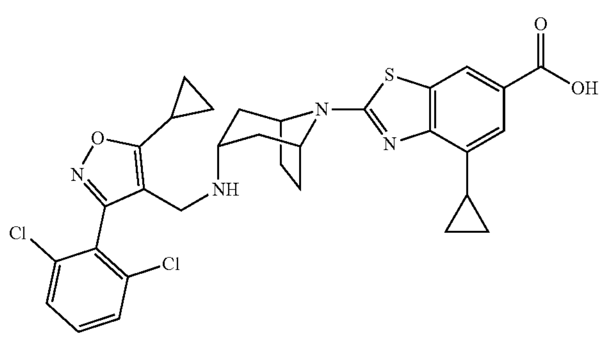 [SMILES: O=C(O)c1cc(C2CC2)c2nc(N3C4CCC3CC(NCc3c(-c5c(Cl)cccc5Cl)noc3C3CC3)C4)sc2c1] | 609.15 (M + H) |
| 323 | 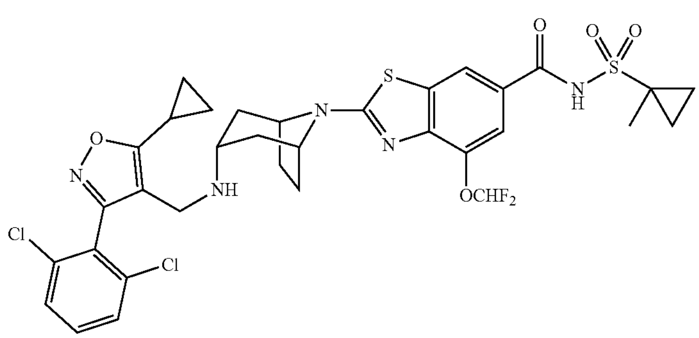 [SMILES: CC1(S(=O)(=O)NC(=O)c2cc(OC(F)F)c3nc(N4C5CCC4CC(NCc4c(-c6c(Cl)cccc6Cl)noc4C4CC4)C5)sc3c2)CC1] | 752.14 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 328 | 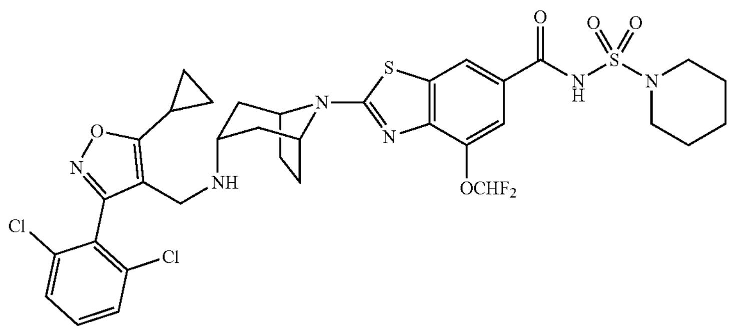 [SMILES: O=C(NS(=O)(=O)N1CCCCC1)c1cc(OC(F)F)c2nc(N3C4CCC3CC(NCc3c(-c5c(Cl)cccc5Cl)noc3C3CC3)C4)sc2c1] | 781.16 (M + H) |
| 342 | 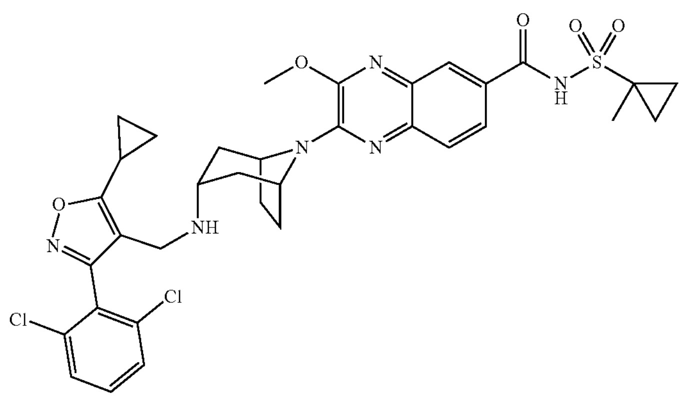 [SMILES: COc1nc2cc(C(=O)NS(=O)(=O)C3(C)CC3)ccc2nc1N1C2CCC1CC(NCc1c(-c3c(Cl)cccc3Cl)noc1C1CC1)C2] | 711.22 (M + H) |
| 400-1 | 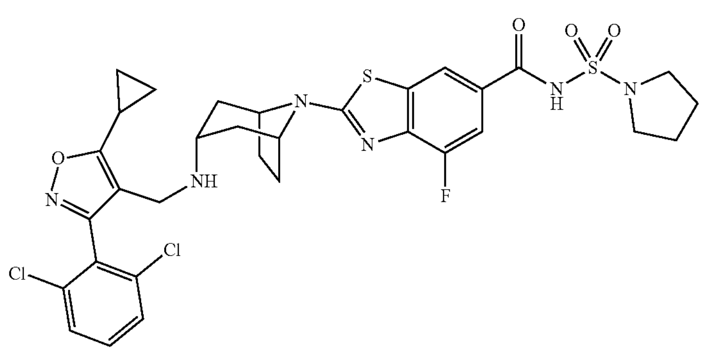 [SMILES: O=C(NS(=O)(=O)N1CCCC1)c1cc(F)c2nc(N3C4CCC3CC(NCc3c(-c5c(Cl)cccc5Cl)noc3C3CC3)C4)sc2c1] | 719.14 (M + H) |
| 400-3 | 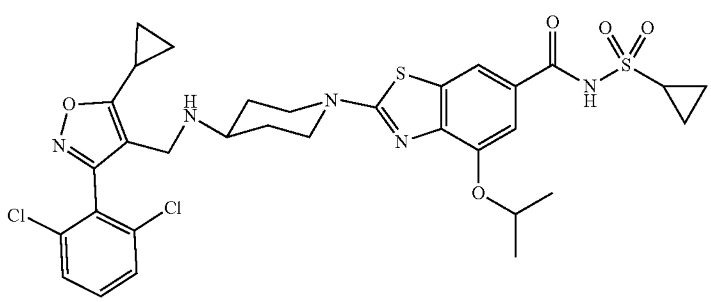 [SMILES: CC(C)Oc1cc(C(=O)NS(=O)(=O)C2CC2)cc2sc(N3CCC(NCc4c(-c5c(Cl)cccc5Cl)noc4C4CC4)CC3)nc12] | 704.17 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 400-4 | 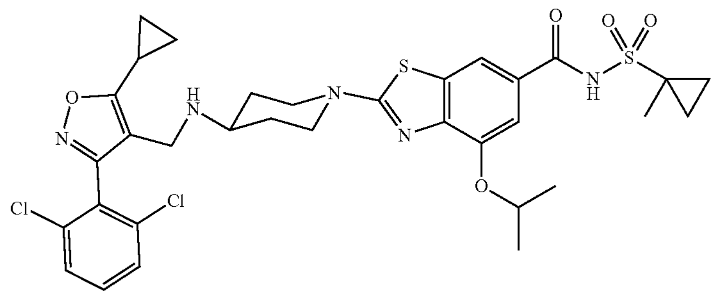 [SMILES: CC(C)Oc1cc(C(=O)NS(=O)(=O)C2(C)CC2)cc2sc(N3CCC(NCc4c(-c5c(Cl)cccc5Cl)noc4C4CC4)CC3)nc12] | 718.19 (M + H) |
| 400-5 | 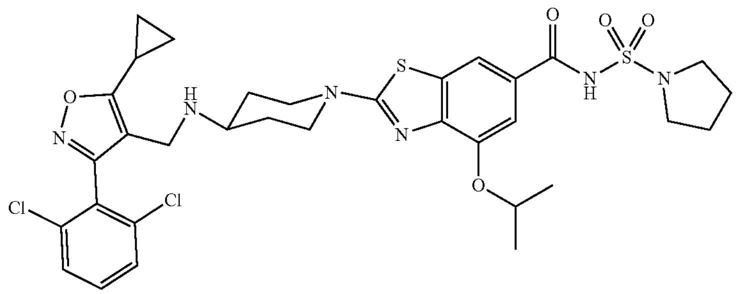 [SMILES: CC(C)Oc1cc(C(=O)NS(=O)(=O)N2CCCC2)cc2sc(N3CCC(NCc4c(-c5c(Cl)cccc5Cl)noc4C4CC4)CC3)nc12] | 733.20 (M + H) |
| 400-6 | 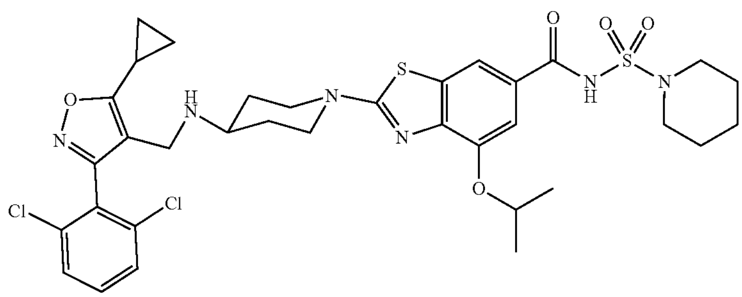 [SMILES: CC(C)Oc1cc(C(=O)NS(=O)(=O)N2CCCCC2)cc2sc(N3CCC(NCc4c(-c5c(Cl)cccc5Cl)noc4C4CC4)CC3)nc12] | 747.22 (M + H) |
| 400-7 | 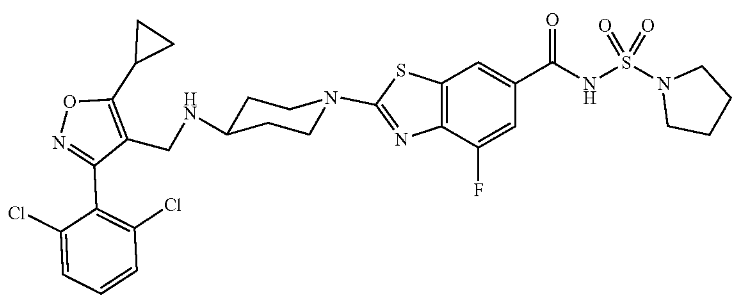 [SMILES: O=C(NS(=O)(=O)N1CCCC1)c1cc(F)c2nc(N3CCC(NCc4c(-c5c(Cl)cccc5Cl)noc4C4CC4)CC3)sc2c1] | 693.15 (M + H) |
| 400-8 | 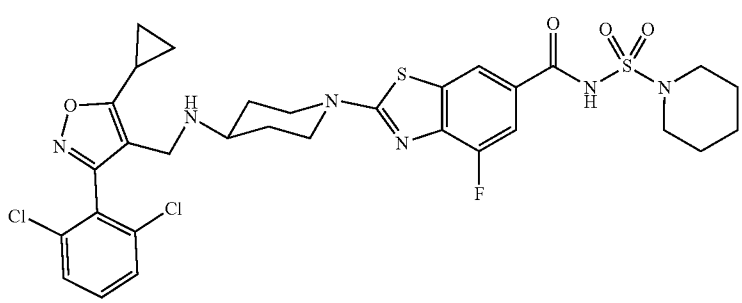 [SMILES: O=C(NS(=O)(=O)N1CCCCC1)c1cc(F)c2nc(N3CCC(NCc4c(-c5c(Cl)cccc5Cl)noc4C4CC4)CC3)sc2c1] | 707.16 (M + H) |

TABLE 8a-continued
The following examples listed in TABLE 8a werre prepared according to the procedures described for Example 189, Example 190 and Example 323.
| Example | Structure | MS Data |
|---|---|---|
| 400-9 | 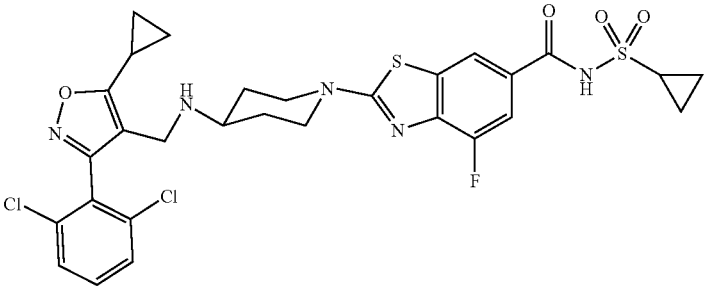 [SMILES: O=C(NS(=O)(=O)C1CC1)c1cc(F)c2nc(N3CCC(NCc4c(-c5c(Cl)cccc5Cl)noc4C4CC4)CC3)sc2c1] | 664.12 (M + H) |
| 400-10 | 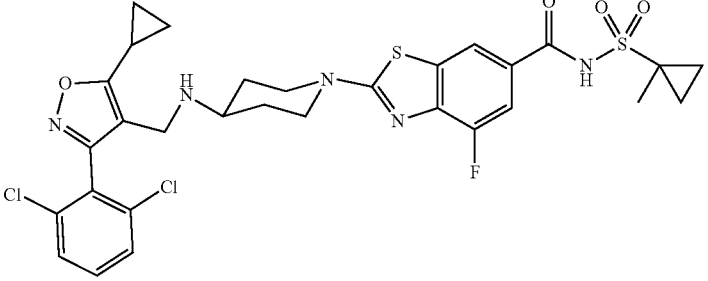 | 678.14 (M + H) |
| 400-11 | 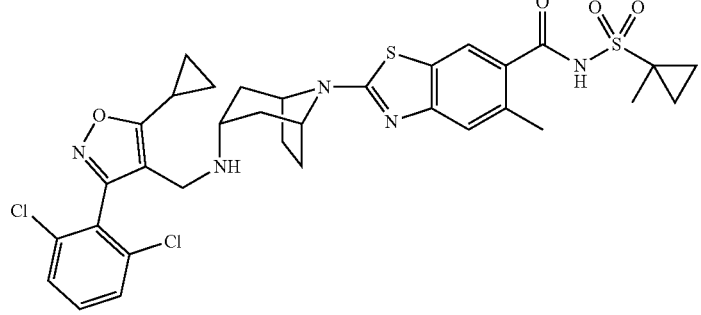 | 700.19 (M + H) |
| 400-12 | 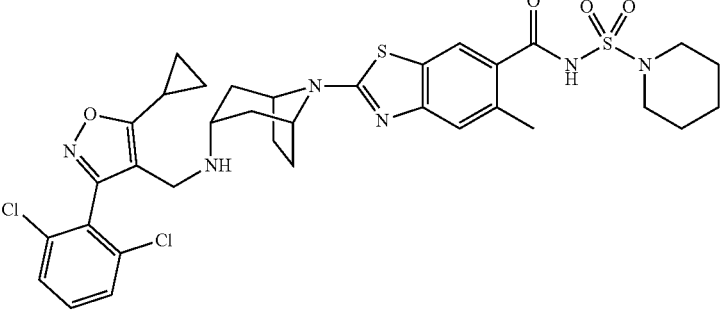 | 729.22 (M + H) |

TABLE 8a-continued

The following examples listed in TABLE 8a werre prepared according to the procedures described for Example 189, Example 190 and Example 323.

| Example | Structure | MS Data |
| --- | --- | --- |
| 400-13 | 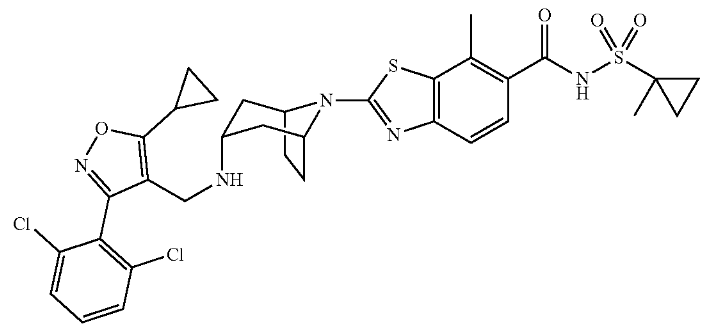 [SMILES: Cc1c(C(=O)NS(=O)(=O)C2(C)CC2)ccc2nc(N3C4CCC3CC(NCc3c(-c5c(Cl)cccc5Cl)noc3C3CC3)C4)sc12] | 700.19 (M + H) |
| 400-14 | 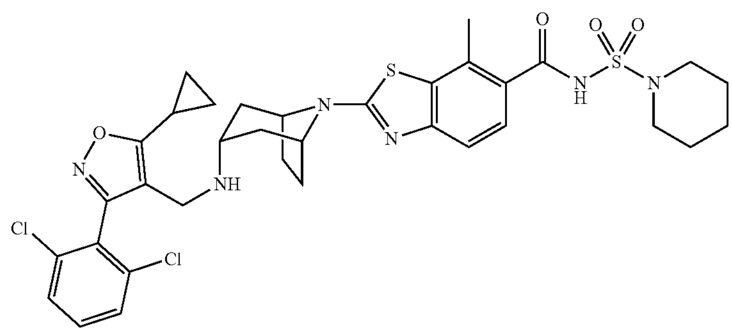 [SMILES: Cc1c(C(=O)NS(=O)(=O)N2CCCCC2)ccc2nc(N3C4CCC3CC(NCc3c(-c5c(Cl)cccc5Cl)noc3C3CC3)C4)sc12] | 729.22 (M + H) |
| 400-15 | 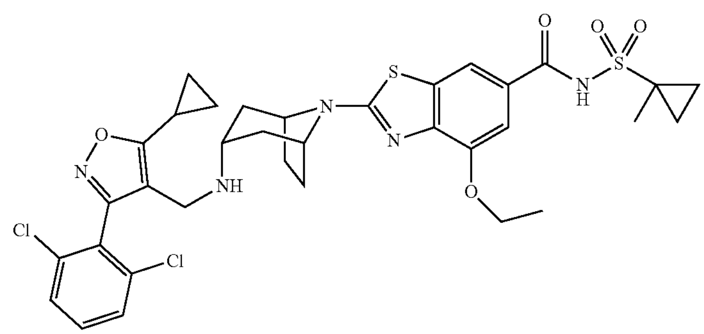 [SMILES: CCOc1cc(C(=O)NS(=O)(=O)C2(C)CC2)cc2sc(N3C4CCC3CC(NCc3c(-c5c(Cl)cccc5Cl)noc3C3CC3)C4)nc12] | 730.17 (M + H) |
| 400-16 | 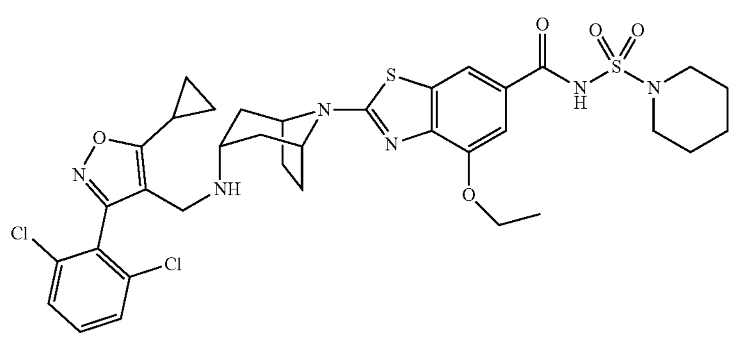 [SMILES: CCOc1cc(C(=O)NS(=O)(=O)N2CCCCC2)cc2sc(N3C4CCC3CC(NCc3c(-c5c(Cl)cccc5Cl)noc3C3CC3)C4)nc12] | 759.20 (M + H) |

TABLE 8a-continued
The following examples listed in TABLE 8a werre prepared according to the procedures described for Example 189, Example 190 and Example 323.
| Example | Structure | MS Data |
|---|---|---|
| 400-18 | 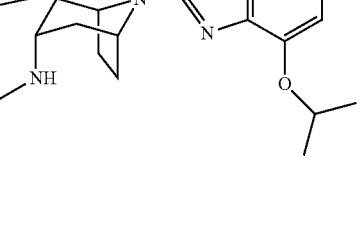 | 744.19 (M + H) |
| 400-20 | 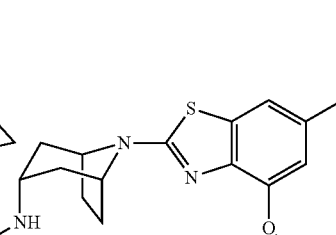 | 773.21 (M + H) |
| 400-22 | 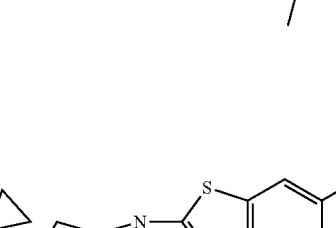 | 704.14 (M + H) |
| 400-24 | 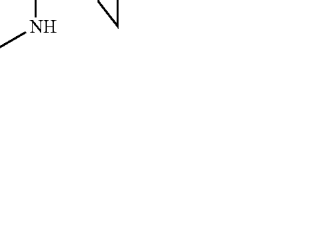 | 733.16 (M + H) |

TABLE 8a-continued
The following examples listed in TABLE 8a werre prepared according to the procedures described for Example 189, Example 190 and Example 323.
| Example | Structure | MS Data |
| --- | --- | --- |
| 400-25 | 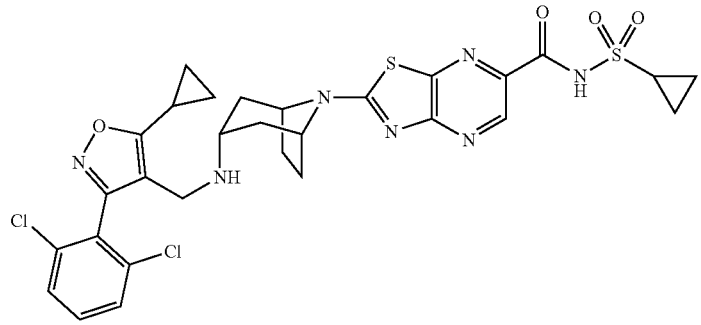 [SMILES: O=C(NS(=O)(=O)C1CC1)c1cnc2nc(N3C4CCC3CC(NCc3c(-c5c(Cl)cccc5Cl)noc3C3CC3)C4)sc2n1] | 674.13 (M + H) |
| 400-26 | 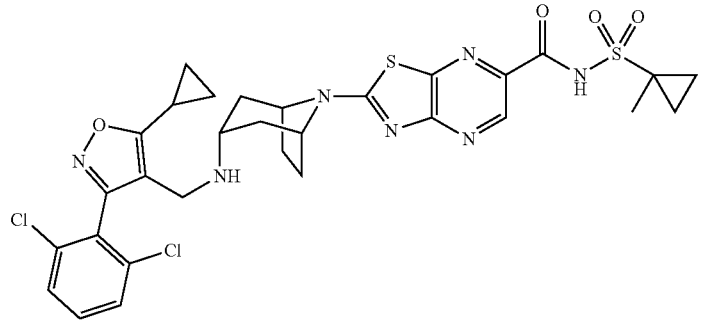 [SMILES: CC1(S(=O)(=O)NC(=O)c2cnc3nc(N4C5CCC4CC(NCc4c(-c6c(Cl)cccc6Cl)noc4C4CC4)C5)sc3n2)CC1] | 688.14 (M + H) |
| 400-29 | 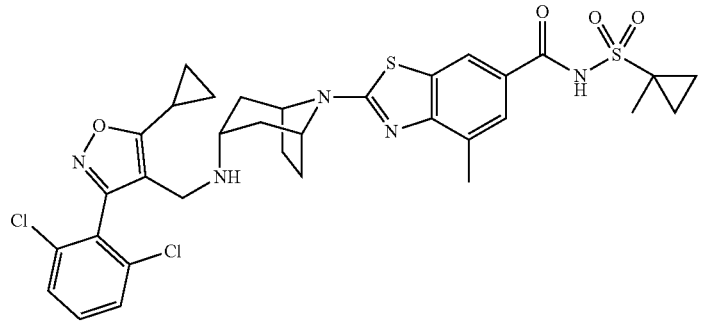 [SMILES: Cc1cc(C(=O)NS(=O)(=O)C2(C)CC2)cc2sc(N3C4CCC3CC(NCc3c(-c5c(Cl)cccc5Cl)noc3C3CC3)C4)nc12] | 700.16 (M + H) |
| 400-32 | 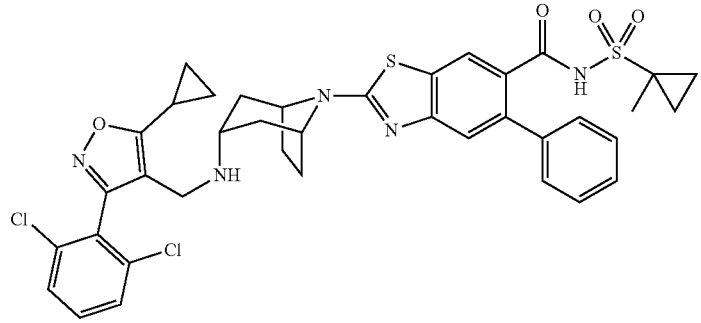 [SMILES: CC1(S(=O)(=O)NC(=O)c2cc3sc(N4C5CCC4CC(NCc4c(-c6c(Cl)cccc6Cl)noc4C4CC4)C5)nc3cc2-c2ccccc2)CC1] | 762.18 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 400-33 | 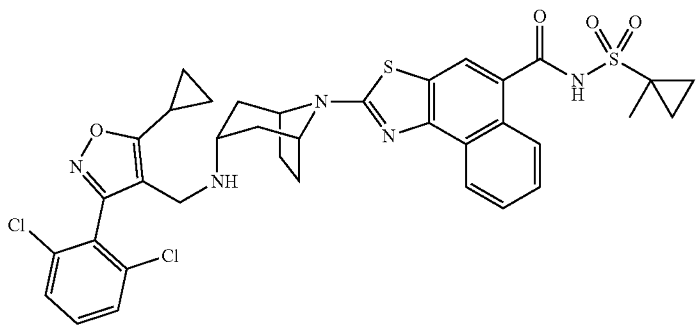 [SMILES: CC1(S(=O)(=O)NC(=O)c2cc3sc(N4C5CCC4CC(NCc4c(-c6c(Cl)cccc6Cl)noc4C4CC4)C5)nc3c3ccccc23)CC1] | 736.16 (M + H) |
| 400-35 | 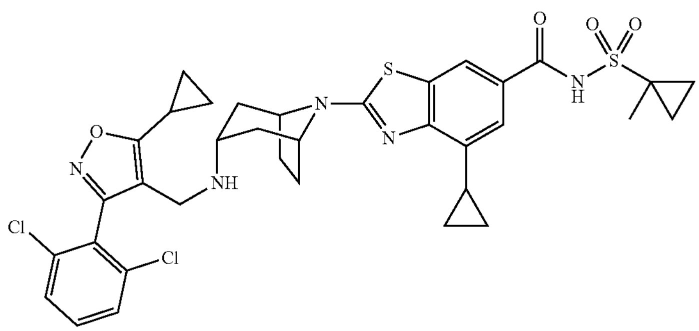 [SMILES: CC1(S(=O)(=O)NC(=O)c2cc(C3CC3)c3nc(N4C5CCC4CC(NCc4c(-c6c(Cl)cccc6Cl)noc4C4CC4)C5)sc3c2)CC1] | 726.19 (M + H) |
| 400-37 | 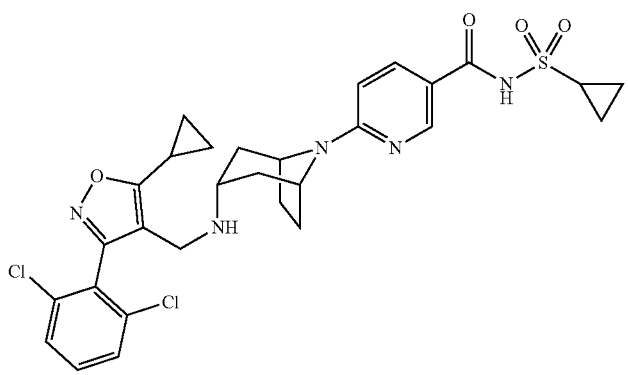 [SMILES: O=C(NS(=O)(=O)C1CC1)c1ccc(N2C3CCC2CC(NCc2c(-c4c(Cl)cccc4Cl)noc2C2CC2)C3)nc1] | 616.16 (M + H) |
| 402 | 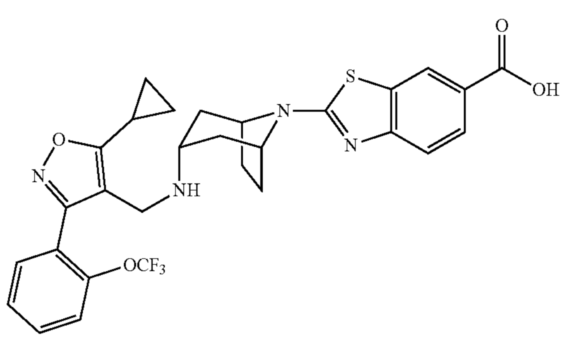 [SMILES: O=C(O)c1ccc2nc(N3C4CCC3CC(NCc3c(-c5ccccc5OC(F)(F)F)noc3C3CC3)C4)sc2c1] | 585.18 (M + H) |

TABLE 8a-continued
The following examples listed in TABLE 8a werre prepared according to the procedures described for Example 189, Example 190 and Example 323.
| Example | Structure | MS Data |
|---|---|---|
| 403 | 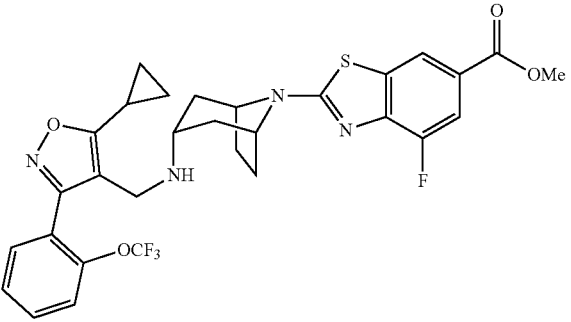 | 617.19 (M + H) |
| 404 | 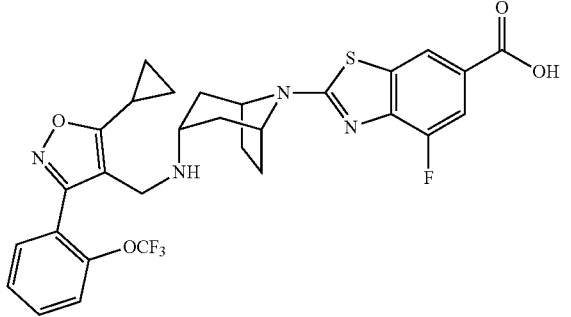 [SMILES: O=C(O)c1cc(F)c2nc(N3C4CCC3CC(NCc3c(-c5ccccc5OC(F)(F)F)noc3C3CC3)C4)sc2c1] | 603.17 (M + H) |
| 413 | 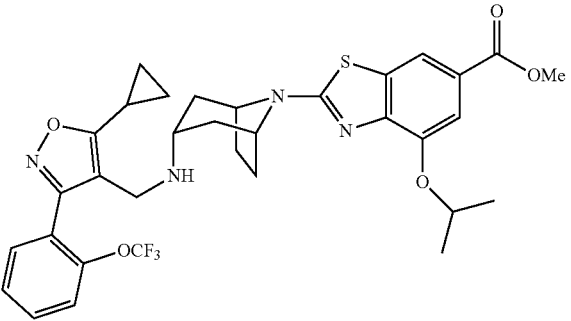 | 657.24 (M + H) |
| 414 | 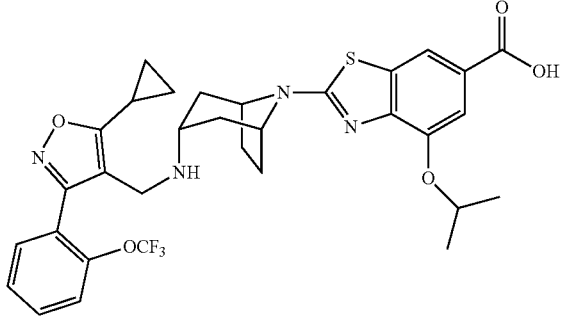 [SMILES: CC(C)Oc1cc(C(=O)O)cc2sc(N3C4CCC3CC(NCc3c(-c5ccccc5OC(F)(F)F)noc3C3CC3)C4)nc12] | 643.22 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 510 | 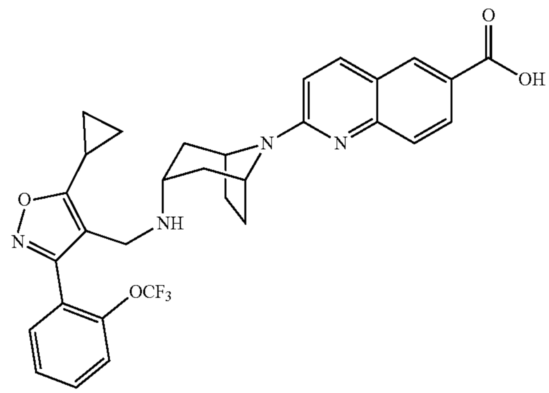 [SMILES: O=C(O)c1ccc2nc(N3C4CCC3CC(NCc3c(-c5ccccc5OC(F)(F)F)noc3C3CC3)C4)ccc2c1] | 587.17 (M + H) |
| 514 | 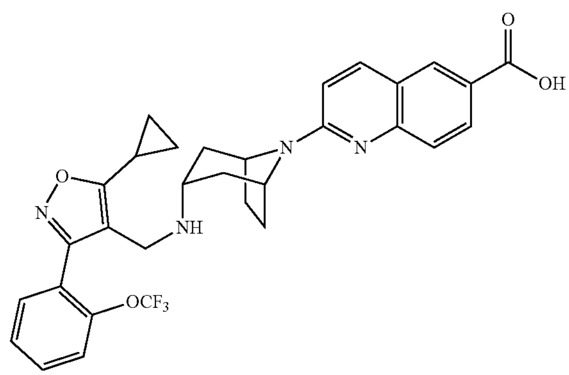 [SMILES: O=C(O)c1ccc2nc(N3C4CCC3CC(NCc3c(-c5ccccc5OC(F)(F)F)noc3C3CC3)C4)ccc2c1] | 579.22 (M + H) |
| 597 | 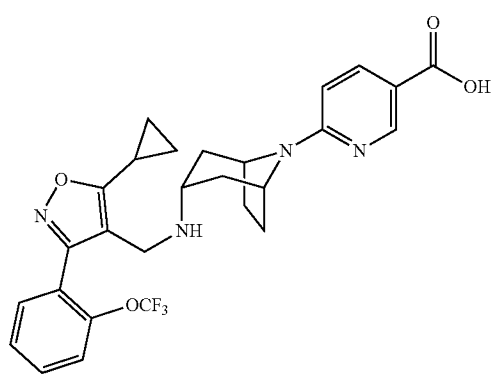 [SMILES: O=C(O)c1ccc(N2C3CCC2CC(NCc2c(-c4ccccc4OC(F)(F)F)noc2C2CC2)C3)nc1] | 528.52 (M + H) |
| 638 | 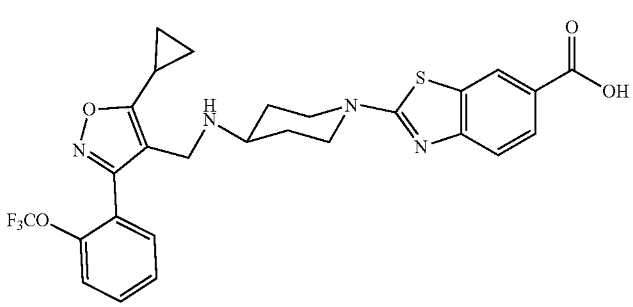 [SMILES: O=C(O)c1ccc2nc(N3CCC(NCc4c(-c5ccccc5OC(F)(F)F)noc4C4CC4)CC3)sc2c1] | 559.16 (M + H) |

US 11,034,684 B2
507                                                                                                                                       508
TABLE 8a-continued
The following examples listed in TABLE 8a werre prepared according to the procedures described for Example 189, Example 190 and Example 323.
| Example | Structure | MS Data |
|---|---|---|
| 639 | 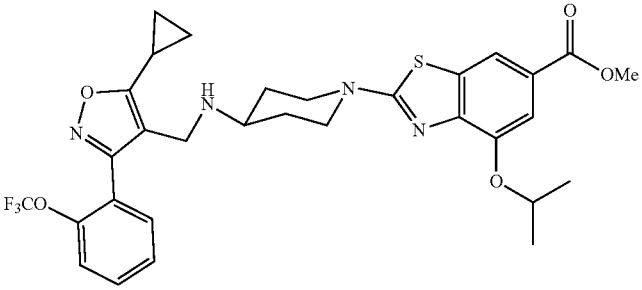 [SMILES: COC(=O)c1cc(OC(C)C)c2nc(N3CCC(NCc4c(-c5ccccc5OC(F)(F)F)noc4C4CC4)CC3)sc2c1] | 631.23 (M + H) |
| 640 | 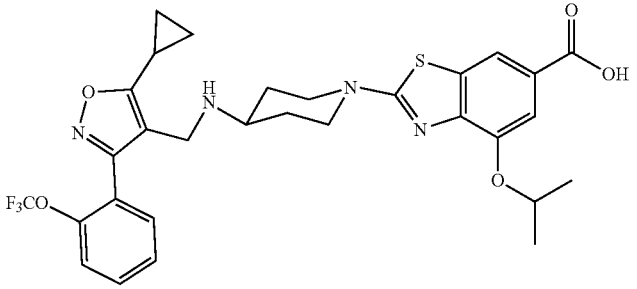 [SMILES: CC(C)Oc1cc(C(=O)O)cc2sc(N3CCC(NCc4c(-c5ccccc5OC(F)(F)F)noc4C4CC4)CC3)nc12] | 617.21 (M + H) |
| 641 | 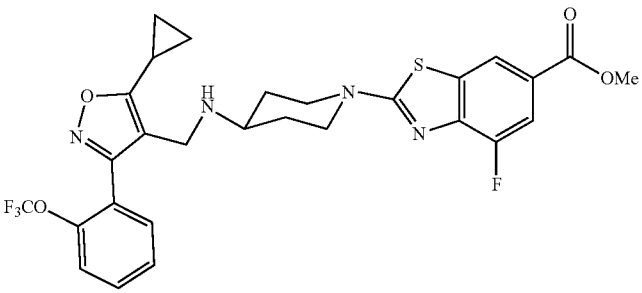 [SMILES: COC(=O)c1cc(F)c2nc(N3CCC(NCc4c(-c5ccccc5OC(F)(F)F)noc4C4CC4)CC3)sc2c1] | 591.17 (M + H) |
| 642 | 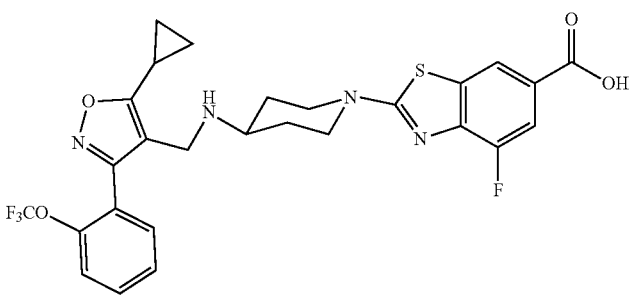 | 577.15 (M + H) |
| 643 | 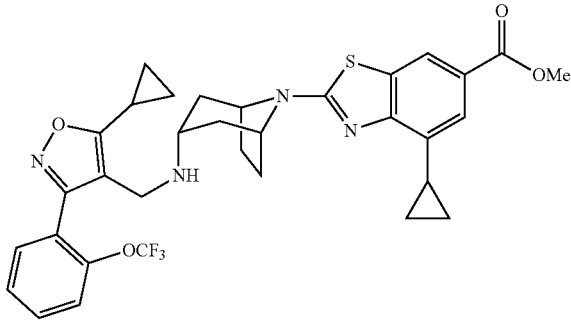 [SMILES: COC(=O)c1cc(C2CC2)c2nc(N3C4CCC3CC(NCc3c(-c5ccccc5OC(F)(F)F)noc3C3CC3)C4)sc2c1] | 639.22 (M + H) |

TABLE 8a-continued

The following examples listed in TABLE 8a werre prepared according to the procedures described for Example 189, Example 190 and Example 323.

| Example | Structure | MS Data |
| --- | --- | --- |
| 644 | 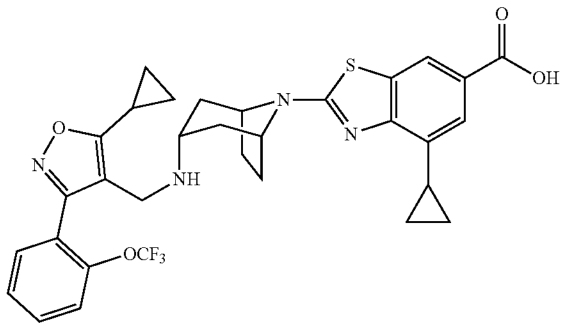 [SMILES: O=C(O)c1cc(C2CC2)c2nc(N3C4CCC3CC(NCc3c(-c5ccccc5OC(F)(F)F)noc3C3CC3)C4)sc2c1] | 625.21 (M + H) |
| 646 | 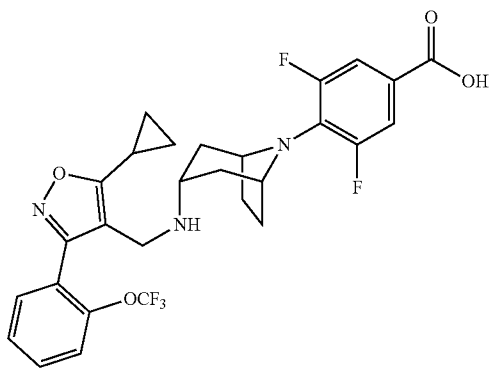 [SMILES: O=C(O)c1cc(F)c(N2C3CCC2CC(NCc2c(-c4ccccc4OC(F)(F)F)noc2C2CC2)C3)c(F)c1] | 564.19 (M + H) |
| 693 | 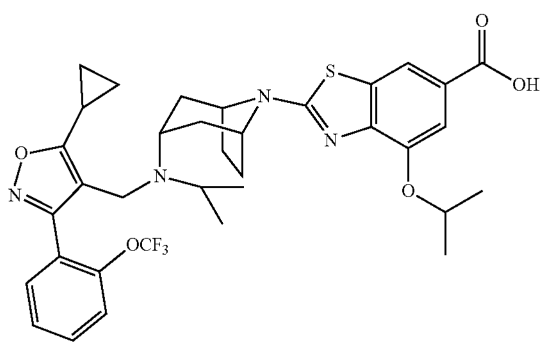 [SMILES: CC(C)Oc1cc(C(=O)O)cc2sc(N3C4CCC3CC(N(Cc3c(-c5ccccc5OC(F)(F)F)noc3C3CC3)C(C)C)C4)nc12] | 685.25 (M + H) |
| 695 | 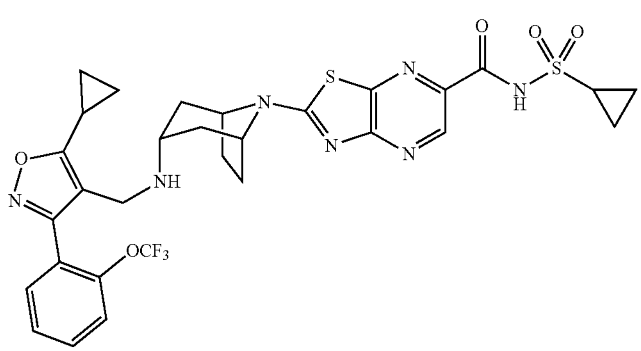 [SMILES: O=C(NS(=O)(=O)C1CC1)c1cnc2nc(N3C4CCC3CC(NCc3c(-c5ccccc5OC(F)(F)F)noc3C3CC3)C4)sc2n1] | 688.16 (M − H) |

TABLE 8a-continued

The following examples listed in TABLE 8a werre prepared according to the procedures described for Example 189, Example 190 and Example 323.

| Example | Structure | MS Data |
|---------|-----------|---------|
| 696 | 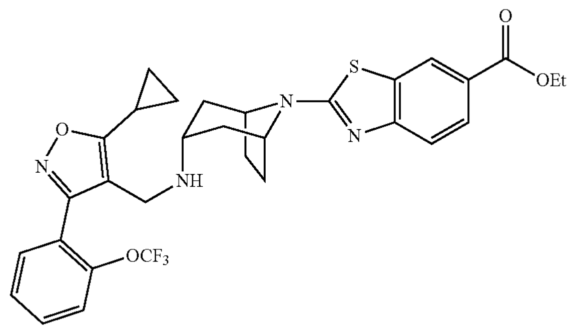 [SMILES: CCOC(=O)c1ccc2nc(N3C4CCC3CC(NCc3c(-c5ccccc5OC(F)(F)F)noc3C3CC3)C4)sc2c1] | 613.21 (M + H) |
| 702 | 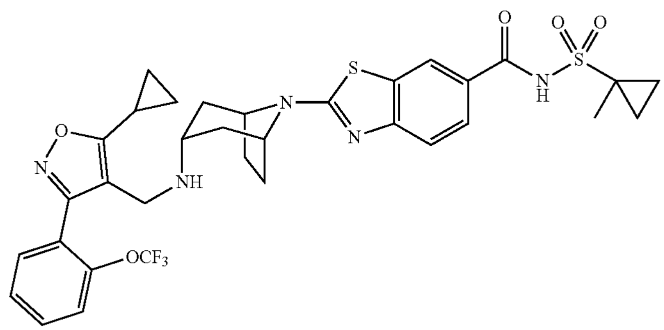 [SMILES: CC1(S(=O)(=O)NC(=O)c2ccc3nc(N4C5CCC4CC(NCc4c(-c6ccccc6OC(F)(F)F)noc4C4CC4)C5)sc3c2)CC1] | 700.45 (M − H) |
| 791 | 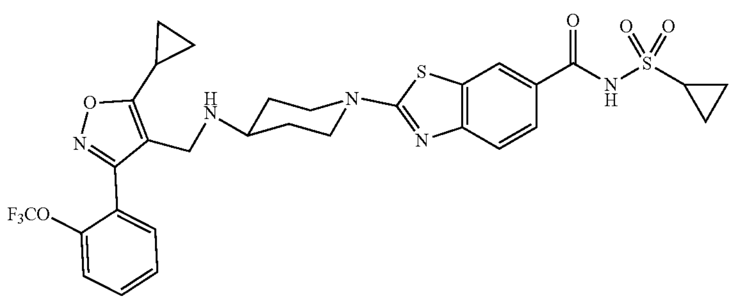 [SMILES: O=C(NS(=O)(=O)C1CC1)c1ccc2nc(N3CCC(NCc4c(-c5ccccc5OC(F)(F)F)noc4C4CC4)CC3)sc2c1] | 662.19 (M + H) |
| 900-1 | 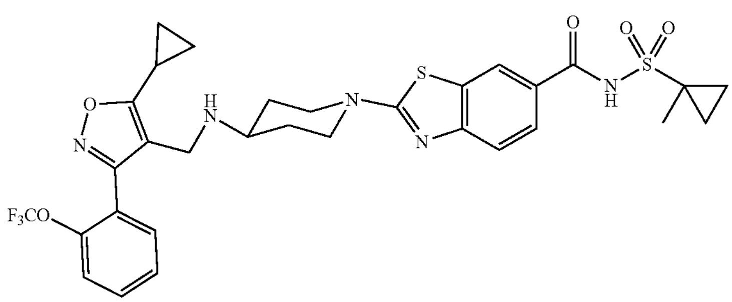 [SMILES: CC1(S(=O)(=O)NC(=O)c2ccc3nc(N4CCC(NCc5c(-c6ccccc6OC(F)(F)F)noc5C5CC5)CC4)sc3c2)CC1] | 676.20 (M + H) |

TABLE 8a-continued

The following examples listed in TABLE 8a werre prepared according to the procedures described for Example 189, Example 190 and Example 323.

| Example | Structure | MS Data |
|---|---|---|
| 900-2 | 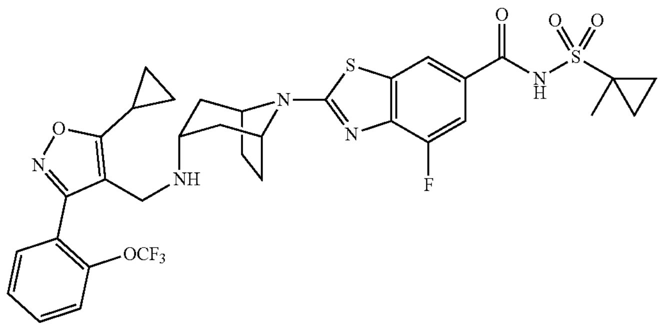 [SMILES: CC1(S(=O)(=O)NC(=O)c2cc(F)c3nc(N4C5CCC4CC(NCc4c(-c6ccccc6OC(F)(F)F)noc4C4CC4)C5)sc3c2)CC1] | 720.23 (M + H) |
| 900-3 | 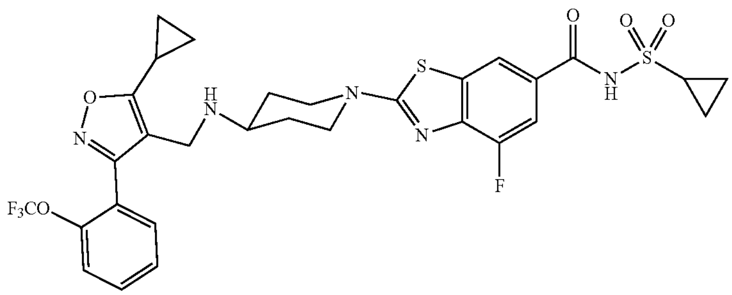 [SMILES: O=C(NS(=O)(=O)C1CC1)c1cc(F)c2nc(N3CCC(NCc4c(-c5ccccc5OC(F)(F)F)noc4C4CC4)CC3)sc2c1] | 680.18 (M + H) |
| 900-4 | 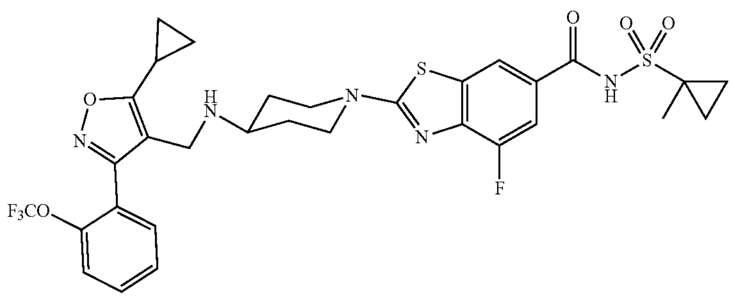 [SMILES: CC1(S(=O)(=O)NC(=O)c2cc(F)c3nc(N4CCC(NCc5c(-c6ccccc6OC(F)(F)F)noc5C5CC5)CC4)sc3c2)CC1] | 694.20 (M + H) |
| 900-5 | 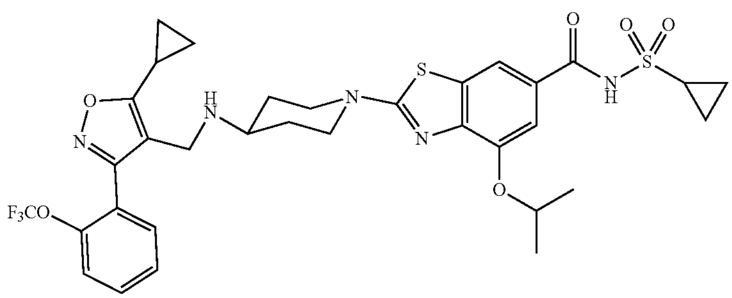 | 720.24 (M + H) |
| 900-6 | 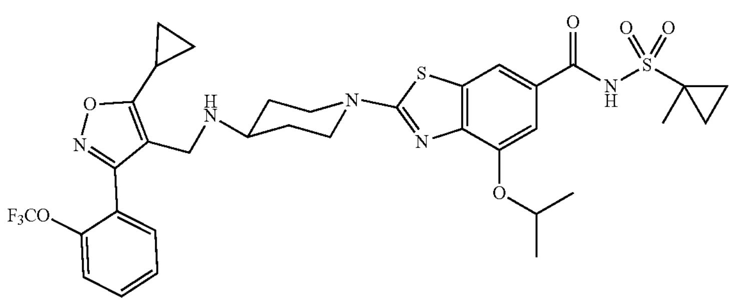 [SMILES: CC(C)Oc1cc(C(=O)NS(=O)(=O)C2(C)CC2)cc2sc(N3CCC(NCc4c(-c5ccccc5OC(F)(F)F)noc4C4CC4)CC3)nc12] | 734.25 (M + H) |

TABLE 8a-continued

The following examples listed in TABLE 8a werre prepared according to the procedures described for Example 189, Example 190 and Example 323.

| Example | Structure | MS Data |
|---|---|---|
| 900-9 | 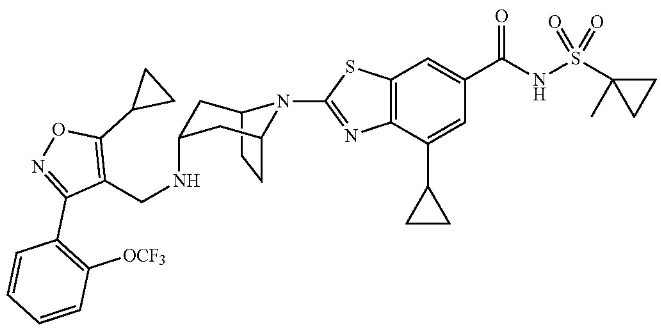 [SMILES: CC1(S(=O)(=O)NC(=O)c2cc(C3CC3)c3nc(N4C5CCC4CC(NCc4c(-c6ccccc6OC(F)(F)F)noc4C4CC4)C5)sc3c2)CC1] | 742.26 (M + H) |
| 900-11 | 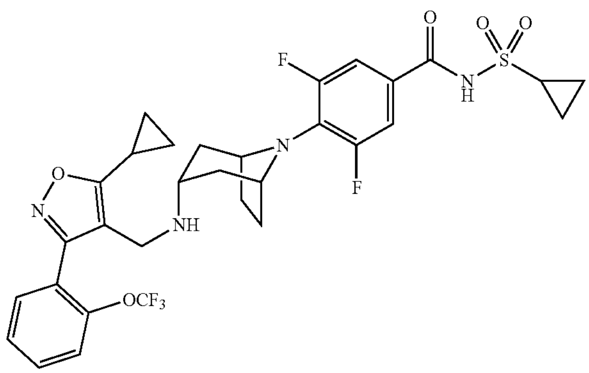 [SMILES: O=C(NS(=O)(=O)C1CC1)c1cc(F)c(N2C3CCC2CC(NCc2c(-c4ccccc4OC(F)(F)F)noc2C2CC2)C3)c(F)c1] | 667.22 (M + H) |
| 900-12 | 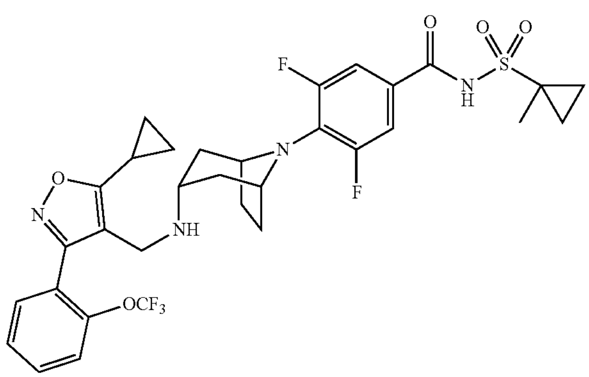 [SMILES: CC1(S(=O)(=O)NC(=O)c2cc(F)c(N3C4CCC3CC(NCc3c(-c5ccccc5OC(F)(F)F)noc3C3CC3)C4)c(F)c2)CC1] | 681.23 (M + H) |
| 900-13 | 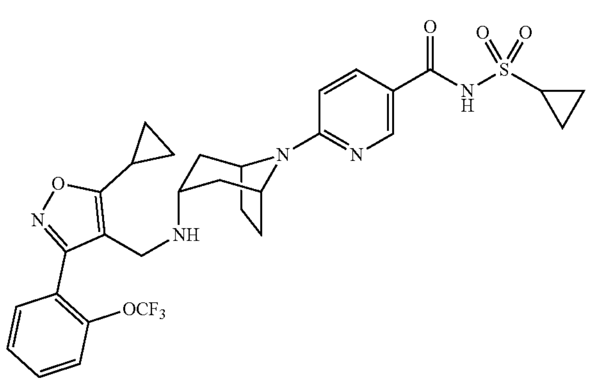 [SMILES: O=C(NS(=O)(=O)C1CC1)c1ccc(N2C3CCC2CC(NCc2c(-c4ccccc4OC(F)(F)F)noc2C2CC2)C3)nc1] | 632.23 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 900-14 | 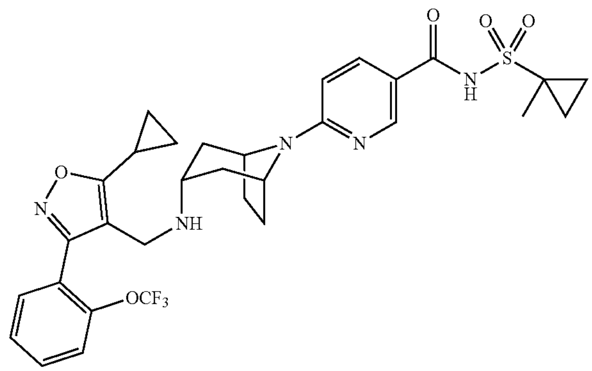 [SMILES: CC1(S(=O)(=O)NC(=O)c2ccc(N3C4CCC3CC(NCc3c(-c5ccccc5OC(F)(F)F)noc3C3CC3)C4)nc2)CC1] | 646.24 (M + H) |
| 900-15 | 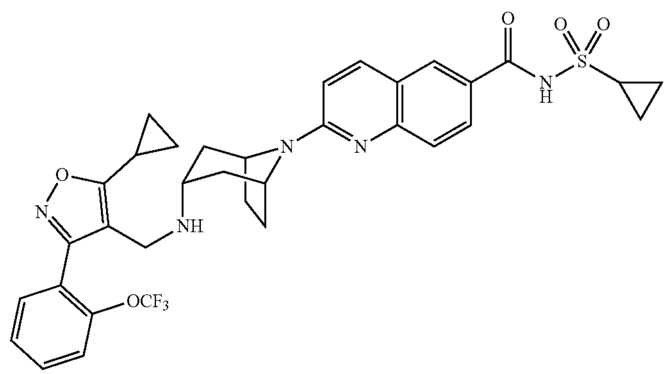 [SMILES: O=C(NS(=O)(=O)C1CC1)c1ccc2nc(N3C4CCC3CC(NCc3c(-c5ccccc5OC(F)(F)F)noc3C3CC3)C4)ccc2c1] | 682.25 (M + H) |
| 1202 | 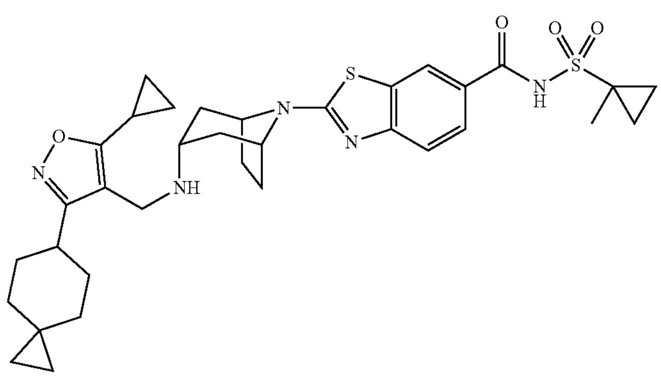 [SMILES: CC1(S(=O)(=O)NC(=O)c2ccc3nc(N4C5CCC4CC(NCc4c(C6CCC7(CC6)CC7)noc4C4CC4)C5)sc3c2)CC1] | 650.55 (M + H) |
| 1401 | 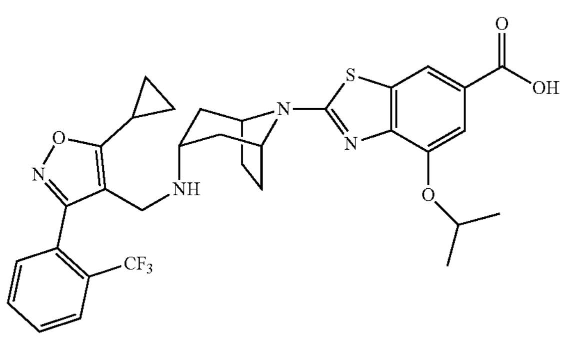 [SMILES: CC(C)Oc1cc(C(=O)O)cc2sc(N3C4CCC3CC(NCc3c(-c5ccccc5C(F)(F)F)noc3C3CC3)C4)nc12] | 627.24 (M + H) |

TABLE 8a-continued

The following examples listed in TABLE 8a werre prepared according to the procedures described for Example 189, Example 190 and Example 323.

| Example | Structure | MS Data |
|---|---|---|
| 1402 | 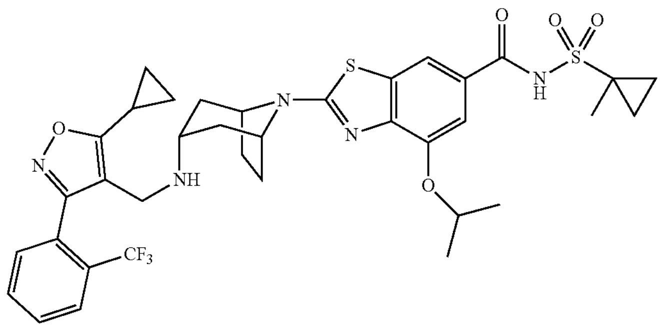 [SMILES: CC(C)Oc1cc(C(=O)NS(=O)(=O)C2(C)CC2)cc2sc(N3C4CCC3CC(NCc3c(-c5ccccc5C(F)(F)F)noc3C3CC3)C4)nc12] | 744.28 (M + H) |
| 1403 | 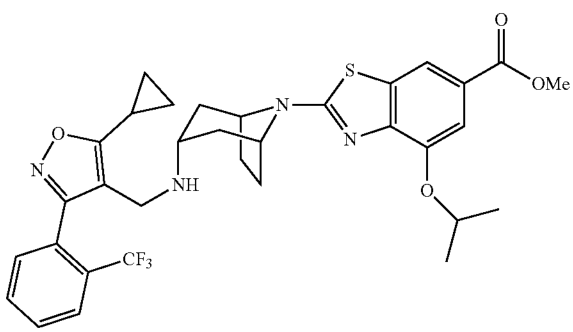 [SMILES: COC(=O)c1cc(OC(C)C)c2nc(N3C4CCC3CC(NCc3c(-c5ccccc5C(F)(F)F)noc3C3CC3)C4)sc2c1] | 641.25 (M + H) |
| 1404 | 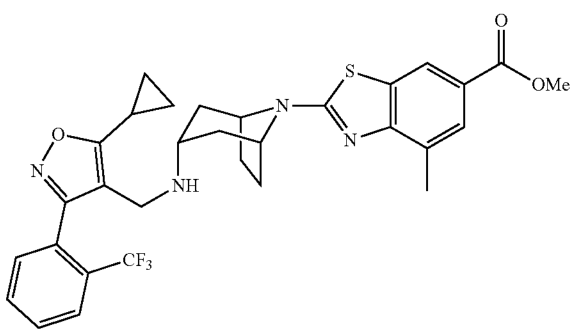 [SMILES: COC(=O)c1cc(C)c2nc(N3C4CCC3CC(NCc3c(-c5ccccc5C(F)(F)F)noc3C3CC3)C4)sc2c1] | 597.22 (M + H) |
| 1405 | 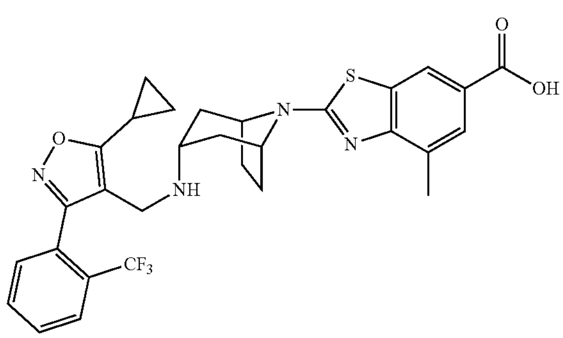 [SMILES: Cc1cc(C(=O)O)cc2sc(N3C4CCC3CC(NCc3c(-c5ccccc5C(F)(F)F)noc3C3CC3)C4)nc12] | 583.20 (M + H) |

TABLE 8a-continued

The following examples listed in TABLE 8a werre prepared according to the procedures described for Example 189, Example 190 and Example 323.

| Example | Structure | MS Data |
|---|---|---|
| 1406 | 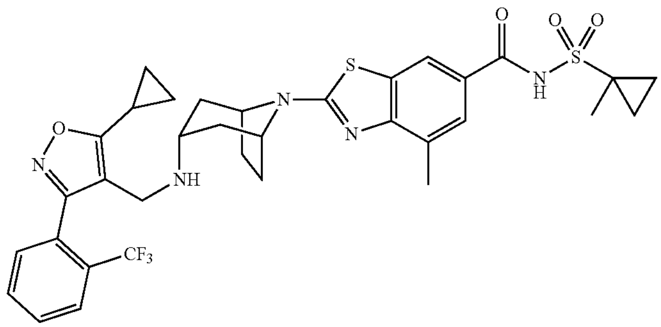 [SMILES: Cc1cc(C(=O)NS(=O)(=O)C2(C)CC2)cc2sc(N3C4CCC3CC(NCc3c(-c5ccccc5C(F)(F)F)noc3C3CC3)C4)nc12] | 700.25 (M + H) |
| 1407 | 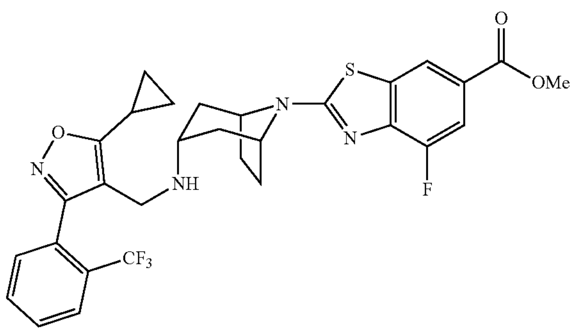 | 601.20 (M + H) |
| 1408 | 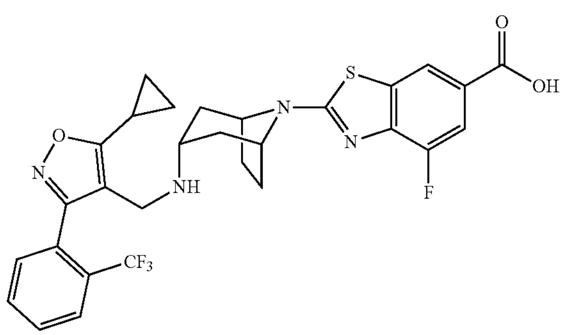 [SMILES: O=C(O)c1cc(F)c2nc(N3C4CCC3CC(NCc3c(-c5ccccc5C(F)(F)F)noc3C3CC3)C4)sc2c1] | 587.18 (M + H) |
| 1409 | 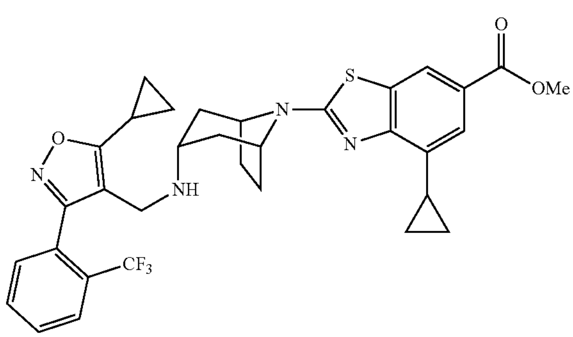 | 623.24 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 1410 | 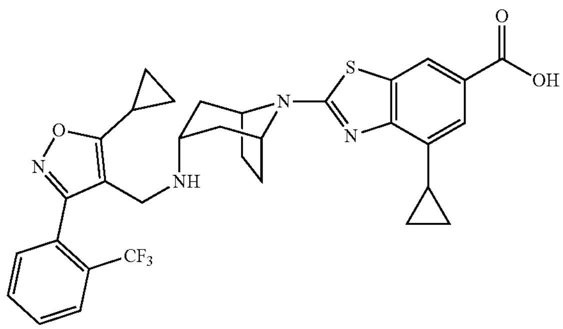 [SMILES: O=C(O)c1cc(C2CC2)c2nc(N3C4CCC3CC(NCc3c(-c5ccccc5C(F)(F)F)noc3C3CC3)C4)sc2c1] | 609.22 (M + H) |
| 1411 | 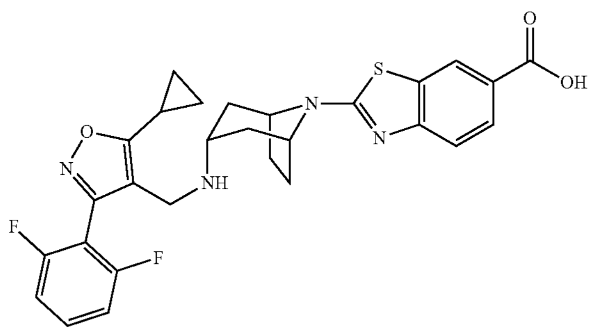 [SMILES: O=C(O)c1ccc2nc(N3C4CCC3CC(NCc3c(-c5c(F)cccc5F)noc3C3CC3)C4)sc2c1] | 537.17 (M + H) |
| 1412 | 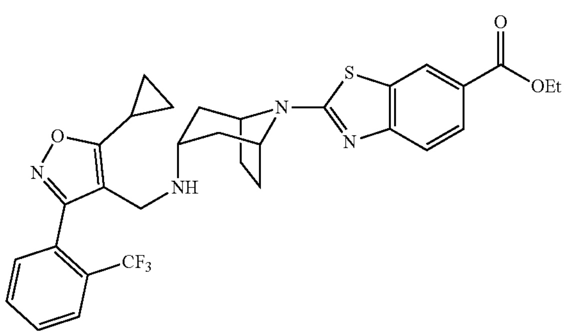 [SMILES: CCOC(=O)c1ccc2nc(N3C4CCC3CC(NCc3c(-c5ccccc5C(F)(F)F)noc3C3CC3)C4)sc2c1] | 597.22 (M + H) |
| 1413 | 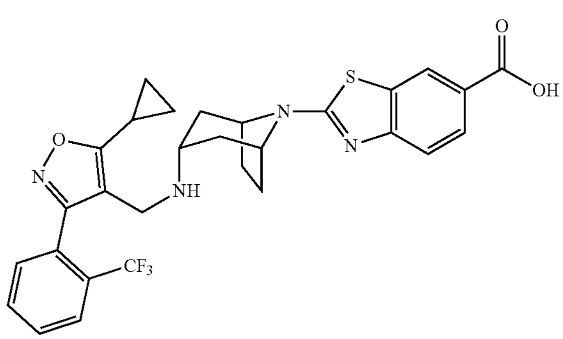 [SMILES: O=C(O)c1ccc2nc(N3C4CCC3CC(NCc3c(-c5ccccc5C(F)(F)F)noc3C3CC3)C4)sc2c1] | 569.19 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 1414 | 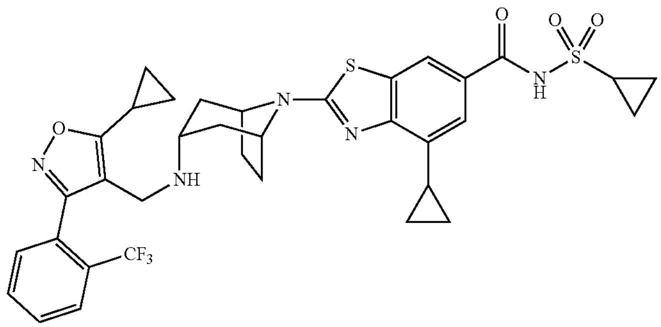 [SMILES: O=C(NS(=O)(=O)C1CC1)c1cc(C2CC2)c2nc(N3C4CCC3CC(NCc3c(-c5ccccc5C(F)(F)F)noc3C3CC3)C4)sc2c1] | 712.25 (M + H) |
| 1415 | 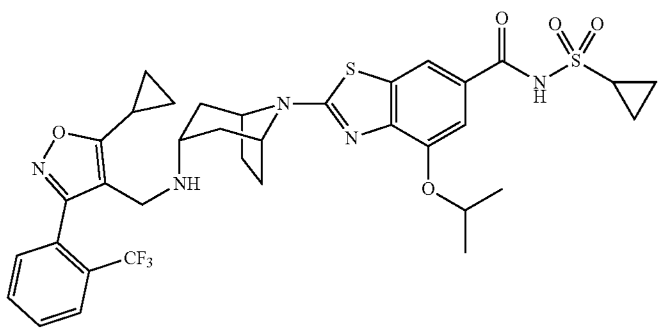 [SMILES: CC(C)Oc1cc(C(=O)NS(=O)(=O)C2CC2)cc2sc(N3C4CCC3CC(NCc3c(-c5ccccc5C(F)(F)F)noc3C3CC3)C4)nc12] | 730.26 (M + H) |
| 1416 | 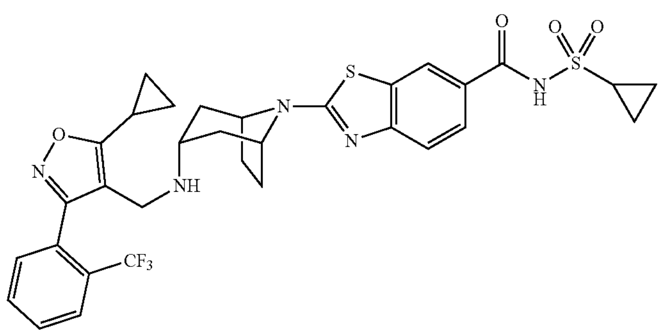 [SMILES: O=C(NS(=O)(=O)C1CC1)c1ccc2nc(N3C4CCC3CC(NCc3c(-c5ccccc5C(F)(F)F)noc3C3CC3)C4)sc2c1] | 672.21 (M + H) |
| 1417 | 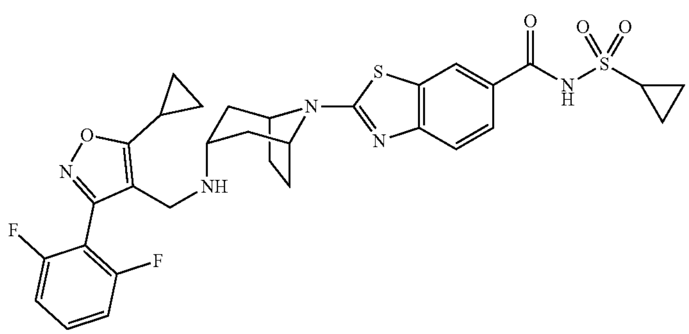 [SMILES: O=C(NS(=O)(=O)C1CC1)c1ccc2nc(N3C4CCC3CC(NCc3c(-c5c(F)cccc5F)noc3C3CC3)C4)sc2c1] | 640.20 (M + H) |

TABLE 8a-continued
The following examples listed in TABLE 8a werre prepared according to the procedures described for Example 189, Example 190 and Example 323.
| Example | Structure | MS Data |
|---------|-----------|---------|
| 1418 | 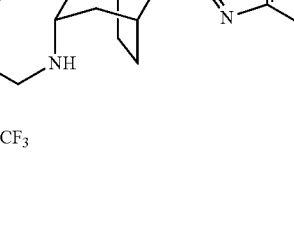 | 553.21 (M + H) |
| 1419 | 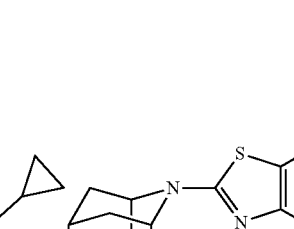 | 577.21 (M + H) |
| 1420 | 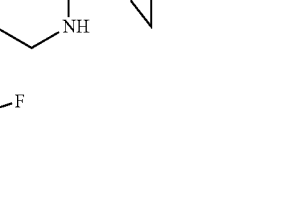 | 686.45 (M + H) |
| 1421 | 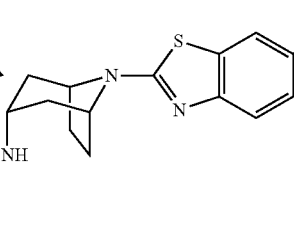 | 652.40 (M − H) |

TABLE 8a-continued

The following examples listed in TABLE 8a werre prepared according to the procedures described for Example 189, Example 190 and Example 323.

| Example | Structure | MS Data |
| --- | --- | --- |
| 1422 | 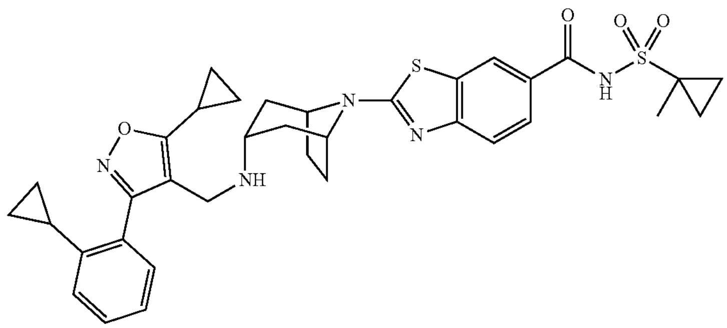 [SMILES: CC1(S(=O)(=O)NC(=O)c2ccc3nc(N4C5CCC4CC(NCc4c(-c6ccccc6C6CC6)noc4C4CC4)C5)sc3c2)CC1] | 658.5 (M + H) |
| 1423 | 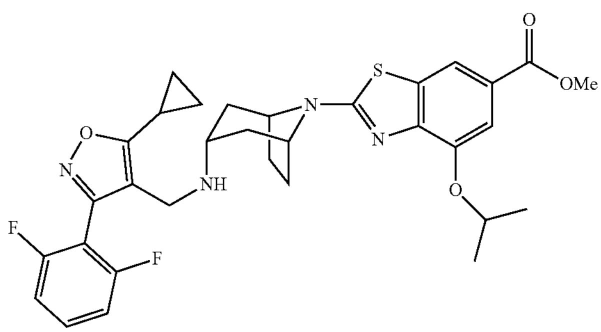 [SMILES: COC(=O)c1cc(OC(C)C)c2nc(N3C4CCC3CC(NCc3c(-c5c(F)cccc5F)noc3C3CC3)C4)sc2c1] | 609.23 (M + H) |
| 1424 | 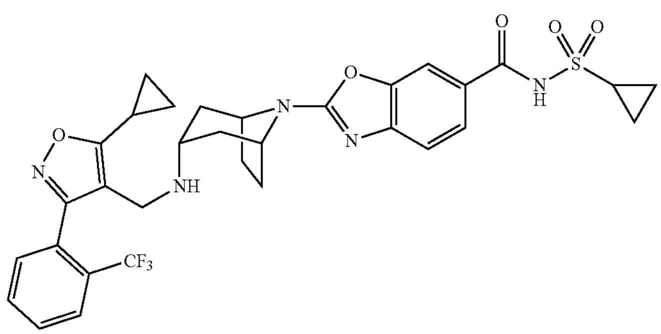 [SMILES: O=C(NS(=O)(=O)C1CC1)c1ccc2nc(N3C4CCC3CC(NCc3c(-c5ccccc5C(F)(F)F)noc3C3CC3)C4)oc2c1] | 656.23 (M + H) |
| 1425 | 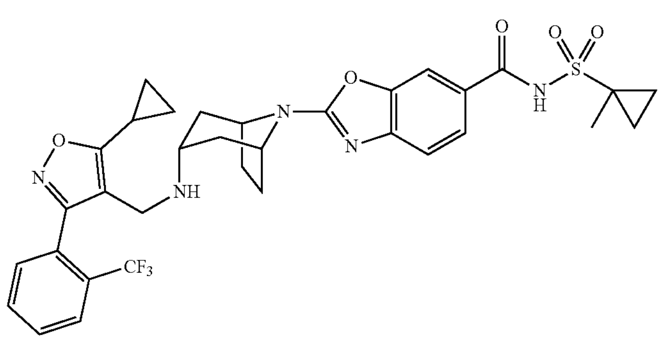 [SMILES: CC1(S(=O)(=O)NC(=O)c2ccc3nc(N4C5CCC4CC(NCc4c(-c6ccccc6C(F)(F)F)noc4C4CC4)C5)oc3c2)CC1] | 670.00 (M + H) |

TABLE 8a-continued

The following examples listed in TABLE 8a werre prepared according to the procedures described for Example 189, Example 190 and Example 323.

| Example | Structure | MS Data |
|---------|-----------|---------|
| 1426 | 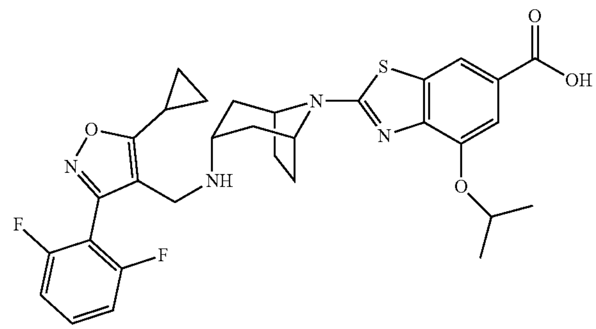 [SMILES: CC(C)Oc1cc(C(=O)O)cc2sc(N3C4CCC3CC(NCc3c(-c5c(F)cccc5F)noc3C3CC3)C4)nc12] | 595.22 (M + H) |
| 1428 | 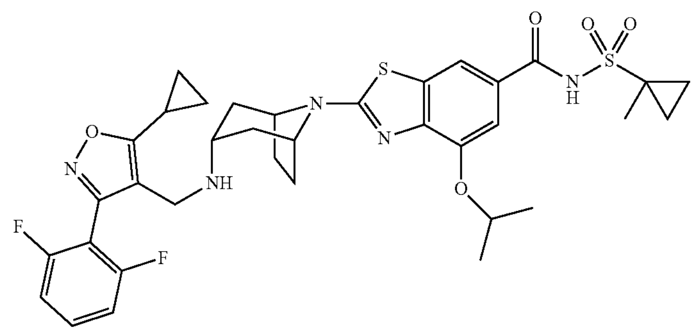 [SMILES: CC(C)Oc1cc(C(=O)NS(=O)(=O)C2(C)CC2)cc2sc(N3C4CCC3CC(NCc3c(-c5c(F)cccc5F)noc3C3CC3)C4)nc12] | 712.24 (M + H) |
| 1429 | 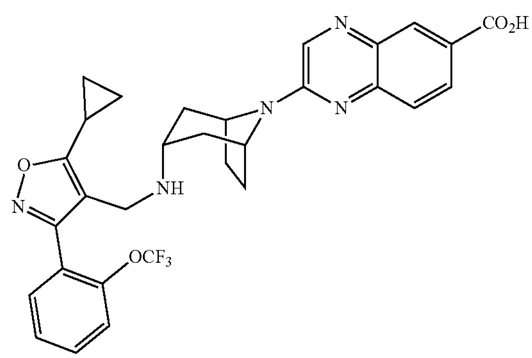 [SMILES: O=C(O)c1ccc2nc(N3C4CCC3CC(NCc3c(-c5ccccc5OC(F)(F)F)noc3C3CC3)C4)cnc2c1] | 580.22 (M + H) |
| 1430 | 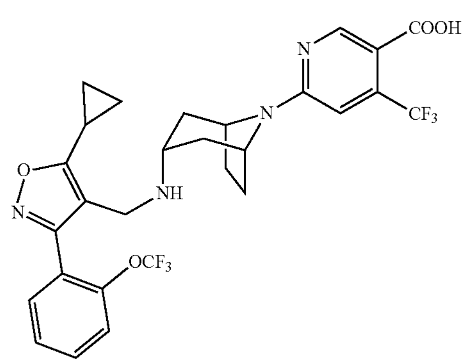 [SMILES: O=C(O)c1cnc(N2C3CCC2CC(NCc2c(-c4ccccc4OC(F)(F)F)noc2C2CC2)C3)cc1C(F)(F)F] | 597.20 (M + H) |

TABLE 8a-continued

The following examples listed in TABLE 8a werre prepared according to the procedures described for Example 189, Example 190 and Example 323.

| Example | Structure | MS Data |
|---|---|---|
| 1431 | 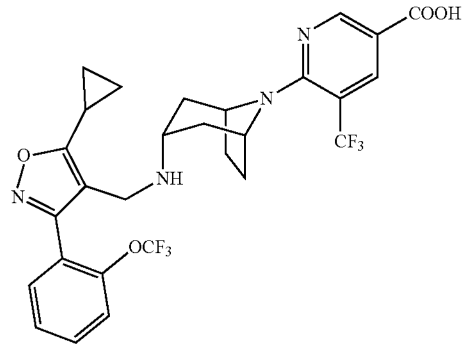 [SMILES: O=C(O)c1cnc(N2C3CCC2CC(NCc2c(-c4ccccc4OC(F)(F)F)noc2C2CC2)C3)c(C(F)(F)F)c1] | 597.20 (M + H) |

Assays

Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 µl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 µl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

To assess the FXR agonistic potency of the example compounds as well as for reference compound, potency ranges were determined in the Human FXR (NR1H4) Assay as listed below in Table 9. The efficacy was normalized to CDCA set as 100%. (A=EC50<0.001 µM; B 0.001 µM<EC50<0.1 µM; C=0.1 µM<EC50<1.0 µM; D=EC50>1.0 µM)

TABLE 9

| Example | EC50 | Efficacy (%) |
|---|---|---|
| CDCA | D | 100 |
| 6-ECDCA | C | 223 |
| 1 | D | 74% |
| 2 | B | 244% |
| 3 | B | 137% |
| 4 | A | 169% |
| 5 | B | 145% |
| 6 | A | 153% |
| 19 | C | 78% |
| 20 | B | 56% |
| 49 | B | 135% |
| 50 | A | 186% |
| 95 | B | 128% |
| 96 | B | 136% |
| 138 | A | 155% |
| 153 | B | 113% |
| 165 | B | 236% |
| 169 | D | 38% |
| 170 | C | 105% |
| 172 | C | 257% |
| 173 | D | 116% |
| 174 | B | 132% |
| 176 | C | 228% |
| 178 | D | 108% |
| 179 | C | 148% |
| 183 | D | 119% |
| 186 | D | 45% |
| 187 | D | 64% |
| 188 | D | 15% |

TABLE 9-continued

| Example | EC50 | Efficacy (%) |
|---|---|---|
| 189 | B | 73% |
| 190 | A | 96% |
| 201 | A | 282% |
| 202 | A | 279% |
| 225 | A | 126% |
| 227 | A | 256% |
| 228 | B | 140% |
| 231 | A | 277% |
| 234 | C | 146% |
| 235 | B | 240% |
| 236 | B | 75% |
| 237 | B | 226% |
| 239 | B | 201% |
| 240 | A | 245% |
| 257 | B | 203% |
| 262 | A | 289% |
| 268 | C | 129% |
| 279 | C | 158% |
| 280 | B | 242% |
| 281 | B | 171% |
| 282 | B | 142% |
| 283 | D | 246% |
| 284 | D | 54% |
| 285 | C | 126% |
| 286 | D | 67% |
| 287 | D | 98% |
| 288 | C | 114% |
| 289 | D | 207% |
| 290 | D | 85% |
| 291 | B | 171% |
| 292 | B | 212% |
| 293 | B | 92% |
| 294 | D | 130% |
| 295 | B | 152% |
| 296 | A | 184% |
| 297 | A | 150% |
| 298 | B | 155% |
| 299 | B | 154% |
| 300 | A | 143% |
| 301 | A | 63% |
| 302 | B | 62% |
| 303 | A | 175% |
| 304 | A | 139% |
| 305 | C | 139% |
| 7 | B | 37% |
| 8 | A | 109% |
| 64 | B | 40% |
| 122 | B | 90% |
| 125 | B | 86.5% |
| 194 | A | 81% |
| 196 | B | 83.5% |
| 197 | C | 115% |
| 198 | B | 140% |
| 199 | C | 58% |
| 200-1 | B | 10% |
| 200-3 | C | 35% |
| 200-4 | B | 106% |
| 200-5 | C | 72% |
| 200-6 | B | 86.5% |
| 200-7 | B | 74.5% |
| 200-8 | A | 73.5% |
| 200-9 | B | 81% |
| 200-10 | A | 92.5% |
| 200-11 | B | 75% |
| 200-12 | B | 16.5% |
| 200-13 | A | 96% |
| 200-14 | A | 93.5% |
| 200-15 | B | 75.8% |
| 200-16 | B | 109% |
| 200-17 | B | 51.5% |
| 200-18 | B | 91.3% |
| 200-19 | B | 50.5% |
| 200-21 | B | 58% |
| 200-23 | B | 76.5% |
| 200-24 | B | 96.2% |
| 200-25 | B | 58.5% |
| 200-27 | B | 28.3% |
| 200-28 | A | 132% |

TABLE 9-continued

| Example | EC50 | Efficacy (%) |
|---|---|---|
| 200-29 | B | 94% |
| 200-30 | A | 108% |
| 323 | A | 150% |
| 328 | A | 146% |
| 342 | B | 76% |
| 400-1 | B | 210% |
| 400-3 | B | 104% |
| 400-4 | B | 97.5% |
| 400-5 | B | 110% |
| 400-6 | B | 73.5% |
| 400-7 | B | 91% |
| 400-8 | B | 79% |
| 400-9 | C | 37.5% |
| 400-10 | C | 68% |
| 400-11 | A | 79.3% |
| 400-12 | A | 115% |
| 400-13 | B | 83.3% |
| 400-14 | A | 119% |
| 400-15 | A | 104% |
| 400-16 | A | 87.3% |
| 400-18 | A | 98% |
| 400-20 | B | 43.6% |
| 400-22 | A | 83.2% |
| 400-24 | A | 88.2% |
| 400-25 | B | 72% |
| 400-26 | A | 97.2% |
| 400-29 | A | 118% |
| 400-32 | A | 116% |
| 400-33 | A | 91% |
| 400-35 | B | 117% |
| 400-37 | B | 82.5% |
| 402 | B | 112% |
| 403 | B | 61% |
| 404 | B | 88% |
| 413 | B | 118% |
| 414 | A | 121% |
| 510 | B | 41% |
| 514 | B | 100% |
| 597 | B | 83.5% |
| 638 | C | 107% |
| 639 | C | 13% |
| 640 | B | 92.3% |
| 641 | C | 40% |
| 642 | C | 85.3% |
| 643 | B | 52% |
| 644 | A | 94.5% |
| 646 | B | 105% |
| 695 | B | 75% |
| 696 | B | 59.1% |
| 702 | B | 113% |
| 791 | D | 63% |
| 900-1 | C | 80.5% |
| 900-2 | B | 109% |
| 900-3 | C | 44.8% |
| 900-4 | D | 84.8% |
| 900-5 | C | 68.5% |
| 900-6 | B | 112% |
| 900-9 | A | 122% |
| 900-11 | B | 70.5% |
| 900-12 | B | 67% |
| 900-13 | B | 59.5% |
| 900-14 | C | 46.5% |
| 900-15 | B | 82.5% |
| 1202 | B | 85.5% |
| 1401 | C | 125% |
| 1402 | B | 136% |
| 1403 | B | 119% |
| 1404 | C | 46% |
| 1405 | B | 125% |
| 1406 | A | 133% |
| 1407 | B | 92.5% |
| 1408 | B | 103% |
| 1409 | B | 52% |
| 1410 | A | 74.5% |
| 1411 | B | 94.7% |
| 1412 | C | 75% |
| 1413 | B | 90.7% |
| 1414 | A | 89.5% |

TABLE 9-continued

| Example | EC50 | Efficacy (%) |
| --- | --- | --- |
| 1415 | B | 106% |
| 1416 | B | 87.5% |
| 1417 | B | 69% |
| 1418 | B | 102% |
| 1419 | B | 107% |
| 1420 | B | 91% |
| 1421 | B | 101% |
| 1422 | B | 94% |
| 1423 | D | 78% |
| 1424 | B | 148% |
| 1425 | C | 74% |
| 1426 | C | 73.2% |
| 1428 | B | 86% |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (I):

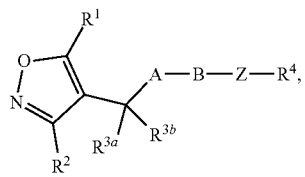

(I)

or a pharmaceutically acceptable salt thereof, wherein:
$R^1$ is isopropyl, cyclopropyl or t-butyl;
$R^2$ is optionally substituted phenyl;
$R^{3a}$ and $R^{3b}$ are independently hydrogen or halogen;
A is

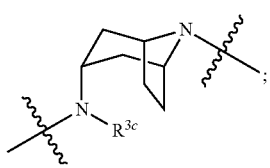

$R^{3c}$ is hydrogen, methyl or formyl;
B is

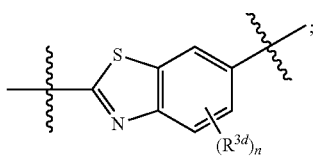

n is 0 or 1;
$R^{3d}$ is selected from the group consisting of halogen, —CN, —NO$_2$, —NH$_2$, optionally substituted C$_1$-C$_6$ alkyl, optionally substituted C$_1$-C$_6$ alkoxy, optionally substituted C$_3$-C$_6$ cycloalkyl, optionally substituted C$_3$-C$_6$ cycloalkenyl, optionally substituted aryl, and optionally substituted heteroaryl;

Z is absent;
$R^4$ is —CO$_2$R$^5$; and
$R^5$ is hydrogen, methyl, ethyl or t-butyl.

2. The compound of claim 1, wherein $R^1$ is cyclopropyl.

3. The compound of claim 1, wherein $R^2$ is

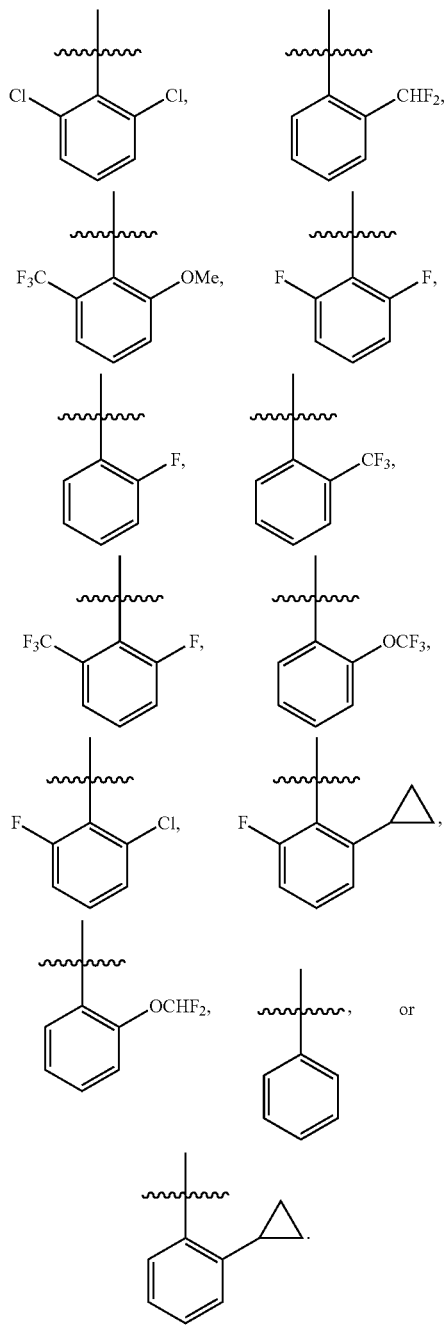

4. The compound of claim 1, wherein $R^{3a}$, $R^{3b}$, $R^{3c}$ and $R^5$ are all hydrogen.

5. The compound of claim 1, wherein n is 1 and $R^{3d}$ is iPrO-, fluoro, or cyclopropyl.

6. The compound of claim 1, selected from the compounds set forth in the table below,

| Example No. | Structure |
|---|---|
| 414 | 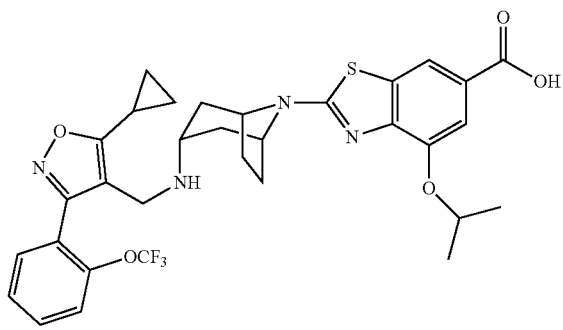 [SMILES: CC(C)Oc1cc(C(=O)O)cc2sc(N3C4CCC3CC(NCc3c(-c5ccccc5OC(F)(F)F)noc3C3CC3)C4)nc12] |
| 644 | 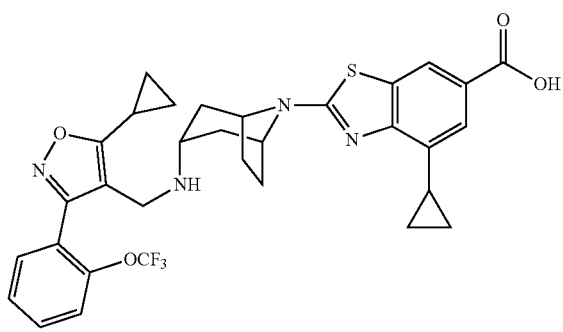 [SMILES: O=C(O)c1cc(C2CC2)c2nc(N3C4CCC3CC(NCc3c(-c5ccccc5OC(F)(F)F)noc3C3CC3)C4)sc2c1] |
| 200-30 | 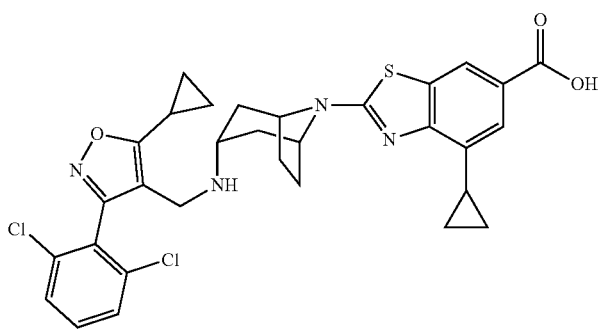 [SMILES: O=C(O)c1cc(C2CC2)c2nc(N3C4CCC3CC(NCc3c(-c5c(Cl)cccc5Cl)noc3C3CC3)C4)sc2c1] |
| 200-14 | 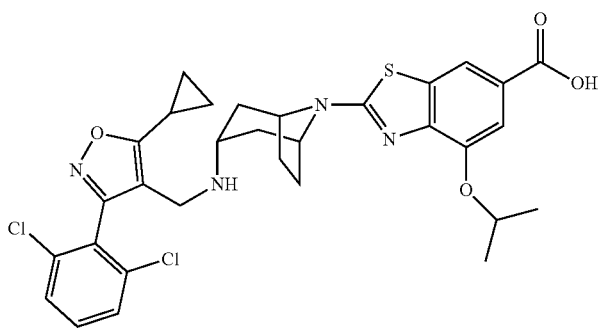 [SMILES: CC(C)Oc1cc(C(=O)O)cc2sc(N3C4CCC3CC(NCc3c(-c5c(Cl)cccc5Cl)noc3C3CC3)C4)nc12] |

| Example No. | Structure |
|---|---|
| 404 | 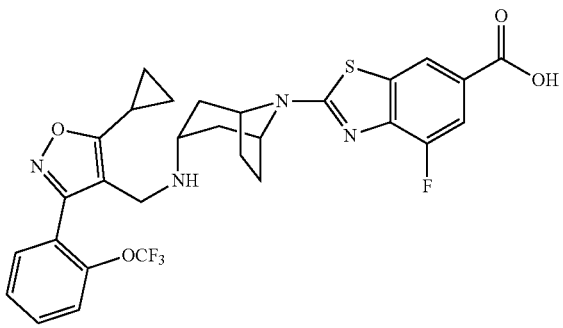 [SMILES: O=C(O)c1cc(F)c2nc(N3C4CCC3CC(NCc3c(-c5ccccc5OC(F)(F)F)noc3C3CC3)C4)sc2c1] |
| 1408 | 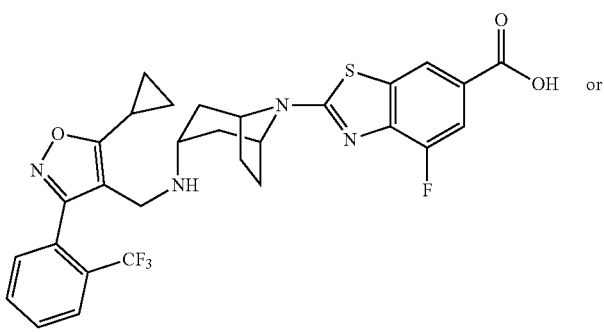 [SMILES: O=C(O)c1cc(F)c2nc(N3C4CCC3CC(NCc3c(-c5ccccc5C(F)(F)F)noc3C3CC3)C4)sc2c1] or |
| 4 | 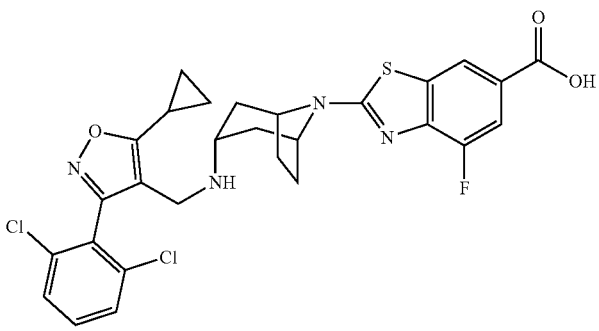 |
or a pharmaceutically acceptable salt thereof.
7. The compound of claim 6, having the structure
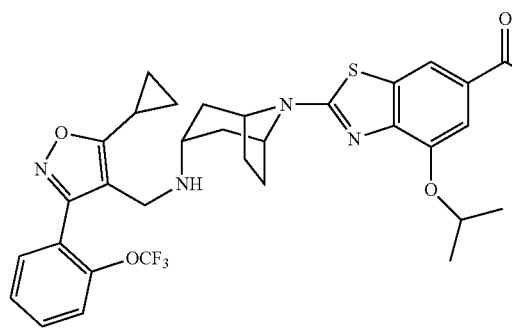
or a pharmaceutically acceptable salt thereof.
8. The compound of claim 6, having the structure
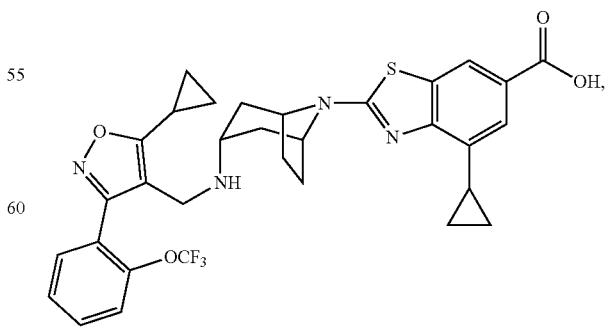
or a pharmaceutically acceptable salt thereof.

9. The compound of claim 6, having the structure

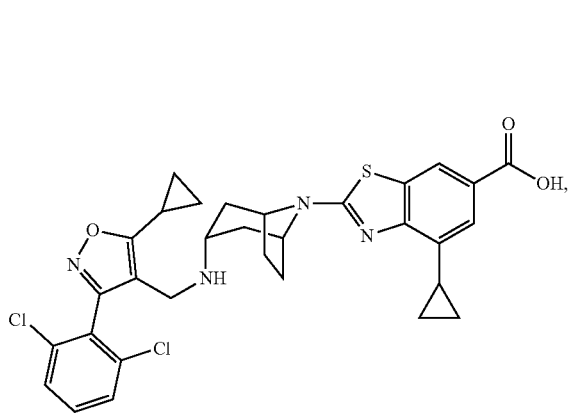 [SMILES: O=C(O)c1cc(C2CC2)c2nc(N3C4CCC3CC(NCc3c(-c5c(Cl)cccc5Cl)noc3C3CC3)C4)sc2c1]

or a pharmaceutically acceptable salt thereof.

10. The compound of claim 6, having the structure

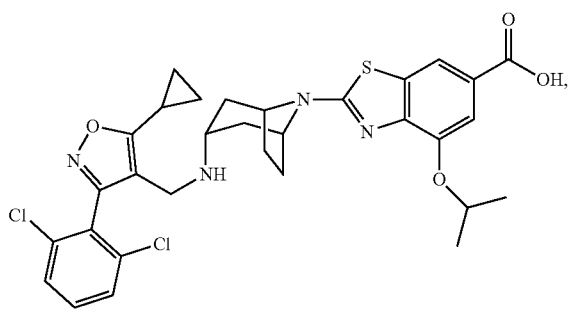 [SMILES: CC(C)Oc1cc(C(=O)O)cc2sc(N3C4CCC3CC(NCc3c(-c5c(Cl)cccc5Cl)noc3C3CC3)C4)nc12]

or a pharmaceutically acceptable salt thereof.

11. The compound of claim 6, having the structure

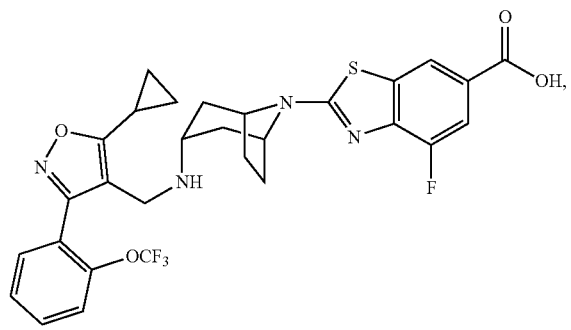 [SMILES: O=C(O)c1cc(F)c2nc(N3C4CCC3CC(NCc3c(-c5ccccc5C(F)(F)F)noc3C3CC3)C4)sc2c1]

or a pharmaceutically acceptable salt thereof.

12. The compound of claim 6, having the structure

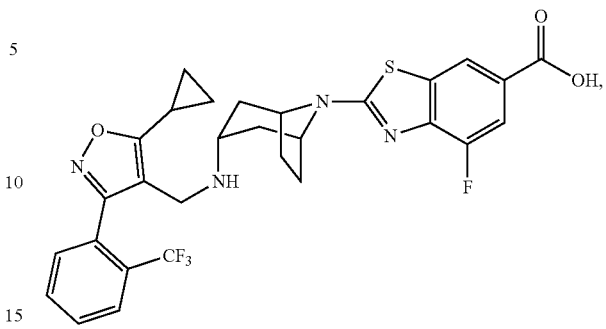 [SMILES: O=C(O)c1cc(F)c2nc(N3C4CCC3CC(NCc3c(-c5c(Cl)cccc5Cl)noc3C3CC3)C4)sc2c1]

or a pharmaceutically acceptable salt thereof.

13. The compound of claim 6, having the structure

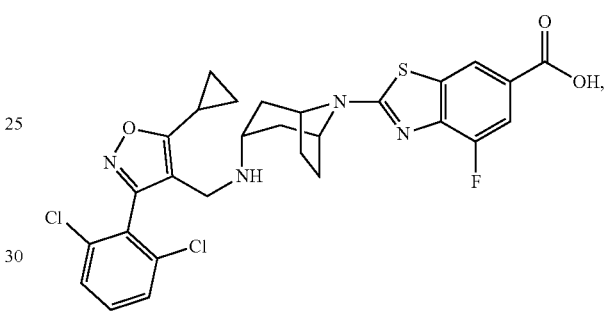

or a pharmaceutically acceptable salt thereof.

14. A method for treating an FXR-mediated disease or condition in a subject in need thereof, comprising administering to the subject a therapeutically effective amount of a compound according to claim 1.

15. The method according to claim 14, wherein the FXR-mediated disease or condition is selected from the group consisting of chronic liver disease, gastrointestinal disease, renal disease, cardiovascular disease, fibrotic diseases, and metabolic disease.

16. The method according to claim 15, wherein the FXR-mediated disease or condition is a fibrotic disease selected from primary biliary cirrhosis, primary sclerosing cholangitis, pulmonary fibrosis, renal fibrosis, and liver fibrosis.

17. The method according to claim 15, wherein the FXR-mediated disease or condition is a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

18. The method according to claim 15, wherein the FXR-mediated disease or condition is a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

19. The method according to claim 15, wherein the FXR-mediated disease or condition is a cardiovascular disease selected from the group consisting of atherosclerosis, arteriosclerosis, dyslipidemia, hypercholesterolemia, and hypertriglyceridemia.

20. The method according to claim 15, wherein the FXR-mediated disease or condition is a metabolic disease selected from the group consisting of insulin resistance, Type I and Type II diabetes, and obesity.

21. A pharmaceutical composition comprising a compound according to claim 1 and a pharmaceutically acceptable carrier.

22. A pharmaceutical composition comprising a compound according to claim 6 and a pharmaceutically acceptable carrier.

\* \* \* \* \*